United States Patent
Patten et al.

(10) Patent No.: US 7,531,324 B2
(45) Date of Patent: May 12, 2009

(54) INTERFERON-ALPHA POLYPEPTIDES AND CONJUGATES

(75) Inventors: Phillip A. Patten, Portola Valley, CA (US); Sridhar Viswanathan, Menlo Park, CA (US); Torben Lauesgaard Nissen, London (GB); Anne Vogt, Loerrach (DE); Harald Kropshofer, Loerrach (DE); Ralf Schumacher, Penzberg (DE); Stephan Fischer, Polling (DE); Stefan Seeber, Penzberg (DE); Andreas Schaubmar, Penzberg (DE); Roberto Falkenstein, Munich (DE)

(73) Assignee: Maxygen, Inc., Redwood City, CA (US)

( * ) Notice: Subject to any disclaimer, the term of this patent is extended or adjusted under 35 U.S.C. 154(b) by 416 days.

(21) Appl. No.: 11/531,557

(22) Filed: Sep. 13, 2006

(65) Prior Publication Data

US 2007/0025966 A1    Feb. 1, 2007

Related U.S. Application Data

(62) Division of application No. 11/132,722, filed on May 18, 2005, now Pat. No. 7,318,918.

(60) Provisional application No. 60/572,504, filed on May 19, 2004.

(51) Int. Cl.
*C12N 15/00* (2006.01)
*C12N 15/63* (2006.01)
*C12P 21/00* (2006.01)
*C07H 21/04* (2006.01)

(52) U.S. Cl. .................. 435/69.1; 435/320.1; 435/471; 435/325; 435/70.1; 435/71.1; 536/23.1; 536/23.52

(58) Field of Classification Search .................... None
See application file for complete search history.

(56) References Cited

U.S. PATENT DOCUMENTS

| | | |
|---|---|---|
| 4,414,150 A | 11/1983 | Goeddel |
| 4,695,623 A | 9/1987 | Stabinsky |
| 4,885,166 A | 12/1989 | Meyer et al. |
| 5,382,657 A | 1/1995 | Karasiewicz et al. |
| 5,539,063 A | 7/1996 | Hakimi et al. |
| 5,559,213 A | 9/1996 | Hakimi et al. |
| 5,747,646 A | 5/1998 | Hakimi et al. |
| 5,792,834 A | 8/1998 | Hakimi et al. |
| 5,834,594 A | 11/1998 | Hakimi et al. |
| 5,849,860 A | 12/1998 | Hakimi et al. |
| 5,985,262 A | 11/1999 | Kinstler et al. |
| 6,303,344 B1 | 10/2001 | Patten |
| 6,610,830 B1 | 8/2003 | Goeddel et al. |
| 2004/0002474 A1 | 1/2004 | Heinrichs et al. |
| 2004/0030101 A1 | 2/2004 | Bailon et al. |
| 2004/0219131 A1 | 11/2004 | Patten et al. |
| 2004/0223950 A1 | 11/2004 | Brugger et al. |

FOREIGN PATENT DOCUMENTS

| | | |
|---|---|---|
| EP | 0 051 873 A2 | 5/1982 |
| EP | 0 205 404 A2 | 12/1986 |
| EP | 0 422 697 A1 | 4/1991 |
| EP | 0 510 356 B1 | 10/1992 |
| EP | 0 593 868 B1 | 4/1994 |
| EP | 0 809 996 A2 | 12/1997 |
| EP | 0 911 033 A2 | 4/1999 |
| EP | 0 911 033 B1 | 11/2003 |
| KR | 2002-0067105 | 8/2002 |
| WO | WO 83/02461 A1 | 7/1983 |
| WO | WO 92/06707 A1 | 4/1992 |
| WO | WO 95/24212 A1 | 9/1995 |
| WO | WO 99/03887 A1 | 1/1999 |
| WO | WO 00/42175 A1 | 7/2000 |
| WO | 0052153 A2 | 9/2000 |
| WO | 0069913 A1 | 11/2000 |
| WO | WO 01/25438 A2 | 4/2001 |
| WO | WO 01/87925 A2 | 11/2001 |
| WO | 0244197 A2 | 6/2002 |
| WO | 2004045648 A1 | 6/2004 |
| WO | WO 2004/046365 A2 | 6/2004 |

OTHER PUBLICATIONS

Allen G., Diaz M.O. (1996) Nomenclature of the human interferon proteins. J. Interferon Cytokine Res. Feb. 1996; 16(2):181-184.

Alton, K. et al. (1983) Production, characterization and biological effects of recombinant DNA derived IFN-α and IFN-γ analogs. in The Biology of the Interferon System, 1983, eds. E. DeMaeyer and H. Schellekens, Elsevier Science Publications pp. 119-128.

Altrock B.W., et al. (1986) Antiviral and antitumor effects of a human interferon analog, IFN-alpha Con1, assessed in hamsters. J Interferon Res. Aug. 1986; 6(4):405-415.

Blatt L.M., et al. (1996) The biologic activity and molecular characterization of a novel synthetic interferon-alpha species, consensus interferon. J Interferon Cytokine Res. Jul. 1996; 16(7):489-499.

Chang C.C., et al. (1999) Evolution of a cytokine using DNA family shuffling. Nat Biotechnol. Aug. 1999;17(8):793-797.

Cheetham B.F., et al. (1991) Structure-function studies of human interferons-alpha: enhanced activity on human and murine cells. Antiviral Res. Jan. 1991;15(1):27-39.

(Continued)

*Primary Examiner*—Christine J Saoud
*Assistant Examiner*—Jegatheesan Seharaseyon
(74) *Attorney, Agent, or Firm*—Joanne R. Petithory; Norman J. Kruse

(57) ABSTRACT

The present invention provides interferon-alpha polypeptides and conjugates, and nucleic acids encoding the polypeptides. The invention also includes compositions comprising these polypeptides, conjugates, and nucleic acids; cells containing or expressing the polypeptides, conjugates, and nucleic acids; methods of making the polypeptides, conjugates, and nucleic acids; and methods of using the polypeptides, conjugates, and nucleic acids.

13 Claims, 9 Drawing Sheets

OTHER PUBLICATIONS

Diaz M.O., et al. (1996) Nomenclature of the human interferon genes. J Interferon Cytokine Res. Feb. 1996;16(2):179-80.

Fish E.N., et al. (1989) The role of three domains in the biological activity of human interferon-alpha. J Interferon Res. Feb. 1989;9(1):97-114.

Foser S, et al. (2003) Isolation, structural characterization, and antiviral activity of positional isomers of monopegylated interferon alpha-2a (PEGASYS). Protein Expr Purif. Jul. 2003;30(1):78-87.

Gangemi J.D., et al. (1989) Significant differences in therapeutic responses to a human interferon-alpha B/D hybrid in Rauscher or Friend murine leukemia virus infections. J Interferon Res. Jun. 1989;9(3):275-283.

Henco K., et al. (1985) Structural relationship of human interferon alpha genes and pseudogenes. J Mol Biol. Sep. 20, 1985;185(2):227-260.

Meister A., et al. (1986) Biological activities and receptor binding of two human recombinant interferons and their hybrids. J Gen Virol. Aug. 1986; 67 (Pt 8):1633-1643.

Ozes O.N., et al. (1992) A comparison of interferon-Con1 with natural recombinant interferons-alpha: antiviral, antiproliferative, and natural killer-inducing activities. J Interferon Res. Feb. 1992;12(1):55-59.

Weck P.K., et al. (1981) Antiviral activities of hybrids of two major human leukocyte interferons. Nucleic Acids Res. Nov. 25, 1981; 9(22):6153-66.

Goeddel D.V., et al. The structure of eight distinct cloned human leukocyte interferon cDNAs. Nature, Mar. 5, 1981; vol. 290(5801):20-26.

Bailon P., et al. Rational design of a potent, long-lasting form of interferon: a 40 kDa branched polyethylene glycol-conjugated interferon alpha-2a for the treatment of hepatitis C. Bioconjugugate Chemistry, Mar.-Apr. 2001; vol. 12(2):195-202.

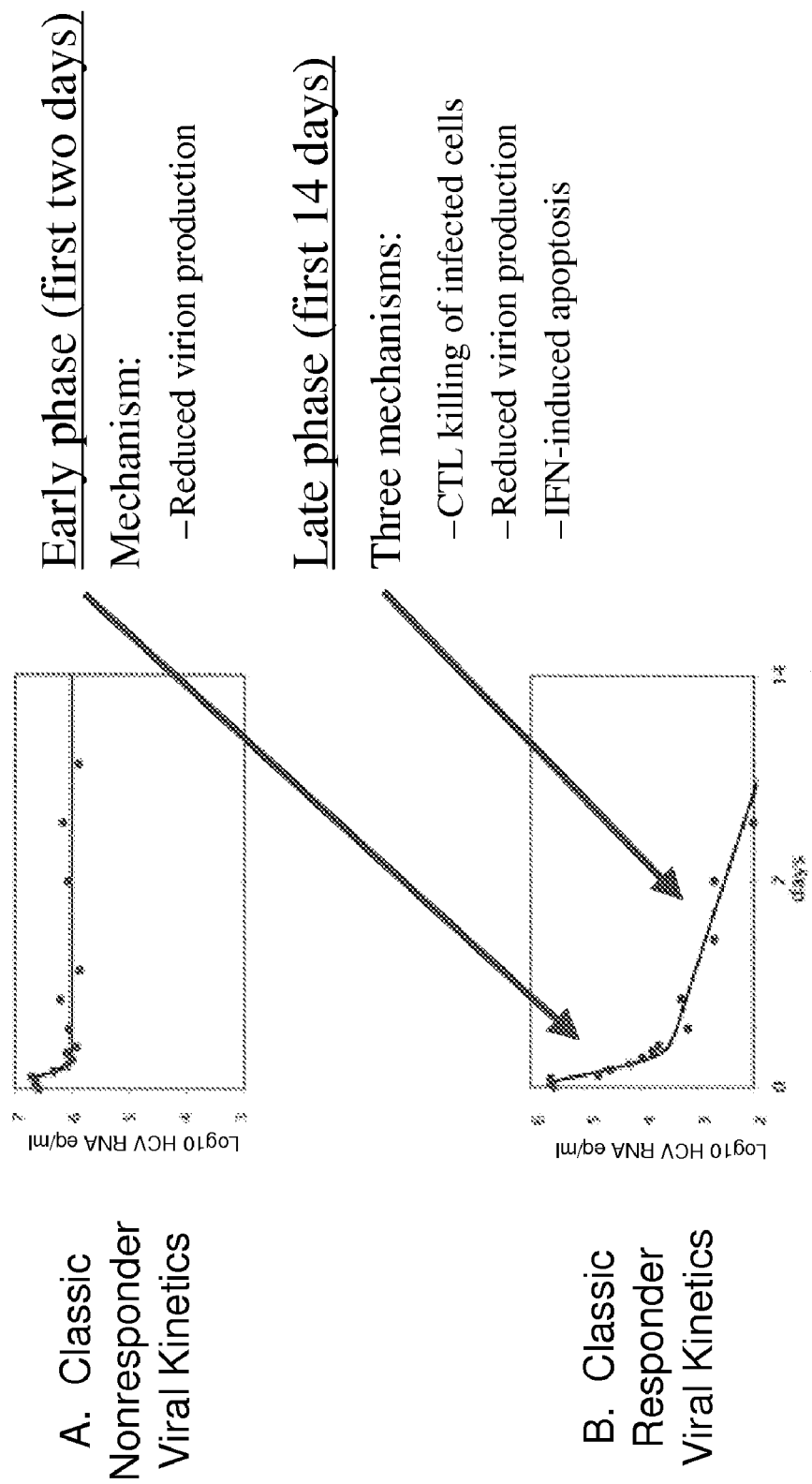

```
                      *        20         *        40         *        60         *        80
14epi18    : CDLPQTHSLGHRRTMMLLAQMRRISLFSCLKDRHDFRFPQEEFDGNHAQKVQAIFLFYEMMQQTFNLFSTKDSSAAWDETLLEKF :  85
hIFNa-1a   : ....E....DN...L......S...PS...M.....G.........QF..AP..SVLH.LI..I....T..........D..D.. :  85
hIFNa-2b   : ..........S...L.....................G......-..QF..AET.PVLH..I..I..................D.. :  84
hIFNa-4b   : ..........N..ALI.....G...H..........G..E.....HQF..T...SVLH..I.........E......EQS..... :  85
hIFNa-5    : .........SN...L.IM...G...P..........G.........QF..A...SVLH..I..............T......D.. :  85
hIFNa-6    : ..............................................QF..AE..SVLH.VI.............V....R..D.L :  85
hIFNa-7    : .........RN..ALI.....G...P........E....E.....HQF..T...SVLH..I.........E......EQS..... :  85
hIFNa-8b   : ..........N..ALI.........P..........E.......DKQF..A...SVLH..I...............L.....DE. :  85
hIFNa-10a  : ..........N..ALI..G..G...P...........I........QF..A...SVLH..I.........E......EQS..... :  85
hIFNa-14a  : .N.S.....NN...L..M.......P..........E.........QF..A...SVLH.............N............. :  85
hIFNa-16   : ..........N..ALI.....G...H.......Y..G....V....QF..A...SA.H..I.....................D.. :  85
hIFNa-17b  : ..........N..ALI.....G...P..........GL........QF..T...SVLH..I.........E......EQS..... :  85
hIFNa-21b  : ..........N..ALI.....G...P..........G.........QF..A...SVLH..I..............T.EQS..... :  85

*        100         *        120         *        140         *        160
14epi18    : YIELFQQMNDLEACVMQEVGVEETPLMNVDSILAVRKYFQRITLYLTEKKYSPCAWEVVRAEIMRSFSFSTNLQESLRSKE : 166
hIFNa-1a   : CT..Y..L..........ER.G......A......K...R..........................L.L......R..R.. : 166
hIFNa-2b   : .T..Y..L.......I.G...T.....KE.................K.....................L............ : 165
hIFNa-4b   : ST..Y..L.......I..................................................L.......KR..R.D : 166
hIFNa-5    : .T..Y..L......M.......D..........T..................................L.A....R..R.. : 166
hIFNa-6    : .T..Y..L...........W.GG.....E.......................................S.R....R..R.. : 166
hIFNa-7    : ST..Y..L.......I............E.F...............M..........................KKG..R.D : 166
hIFNa-8b   : ....D..L....S........I.S...YE.......................S...............L.I...KR.K... : 166
hIFNa-10a  : ST..Y..L.......I............E.................I.R.................L.......KR..R.D : 166
hIFNa-14a  : ...............I............E.................M...........................KR..R.D : 166
hIFNa-16   : .......L.......T.......IA...E.................MG..........................KG..R.D : 166
hIFNa-17b  : ST..Y..L.N.....I....M.......E.....................................L.......KI..R.D : 166
hIFNa-21b  : ST..N..L.......I...................K................................L.KIF..R..R.. : 166
```

Fig. 2

```
                    *        20         *        40         *        60         *        80
25epi19   : CDLPQTHSLSNRRTLMLMAQMRRISPFSCLKDRHDFGFPEEEFDGHQAQKVQAIFLLYELIQQTFNLFSTKDSSAAWDETLLEKF :  85
hIFNa-1a  : ....E....D.......L...S....S...M........Q.....N.F..AP..SV.H.....I....T..........D..D.. :  85
hIFNa-2b  : .........GS......L.......L.............Q...−.N.F..AET.PV.H.M...I..................D.. :  84
hIFNa-4b  : .........G...A.I.L...G...H.....................F..T...SV.H.M..........E......EQS..... :  85
hIFNa-5   : ................I....G.................Q.....N.F..A...SV.H.M...............T......D.. :  85
hIFNa-6   : .........GH...M..L.......L..........R..Q.....N.F..AE..SV.H.V..............V....R..D.L :  85
hIFNa-7   : .........R...A.I.L...G............E.R..........F..T...SV.H.M..........E......EQS..... :  85
hIFNa-8b  : .........G...A.I.L..................E..Q....DK.F..A...SV.H.M................L.....DE. :  85
hIFNa-10a : .........G...A.I.LG..G..............RI.Q.....N.F..A...SV.H.M..........E......EQS..... :  85
hIFNa-14a : .N.S.....N..........................E..Q.....N.F..A...SV.H.MM..........N............. :  85
hIFNa-16  : .........G...A.I.L...G...H.......Y.....Q.V...N.F..A...SAFH.M......................D.. :  85
hIFNa-17b : .........G...A.I.L...G...............L.Q.....N.F..T...SV.H.M..........E......EQS..... :  85
hIFNa-21b : .........G...A.I.L...G.................Q.....N.F..A...SV.H.M...............T.EQS..... :  85

*        100         *       120         *       140         *       160
25epi19   : YIELFQQMNNLEACVIQEVGVEEIALMNVDSILAVRKYFRRITLYLTEKKYSPCAWEVVRAEIMRSFSFSTNLQESLRSKE : 166
hIFNa-1a  : CT..Y..L.D.....M..ER.G.TP...A......K..............................L.L......R..R.. : 166
hIFNa-2b  : .T..Y..L.D.......G...T.TP...KE.........Q......K.....................L............ : 165
hIFNa-4b  : ST..Y..L.D.............TP..............Q..........................L.......KR..R.D : 166
hIFNa-5   : .T..Y..L.D....MM......DTP........T.....Q............................L.A....R..R.. : 166
hIFNa-6   : .T..Y..L.D.....M...W.GGTP...E..........Q............................S.R....R..R.. : 166
hIFNa-7   : ST..Y..L.D.............TP...E.F........Q......M..........................KKG..R.D : 166
hIFNa-8b  : ....D..L.D..S..M.....I.SP...YE.........Q............S...............L.I...KR.K... : 166
hIFNa-10a : ST..Y..L.D.............TP...E..........Q......I.R.................L.......KR..R.D : 166
hIFNa-14a : .........D.............TP...E..........Q......M...........................KR..R.D : 166
hIFNa-16  : .......L.D.....T............E..........Q......MG..........................KG..R.D : 166
hIFNa-17b : ST..Y..L............M..TP...E..........Q..........................L.......KI..R.D : 166
hIFNa-21b : ST..N..L.D.............TP..........K...Q............................L.KIF..R..R.. : 166
```

Fig. 3

BLOSUM62 SUBSTITUTION MATRIX

|   | A | R | N | D | C | Q | E | G | H | I | L | K | M | F | P | S | T | W | Y | V | B | Z | X | * |
|---|---|---|---|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 | -2 | -1 | 0 | -4 |
| R | -1 | 5 | 0 | -2 | -3 | 1 | 0 | -2 | 0 | -3 | -2 | 2 | -1 | -3 | -2 | -1 | -1 | -3 | -2 | -3 | -1 | 0 | -1 | -4 |
| N | -2 | 0 | 6 | 1 | -3 | 0 | 0 | 0 | 1 | -3 | -3 | 0 | -2 | -3 | -2 | 1 | 0 | -4 | -2 | -3 | 3 | 0 | -1 | -4 |
| D | -2 | -2 | 1 | 6 | -3 | 0 | 2 | -1 | -1 | -3 | -4 | -1 | -3 | -3 | -1 | 0 | -1 | -4 | -3 | -3 | 4 | 1 | -1 | -4 |
| C | 0 | -3 | -3 | -3 | 9 | -3 | -4 | -3 | -3 | -1 | -1 | -3 | -1 | -2 | -3 | -1 | -1 | -2 | -2 | -1 | -3 | -3 | -2 | -4 |
| Q | -1 | 1 | 0 | 0 | -3 | 5 | 2 | -2 | 0 | -3 | -2 | 1 | 0 | -3 | -1 | 0 | -1 | -2 | -1 | -2 | 0 | 3 | -1 | -4 |
| E | -1 | 0 | 0 | 2 | -4 | 2 | 5 | -2 | 0 | -3 | -3 | 1 | -2 | -3 | -1 | 0 | -1 | -3 | -2 | -2 | 1 | 4 | -1 | -4 |
| G | 0 | -2 | 0 | -1 | -3 | -2 | -2 | 6 | -2 | -4 | -4 | -2 | -3 | -3 | -2 | 0 | -2 | -2 | -3 | -3 | -1 | -2 | -1 | -4 |
| H | -2 | 0 | 1 | -1 | -3 | 0 | 0 | -2 | 8 | -3 | -3 | -1 | -2 | -1 | -2 | -1 | -2 | -2 | 2 | -3 | 0 | 0 | -1 | -4 |
| I | -1 | -3 | -3 | -3 | -1 | -3 | -3 | -4 | -3 | 4 | 2 | -3 | 1 | 0 | -3 | -2 | -1 | -3 | -1 | 3 | -3 | -3 | -1 | -4 |
| L | -1 | -2 | -3 | -4 | -1 | -2 | -3 | -4 | -3 | 2 | 4 | -2 | 2 | 0 | -3 | -2 | -1 | -2 | -1 | 1 | -4 | -3 | -1 | -4 |
| K | -1 | 2 | 0 | -1 | -3 | 1 | 1 | -2 | -1 | -3 | -2 | 5 | -1 | -3 | -1 | 0 | -1 | -3 | -2 | -2 | 0 | 1 | -1 | -4 |
| M | -1 | -1 | -2 | -3 | -1 | 0 | -2 | -3 | -2 | 1 | 2 | -1 | 5 | 0 | -2 | -1 | -1 | -1 | -1 | 1 | -3 | -1 | -1 | -4 |
| F | -2 | -3 | -3 | -3 | -2 | -3 | -3 | -3 | -1 | 0 | 0 | -3 | 0 | 6 | -4 | -2 | -2 | 1 | 3 | -1 | -3 | -3 | -1 | -4 |
| P | -1 | -2 | -2 | -1 | -3 | -1 | -1 | -2 | -2 | -3 | -3 | -1 | -2 | -4 | 7 | -1 | -1 | -4 | -3 | -2 | -2 | -1 | -2 | -4 |
| S | 1 | -1 | 1 | 0 | -1 | 0 | 0 | 0 | -1 | -2 | -2 | 0 | -1 | -2 | -1 | 4 | 1 | -3 | -2 | -2 | 0 | 0 | 0 | -4 |
| T | 0 | -1 | 0 | -1 | -1 | -1 | -1 | -2 | -2 | -1 | -1 | -1 | -1 | -2 | -1 | 1 | 5 | -2 | -2 | 0 | -1 | -1 | 0 | -4 |
| W | -3 | -3 | -4 | -4 | -2 | -2 | -3 | -2 | -2 | -3 | -2 | -3 | -1 | 1 | -4 | -3 | -2 | 11 | 2 | -3 | -4 | -3 | -2 | -4 |
| Y | -2 | -2 | -2 | -3 | -2 | -1 | -2 | -3 | 2 | -1 | -1 | -2 | -1 | 3 | -3 | -2 | -2 | 2 | 7 | -1 | -3 | -2 | -1 | -4 |
| V | 0 | -3 | -3 | -3 | -1 | -2 | -2 | -3 | -3 | 3 | 1 | -2 | 1 | -1 | -2 | -2 | 0 | -3 | -1 | 4 | -3 | -2 | -1 | -4 |
| B | -2 | -1 | 3 | 4 | -3 | 0 | 1 | -1 | 0 | -3 | -4 | 0 | -3 | -3 | -2 | 0 | -1 | -4 | -3 | -3 | 4 | 1 | -1 | -4 |
| Z | -1 | 0 | 0 | 1 | -3 | 3 | 4 | -2 | 0 | -3 | -3 | 1 | -1 | -3 | -1 | 0 | -1 | -3 | -2 | -2 | 1 | 4 | -1 | -4 |
| X | 0 | -1 | -1 | -1 | -2 | -1 | -1 | -1 | -1 | -1 | -1 | -1 | -1 | -1 | -2 | 0 | 0 | -2 | -1 | -1 | -1 | -1 | -1 | -4 |
| * | -4 | -4 | -4 | -4 | -4 | -4 | -4 | -4 | -4 | -4 | -4 | -4 | -4 | -4 | -4 | -4 | -4 | -4 | -4 | -4 | -4 | -4 | -4 | 1 |



INTERFERON-ALPHA POLYPEPTIDES AND CONJUGATES

CROSS-REFERENCE TO RELATED APPLICATIONS

This application is divisional of U.S. application Ser. No. 11/132,722 filed on May 18, 2005 (now U.S. Pat. No. 7,318, 918), which claims the benefit of U.S. Provisional Application Ser. No. 60/572,504 filed on May 19, 2004, the disclosure of each of which are incorporated by reference herein in its entirety for all purposes.

FIELD OF THE INVENTION

The present invention relates generally to polynucleotides and polypeptides encoded therefrom, conjugates of the polypeptides, as well as vectors, cells, antibodies, and methods for using and producing the polynucleotides, polypeptides, and conjugates.

BACKGROUND OF THE INVENTION

Interferon-alphas are members of the diverse helical-bundle superfamily of cytokine genes (Sprang, S. R. et al. (1993) Curr. Opin. Struct. Biol. 3:815-827). The human interferon-alphas are encoded by a family of over 20 tandemly duplicated nonallelic genes and psuedogenes that share 85-98% sequence identity at the amino acid level (Henco, K. et al. (1985) J. Mol. Biol. 185:227-260). Genes which express active interferon-alpha proteins have been grouped into 13 families according to genetic loci. Known expressed human interferon-alpha proteins and their allelic variations are tabulated in Allen G. and Diaz M. O. (1996) J. Interferon and Cytokine Res. 16:181-184.

Interferon-alphas have been shown to inhibit various types of cellular proliferation, and are especially useful for the treatment of a variety of cellular proliferation disorders frequently associated with cancer, particularly hematologic malignancies such as leukemias. These proteins have shown antiproliferative activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, E. M. et al. (1984) J. Biol. Response Modifiers 3:580; Oldham, R. K. (1985) Hospital Practice 20:71).

Interferon-alphas are also useful against various types of viral infections (Finter, N. B. et al. (1991) Drugs 42(5):749). Interferon-alphas have activity against human papillomavirus infection, Hepatitis B, and Hepatitis C infections (Finter, N. B. et al., 1991, supra; Kashima, H. et al. (1988) Laryngoscope 98:334; Dusheiko, G. M. et al. (1986) J. Hematology 3 (Supple. 2):S199; Davis, G L et al. (1989) N. England J. Med. 321:1501). The role of interferons and interferon receptors in the pathogenesis of certain autoimmune and inflammatory diseases has also been investigated (Benoit, P. et al. (1993) J. Immunol. 150(3):707).

Although these proteins possess therapeutic value in the treatment of a number of diseases, they have not been optimized for use as pharmaceuticals. For example, dose-limiting toxicity, receptor cross-reactivity, and short serum half-lives significantly reduce the clinical utility of many of these cytokines (Dusheiko, G. (1997) Hepatology 26:112S-121S; Vial, T. and Descotes, J. (1994) Drug Experience 10:115-150; Funke, I. et al. (1994) Ann. Hematol. 68:49-52; Schomburg, A. et al. (1993) J. Cancer Res. Clin. Oncol. 119:745-755). Diverse and severe side effect profiles which accompany interferon administration include flu-like symptoms, fatigue, hallucination, fever, hepatic enzyme elevation, and leukopenia (Pontzer, C. H. et al. (1991) Cancer Res. 51:5304; Oldham, 1985, supra).

Hepatitis-C virus (HCV) is a nonhost integrated RNA virus with a very high rate of replication and is therefore associated with a large degree of genetic diversity. At least six genotypes and more than thirty subtypes of HCV RNA have been identified. HCV genotype has been shown to be a predictor of response to IFN-alpha therapy. Patients infected with HCV genotypes 2 and 3 have been found to generally respond well to interferon therapy. Patients infected with genotypes 4, 5 and 6 tend to respond less well. Patients infected with HCV genotype 1 tend to respond very poorly to interferon therapy, with about 50% of Genotype 1 patients classified as "nonresponders" towards IFN-alpha therapy. Genotype 1 is currently the most prevalent form of Hepatitis C, infecting approximately 70% of patients in the US and 50% of patients in Europe. Clearly, there is a pressing need for more effective therapies for HCV infection, particularly of the Genotype 1 variety.

There is genetic and biochemical evidence that Genotype 1 HCV (and other subtypes) actively attenuate the IFN-alpha signaling pathway by inhibiting key IFN responsive proteins such as the dsRNA-activated serine/threonine protein kinase PKR (Katze M. G., et al. (2002) Nat. Rev. Immunol. 2(9): 675-687). As a likely consequence of this genetic diversity and active inhibition of the antiviral response, HCV (particularly Genotype 1) has the ability to escape the host's immune surveillance, leading to a high rate of chronic infection. The extensive genetic heterogeneity of HCV has important diagnostic and clinical implications, potentially accounting for variations in clinical course, difficulties in vaccine development, and lack of response to therapy.

The present invention addresses the need for interferon-alpha molecules which exhibit enhanced antiviral and/or immunomodulatory efficacy. The invention provides novel interferon-alpha polypeptides and polypeptide conjugates, nucleic acids encoding the polypeptides, and methods of using such molecules. Such molecules would be of beneficial use in a variety of applications, including, e.g., therapeutic and prophylactic treatments, particularly for viral infections and diseases and conditions associated with viral infections. The present invention fulfills these and other needs.

SUMMARY OF THE INVENTION

The present invention provides novel polypeptides, including variants thereof and fusion proteins comprising such polypeptides. The invention also provides conjugates comprising a polypeptide of the invention covalently linked to one or more non-polypeptide moieties. The invention also provides nucleic acids encoding any of the polypeptides of the invention, and vectors and host cells comprising such nucleic acids. In addition, the invention provides methods of making and using such polypeptides, conjugates, and nucleic acids, and other features apparent upon further review.

In one aspect, the invention provides an isolated or recombinant polypeptide, the polypeptide comprising a sequence identified as one of SEQ ID NOs:2-35 and SEQ ID NOs: 37-44 (such as one of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:10, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:37, SEQ ID NO:38, SEQ ID NO:39, SEQ ID NO:40, SEQ ID NO:41, SEQ ID NO:42, SEQ ID NO:43, and SEQ ID NO:44). The invention also provides fusion proteins and conjugates comprising any of these polypeptides, nucleic acids encoding these polypeptides, and methods of making and using these polypeptides.

The invention also provides isolated or recombinant polypeptides which each comprise a sequence which (a) differs in 1 to 16 amino acid positions from SEQ ID NO:1 and (b) comprises one or more substitutions relative to SEQ ID NO:1 selected from the group consisting of F48A/L; V51P; F55A; F65A; F68P; L111A; and V114P. Some such polypeptides comprise a sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitutions relative to SEQ ID NO:1 selected from the group consisting of H47Q; V51A; Q52P/E; A53T; F55S; L56V; F57L; Y58H; M61I; N113K; V114E; and E160D. In some instances, the polypeptide exhibits an interferon-alpha activity (such as, e.g., antiviral activity, $T_H1$ differentiation activity, and/or antiproliferative activity). The invention also provides fusion proteins and conjugates comprising any of these polypeptides, nucleic acids encoding such polypeptides, and methods of making and using such polypeptides.

The invention also provides isolated or recombinant polypeptides which each comprise a sequence which (a) differs in 0 to 16 amino acid positions from SEQ ID NO:13 and (b) comprises one or more of: Ala or Leu at position 48; Pro at position 51; Ala at position 55; Ala at position 65; Pro at position 68; Ala at position 111; and Pro at position 114 (position numbering relative to SEQ ID NO:13). Some such polypeptides comprise a sequence which differs from SEQ ID NO:13 in 0, 1, 2, 3, 4, 5, 6, 7, 8, 9, 10, 11, 12, 13, 14, 15, or 16 amino acid positions, e.g., in 0-15 amino acid positions, in 0-14 amino acid positions, in 0-13 amino acid positions, in 0-12 amino acid positions, in 0-11 amino acid positions, in 0-10 amino acid positions, in 0-9 amino acid positions, in 0-8 amino acid positions, in 0-7 amino acid positions, in 0-6 amino acid positions, in 0-5 amino acid positions, in 0-4 amino acid positions, in 0-3 amino acid positions, in 0-2 amino acid positions, or in 0-1 amino acid positions. Some such polypeptides comprise an Ala or a Leu at position 48. Some such polypeptides comprise an Ala at position 48. In some instances, the polypeptide further comprises one or more substitution(s) relative to SEQ ID NO:13 selected from the group consisting of H47Q; V51A; Q52P/E; A53T; F55S; L56V; F57L; Y58H; M61I; N113K; V114E; and E160D. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:36 and (b) comprises one or more substitutions relative to SEQ ID NO:36 selected from the group consisting of M21A; I24P; F48A/L; T51P; S55A; F65A; F68P; F90A; M93P; L111A; V114P; F124A; I127P and E160D. Some such polypeptides comprise a sequence which differs from SEQ ID NO:36 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitutions relative to SEQ ID NO:36 selected from the group consisting of P26L; H47Q; T51V; S55P/F; V56L; H58Y; L60M; F90Y; M93L; N95D; N113K; V114E; R125Q; T132K; and L154F. In some instances, the polypeptide exhibits an interferon-alpha activity (such as, e.g., antiviral activity, $T_H1$ differentiation activity, and/or antiproliferative activity). The invention also provides fusion proteins and conjugates comprising any of these polypeptides, nucleic acids encoding such polypeptides, and methods of making and using such polypeptides.

The invention also provides isolated or recombinant polypeptides which each comprise a sequence which (a) differs in 0 to 16 amino acid positions from SEQ ID NO:38 and (b) comprises one or more of: Ala at position 21; Pro at position 24; Ala or Leu at position 48; Pro at position 51; Ala at position 55; Ala at position 65; Pro at position 68; Ala at position 90; Pro at position 93; Ala at position 111; Pro at position 114; Ala at position 124; Pro at position 127; and Glu at position 160 (position numbering relative to SEQ ID NO:38). Some such polypeptides comprise a sequence which differs from SEQ ID NO:38 in 0, 1, 2, 3, 4, 5, 6, 7, 8, 9, 10, 11, 12, 13, 14, 15, or 16 amino acid positions, e.g., in 0-15 amino acid positions, in 0-14 amino acid positions, in 0-13 amino acid positions, in 0-12 amino acid positions, in 0-11 amino acid positions, in 0-10 amino acid positions, in 0-9 amino acid positions, in 0-8 amino acid positions, in 0-7 amino acid positions, in 0-6 amino acid positions, in 0-5 amino acid positions, in 0-4 amino acid positions, in 0-3 amino acid positions, in 0-2 amino acid positions, or in 0-1 amino acid positions. Some such polypeptides comprise an Ala or a Leu at position 48. Some such polypeptides comprise an Ala at position 48. In some instances, the polypeptide further comprises one or more substitution(s) relative to SEQ ID NO:38 selected from the group consisting of P26L; H47Q; V51T; F55P/S; L56V; Y58H; L60M; F90Y; M93L; N95D; N113K; V114E; R125Q; T132K; and F154L. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, nucleic acids encoding such polypeptides, and methods of making and using such polypeptides.

The invention also provides conjugates comprising a polypeptide of the invention, such as any of the polypeptides of the invention described above, and at least one non-polypeptide moiety attached to an attachment group of the polypeptide, wherein the conjugate exhibits an interferon-alpha activity. In some instances, the non-polypeptide moiety is a polymer (for example, a polyalkylene oxide molecule, such as a polyethylene glycol (PEG), such as a monomethoxypolyethylene glycol (mPEG)), or a sugar moiety. The at least one non-polypeptide moiety may, for example, be attached to a cysteine, to a lysine, to the N-terminal amino group of the polypeptide, or to an in vivo glycosylation site of the polypeptide. The invention also provides methods of making and using such conjugates.

The invention also provides isolated or recombinant nucleic acids encoding any of the polypeptides of the invention. The invention also provides vectors and host cells comprising such nucleic acids, and methods of making polypeptides of the invention comprising culturing host cells comprising such nucleic acids.

In another aspect, the invention provides a method of inhibiting viral replication in virus-infected cells, the method comprising contacting the virus-infected cells with a polypeptide or a conjugate of the invention. The invention also provides a method of reducing the number of copies of a virus in virus-infected cells, comprising contacting the virus-infected cells with a polypeptide or a conjugate of the invention.

In another aspect, the invention provides a method of treating a condition which is responsive to interferon-alpha, comprising administering to a subject afflicted with the condition a composition comprising a polypeptide of the invention or a conjugate of the invention in an amount effective to ameliorate a symptom associated with the condition. Such conditions include Chronic Hepatitis C infection, Chronic Hepatitis B infection, Hairy Cell Leukemia, Malignant Melanoma, Follicular Lymphoma, Condylomata Acuminata, AIDS-related Kaposi's Sarcoma, Non-Hodgkin's Lymphoma, Chronic Melogenous Leukemia, Basal Cell Carcinoma, Multiple Myeloma, carcinoid tumors, bladder cancer, Crohn's Disease, Cutaneous T Cell Lymphoma, Renal Cell Carcinoma, Multiple Sclerosis, and AIDS. The invention also includes the use of a composition comprising a polypeptide of the invention or a conjugate of the invention to treat a condition which is responsive to interferon-alpha, such as for example a condition described above.

These and other objects and features of the invention will become more fully apparent when the following detailed description is read in conjunction with the accompanying figures.

BRIEF DESCRIPTION OF THE FIGURES

FIGS. 1A and 1B show biphasic timecourses for viral clearance from HCV-infected cells following IFN-alpha treatment (A. Nonresponder kinetics; B. Responder kinetics).

FIG. 2 shows an alignment of the sequence of a polypeptide of the invention (SEQ ID NO:13) with the following human interferon-alpha (huIFN-alpha) polypeptide sequences: huIFN-alpha 1a (SEQ ID NO:45), huIFN-alpha 2b (SEQ ID NO:46), huIFN-alpha 4b (SEQ ID NO:48), huIFN-alpha 5 (SEQ ID NO:49), huIFN-alpha 6 (SEQ ID NO:50), huIFN-alpha 7 (SEQ ID NO:51), huIFN-alpha 8b (SEQ ID NO:52), huIFN-alpha 10a (SEQ ID NO:53), huIFN-alpha 14a (SEQ ID NO:54), huIFN-alpha 16 (SEQ ID NO:55), huIFN-alpha 17b (SEQ ID NO:56) and huIFN-alpha 21b (SEQ ID NO:57). The naming conventions for the huIFN-alpha sequences are according to Allen G. and Diaz M. O. (1996) J. Interferon and Cytokine Res. 16:181-184. Amino acid residue positions in SEQ ID NOs:45-46 and 48-57 which are identical to SEQ ID NO:13 are indicated with a period (.), and gaps in the sequence are indicated with a dash (-).

FIG. 3 shows an alignment of the sequence of a polypeptide of the invention (SEQ ID NO:38) with human interferon-alpha polypeptide sequences SEQ ID NOs:45-46 and 48-57. Amino acid residue positions in SEQ ID NOs:45-46 and 48-57 which are identical to SEQ ID NO:38 are indicated with a period (.), and gaps in the sequence are indicated with a dash (-).

FIG. 4 shows the BLOSUM62 substitution matrix.

FIGS. 5A, 5B and 5C show examples of calculations of alignment scores used to determine optimal sequence alignments, using the following parameters: BLOSUM62 matrix, gap open penalty=11, and gap extension penalty=1.

DETAILED DESCRIPTION OF THE INVENTION

Definitions

Figure 6:
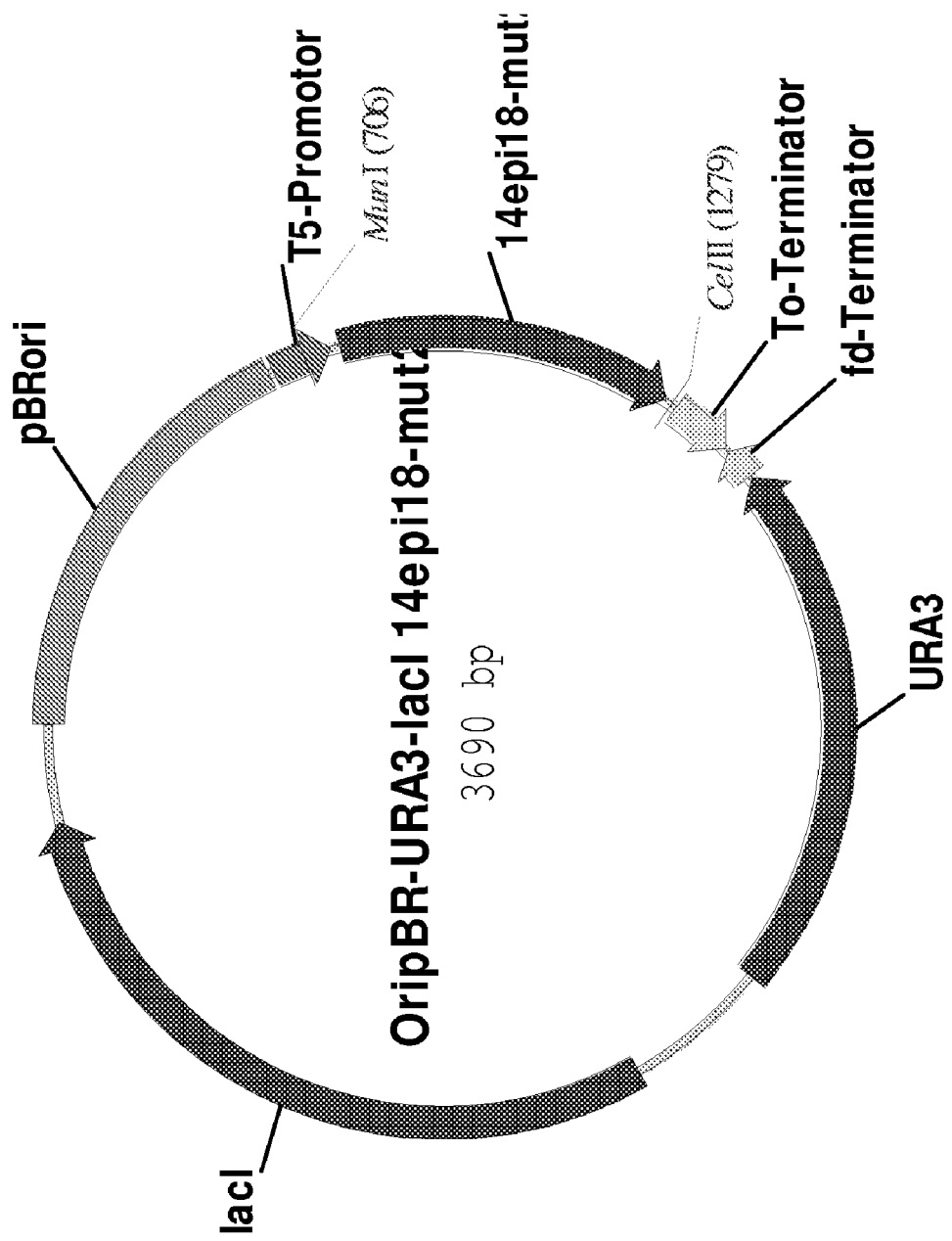
FIGS. 6 and 7 show *E. coli* expression vectors designated OripBR-URA3-lacI__14epi18-mut2 and OripBR-URA3-lacI__25epi19-mut, respectively.

Unless otherwise defined herein or in the remainder of the specification, all technical and scientific terms used herein have the same meaning as commonly understood by those of ordinary skill in the art to which the invention belongs.

A "polypeptide sequence" (e.g., a protein, polypeptide, peptide, etc.) is a polymer of amino acids comprising naturally occurring amino acids or artificial amino acid analogues, or a character string representing an amino acid polymer, depending on context. Given the degeneracy of the genetic code, one or more nucleic acids, or the complementary nucleic acids thereof, that encode a specific polypeptide sequence can be determined from the polypeptide sequence.

A "polynucleotide sequence" (e.g., a nucleic acid, polynucleotide, oligonucleotide, etc.) is a polymer of nucleotides comprising nucleotides A,C,T,U,G, or other naturally occurring nucleotides or artificial nucleotide analogues, or a character string representing a nucleic acid, depending on context. Either the given nucleic acid or the complementary nucleic acid can be determined from any specified polynucleotide sequence.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or an equivalent position in the selected amino acid or nucleic acid polymer, rather than by the actual numerical position of the component in the given polymer. Thus, for example, the numbering of a given amino acid position in a given polypeptide sequence corresponds to the same or equivalent amino acid position in a selected polypeptide sequence used as a reference sequence.

An "equivalent position" (for example, an "equivalent amino acid position" or "equivalent nucleic acid position" or "equivalent residue position") is defined herein as a position (such as, an amino acid position or nucleic acid position or residue position) of a test polypeptide (or test polynucleotide) sequence which aligns with a corresponding position of a reference polypeptide (or reference polynucleotide) sequence, when optimally aligned using an alignment algorithm as described herein. The equivalent amino acid position of the test polypeptide need not have the same numerical position number as the corresponding position of the reference polypeptide; likewise, the equivalent nucleic acid position of the test polynucleotide need not have the same numerical position number as the corresponding position of the reference polynucleotide. As an example, FIG. 2 shows the sequence of a polypeptide of the invention (SEQ ID NO:13) optimally aligned with various known human interferon-alpha polypeptide sequences. In this example, amino acid position number 48 of SEQ ID NO:13 is considered to be an equivalent amino acid position to (i.e. is "equivalent to") that of amino acid position number 47 of SEQ ID NO:46 (huIFN-alpha 2b), since amino acid number 48 of SEQ ID NO:13 aligns with amino acid number 47 of SEQ ID NO:46. In other words, amino acid position 48 of SEQ ID NO:13 "corresponds to" amino acid position 47 of SEQ ID NO:46. Likewise, residue A48 (Ala48) in SEQ ID NO:13 is understood to correspond to residue F48 (Phe48) in, e.g., SEQ ID NO:1, so that for example the substitution A48L relative to SEQ ID NO:13 is understood to correspond to the substitution F48L relative to, e.g., SEQ ID NO:1 (and so on).

Two polypeptide sequences are "optimally aligned" when they are aligned using defined parameters, i.e., a defined amino acid substitution matrix, gap existence penalty (also termed gap open penalty), and gap extension penalty, so as to arrive at the highest similarity score possible for that pair of sequences. The BLOSUM62 matrix (Henikoff and Henikoff (1992) Proc. Natl. Acad. Sci. USA 89(22):10915-10919) is often used as a default scoring substitution matrix in polypeptide sequence alignment algorithms (such as BLASTP). The gap existence penalty is imposed for the introduction of a single amino acid gap in one of the aligned sequences, and the gap extension penalty is imposed for each residue position in the gap. Unless otherwise stated, alignment parameters employed herein are: BLOSUM62 scoring matrix, gap existence penalty=11, and gap extension penalty=1. The alignment score is defined by the amino acid positions of each sequence at which the alignment begins and ends (e.g. the alignment window), and optionally by the insertion of a gap or multiple gaps into one or both sequences, so as to arrive at the highest possible similarity score, as described in more detail below in the section entitled "Percent Sequence Identity".

The terminology used for identifying amino acid positions and amino acid substitutions is illustrated as follows: F48 indicates position number 48 is occupied by a phenylalanine (Phe) residue in a reference amino acid sequence, such as SEQ ID NO:1. F48A indicates that the phenylalanine residue of position 48 has been substituted with a alanine (Ala) residue. Alternative substitutions are indicated with a "/", e.g., F48A/L means an amino acid sequence in which the phenylalanine residue at position 48 is substituted with an alanine or a leucine residue. Multiple substitutions may sometimes be indicated with a "+", e.g. H47Q+F48A/L means an amino acid sequence which comprises a substitution of the histidine residue at position 47 with an glutamine residue and a substitution of the phenylalanine residue in position 48 with an alanine or a leucine residue Deletions are indicated by an asterix. For example, H47* indicates that the histidine residue in position 47 has been deleted. Deletions of two or more continuous amino acids may be indicated as follows, e.g., R161*-E166* indicates the deletion of residues R161-E166 inclusive (that is, residues 161, 162, 163, 164, 164, and 166 are deleted). Insertions are indicated the following way: Insertion of an additional serine residue after the histidine residue located at position 47 is indicated as H47HS. Combined substitutions and insertions are indicated in the following way: Substitution of the histidine residue at position 47 with a serine residue and insertion of an alanine residue after the position 47 amino acid residue is indicated as H47SA.

Unless otherwise indicated, the position numbering of amino acid residues recited herein is relative to the amino acid sequence SEQ ID NO:1. It is to be understood that while the examples and modifications to the parent polypeptide are generally provided herein relative to the sequence SEQ ID NO:1 (or relative to another specified sequence), the examples pertain to other polypeptides of the invention, and the modifications described herein may be made in equivalent amino acid positions of any of the other polypeptides described herein. Thus, as an example, the substitution F48L relative to SEQ ID NO:1 is understood to correspond to the substitution A48L in SEQ ID NO:13, and so on.

The term "exhibiting (e.g., exhibits, or having, or has) an interferon-alpha activity" is intended to indicate that the polypeptide or conjugate of the invention has at least one activity exhibited by a reference interferon-alpha polypeptide (such as, for example, a human interferon-alpha polypeptide, e.g., huIFN-alpha 2b identified herein as SEQ ID NO:46, huIFN-alpha 2a identified herein as SEQ ID NO:47, hIFN-alpha 8b identified herein as SEQ ID NO: 51, or any other interferon alpha polypeptide known in the art, such as, for example, those listed in Allen G. and Diaz M. O. (1996, supra)). Such activity includes the ability to signal through an interferon-alpha receptor, as evidenced by, for example, one or more of: inhibition of viral replication in virus-infected cells ("antiviral activity"); enhancement of differentiation of naïve T-cells to a $T_H1$ phenotype and/or suppression of differentiation of naïve T-cells to a $T_H2$ phenotype ("$T_H1$ differentiation activity"); or inhibition of cell proliferation ("antiproliferative activity"). The one or more interferon-alpha activity is assayed using assays known in the art and/or described in the Examples.

A polypeptide or a conjugate exhibiting an interferon-alpha activity is considered to have such activity when it displays a measurable activity, e.g., a measurable antiviral activity, antiproliferative activity, or $T_H1$ differentiation activity (e.g., as determined by assays known in the art and/or described in the Examples). One of skill in the art recognizes that what constitutes a measurable activity depends in part on the nature of the assay being undertaken, but as a general guideline a measurable activity is one in which the assay signal generated in the presence of the test compound (e.g., a polypeptide of the invention) is quantifiably different than the assay signal generated in the absence of the test compound. It is to be understood that a polypeptide or conjugate of the invention need not exhibit all of the known activities of a particular reference interferon-alpha, or exhibit such activities to the same extent as the reference interferon-alpha. In some instances the activity exhibited by a polypeptide or conjugate of the invention (as evidenced, e.g., by an $EC_{50}$, specific activity, or other value related to activity) may be about equal to, be less than, or be greater than that of the particular activity exhibited by the reference interferon-alpha.

A "variant" is a polypeptide comprising a sequence which differs in one or more amino acid position(s) from that of a parent polypeptide sequence. For example, a variant may comprise a sequence which differs from the parent polypeptides sequence in up to 10% of the total number of residues of the parent polypeptide sequence, such as in up to 8% of the residues, e.g., in up to 6%, 5%, 4%, 3% 2% or 1% of the total number of residue of the parent polypeptide sequence. For example, a variant of SEQ ID NO:1 may comprise a sequence which differs from SEQ ID NO:1 in 1-16 amino acid positions (such as in 1, 2, 3, 4, 5, 6, 7, 8, 9, 10, 11, 12, 13, 14, 15, or 16 amino acid positions), e.g. in 1-15 amino acid positions, in 1-14 amino acid positions, in 1-13 amino acid positions, in 1-12 amino acid positions, in 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions.

The term "parent polypeptide" or "parent interferon-alpha" is intended to indicate the polypeptide sequence to be modified in accordance with the present invention. The parent polypeptide sequence may be that of a naturally occurring IFN-alpha (such as a mammalian IFN-alpha, e.g., a primate IFN-alpha, such as a human IFN-alpha, such as a huIFN-alpha polypeptide identified herein as SEQ ID NOs:45-57, or other huIFN-alpha sequence such as those described herein and/or in Allen G. and Diaz M. O. (1996), supra). The parent polypeptide sequence may be that of a non-naturally occurring (i.e., "synthetic") interferon-alpha, such as IFN-alpha Con1 (SEQ ID NO:58). In some instances, the parent polypeptide to be modified may itself be a polypeptide of the invention, such as, for example, any one of SEQ ID NOs:2-35 and SEQ ID NOs:37-44.

"Naturally occurring" as applied to an object refers to the fact that the object can be found in nature as distinct from being artificially produced by man. For example, a polypeptide or polynucleotide sequence that is present in an organism (including viruses, bacteria, protozoa, insects, plants or mammalian tissue) that can be isolated from a source in nature and which has not been intentionally modified by man in the laboratory is naturally occurring. "Non-naturally occurring" (also termed "synthetic" or "artificial") as applied to an object means that the object is not naturally-occurring—i.e., the object cannot be found in nature as distinct from being artificially produced by man.

A "fragment" or "subsequence" is any portion of an entire sequence, up to but not including the entire sequence. Thus, a fragment or subsequence refers to a sequence of amino acids or nucleic acids that comprises a part of a longer sequence of amino acids (e.g., polypeptide) or nucleic acids (e.g., polynucleotide).

One type of fragment contemplated by the present invention is a fragment in which amino acid residues are removed from the N-terminus or the C-terminus of the parent polypeptide (or both); such a polypeptide is considered to be "N-terminally truncated" or "C-terminally truncated", respectively. It is known that deletion of at least the first four amino acids from the N-terminus does not significantly affect interferon-alpha activity (Lydon, N. B. et al. (1985) Biochemistry 24: 4131-41). Furthermore, variants retaining interferon-alpha activity have been described wherein between 7 and 11 amino acids have been deleted from the C-terminus (Cheetham B. F. et al. (1991) Antiviral Res. 15(1):27-39; Chang N. T. et al. (1983) Arch. Biochem Biophys. 221(2): 585-589; Franke A. E. et al. (1982) DNA 1(3):223-230).

A "receptor" e.g., an "interferon-alpha receptor" (also known as a "Type I interferon receptor") is a receptor which is activated in cells by an interferon-alpha, e.g., binds an interferon-alpha and initiates intracellular signaling, such as a type I interferon receptor comprising receptor subunits IFNAR-2 and IFNAR-1 (Domanski et al. (1998) J. Biol. Chem. 273(6):3144-3147; Mogensen et al., (1999) Journal of Interferon and Cytokine Research, 19:1069-1098). In the context of this invention, receptor is also meant to include truncated forms of a full-length receptor molecule, such as for example a receptor molecule which lacks a membrane-binding portion, such as a soluble form of a receptor molecule (also known as a "soluble receptor") which comprises an extracellular binding domain, which binds an interferon-alpha, but may not necessarily bind to a membrane and/or initiate intracellular signaling.

A "specific binding affinity" between two molecules, e.g., a ligand and a receptor, means a preferential binding of one molecule for another in a mixture of molecules. The binding of the molecules is typically considered specific if the binding affinity is about $1 \times 10^4 M^{-1}$ to about $1 \times 10^9 M^{-1}$ or greater (i.e., $K_D$ of about $10^{-4}$ to $10^{-9}$ M or less). Binding affinity of a ligand and a receptor may be measured by standard techniques known to those of skill in the art. Non-limiting examples of well-known techniques for measuring binding affinities include Biacore® technology (Biacore AB, Sweden), isothermal titration microcalorimetry (MicroCal LLC, Northampton, Mass. USA), ELISA, and FACS. For example, FACS or other sorting methods may be used to select for populations of molecules (such as for example, cell surface-displayed ligands) which specifically bind to the associated binding pair member (such as a receptor, e.g., a soluble receptor). Ligand-receptor complexes may be detected and sorted e.g., by fluorescence (e.g., by reacting the complex with a fluorescent antibody that recognizes the complex). Molecules of interest which bind an associated binding pair member (e.g., receptor) are pooled and re-sorted in the presence of lower concentrations of receptor. By performing multiple rounds sorting in the presence of decreasing concentrations of receptor (an exemplary concentration range being on the order of $10^{-6}$ M down to $10^{-9}$ M, i.e., 1 micromolar (μM) down to 1 nanomolar (nM), or less, depending on the nature of the ligand-receptor interaction), populations of the molecule of interest exhibiting specific binding affinity for the receptor may be isolated.

A polypeptide, nucleic acid, or other component is "isolated" when it is partially or completely separated from components with which it is normally associated (other peptides, polypeptides, proteins (including complexes, e.g., polymerases and ribosomes which may accompany a native sequence), nucleic acids, cells, synthetic reagents, cellular contaminants, cellular components, etc.), e.g., such as from other components with which it is normally associated in the cell from which it was originally derived. A polypeptide, nucleic acid, or other component is isolated when it is partially or completely recovered or separated from other components of its natural environment such that it is the predominant species present in a composition, mixture, or collection of components (i.e., on a molar basis it is more abundant than any other individual species in the composition). In some instances, the preparation consists of more than about 60%, 70% or 75%, typically more than about 80%, or preferably more than about 90% of the isolated species.

A "substantially pure" or "isolated" nucleic acid (e.g., RNA or DNA), polypeptide, protein, or composition also means where the object species (e.g., nucleic acid or polypeptide) comprises at least about 50, 60, or 70 percent by weight (on a molar basis) of all macromolecular species present. A substantially pure or isolated composition can also comprise at least about 80, 90, or 95 percent by weight of all macromolecular species present in the composition. An isolated object species can also be purified to essential homogeneity (contaminant species cannot be detected in the composition by conventional detection methods) wherein the composition consists essentially of derivatives of a single macromolecular species. The term "purified" generally denotes that a nucleic acid, polypeptide, or protein gives rise to essentially one band in an electrophoretic gel. It typically means that the nucleic acid, polypeptide, or protein is at least about 50% pure, 60% pure, 70% pure, 75% pure, more preferably at least about 85% pure, and most preferably at least about 99% pure.

The term "isolated nucleic acid" may refer to a nucleic acid (e.g., DNA or RNA) that is not immediately contiguous with both of the coding sequences with which it is immediately contiguous (i.e., one at the 5' and one at the 3' end) in the naturally occurring genome of the organism from which the nucleic acid of the invention is derived. Thus, this term includes, e.g., a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including, e.g., a virus, from which it was originally derived, linked to an additional coding sequence to form a hybrid gene encoding a chimeric polypeptide, or independent of any other DNA sequences. The DNA may be double-stranded or single-stranded, sense or antisense.

A "recombinant polynucleotide" or a "recombinant polypeptide" is a non-naturally occurring polynucleotide or polypeptide which may include nucleic acid or amino acid sequences, respectively, from more than one source nucleic acid or polypeptide, which source nucleic acid or polypeptide can be a naturally occurring nucleic acid or polypeptide, or can itself have been subjected to mutagenesis or other type of modification. A nucleic acid or polypeptide may be deemed "recombinant" when it is synthetic or artificial or engineered, or derived from a synthetic or artificial or engineered polypeptide or nucleic acid. A recombinant nucleic acid (e.g., DNA or RNA) can be made by the combination (e.g., artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or artificially synthesized. A "recombinant polypeptide" often refers to a polypeptide that results from a cloned or recombinant nucleic acid. The source polynucleotides or polypeptides from which the different nucleic acid or amino acid sequences are derived are sometimes homologous (i.e., have, or encode a polypeptide that encodes, the same or a similar structure and/or function), and are often from different isolates, serotypes, strains, species, of organism or from different disease states, for example.

The term "recombinant" when used with reference, e.g., to a cell, polynucleotide, vector, protein, or polypeptide typically indicates that the cell, polynucleotide, or vector has been modified by the introduction of a heterologous (or foreign) nucleic acid or the alteration of a native nucleic acid, or that the protein or polypeptide has been modified by the introduction of a heterologous amino acid, or that the cell is derived from a cell so modified. Recombinant cells express nucleic acid sequences that are not found in the native (non-recombinant) form of the cell or express native nucleic acid sequences that would otherwise be abnormally expressed, under-expressed, or not expressed at all. The term "recombinant" when used with reference to a cell indicates that the cell replicates a heterologous nucleic acid, or expresses a polypeptide encoded by a heterologous nucleic acid. Recombinant cells can contain coding sequences that are not found within the native (non-recombinant) form of the cell. Recombinant cells can also contain coding sequences found in the native form of the cell wherein the coding sequences are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, recombination, and related techniques.

The term "recombinantly produced" refers to an artificial combination usually accomplished by either chemical synthesis means, recursive sequence recombination of nucleic acid segments or other diversity generation methods (such as, e.g., shuffling) of nucleotides, or manipulation of isolated segments of nucleic acids, e.g., by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo where it may be expressed or propagated.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

An "immunogen" refers to a substance capable of provoking an immune response, and includes, e.g., antigens, autoantigens that play a role in induction of autoimmune diseases, and tumor-associated antigens expressed on cancer cells. An immune response generally refers to the development of a cellular or antibody-mediated response to an agent, such as an antigen or fragment thereof or nucleic acid encoding such agent. In some instances, such a response comprises a production of at least one or a combination of CTLs, B cells, or various classes of T cells that are directed specifically to antigen-presenting cells expressing the antigen of interest.

An "antigen" refers to a substance that is capable of eliciting the formation of antibodies in a host or generating a specific population of lymphocytes reactive with that substance. Antigens are typically macromolecules (e.g., proteins and polysaccharides) that are foreign to the host.

An "adjuvant" refers to a substance that enhances an antigen's immune-stimulating properties or the pharmacological effect(s) of a drug. An adjuvant may non-specifically enhance the immune response to an antigen. "Freund's Complete Adjuvant," for example, is an emulsion of oil and water containing an immunogen, an emulsifying agent and mycobacteria. Another example, "Freund's incomplete adjuvant," is the same, but without mycobacteria.

A vector is a component or composition for facilitating cell transduction or transfection by a selected nucleic acid, or expression of the nucleic acid in the cell. Vectors include, e.g., plasmids, cosmids, viruses, YACs, bacteria, poly-lysine, etc. An "expression vector" is a nucleic acid construct or sequence, generated recombinantly or synthetically, with a series of specific nucleic acid elements that permit transcription of a particular nucleic acid in a host cell. The expression vector can be part of a plasmid, virus, or nucleic acid fragment. The expression vector typically includes a nucleic acid to be transcribed operably linked to a promoter. The nucleic acid to be transcribed is typically under the direction or control of the promoter.

"Substantially the entire length of a polynucleotide sequence" or "substantially the entire length of a polypeptide sequence" refers to at least 50%, generally at least about 60%, 70%, or 75%, usually at least about 80%, or typically at least about 85%, 90%, 91%, 92%, 93%, 94%, 95%, 96%, 97%, 98%, 99% or more of a length of a polynucleotide sequence or polypeptide sequence.

The term "immunoassay" includes an assay that uses an antibody or immunogen to bind or specifically bind an antigen. The immunoassay is typically characterized by the use of specific binding properties of a particular antibody to isolate, target, and/or quantify the antigen.

The term "subject" as used herein includes, but is not limited to, an organism; a mammal, including, e.g., a human, non-human primate (e.g., baboon, orangutan, monkey), mouse, pig, cow, goat, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier.

The term "effective amount" means a dosage or amount sufficient to produce a desired result. The desired result may comprise an objective or subjective improvement in the recipient of the dosage or amount.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as a nucleic acid, vector, gene, polypeptide, protein, substance, or composition thereof that, when administered to a subject who does not display signs or symptoms of pathology, disease or disorder, or who displays only early signs or symptoms of pathology, disease, or disorder, diminishes, prevents, or decreases the risk of the subject developing a pathology, disease, or disorder. A "prophylactically useful" agent or compound (e.g., nucleic acid or polypeptide) refers to an agent or compound that is useful in diminishing, preventing, treating, or decreasing development of pathology, disease or disorder.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as a nucleic acid, vector, gene, polypeptide, protein, substance, or composition thereof, that eliminates or diminishes signs or symptoms of pathology, disease or disorder, when administered to a subject suffering from such signs or symptoms. A "therapeutically useful" agent or compound (e.g., nucleic acid or polypeptide) indicates that an agent or compound is useful in diminishing, treating, or eliminating such signs or symptoms of a pathology, disease or disorder.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins (e.g., promoter, enhancer, or other regulatory regions). Genes can be obtained from a variety of sources, including cloning from a source of interest or synthesizing from known or predicted sequence information, and may include sequences designed to have desired parameters.

Generally, the nomenclature used hereafter and the laboratory procedures in cell culture, molecular genetics, molecular biology, nucleic acid chemistry, and protein chemistry described below are those well known and commonly employed by those of ordinary skill in the art. Standard techniques, such as described in Sambrook et al., Molecular Cloning—A Laboratory Manual (2nd Ed.), Vols. 1-3, Cold Spring Harbor Laboratory, Cold Spring Harbor, N.Y., 1989 (hereinafter "Sambrook") and Current Protocols in Molecular Biology, F. M. Ausubel et al., eds., Current Protocols, a joint venture between Greene Publishing Associates, Inc. and John Wiley & Sons, Inc. (1994, supplemented through 1999) (hereinafter "Ausubel"), are used for recombinant nucleic acid methods, nucleic acid synthesis, cell culture methods, and transgene incorporation, e.g., electroporation, injection, gene gun, impressing through the skin, and lipofection. Generally, oligonucleotide synthesis and purification steps are performed according to specifications. The techniques and procedures are generally performed according to conventional methods in the art and various general references which are provided throughout this document. The procedures therein are believed to be well known to those of ordinary skill in the art and are provided for the convenience of the reader.

As used herein, an "antibody" refers to a protein comprising one or more polypeptides substantially or partially encoded by immunoglobulin genes or fragments of immunoglobulin genes. The term antibody is used to mean whole antibodies and binding fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 KDa) and one "heavy" chain (about 50-70 KDa). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies also include single-armed composite monoclonal antibodies, single chain antibodies, including single chain Fv (sFv) antibodies in which a variable heavy and a variable light chain are joined together (directly or through a peptide linker) to form a continuous polypeptide, as well as diabodies, tribodies, and tetrabodies (Pack et al. (1995) J Mol Biol 246:28; Biotechnol 11:1271; and Biochemistry 31:1579). The antibodies are, e.g., polyclonal, monoclonal, chimeric, humanized, single chain, Fab fragments, fragments produced by an Fab expression library, or the like.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An "antigen-binding fragment" of an antibody is a peptide or polypeptide fragment of the antibody that binds an antigen. An antigen-binding site is formed by those amino acids of the antibody that contribute to, are involved in, or affect the binding of the antigen. See Scott, T. A. and Mercer, E. I., Concise Encyclopedia: Biochemistry and Molecular Biology (de Gruyter, 3d ed. 1997), and Watson, J. D. et al., Recombinant DNA (2d ed. 1992) (hereinafter "Watson, Recombinant DNA"), each of which is incorporated herein by reference in its entirety for all purposes.

The term "screening" describes, in general, a process that identifies optimal molecules of the present invention, such as, e.g., polypeptides of the invention, and related fusion polypeptides including the same, and nucleic acids encoding all such molecules. Several properties of these respective molecules can be used in selection and screening, for example: an ability of a respective molecule to bind a ligand or to a receptor, to inhibit cell proliferation, to inhibit viral replication in virus-infected cells, to induce or inhibit cellular cytokine production, to alter an immune response, e.g., induce or inhibit a desired immune response, in a test system or an in vitro, ex vivo or in vivo application. In the case of antigens, several properties of the antigen can be used in selection and screening including antigen expression, folding, stability, immunogenicity and presence of epitopes from several related antigens.

"Selection" is a form of screening in which identification and physical separation are achieved simultaneously by, e.g., expression of a selection marker, which, in some genetic circumstances, allows cells expressing the marker to survive while other cells die (or vice versa). Screening markers include, for example, luciferase, beta-galactosidase and green fluorescent protein, and the like. Selection markers include drug and toxin resistance genes, and the like. Another mode of selection involves physical sorting based on a detectable event, such as binding of a ligand to a receptor, reaction of a substrate with an enzyme, or any other physical process which can generate a detectable signal either directly (e.g., by utilizing a chromogenic substrate or ligand) or indirectly (e.g., by reacting with a chromogenic secondary antibody). Selection by physical sorting can by accomplished by a variety of methods, such as by FACS in whole cell or microdroplet formats.

An "exogenous" "nucleic acid," "exogenous DNA segment," "heterologous sequence," or "heterologous nucleic acid," as used herein, is one that originates from a source foreign to the particular host cell, or, if from the same source, is modified from its original form. Thus, a heterologous gene in a host cell includes a gene that is endogenous to the particular host cell, but has been modified. Modification of a heterologous sequence in the applications described herein typically occurs through the use of recursive sequence recombination. The terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res 19:5081; Ohtsuka et al. (1985) J Biol Chem 260: 2605-2608; Cassol et al. (1992); Rossolini et al. (1994) Mol Cell Probes 8:91-98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample. A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "cytokine" includes, for example, interleukins, interferons, chemokines, hematopoietic growth factors, tumor necrosis factors and transforming growth factors. In general these are low molecular weight proteins that regulate maturation, activation, proliferation, and differentiation of cells of the immune system.

In the present description and claims, any reference to "a" component, e.g. in the context of a non-polypeptide moiety, an amino acid residue, a substitution, a buffer, a cation, etc., is intended to refer to one or more of such components, unless stated otherwise or unless it is clear from the particular context that this is not the case. For example, the expression "a component selected from the group consisting of A, B and C" is intended to include all combinations of A, B and C, e.g., A, B, C, A+B, A+C, B+C or A+B+C.

Various additional terms are defined or otherwise characterized herein.

Molecules and Methods of the Invention

Molecules of the invention (e.g., polypeptides of the invention, conjugates of the invention, and nucleic acids encoding said polypeptides) are useful for the treatment of diseases and disorders which are responsive to treatment by interferon-alpha, particularly diseases associated with viral infection, such as, for example, infection by HCV.

Patients with chronic HCV infection have viral loads typically in the range of $10^4$-$10^7$ copies of HCV RNA/ml of serum prior to treatment. Upon treatment with IFN-alpha, viral load in these patients characteristically undergoes two distinct log-linear phases of decline (FIG. 1B; Neumann A. U., et al. (1998) Science 282:103-107). The initial rapid drop in viral load that occurs within the first two days of IFN-alpha therapy is believed to be due to interferon-alpha mediated reduction in virus production in the infected liver cells and concomitant protection of naïve cells against infection. The rate of viral production reaches a new steady state at about two days, at which time a second less rapid log-linear phase of viral clearance is observed. This second phase of viral clearance is generally believed to be due in part to T-cell mediated killing of infected liver cells (Neumann, et al., supra). IFN-alpha is believed to play a key role in this biological response through the stimulation of antigen specific T cells to differentiate into $T_H1$ cells. Furthermore, the mode of action of Ribavirin is believed to be due to augmentation of the $T_H1$ response, and is thought to be the mechanistic basis of its efficacy in combination therapy with IFN-alpha. HCV-infected patients who are non-responsive to interferon-alpha therapies currently in use (generally termed "non-responders") exhibit much shallower viral load clearance profiles (FIG. 1A).

Although the present invention is not intended to be limited by a particular theory of underlying mechanism, it is proposed that antiviral activity in surrogate assay systems (such as those described in more detail herein) may be predictive of interferon-alpha efficacy, in for example the first phase of viral clearance. Exemplary antiviral assays, described in the Examples section, monitor the effectiveness of IFN-alpha in protecting against the cytopathic effect of Encephalomyocarditis Virus (EMCV) in HuH7 human liver-derived cells as a surrogate system for effectiveness against HCV in human liver cells. Other useful virus/cell assay systems include EMCV in WISH human amnion-derived cells, EMCV in HeLa human cervical carcinoma cells, Vesicular Stomatitis Virus (VSV) in HuH7 cells, Vaccinia Virus (VV) in HeLa cells, Yellow Fever Virus (YFV) in HepG2 human hepatocarcinoma cells, as well as Human Immunodeficiency Virus (HIV) in primary CD4+ T-cells. Example 2 shows antiviral activities of representative polypeptides of the invention in the EMCV/HuH7 and EMCV/HeLa antiviral activity assays.

Other surrogate assay systems useful for monitoring effectiveness against HCV in infected hepatocytes include HCV replicon systems, as described, for example, by Lohmann V., et al., (1999) Science 285(5424):285-293; Randall G. and Rice C. M. (2001) Curr Opin Infect Dis 14(6):743-7477; and Bartenschlager, R. (2002) Nature Reviews/Drug Discovery 1:911. An example of a useful in vivo host system for monitoring HCV antiviral efficacy is a chimeric human liver SCID mouse, as described by Mercer, et al. (2001) Nature Medicine 7(8):927-933.

It is furthermore proposed, without being limited by theory, that enhancement of $T_H1$ differentiation and/or suppression of $T_H2$ differentiation by IFN-alpha may be a contributing factor to interferon-alpha efficacy, for example, in the second phase of viral clearance. According to this theory, evolved IFN-alphas with increased potency in these biological activities (i.e., enhancement of $T_H1$ differentiation and/or suppression of $T_H2$ differentiation) would be predicted to have increased efficacy relative to, for example, currently approved therapeutic interferon-alpha molecules administered at the same dosage. An exemplary assay, described in the Examples section herein, monitors the enhancement of $T_H1$ differentiation and/or suppression of $T_H2$ differentiation by IFN-alpha on naïve $T_H0$ cells, by measuring production of cytokines associated with the $T_H1$-phenotype (e.g., IFN-gamma) and/or the $T_H2$-phenotype (e.g., IL-5, IL4) via ELISA or via intracellular staining and FACS sorting. Example 3 shows $T_H1$ differentiation activities of representative polypeptides of the invention.

The therapeutic efficacy of IFN-alpha molecules tends to be diminished in part due to dose-limiting toxicities, e.g. thrombocytopenia and neutropenia. Although the present invention is not intended to be limited by a particular theory of underlying mechanism, it is proposed that such toxicity may be associated with anti-proliferative effects of IFN-alpha on platelet and neutrophil precursors, and that antiproliferative activity in surrogate assay systems (such as those described herein) may be predictive of the relative toxicity of an interferon-alpha molecule. Thus, dose-limiting toxicities associated with IFN-alpha therapy may be diminished in IFN-alpha molecules that exhibit reduced antiproliferative activity relative to, for example, currently approved therapeutic interferon-alpha molecules, such as ROFERON®-A (Interferon alfa-2a, recombinant; Hoffmann-La Roche Inc.), INTRON® A (Interferon alfa-2b, recombinant; Schering Corporation), and INFERGEN® (interferon alfacon-1; InterMune, Inc.). An exemplary antiproliferative activity assay, described in the Examples section herein, monitors the effect of IFN-alpha on the proliferation of human Daudi lymphoid cells. Alternatively, or in addition, dose-limiting toxicities may be reduced as a result of administering more therapeutically active molecules, which would permit dosing in lower concentrations or at lower frequency than currently approved molecules. Example 4 shows the Daudi antiproliferative activities of representative polypeptides of the invention.

It is an object of the invention to provide novel interferon-alpha polypeptides, and nucleic acids which encode the polypeptides. Polypeptides of the invention are useful for the treatment of diseases and disorders which are responsive to treatment by interferon-alpha, particularly diseases associated with viral infection, such as, for example, infection by HCV. Some polypeptides of the invention exhibit an interferon-alpha activity, such as, for example, antiviral activity, antiproliferative activity, and/or $T_H1$ differentiation activity. Some polypeptides of the invention exhibit one or more of the following properties: increased or decreased antiviral activity compared to a reference IFN-alpha polypeptide; increased or decreased $T_H1$ differentiation activity compared to a reference IFN-alpha polypeptide; increased or decreased antiproliferative activity compared to a reference IFN-alpha polypeptide. The reference IFN-alpha polypeptide may comprise a sequence of a non-naturally occurring interferon-alpha, such as IFN-alpha Con1 (SEQ ID NO:58), or may comprise a sequence of a naturally-occurring (i.e., wild-type) interferon-alpha polypeptide. Examples of sequences of naturally occurring interferon-alpha polypeptides include sequences of human IFN-alpha polypeptides, such as, for example, huIFN-alpha 2b (SEQ ID NO:46), huIFN-alpha 2a (SEQ ID NO:47), huIFN-alpha 2c (SEQ ID NO:46 with position 34=Arg), huIFN-alpha 8b (SEQ ID NO:52), huIFN-alpha 8a (SEQ ID NO:52 with positions 98=Val, 99=Leu, 100=Cys, and 101=Asp), huIFN-alpha 8c (SEQ ID NO:52 with position 161=Asp and amino acids at positions 162-166 deleted), huIFN-alpha 14a (SEQ ID NO:54), huIFN-alpha 14c (SEQ ID NO:54 with position 152=Leu), or a sequence of any other naturally occurring human interferon alpha polypeptide, such as those listed in Allen G. and Diaz M. O. (1996), supra.

In another aspect, the invention provides interferon-alpha polypeptides which exhibit enhanced efficacy in clearing a virus from virus-infected cells, compared to a reference interferon-alpha molecule, such as one currently employed as a therapeutic (such as, for example, ROFERON-A, INTRON A, or INFERGEN). Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus;

viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus. Such enhanced efficacy may arise from enhanced antiviral activity, enhanced $T_H1$-differentiation activity, or both, relative to the reference molecule. For example, some interferon-alpha polypeptides of the invention may be particularly useful in clearing viruses or viral strains that show poor response to treatment with interferon-alpha molecules currently in use, such as, for example, Genotype 1 of HCV.

Some polypeptides of the invention exhibit an increased ratio of (antiviral activity/antiproliferative activity) compared to the reference IFN-alpha molecule, and/or an increased ratio of ($T_H1$ differentiation activity/antiproliferative activity) compared to the reference IFN-alpha molecule. Polypeptides exhibiting such properties may be particularly effective in treatment of viral infections, such as, for example, infection by a virus listed above. Some such polypeptides may, for example, provide enhanced therapeutic efficacy over currently-approved interferon-alpha molecules in the treatment of HCV, in one or both phases of the biphasic viral clearance profile, and/or may exhibit reduced toxicity. Some such polypeptides may provide enhanced therapeutic efficacy over currently-approved interferon-alpha molecules in the treatment of Genotype 1 HCV.

It is another object of the invention to provide conjugates, such conjugates comprising one or more non-polypeptide moiety linked to a polypeptide of the invention, which conjugate exhibits an interferon-alpha activity (such as one or more of the activities listed above), and which optionally exhibits other desirable properties, such as increased serum half-life and/or functional in vivo half-life, and/or decreased antigenicity, compared to the non-conjugated polypeptide. Some such conjugates may exhibit enhanced efficacy in clearing a virus from cells infected with the virus, compared to a reference interferon-alpha molecule, such as an interferon-alpha conjugate currently employed as a therapeutic (such as, for example, PEGASYS® (Peginterferon alfa-2a; Hoffmann-La Roche, Inc.) or PEG-INTRON® (peginterferon alfa-2b; Schering Corporation). Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus; viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus. Such enhanced efficacy may arise from enhanced antiviral activity, enhanced $T_H1$-differentiation activity, or both, relative to the reference molecule. For example, some interferon-alpha conjugates of the invention may be particularly useful in clearing viruses or viral strains that show poor response to treatment with interferon-alpha molecules currently in use, such as, for example, Genotype 1 of HCV.

Some conjugates of the invention exhibit an increased ratio of (antiviral activity/antiproliferative activity) compared to the reference IFN-alpha molecule, and/or an increased ratio of ($T_H1$ differentiation activity/antiproliferative activity) compared to the reference IFN-alpha molecule. Conjugates exhibiting such properties may be particularly effective in treatment of viral infections, such as infection by a virus listed above, such as, for example, HCV. Some such conjugates may, for example, provide enhanced therapeutic efficacy over currently-approved interferon-alpha molecules in the treatment of HCV, in one or both phases of the biphasic viral clearance profile, and/or may exhibit reduced toxicity. Some such conjugates may provide enhanced therapeutic efficacy over currently-approved interferon-alpha molecules in the treatment of Genotype 1 HCV.

It is another object of the invention to provide a method of inhibiting viral replication in virus-infected cells, the method comprising administering to the virus-infected cells a polypeptide or conjugate of the invention in an amount effective to inhibit viral replication in said cells. The invention also provides a method of reducing the number of copies of a virus in virus-infected cells, comprising administering to the virus-infected cells a polypeptide or conjugate of the invention in an amount effective to reduce the number of copies of the virus in said cells. The virus may be a virus of the Flaviviridae family, such as, for example, Hepatitis C Virus, Yellow Fever Virus, West Nile Virus, Japanese Encephalitis Virus, Dengue Virus, or Bovine Viral Diarrhea Virus; a virus of the Hepadnaviridae family, such as, for example, Hepatitis B Virus; a virus of the Picornaviridae family, such as, for example, Encephalomyocarditis Virus, Human Rhinovirus, or Hepatitis A Virus; a virus of the Retroviridae family, such as, for example, Human Immunodeficiency Virus, Simian Immunodeficiency Virus, Human T-Lymphotropic Virus, or Rous Sarcoma Virus; a virus of the Coronaviridae family, such as, for example, SARS coronavirus; a virus of the Rhabdoviridae family, such as, for example, Rabies Virus or Vesicular Stomatitis Virus; a virus of the Paramyxoviridae family, such as, for example, Respiratory Syncytial Virus or Parainfluenza Virus; a virus of the Papillomaviridae family, such as, for example, Human Papillomavirus; or a virus of the Herpesviridae family, such as, for example, Herpes Simplex Virus. The virus may for example be an RNA virus, such as HCV, a DNA virus, such as HBV, or a retrovirus, such as HIV. The cells may be in culture or otherwise isolated from a mammal (i.e., in vitro or ex vivo), or may be in vivo, e.g., in a mammal (e.g. such as a SCID mouse model as described by Mercer, et al. (2001) Nature Medicine. 7(8): 927-933), in a primate, or in man.

The invention also provides a method of enhancing $T_H1$ differentiation of $T_H0$ cells, comprising administering to a population comprising $T_H0$ cells a polypeptide or conjugate of the invention in an amount effective to increase the production of a cytokine associated with the $T_H1$-phenotype (e.g., IFN-gamma) and/or decrease the production of a cytokine associated with the $T_H2$-phenotype (e.g., IL-4 or IL-5) in said population. The population may be in culture or otherwise isolated from a mammal (i.e., in vitro or ex vivo), or may be in vivo, e.g., in a mammal, in a primate, or in man.

The invention also provides a method of inhibiting proliferation of a cell population, comprising contacting the cell population with a polypeptide, variant, or conjugate of the invention in an amount effective to decrease proliferation of the cell population. The cell population may be in culture or otherwise isolated from a mammal (i.e., in vitro or ex vivo), or may be in vivo, e.g., in a mammal, a primate, or man.

These and other objects of the invention are discussed in more detail below.

Polypeptides of the Invention

The invention provides novel interferon-alpha polypeptides, collectively referred to herein as "polypeptides of the invention". The term "polypeptide(s) of the invention" is intended throughout to include variants of the polypeptide sequences disclosed herein. Also included in this invention are fusion proteins comprising polypeptides of the invention, and conjugates comprising polypeptides of the invention.

Fragments of various interferon-alpha coding sequences were recursively recombined to form libraries comprising recombinant polynucleotides, from which polypeptides of the invention were derived. Methods for obtaining libraries of recombinant polynucleotides and/or for obtaining diversity in nucleic acids used as the substrates for recursive sequence recombination are also described infra.

Exemplary polypeptides of the invention include polypeptides comprising sequences identified herein as SEQ ID NOs: 2-35 and SEQ ID NOs: 37-44 (i.e., SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:10, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:37, SEQ ID NO:38, SEQ ID NO:39, SEQ ID NO:40, SEQ ID NO:41, SEQ ID NO:42, SEQ ID NO:43, and SEQ ID NO:44). Some such polypeptides further comprise one or more additional amino acid(s), such as, for example, a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:1 and (b) comprises one or more substitution(s) relative to SEQ ID NO:1 selected from the group consisting of F48A/L; V51P; F55A; F65A; F68P; L111A; and V114P. Some such polypeptides comprise a sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitution(s) relative to SEQ ID NO:1 selected from the group consisting of H47Q; V51A; Q52P/E; A53T; F55S; L56V; F57L; Y58H; M61I; N113K; V114E; and E160D. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:1 and (b) comprises the substitution F48A/L relative to SEQ ID NO:1. Some such polypeptides comprise a sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. Some such polypeptides comprise the substitution F48A relative to SEQ ID NO:1. In some instances, the polypeptide further comprises one or more substitution(s) relative to SEQ ID NO:1 selected from the group consisting of H47Q; V51A/P; Q52P/E; A53T; F55A/S; L56V; F65A; F57L; Y58H; M61I; F68P; L111A; N113K; V114E/P; and E160D. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:1 and (b) comprises the substitution F55A relative to SEQ ID NO:1. Some such polypeptides comprise a sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitution(s) relative to SEQ ID NO:1 selected from the group consisting of H47Q; F48A/L; V51A/P; Q52P/E; A53T; L56V; F65A; F57L; Y58H; M61I; F68P; L111A; N113K; V114E/P; and E160D. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:1 and (b) comprises the substitution F65A relative to SEQ ID NO:1. Some such polypeptides comprise a sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitutions relative to SEQ ID NO:1 selected from the group consisting of H47Q; F48A/L; V51A/P; Q52P/E; A53T; F55A/S; L56V; F57L; Y58H; M61I; F68P; L111A; N113K; V114E/P; and E160D. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:1 and (b) comprises the substitution L111A relative to SEQ ID NO:1. Some such polypeptides comprise a sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitutions relative to SEQ ID NO:1 selected from the group consisting of H47Q; F48A/L; V51A/P; Q52P/E; A53T; F55A/S; L56V; F65A; F57L; Y58H; M61I; F68P; N113K; V114E/P; and E160D. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 0 to 16 amino acid positions from SEQ ID NO:13 and (b) comprises one or more of: Ala or Leu at position 48; Pro at position 51; Ala at position 55; Ala at position 65; Pro at position 68; Ala at position 111; and Pro at position 114 (position numbering relative to SEQ ID NO:13). Some such polypeptides comprise a sequence which differs from SEQ ID NO:13 in 0, 1, 2, 3, 4, 5, 6, 7, 8, 9, 10, 11, 12, 13, 14, 15, or 16 amino acid positions, e.g., in 0-15 amino acid positions, in 0-14 amino acid positions, in 0-13 amino acid positions, in 0-12 amino acid positions, in 0-11 amino acid positions, in 0-10 amino acid positions, in 0-9 amino acid positions, in 0-8 amino acid positions, in 0-7 amino acid positions, in 0-6 amino acid positions, in 0-5 amino acid positions, in 0-4 amino acid positions, in 0-3 amino acid positions, in 0-2 amino acid positions, or in 0-1 amino acid positions. Some such polypeptides comprise an Ala or a Leu at position 48. Some such polypeptides comprise an Ala at position 48. In some instances, the polypeptide further comprises one or more substitution(s) relative to SEQ ID NO:13 selected from the group consisting of H47Q; V51A; Q52P/E; A53T; F55S; L56V; F57L; Y58H; M61I; N113K; V114E; and E160D. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:36 and (b) comprises one or more substitution(s) relative to SEQ ID NO:36 selected from the group consisting of M21A; I24P; F48A/L; T51P; S55A; F65A; F68P; F90A; M93P; L111A; V114P; F124A; I127P; and E160D. Some such polypeptides comprise a sequence which differs from SEQ ID NO:36 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitution(s) relative to SEQ ID NO:36 selected from the group consisting of P26L; H47Q; T51V; S55P/F; V56L; H58Y; L60M; F90Y; M93L; N95D; N113K; V114E; R125Q; T132K; and L154F. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:36 and (b) comprises the substitution F48A/L relative to SEQ ID NO:36. Some such polypeptides comprise a sequence which differs from SEQ ID NO:36 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. Some such polypeptides comprise the substitution F48A relative to SEQ ID NO:36. In some instances, the polypeptide further comprises one or more substitution(s) relative to SEQ ID NO:36 selected from the group consisting of M21A; I24P; P26L; H47Q; T51V/P; S55P/F/A; V56L; H58Y; L60M; F65A; F68P; F90Y/A; M93L/P; N95D; L111A; N113K; V114E/P; F124A; R125Q; I127P; T132K; L154F; and E160D. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:36 and (b) comprises the substitution F90A relative to SEQ ID NO:36. Some such polypeptides comprise a sequence which differs from SEQ ID NO:36 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitution(s) relative to SEQ ID NO:36 selected from the group consisting of M21A; I24P; P26L; H47Q; F48A/L; T51V/P; S55P/F/A; V56L; H58Y; L60M; F65A; F68P; M93L/P; N95D; L111A; N113K; V114E/P; F124A; R125Q; I127P; T132K; L154F; and E160D, In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 1 to 16 amino acid positions from SEQ ID NO:36 and (b) comprises the substitution E160D relative to SEQ ID NO:36. Some such polypeptides comprise a sequence which differs from SEQ ID NO:36 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide further comprises one or more substitution(s) relative to SEQ ID NO:36 selected from the group consisting of M21A; I24P; P26L; H47Q; F48A/L; T51V/P; S55P/F/A; V56L; H58Y; L60M; F65A; F68P; F90Y/A; M93L/P; N95D; L111A; N113K; V114E/P; F124A; R125Q; I127P; T132K; and L154F. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

The invention also provides isolated or recombinant polypeptides which each comprise a sequence which (a) differs in 0 to 16 amino acid positions from SEQ ID NO:38 and (b) comprises one or more of: Ala at position 21; Pro at position 24; Ala or Leu at position 48; Pro at position 51; Ala at position 55; Ala at position 65; Pro at position 68; Ala at position 90; Pro at position 93; Ala at position 111; Pro at position 114; Ala at position 124; Pro at position 127; and Glu at position 160 (position numbering relative to SEQ ID NO:38). Some such polypeptides comprise a sequence which differs from SEQ ID NO:38 in 0, 1, 2, 3, 4, 5, 6, 7, 8, 9, 10, 11, 12, 13, 14, 15, or 16 amino acid positions, e.g., in 0-15 amino acid positions, in 0-14 amino acid positions, in 0-13 amino acid positions, in 0-12 amino acid positions, in 0-11 amino acid positions, in 0-10 amino acid positions, in 0-9 amino acid positions, in 0-8 amino acid positions, in 0-7 amino acid positions, in 0-6 amino acid positions, in 0-5 amino acid positions, in 0-4 amino acid positions, in 0-3 amino acid positions, in 0-2 amino acid positions, or in 0-1 amino acid positions. Some such polypeptides comprise an Ala or a Leu at position 48. Some such polypeptides comprise an Ala at position 48. In some instances, the polypeptide further comprises one or more substitution(s) relative to SEQ ID NO:38 selected from the group consisting of P26L; H47Q; V51T; F55P/S; L56V; Y58H; L60M; F90Y; M93L; N95D; N113K; V114E; R125Q; T132K; and F154L. In some instances, the polypeptide exhibits an interferon-alpha activity (e.g., antiviral activity, $T_H1$ differentiation activity, and/or antiproliferative activity). Some such polypeptides further comprise one or more additional amino acid(s), such as a methionine added to the N-terminus. The invention also provides fusion proteins and conjugates comprising these polypeptides, and isolated or recombinant nucleic acids encoding these polypeptides.

Other modifications contemplated for polypeptides of the invention include those described below and in the section entitled "INTERFERON-ALPHA CONJUGATES".

It is to be understood that while the examples and modifications to the parent polypeptide are generally provided herein relative to the sequence SEQ ID NO:1 (or relative to SEQ ID NO:36, or relative to some other specified sequence), the disclosed modifications may also be made in equivalent amino acid positions of any of the other polypeptides of the invention (such as a polypeptide comprising a sequence selected from SEQ ID NOs:2-35 and SEQ ID NOs:37-44) described herein. Thus, as an example, the substitution F48L relative to SEQ ID NO:1 is understood to correspond to the substitution A48L in SEQ ID NO:13, and so on.

The following tables provide sequences of some interferon-alpha polypeptides of the invention. For clarity, the sequences are shown relative to reference sequences SEQ ID NO:1 (Table 1) or SEQ ID NO:36 (Table 2). Some such polypeptides exhibit an interferon-alpha activity, such as antiviral activity, $T_H1$ differentiation activity, and/or antiproliferative activity.

TABLE 1

| Polypeptide Sequence (relative to SEQ ID NO:1) | Clone name | SEQ ID |
|---|---|---|
| SEQ ID NO:1 | B9x14EC4 | SEQ ID NO:1 |
| SEQ ID NO:1 F55P | 14epi07 | SEQ ID NO:2 |
| SEQ ID NO:1 V51A Q52P F55S L56V F57L Y58H | 14epi08 | SEQ ID NO:3 |
| SEQ ID NO:1 V51A Q52E A53T F55P L56V F57L Y58H | 14epi09 | SEQ ID NO:4 |
| SEQ ID NO:1 V51A Q52E F55S L56V F57L Y58H | 14epi10 | SEQ ID NO:5 |
| SEQ ID NO:1 V51A F55S L56A Y58H | 14epi11 | SEQ ID NO:6 |
| SEQ ID NO:1 F48L E160D | 14epi12d | SEQ ID NO:7 |
| SEQ ID NO:1 H47Q | 14epi13 | SEQ ID NO:8 |
| SEQ ID NO:1 M61I | 14epi14 | SEQ ID NO:9 |
| SEQ ID NO:1 F48L | 14epi15 | SEQ ID NO:10 |
| SEQ ID NO:1 F48L F55A | 14epi16 | SEQ ID NO:11 |

TABLE 1-continued

| Polypeptide Sequence (relative to SEQ ID NO:1) | Clone name | SEQ ID |
|---|---|---|
| SEQ ID NO:1 F48L F55S | 14epi17 | SEQ ID NO:12 |
| SEQ ID NO:1 F48A | 14epi18 | SEQ ID NO:13 |
| SEQ ID NO:1 F48A F55A | 14epi19 | SEQ ID NO:14 |
| SEQ ID NO:1 F48A F55S | 14epi20 | SEQ ID NO:15 |
| SEQ ID NO:1 F55A | 14epi21 | SEQ ID NO:16 |
| SEQ ID NO:1 F55S | 14epi22 | SEQ ID NO:17 |
| SEQ ID NO:1 F48A F55S L111A | 14epi23 | SEQ ID NO:18 |
| SEQ ID NO:1 F48A F55S N113K V114E | 14epi24 | SEQ ID NO:19 |
| SEQ ID NO:1 F48L F55S L111A | 14epi25 | SEQ ID NO:20 |
| SEQ ID NO:1 F48L F55S N113K V114E | 14epi26 | SEQ ID NO:21 |
| SEQ ID NO:1 F48A F55S F65A L111A | 14epi27 | SEQ ID NO:22 |
| SEQ ID NO:1 F48A F55S F65A N113K V114E | 14epi28 | SEQ ID NO:23 |
| SEQ ID NO:1 F48A F55S F65A L111A | 14epi29 | SEQ ID NO:24 |
| SEQ ID NO:1 F48A F55A L111A | 14epi30 | SEQ ID NO:25 |
| SEQ ID NO:1 F48A F55A N113K V114E | 14epi31 | SEQ ID NO:26 |
| SEQ ID NO:1 F48L Q52P F55S N113K V114E | 14epi32 | SEQ ID NO:27 |
| SEQ ID NO:1 Q52P F55S N113K V114E | 14epi33 | SEQ ID NO:28 |
| SEQ ID NO:1 Q52P F55S N113K V114E | 14epi34 | SEQ ID NO:29 |
| SEQ ID NO:1 F48L V51A Q52P F55S L56V F57L Y58H N113K V114E | 14epi35 | SEQ ID NO:30 |
| SEQ ID NO:1 V51A Q52E A53T F55P L56V F57L Y58H N113K V114E | 14epi36 | SEQ ID NO:31 |
| SEQ ID NO:1 V51A F55S L56V F57L Y58H N113K V114E | 14epi37 | SEQ ID NO:32 |
| SEQ ID NO:1 V51A Q52P F55S L56V F57L Y58H N113K V114E | 14epi38 | SEQ ID NO:33 |
| SEQ ID NO:1 H47Q F48A F55S | 14epi39 | SEQ ID NO:34 |
| SEQ ID NO:1 H47Q F48A F55S L56V Y58H | 14epi42 | SEQ ID NO:35 |

TABLE 2

| Polypeptide Sequence (relative to SEQ ID NO:36) | Clone name | SEQ ID |
|---|---|---|
| SEQ ID NO:36 | 25epi08 | SEQ ID NO:36 |
| SEQ ID NO:36 F48A L154F | 25epi18 | SEQ ID NO:37 |
| SEQ ID NO:36 F48A T51V S55F V56L H58Y L154F | 25epi19 | SEQ ID NO:38 |
| SEQ ID NO:36 F48A T51V V56L H58Y L154F | 25epi20 | SEQ ID NO:39 |
| SEQ ID NO:36 F48A T51V L154F | 25epi25 | SEQ ID NO:40 |
| SEQ ID NO:36 F48A T51V F90Y M93L N95D L154F | 25epi26 | SEQ ID NO:41 |
| SEQ ID NO:36 F48A T51V F90A R125Q L154F | 25epi27 | SEQ ID NO:42 |
| SEQ ID NO:36 F48A T51V F90Y M93L N95D R125Q L154F | 25epi28 | SEQ ID NO:43 |
| SEQ ID NO:36 L154F E160D | 25epi29 | SEQ ID NO:44 |

Sequence Variations

As noted above, polypeptides of the present invention include polypeptides comprising sequences which differ from SEQ ID NO:1 in 1 to 16 amino acid positions and comprise one or more substitutions relative to SEQ ID NO:1 selected from the group consisting of F48A/L; V51P; F55A; F65A; F68P; L111A; and V114P. Polypeptides of the present invention also include polypeptides comprising sequences which differ from SEQ ID NO:36 in 1 to 16 amino acid positions and comprise one or more substitutions relative to SEQ ID NO:36 selected from the group consisting of M21A; I24P; F48A/L; T51P; S55A; F65A; F68P; F90A; M93P; L111A; V114P; F124A; I127P; and E160D. Some such polypeptides exhibit an interferon-alpha activity.

For example, some polypeptides of the invention comprise a sequence having a length of about 151 amino acids, such as about 151, 152, 153, 154, 155, 156, 157, 158, 159, 160, 161, 162, 163, 164, or 165 amino acids, corresponding to a deletion of between 1 and 15 amino acids relative to a parent polypeptide sequence (such as, for example, one of SEQ ID NOs:2-35 or 37-44). In some instances, between 1 and 11, e.g., between 1 and 10, such as between 1 and 7, e.g. between 1 and 5, such as between 1 and 3 amino acids are deleted from the C-terminus, i.e. the polypeptide is C-terminally truncated compared to the parent polypeptide sequence (such as, for example, one of SEQ ID NOs: 2-35 or 37-44) by 1-11 amino acid residues (e.g. by 1, 2, 3, 4, 5, 6, 7, 8, 9, 10, or 11 amino acid residues), such as by 1-10, 1-7, e.g., by 1-5 or by 1-3 amino acid residues. Alternatively, or in addition, some such polypeptides are N-terminally truncated compared to the parent polypeptide sequence (such as, one of SEQ ID NOs: 2-35 or 37-44) by 1-4 amino acid residues (e.g. by 1, 2, 3, or 4 amino acid residues), e.g., 1-4, 1-3, 1-2 or 1 amino acid residue(s) are removed from the N-terminus. Some such polypeptides further comprise a methionine at the N-terminus. Some such polypeptides exhibit an interferon-alpha activity.

As another example, some polypeptides of the invention comprise a sequence containing between 1 and 16 amino acid substitutions relative to SEQ ID NO:1 (e.g. 1, 2, 3, 4, 5, 6, 7, 8, 9, 10, 11, 12, 13, 14, 15, or 16 amino acid substitutions), such as 1-14 or 1-12 or 1-10 or 1-8 or 1-6 or 1-5 or 1-4 or 1-3 or 1-2 amino acid substitutions, in which at least one of the substitutions is selected from the group consisting of F48A/L; V51P; F55A; F65A; F68P; L111A; and V114P. Other polypeptides of the invention comprise a sequence containing between 1 and 16 amino acid substitutions relative to SEQ ID NO:36 (e.g. 1, 2, 3, 4, 5, 6, 7, 8, 9, 10, 11, 12, 13, 14, 15, or 16 amino acid substitutions), such as 1-14 or 1-12 or 1-10 or 1-8 or 1-6 or 1-5 or 1-4 or 1-3 or 1-2 amino acid substitutions, in which at least one of the substitutions is selected from the group consisting of M21A; I24P; F48A/L; T51P; S55A; F65A; F68P; F90A; M93P; L111A; V114P; F124A; I127P; and E160D. One or more additional amino acid substitutions may be made in the polypeptide sequence according to, for example, a substitution group (such as, a conservative substitution group), such as one set forth below. Alternatively, or in addition, one or more additional amino acid substitutions may made in the polypeptide sequence which introduces or removes an amino acid residue comprising an attachment group for a non-polypeptide moiety. Examples include introduction of one or more N-glycosylation site(s), introduction of one or more cysteine residue(s) or lysine residue(s), removal of one or more N-glycosylation site(s), and/or or removal of one or more lysine(s) or histidine(s). Some such polypeptides exhibit an interferon-alpha activity.

As a non-limiting example, a polypeptide of the invention may have a sequence which differs from SEQ ID NO:1 in a total of up to 16 positions (which may be a combination of amino acid substitutions, deletions, and/or insertions, including those described above). In some instances, none, some, or all of the substitutions are substitutions according to a substitution group defined below.

Amino acid substitutions in accordance with the invention may include, but are not limited to, one or more conservative amino acid substitutions. Conservative substitution tables providing functionally similar amino acids are well known in the art. One example is provided in the table below (Table 3), which sets forth six exemplary groups that contain amino acids which may be considered "conservative substitutions" for one another.

TABLE 3

Conservative Substitution Groups

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | Histidine (H) | |
| 5 | Isoleucine (I) | Leucine (L) | Methionine (M) | Valine (V) |
| 6 | Phenylalanine (F) | Tyrosine (Y) | Tryptophan (W) | |

Other substitution groups of amino acids can be envisioned. For example, amino acids can be grouped by similar function or chemical structure or composition (e.g., acidic, basic, aliphatic, aromatic, sulfur-containing). For example, an Aliphatic grouping may comprise: Glycine (G), Alanine (A), Valine (V), Leucine (L), Isoleucine (I). Other groups containing amino acids that are considered conservative substitutions for one another include: Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also Creighton (1984) Proteins, W.H. Freeman and Company, for additional groupings of amino acids. Listing of a polypeptide sequence herein, in conjunction with the above substitution groups, provides an express listing of all conservatively substituted polypeptide sequences.

Percent Sequence Identity

In one aspect, the invention provides isolated or recombinant polypeptides each comprising a sequence having at least 90% sequence identity (e.g., at least about 91%, at least about 92%, at least about 93%, at least about 94%, at least about 95%, at least about 96%, at least about 97%, at least about 98%, or at least about 99% amino acid sequence identity) to any one of SEQ ID NOs:1-35, wherein the sequence comprises one or more of: Ala or Leu at position 48; Pro at position 51; Ala at position 55; Ala at position 65; Pro at position 68; Ala at position 111; and Pro at position 114, amino acid position relative to SEQ ID NO:1. In some instances the polypeptide exhibits an interferon-alpha activity.

The invention also provides isolated or recombinant polypeptides each comprising a sequence having at least 90% sequence identity (e.g., at least about 91%, at least about 92%, at least about 93%, at least about 94%, at least about 95%, at least about 96%, at least about 97%, at least about 98%, or at least about 99% amino acid sequence identity) to any one of SEQ ID NOs:36-44, wherein the sequence comprises one or more of: Ala at position 21; Pro at position 24; Ala or Leu at position 48; Pro at position 51; Ala at position 55; Ala at position 65; Pro at position 68; Ala at position 90; Pro at position 93; Ala at position 111; Pro at position 114; Ala at position 124; Pro at position 127; and Asp at position 160, amino acid position relative to SEQ ID NO:36. In some instances the polypeptide exhibits an interferon-alpha activity.

The degree to which a sequence (polypeptide or nucleic acid) is similar to another provides an indication of similar structural and functional properties for the two sequences. Accordingly, in the context of the present invention, sequences which have a similar sequence to any given exemplar sequence are a feature of the present invention. In particular, sequences that have percent sequence identities as defined below are a feature of the invention.

A variety of methods of determining sequence relationships can be used, including manual alignment and computer assisted sequence alignment and analysis. A variety of computer programs for performing sequence alignments are available, or an alignment can be prepared manually by one of skill, as described below.

As noted above, the sequences of the polypeptides and nucleic acids employed in the subject invention need not be identical, but can be substantially identical to the corresponding sequence of a polypeptide of the invention or nucleic acid of the invention. For example, polypeptides of the invention can be subject to various changes, such as one or more amino acid insertions, deletions, and/or substitutions, either conservative or non-conservative, including where, e.g., such changes might provide for certain advantages in their use, such as, in their therapeutic or prophylactic use or administration or diagnostic application. The nucleic acids of the invention can also be subject to various changes, such as one or more substitutions of one or more nucleic acids in one or more codons such that a particular codon encodes the same or a different amino acid, resulting in either a silent variation (as defined herein) or non-silent variation, or one or more deletions of one or more nucleic acids (or codons) in the sequence. The nucleic acids can also be modified to include one or more codons that provide for optimum expression in an expression system (e.g., bacterial or mammalian), while, if desired, said one or more codons still encode the same amino acid(s). Such nucleic acid changes might provide for certain advantages in their therapeutic or prophylactic use or administration, or diagnostic application. The nucleic acids and polypeptides can be modified in a number of ways so long as they comprise a sequence substantially identical (as defined below) to a sequence in a respective nucleic acid or polypeptide of the invention.

The term "identical" or "identity," in the context of two or more nucleic acid or polypeptide sequences, refers to two or more sequences that are the same or have a specified percentage of amino acid residues or nucleotides that are the same, when compared and aligned for maximum similarity, as determined using the sequence comparison algorithm described below or by visual inspection.

The "percent sequence identity" ("% identity") of a subject sequence to a reference (i.e. query) sequence means that the subject sequence is identical (i.e., on an amino acid-by-amino acid basis for a polypeptide sequence, or a nucleotide-by-nucleotide basis for a polynucleotide sequence) by a specified percentage to the query sequence over a comparison length.

The percent sequence identity of a subject sequence to a query sequence is calculated as follows. First, the optimal alignment of the two sequences is determined using a sequence comparison algorithm with specific alignment parameters. This determination of the optimal alignment may be performed using a computer, or may be manually calculated, as described below. Then, the two optimally aligned sequences are compared over the comparison length, and the number of positions in the optimal alignment at which identical residues occur in both sequences are determined, which provides the number of matched positions. The number of matched positions is then divided by the total number of positions of the comparison length (which, unless otherwise specified, is the length of the query sequence), and then the result is multiplied by 100, to yield the percent sequence identity of the subject sequence to the query sequence.

With regard to polypeptide sequences, typically one sequence is regarded as a "query sequence" (for example, a polypeptide sequence of the invention) to which one or more other sequences, i.e., "subject sequence(s)" (for example, sequences present in a sequence database) are compared. The sequence comparison algorithm uses the designated alignment parameters to determine the optimal alignment between the query sequence and the subject sequence(s). When comparing a query sequence against a sequence database, such as, e.g., GENBANK® (Genetic Sequence Data Bank; U.S. Department of Health and Human Services) or GENESEQ® (Thomson Derwent; also available as DGENE® on STN), usually only the query sequence and the alignment parameters are input into the computer; optimal alignments between the input query sequence and each subject sequence present in the database are returned, generally for up to a desired number of subject sequences.

Two polypeptide sequences are "optimally aligned" when they are aligned using defined parameters, i.e., a defined amino acid substitution matrix, gap existence penalty (also termed gap open penalty), and gap extension penalty, so as to arrive at the highest similarity score possible for that pair of sequences. The BLOSUM62 matrix (Henikoff and Henikoff (1992) Proc. Natl. Acad. Sci. USA 89(22):10915-10919) is often used as a default scoring substitution matrix in polypeptide sequence alignment algorithms (such as BLASTP, described below). The gap existence penalty is imposed for the introduction of a single amino acid gap in one of the aligned sequences, and the gap extension penalty is imposed for each residue position in the gap. Unless otherwise stated, alignment parameters employed herein are: BLOSUM62 scoring matrix, gap existence penalty=11, and gap extension penalty=1. The alignment score is defined by the amino acid positions of each sequence at which the alignment begins and ends (e.g. the alignment window), and optionally by the insertion of a gap or multiple gaps into one or both sequences, so as to arrive at the highest possible similarity score.

While optimal alignment between two or more sequences can be determined manually (as described below), the process is facilitated by the use of a computer-implemented alignment algorithm such as BLAST® (National Library of Medicine), e.g., BLASTP for polypeptide sequences and BLASTN for nucleic acid sequences, described in Altschul et al. (1997) Nucleic Acids Res. 25:3389-3402, and made available to the public through various sources, such as the National Center for Biotechnology Information (NCBI) Website. When using a computerized BLAST interface, if the option exists to use a "low complexity filter", this option should be turned off (i.e., no filter).

Figure 5:
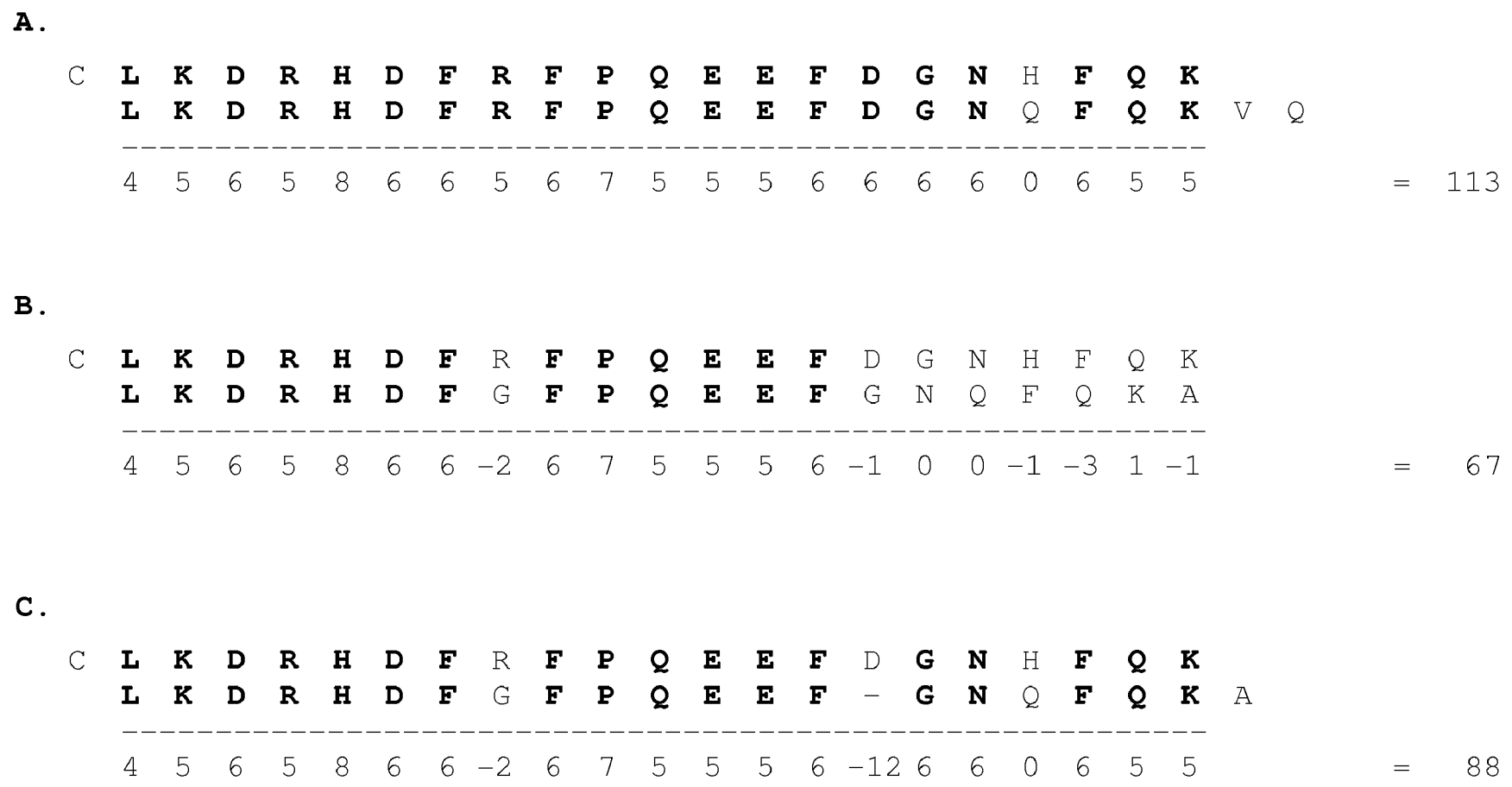

The optimal alignment between two polypeptide sequences can also be determined by a manual calculation of the BLASTP algorithm (i.e., without aid of a computer) using the same alignment parameters specified above (matrix=BLOSUM62, gap open penalty=11, and gap extension penalty=1). To begin, the two sequences are initially aligned by visual inspection. An initial alignment score is then calculated as follows: for each individual position of the alignment (i.e., for each pair of aligned residues), a numerical value is assigned according to the BLOSUM62 matrix (FIG. 4). The sum of the values assigned to each pair of residues in the alignment is the initial alignment score. If the two sequences being aligned are highly similar, often this initial alignment provides the highest possible alignment score. The alignment with the highest possible alignment score is the optimal alignment based on the alignment parameters employed. FIG. 5A shows an example of the calculation of an alignment score for two sequences, a "query" sequence, identified herein as residues 29-50 of SEQ ID NO:1 (upper), and a "subject" sequence, identified herein as residues 30-52 of SEQ ID NO:8 (lower). The sequences were aligned by visual inspection, and the numerical value assigned by the BLOSUM62 matrix for each aligned pair of amino acids is shown beneath each position in the alignment (to aid in visualization, each identical pair of amino acids in the alignment is shown in boldface). In this example, this initial alignment provided the highest possible alignment score (the sum of the values shown beneath each aligned position); any other alignment of these two sequences, with or without gaps, would result in a lower alignment score.

In some instances, a higher alignment score might be obtained by introducing one or more gaps into the alignment. Whenever a gap is introduced into an alignment, a gap open penalty is assigned, and in addition a gap extension penalty is assessed for each residue position within that gap. Therefore, using the alignment parameters described above (including gap open penalty=11 and gap extension penalty=1), a gap of one residue in the alignment would correspond to a value of −(11+(1×1))=−12 assigned to the gap; a gap of three residues would correspond to a value of −(11+(3×1))=−14 assigned to the gap, and so on. This calculation is repeated for each new gap introduced into the alignment. FIGS. 5B and 5C show an example which demonstrates how introduction of a gap into an alignment can result in a higher alignment score, despite the gap penalty. FIG. 5B shows an initial alignment of residues 29-50 of SEQ ID NO:1 (upper, query) and residues 30-50 of SEQ ID NO:46 (lower, subject) made by visual inspection, which results in an initial alignment score of 67. FIG. 5C shows the effect of the introduction of a one-residue gap in SEQ ID NO:46 on the alignment score; despite the gap penalty of −12, the overall alignment score of the two sequences increases to 88. In this example, the alignment shown in FIG. 5C provides the highest possible alignment score, and is thus the optimal alignment of these two sequences; any other alignment of these two sequences (with or without gaps) would result in a lower alignment score.

It is to be understood that the examples of sequence alignment calculations described above, which use relatively short sequences, are provided for illustrative purposes only; in practice, the alignment parameters employed (BLOSUM62 matrix, gap open penalty=11, and gap extension penalty=1) are generally intended for polypeptide sequences 85 amino acids in length or longer. The NCBI website provides the following alignment parameters for sequences of other lengths (which are suitable for computer-aided as well as manual alignment calculation, using the same procedure as described above). For sequences of 50-85 amino acids in length, optimal parameters are BLOSUM80 matrix (Henikoff and Henikoff, supra), gap open penalty=10, and gap extension penalty=1. For sequences of 35-50 amino acids in length, optimal parameters are PAM70 matrix (Dayhoff, M. O., Schwartz, R. M. & Orcutt, B. C. (1978) "A model of evolutionary change in proteins." In Atlas of Protein Sequence and Structure, vol. 5, suppl. 3, M. O. Dayhoff (ed.), pp. 345-352, Natl. Biomed. Res. Found., Washington, D.C.), gap open penalty=10, and gap extension penalty=1. For sequences of less than 35 amino acids in length, optimal parameters are PAM30 matrix (Dayhoff, M. O., supra), gap open penalty=9, and gap extension penalty=1.

Once the sequences are optimally aligned, the percent identity of the subject sequence relative to the query sequence is calculated by counting the number of positions in the optimal alignment which contain identical residue pairs, divide that by the number of residues in the comparison length (which, unless otherwise specified, is the number of residues in the query sequence), and multiplying the resulting number by 100. Referring back to the examples shown in FIG. 5, in each example the sequence designated as the query sequence is 22 amino acids in length. In the alignment of FIG. 5A, 20 pairs of aligned amino acid residues (shown in boldface) are identical in the optimal alignment of the query sequence (upper) with the subject sequence (lower). Thus, this particular subject sequence has (20/22)×100=91.1% identity to the query sequence; in other words, the subject sequence in the alignment of FIG. 5A has at least 91% amino acid sequence identity to the query sequence. In the alignment shown in FIG. 5C, 18 pairs of amino acid residues (shown in boldface) in the optimal alignment are identical; thus this particular subject sequence has (18/22)×100=81.8% identity to the query sequence; in other words, the subject sequence in the alignment of FIG. 5C has at least 81% amino acid sequence identity to the query sequence.

As applied to polypeptides, the term "substantial identity" (or "substantially identical") typically means that when two amino acid sequences (i.e. a query sequence and a subject sequence) are optimally aligned using the BLASTP algorithm (manually or via computer) using appropriate parameters described above, the subject sequence has at least about 60%, 70%, 75%, 80%, 85%, 90%, 91%, 92%, 93%, 94%, 95%, 96%, 97%, 98%, 99%, or more percent amino acid sequence identity to the query sequence. In some instances, the substantial identity exists over a comparison length of at least about 100 amino acid residues, such as, at least about 110, 120, 125, 130, 135, 140, 145, 150, 155, 156, 157, 158, 159, 160, 161, 162, 163, 164, 165, or 166 amino acid residues.

Similarly, as applied in the context of two nucleic acid sequences, the term substantial identity (or substantially identical) means that when two nucleic acid sequences (i.e. a query and a subject sequence) are optimally aligned using the BLASTN algorithm (manually or via computer) using appropriate parameters described below, the subject sequence has at least about 60%, 70%, 75%, 80%, 85%, 90%, 91%, 92%, 93%, 94%, 95%, 96%, 97%, 98%, 99%, or more percent nucleic acid sequence identity to the query sequence. Parameters used for nucleic acid sequence alignments are: match reward 1, mismatch penalty −3, gap existence penalty 5, gap extension penalty 2 (substitution matrices are not used in the BLASTN algorithm). In some instances, the substantial identity exists over a comparison length of at least about 300 nucleotide residues, such as at least about 330, 360, 375, 390, 405, 420, 435, 450, 465, 480, 483, 486, 489, 492, 495, or 498 nucleotides.

Additional Aspects

Any polypeptide of the invention may be present as part of a larger polypeptide sequence, e.g. a fusion protein, such as occurs upon the addition of one or more domains or subsequences for stabilization or detection or purification of the polypeptide. A polypeptide purification subsequence may include, e.g., an epitope tag, a FLAG tag, a polyhistidine sequence, a GST fusion, or any other detection/purification subsequence or "tag" known in the art. These additional domains or subsequences either have little or no effect on the activity of the polypeptide of the invention, or can be removed by post synthesis processing steps such as by treatment with a protease, inclusion of an intein, or the like.

The invention includes fusion proteins comprising a polypeptide of the invention, e.g., as described herein, fused to an Ig molecule, e.g., a human IgG Fc ("fragment crystallizable," or fragment complement binding) hinge, CH2 domain and CH3 domain, and nucleotide sequences encoding such fusion protein. Fc is the portion of the antibody responsible for binding to antibody receptors on cells and the C1q component of complement. These fusion proteins and their encoding nucleic acids are useful as prophylactic and/or therapeutic drugs or as diagnostic tools (see also, e.g., Chalita-Eid, P. et al. (1998) J. Immunol 160:3419-3426; Sturmhoefel, K. et al. (1999) Cancer Res 59:4964-4972). The invention also includes fusion proteins comprising a polypeptide of the invention, fused to an albumin molecule, such as human serum albumin (HSA), as described, for example, in U.S. Pat. No. 5,876,969, and nucleotide sequences encoding the fusion protein. The Ig and albumin fusion proteins may exhibit increased polypeptide serum half-life and/or functional in vivo half-life, reduced polypeptide antigenicity, increased polypeptide storage stability, or increasing bioavailability, e.g. increased $AUC_{sc}$, and are thus may be useful as prophylactic and/or therapeutic drugs.

Any polypeptide of the invention may also comprise one or more modified amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. The presence of modified amino acids may be advantageous in, for example, (a) increasing polypeptide serum half-life and/or functional in vivo half-life, (b) reducing polypeptide antigenicity, (c) increasing polypeptide storage stability, or (d) increasing bioavailability, e.g. increasing the $AUC_{sc}$. Amino acid(s) are modified, for example, co-translationally or post-translationally during recombinant production (e.g., N-linked glycosylation at N-X-S/T motifs during expression in mammalian cells) or modified by synthetic means. This aspect is described in more detail in the section herein entitled "INTERFERON-ALPHA CONJUGATES".

The invention also provides a composition comprising at least one polypeptide of the invention, and an excipient or carrier. The composition may be a composition comprising a pharmaceutically acceptable excipient or carrier. Exemplary compositions and excipients and carriers are described below.

Making Polypeptides

Recombinant methods for producing and isolating polypeptides of the invention are described herein. In addition to recombinant production, the polypeptides may be produced by direct peptide synthesis using solid-phase techniques (see, e.g., Stewart et al. (1969) Solid-Phase Peptide Synthesis, WH Freeman Co, San Francisco; Merrifield J. (1963) J Am Chem Soc 85:2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide full-length polypeptides or fragments thereof. Alternatively, such sequences may be ordered from any number of companies which specialize in production of polypeptides. Most commonly, polypeptides of the invention may be produced by expressing coding nucleic acids and recovering polypeptides, e.g., as described below.

Methods for producing the polypeptides of the invention are also included. One such method comprises introducing into a population of cells any nucleic acid of the invention described herein, which is operatively linked to a regulatory sequence effective to produce the encoded polypeptide, culturing the cells in a culture medium to express the polypeptide, and isolating the polypeptide from the cells or from the culture medium. An amount of nucleic acid sufficient to facilitate uptake by the cells (transfection) and/or expression of the polypeptide is utilized. The nucleic acid is introduced into such cells by any delivery method described herein, including, e.g., injection, gene gun, passive uptake, etc. The nucleic acid may be part of a vector, such as a recombinant expression vector, including a DNA plasmid vector, or any vector described herein. The nucleic acid or vector comprising a nucleic acid of the invention may be prepared and formulated as described herein, above. Such a nucleic acid or expression vector may be introduced into a population of cells of a mammal in vivo, or selected cells of the mammal (e.g., tumor cells) may be removed from the mammal and the nucleic acid expression vector introduced ex vivo into the population of such cells in an amount sufficient such that uptake and expression of the encoded polypeptide results. Or, a nucleic acid or vector comprising a nucleic acid of the invention is produced using cultured cells in vitro. In one aspect, the method of producing a polypeptide of the invention comprises introducing into a population of cells a recombinant expression vector comprising any nucleic acid of the invention described herein in an amount and formula such that uptake of the vector and expression of the encoded polypeptide will result; administering the expression vector into a mammal by any introduction/delivery format described herein; and isolating the polypeptide from the mammal or from a byproduct of the mammal.

Antibodies

In another aspect of the invention, a polypeptide of the invention (or an antigenic fragment thereof) is used to produce antibodies which have, e.g., diagnostic, therapeutic, or prophylactic uses, e.g., related to the activity, distribution, and expression of polypeptides and fragments thereof. Antibodies to polypeptides of the invention may be generated by methods well known in the art. Such antibodies may include, but are not limited to, polyclonal, monoclonal, chimeric, humanized, single chain, Fab fragments and fragments produced by a Fab expression library. Antibodies, e.g., those that block receptor binding, are especially preferred for therapeutic and/or prophylactic use.

Polypeptides for antibody induction do not require biological activity; however, the polypeptides or peptides should be antigenic. Peptides used to induce specific antibodies may have an amino acid sequence consisting of at least about 10 amino acids, preferably at least about 15 or 20 amino acids or at least about 25 or 30 amino acids. Short stretches of a polypeptide may be fused with another protein, such as keyhole limpet hemocyanin, and antibody produced against the chimeric molecule.

Methods of producing polyclonal and monoclonal antibodies are known to those of skill in the art, and many antibodies are available. See, e.g., Current Protocols in Immunology, John Colligan et al., eds., Vols. I-IV (John Wiley & Sons, Inc., NY, 1991 and 2001 Supplement); and Harlow and Lane (1989) Antibodies: A Laboratory Manual Cold Spring Harbor Press, NY; Stites et al. (eds.) Basic and Clinical Immunology (4th ed.) Lange Medical Publications, Los Altos, Calif., and references cited therein; and Goding (1986) Monoclonal Antibodies: Principles and Practice (2d ed.) Academic Press, New York, N.Y.; and Kohler and Milstein (1975) Nature 256:495-497. Other suitable techniques for antibody preparation include selection of libraries of recombinant antibodies in phage or similar vectors. See, Huse et al. (1989) Science 246:1275-1281; and Ward et al. (1989) Nature 341: 544-546. Specific monoclonal and polyclonal antibodies and antisera will usually bind with a $K_D$ of at least about 0.1 μM, preferably at least about 0.01 μM or better, and most typically and preferably, 0.001 μM or better.

Detailed methods for preparation of chimeric (humanized) antibodies can be found in U.S. Pat. No. 5,482,856. Additional details on humanization and other antibody production and engineering techniques can be found in Borrebaeck (ed.) (1995) Antibody Engineering, $2^{nd}$ Edition Freeman and Company, NY (Borrebaeck); McCafferty et al. (1996) Antibody Engineering, A Practical Approach IRL at Oxford Press, Oxford, England (McCafferty), and Paul (1995) Antibody Engineering Protocols Humana Press, Towata, N.J. (Paul).

In one aspect, this invention provides for fully humanized antibodies against the polypeptides of the invention or fragments thereof. Humanized antibodies are especially desirable in applications where the antibodies are used as therapeutics and/or prophylactics in vivo in human patients. Human antibodies consist of characteristically human immunoglobulin sequences. The human antibodies of this invention can be produced in using a wide variety of methods (see, e.g., Larrick et al., U.S. Pat. No. 5,001,065, and Borrebaeck McCafferty and Paul, supra, for a review). In one aspect, the human antibodies of the present invention are produced initially in trioma cells. Genes encoding the antibodies are then cloned and expressed in other cells, such as nonhuman mammalian cells. The general approach for producing human antibodies by trioma technology is described by Ostberg et al. (1983), Hybridoma 2:361-367, Ostberg, U.S. Pat. No. 4,634,664, and Engelman et al., U.S. Pat. No. 4,634,666. The antibody-producing cell lines obtained by this method are called triomas because they are descended from three cells—two human and one mouse. Triomas have been found to produce antibody more stably than ordinary hybridomas made from human cells.

Other uses contemplated for polypeptides of the invention are provided throughout the specification.

Interferon-Alpha Conjugates

In another aspect, the invention relates to a conjugate comprising a polypeptide exhibiting an interferon-alpha activity which comprises an amino acid sequence of any one of SEQ ID NOs:2-35 and SEQ ID NOs:37-44, and at least one non-polypeptide moiety attached to the polypeptide, such as e.g., 1-6, 1-5, 1-4, 1-3, e.g. 1 or 2 non-polypeptide moieties attached to the polypeptide. It will be understood that the conjugate also exhibits an interferon-alpha activity (such as, antiviral activity, $T_H1$ differentiation activity, and/or antiproliferative activity).

In another aspect the conjugate comprises a polypeptide exhibiting an interferon-alpha activity which comprises an amino acid sequence which differs in 1 to 16 amino acid positions from SEQ ID NO:1 and comprises one or more substitutions relative to SEQ ID NO:1 selected from the group consisting of F48A/L; V51P; F55A; F65A; F68P; L111A; and V114P; and at least one non-polypeptide moiety attached to the polypeptide, such as e.g., 1-6, 1-5, 1-4, 1-3, e.g. 1 or 2 non-polypeptide moieties attached to the polypeptide. In some instances, the amino acid sequence further comprises one or more substitutions which introduces an attachment group for the non-polypeptide moiety (e.g., by substitution of an amino acid residue for a different residue which comprises an attachment group for the non-polypeptide moiety, or by insertion of an additional amino acid residue which comprises an attachment group for the non-polypeptide moiety). It will be understood that the conjugate also exhibits an interferon-alpha activity (such as, antiviral activity, $T_H1$ differentiation activity, and/or antiproliferative activity).

The invention also provides conjugates which each comprise a polypeptide comprising a sequence which (a) differs in 1 to 16 amino acid positions from SEQ ID NO:1 and (b) comprises the substitution F48A/L relative to SEQ ID NO:1, and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. Some such conjugates comprise the substitution F48A relative to SEQ ID NO:1. In some instances, the polypeptide part of the conjugate further comprises one or more substitution(s) relative to SEQ ID NO:1 selected from the group consisting of H47Q; V51A/P; Q52P/E; A53T; F55A/S; L56V; F65A; F57L; Y58H; M61I; F68P; L111A; N113K; V114E/P; and E160D. Some such conjugates exhibit an interferon-alpha activity (e.g., antiviral activity, $T_H1$ differentiation activity, and/or antiproliferative activity). Some such conjugates further comprise one or more additional amino acid(s), such as a methionine added to the N-terminus of the polypeptide.

The invention also provides conjugates which each comprise a polypeptide comprising a sequence which (a) differs in 1 to 16 amino acid positions from SEQ ID NO:1 and (b) comprises the substitution F55A relative to SEQ ID NO:1, and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide part of the conjugate further comprises one or more substitution(s) relative to SEQ ID NO:1 selected from the group consisting of H47Q; F48A/L; V51A/P; Q52P/E; A53T; L56V; F65A; F57L; Y58H; M61I; F68P; L111A; N113K; V114E/P; and E160D. Some such conjugates exhibit an interferon-alpha activity (e.g., antiviral activity, $T_H1$ differentiation activity, and/or antiproliferative activity). Some such conjugates further comprise one or more additional amino acid(s), such as a methionine added to the N-terminus of the polypeptide.

The invention also provides conjugates which each comprise a polypeptide comprising a sequence which (a) differs in 1 to 16 amino acid positions from SEQ ID NO:1 and (b) comprises the substitution F65A relative to SEQ ID NO:1, and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide part of the conjugate further comprises one or more substitutions relative to SEQ ID NO:1 selected from the group consisting of H47Q; F48A/L; V51A/P; Q52P/E; A53T; F55A/S; L56V; F57L; Y58H; M61I; F68P; L111A; N113K; V114E/P; and E160D. Some such conjugates exhibit an interferon-alpha activity (e.g., antiviral activity, $T_H1$ differentiation activity, and/or antiproliferative activity). Some such conjugates further comprise one or more additional amino acid(s), such as a methionine added to the N-terminus of the polypeptide.

The invention also provides conjugates which each comprise a polypeptide comprising a sequence which (a) differs in 1 to 16 amino acid positions from SEQ ID NO:1 and (b) comprises the substitution L111A relative to SEQ ID NO:1, and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide sequence which differs from SEQ ID NO:1 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide part of the conjugate further comprises one or more substitutions relative to SEQ ID NO:1 selected from the group consisting of H47Q; F48A/L; V51A/P; Q52P/E; A53T; F55A/S; L56V; F65A; F57L; Y58H; M61I; F68P; N113K; V114E/P; and E160D. Some such conjugates exhibit an interferon-alpha activity (e.g., antiviral activity, $T_H1$ differentiation activity, and/or antiproliferative activity). Some such conjugates further comprise one or more additional amino acid(s), such as a methionine added to the N-terminus of the polypeptide.

The invention also provides conjugates which each comprise a polypeptide comprising a sequence which (a) differs in 0 to 16 amino acid positions from SEQ ID NO:13 and (b) comprises one or more of: Ala or Leu at position 48; Pro at position 51; Ala at position 55; Ala at position 65; Pro at position 68; Ala at position 111; and Pro at position 114 (position numbering relative to SEQ ID NO:13), and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide comprising a sequence which differs from SEQ ID NO:13 in 0, 1, 2, 3, 4, 5, 6, 7, 8, 9, 10, 11, 12, 13, 14, 15, or 16 amino acid positions, e.g., in 0-15 amino acid positions, in 0-14 amino acid positions, in 0-13 amino acid positions, in 0-12 amino acid positions, in 0-11 amino acid positions, in 0-10 amino acid positions, in 0-9 amino acid positions, in 0-8 amino acid positions, in 0-7 amino acid positions, in 0-6 amino acid positions, in 0-5 amino acid positions, in 0-4 amino acid positions, in 0-3 amino acid positions, in 0-2 amino acid positions, or in 0-1 amino acid positions. Some such conjugates comprise a polypeptide sequence which comprises an Ala or a Leu at position 48. Some such conjugates comprise a polypeptide sequence which comprises an Ala at position 48. In some instances, the polypeptide part of the conjugate further comprises one or more substitution(s) relative to SEQ ID NO:13 selected from the group consisting of H47Q; V51A; Q52P/E; A53T; F55S; L56V; F57L; Y58H; M61I; N113K; V114E; and E160D. Some such conjugates exhibit an interferon-alpha activity (e.g., antiviral activity, $T_H1$ differentiation activity, and/or antiproliferative activity). Some such conjugates comprise a polypeptide sequence further comprising one or more additional amino acid(s), such as a methionine added to the N-terminus.

In another aspect the conjugate comprises a polypeptide exhibiting an interferon-alpha activity which comprises an amino acid sequence which differs in 1 to 16 amino acid positions from SEQ ID NO:36 and comprises one or more substitutions relative to SEQ ID NO:36 selected from the group consisting of M21A; I24P; F48A/L; T51P; S55A; F65A; F68P; F90A; M93P; L111A; V114P; F124A; I127P; and E160D; and at least one non-polypeptide moiety attached to the polypeptide, such as e.g., 1-6, 1-5, 1-4, 1-3, e.g. 1 or 2 non-polypeptide moieties attached to the polypeptide. In some instances, the amino acid sequence further comprises one or more substitutions which introduces an attachment group for the non-polypeptide moiety (e.g., by substitution of an amino acid residue for a different residue which comprises an attachment group for the non-polypeptide moiety, or by insertion of an additional amino acid residue which comprises an attachment group for the non-polypeptide moiety).

The invention also provides conjugates which each comprise a polypeptide comprising a sequence which (a) differs in 1 to 16 amino acid positions from SEQ ID NO:36 and (b) comprises the substitution F48A/L relative to SEQ ID NO:36, and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide sequence which differs from SEQ ID NO:36 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. Some such conjugates comprise the substitution F48A relative to SEQ ID NO:36. In some instances, the polypeptide part of the conjugate further comprises one or more substitution(s) relative to SEQ ID NO:36 selected from the group consisting of M21A; I24P; P26L; H47Q; T51V/P; S55P/F/A; V56L; H58Y; L60M; F65A; F68P; F90Y/A; M93L/P; N95D; L111A; N113K; V114E/P; F124A; R125Q; I127P; T132K; L154F; and E160D. Some such conjugates exhibit an interferon-alpha activity (e.g., antiviral activity, $T_H1$ differentiation activity, and/or antiproliferative activity). Some such conjugates further comprise one or more additional amino acid(s), such as a methionine added to the N-terminus of the polypeptide.

The invention also provides conjugates which each comprise a polypeptide comprising a sequence which (a) differs in 1 to 16 amino acid positions from SEQ ID NO:36 and (b) comprises the substitution F90A relative to SEQ ID NO:36, and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide sequence which differs from SEQ ID NO:36 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide part of the conjugate further comprises one or more substitution(s) relative to SEQ ID NO:36 selected from the group consisting of M21A; I24P; P26L; H47Q; F48A/L; T51V/P; S55P/F/A; V56L; H58Y; L60M; F65A; F68P; M93L/P; N95D; L111A; N113K; V114E/P; F124A; R125Q; I127P; T132K; L154F; and E160D. Some such conjugates exhibit an interferon-alpha activity (e.g., antiviral activity, $T_H1$ differentiation activity, and/or antiproliferative activity). Some such conjugates further comprise one or more additional amino acid(s), such as a methionine added to the N-terminus of the polypeptide.

The invention also provides conjugates which each comprise a polypeptide comprising a sequence which (a) differs in 1 to 16 amino acid positions from SEQ ID NO:36 and (b) comprises the substitution E160D relative to SEQ ID NO:36, and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide sequence which differs from SEQ ID NO:36 in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions. In some instances, the polypeptide part of the conjugate further comprises one or more substitution(s) relative to SEQ ID NO:36 selected from the group consisting of M21A; I24P; P26L; H47Q; F48A/L; T51V/P; S55P/F/A; V56L; H58Y; L60M; F65A; F68P; F90Y/A; M93L/P; N95D; L111A; N113K; V114E/P; F124A; R125Q; I127P; T132K; and L154F. Some such conjugates exhibit an interferon-alpha activity (e.g., antiviral activity, $T_H1$ differentiation activity, and/or antiproliferative activity). Some such conjugates further comprise one or more additional amino acid(s), such as a methionine added to the N-terminus of the polypeptide.

The invention also provides conjugates which each comprise a polypeptide comprising a sequence which (a) differs in 0 to 16 amino acid positions from SEQ ID NO:38 and (b) comprises one or more of: Ala at position 21; Pro at position 24; Ala or Leu at position 48; Pro at position 51; Ala at position 55; Ala at position 65; Pro at position 68; Ala at position 90; Pro at position 93; Ala at position 111; Pro at position 114; Ala at position 124; Pro at position 127; and Glu at position 160 (position numbering relative to SEQ ID NO:38), and at least one non-polypeptide moiety attached to the polypeptide, such as e.g., 1-6, 1-5, 1-4, 1-3, e.g. 1 or 2 non-polypeptide moieties attached to the polypeptide. Some such conjugates comprise a polypeptide comprising a sequence which differs from SEQ ID NO:38 in 0, 1, 2, 3, 4, 5, 6, 7, 8, 9, 10, 11, 12, 13, 14, 15, or 16 amino acid positions, e.g., in 0-15 amino acid positions, in 0-14 amino acid positions, in 0-13 amino acid positions, in 0-12 amino acid positions, in 0-11 amino acid positions, in 0-10 amino acid positions, in 0-9 amino acid positions, in 0-8 amino acid positions, in 0-7 amino acid positions, in 0-6 amino acid positions, in 0-5 amino acid positions, in 0-4 amino acid positions, in 0-3 amino acid positions, in 0-2 amino acid positions, or in 0-1 amino acid positions. Some such conjugates comprise a polypeptide sequence which comprises an Ala or a Leu at position 48. Some such conjugates comprise a polypeptide sequence which comprises an Ala at position 48. In some instances, the polypeptide part of the conjugate further comprises one or more substitution(s) relative to SEQ ID NO:38 selected from the group consisting of P26L; H47Q; V51T; F55P/S; L56V; Y58H; L60M; F90Y; M93L; N95D; N113K; V114E; R125Q; T132K; and F154L. Some such conjugates exhibit an interferon-alpha activity (e.g., antiviral activity, $T_H1$ differentiation activity, and/or antiproliferative activity). Some such conjugates comprise a polypeptide sequence further comprising one or more additional amino acid(s), such as a methionine added to the N-terminus.

The term "conjugate" (or interchangeably "polypeptide conjugate" or "conjugated polypeptide") is intended to indicate a heterogeneous (in the sense of composite) molecule formed by the covalent attachment of one or more polypeptides of the invention to one or more non-polypeptide moieties. The term "covalent attachment" means that the polypeptide and the non-polypeptide moiety are either directly covalently joined to one another, or else are indirectly covalently joined to one another through an intervening moiety or moieties, such as a bridge, spacer, or linkage moiety or moieties. Preferably, a conjugated polypeptide is soluble at relevant concentrations and conditions, i.e. soluble in physiological fluids such as blood. Examples of conjugated polypeptides of the invention include glycosylated and/or PEGylated polypeptides. The term "non-conjugated polypeptide" may be used to refer to the polypeptide part of the conjugated polypeptide.

The term "non-polypeptide moiety" is intended to mean a molecule that is capable of conjugating to an attachment group of the polypeptide. Preferred examples of non-polypeptide moieties include polymer molecules, sugar moieties, lipophilic compounds, or organic derivatizing agents, in particular polymer molecules or sugar moieties. It will be understood that the non-polypeptide moiety is linked to the polypeptide through an attachment group of the polypeptide. Except where the number of non-polypeptide moieties, such as polymer molecule(s), attached to the polypeptide is expressly indicated, every reference to "a non-polypeptide moiety" attached to the polypeptide or otherwise used in the present invention shall be a reference to one or more non-polypeptide moieties attached to the polypeptide.

The term "polymer molecule" is defined as a molecule formed by covalent linkage of two or more monomers, wherein none of the monomers is an amino acid residue. The term "polymer" may be used interchangeably with the term "polymer molecule".

The term "sugar moiety" is intended to indicate a carbohydrate molecule attached by in vivo or in vitro glycosylation, such as N- or O-glycosylation.

An "N-glycosylation site" has the sequence N-X-S/T/C, wherein X is any amino acid residue except proline, N is asparagine and S/T/C is either serine, threonine or cysteine, preferably serine or threonine, and most preferably threonine.

An "O-glycosylation site" comprises the OH-group of a serine or threonine residue.

The term "attachment group" is intended to indicate an amino acid residue group capable of coupling to the relevant non-polypeptide moiety such as a polymer molecule or a sugar moiety. Non-limiting examples of useful attachment groups and some corresponding non-polypeptide moieties are provided in Table 4 below.

TABLE 4

Useful attachment groups and examples of corresponding non-polypeptide moieties

| Attachment group | Amino acid | Examples of non-polypeptide moieties | Examples of conjugation method/activated PEG | Reference |
| --- | --- | --- | --- | --- |
| —NH₂ | N-terminus, Lys | Polymer, e.g. PEG | mPEG-SPA mPEG2-NHS mPEG2-butryALD | Nektar Inc. 2003 Catalog |
| —COOH | C-terminus, Asp, Glu | Polymer, e.g. PEG Sugar moiety | mPEG-Hz In vitro coupling | Nektar Inc. 2003 Catalog |
| —SH | Cys | Polymer, e.g. PEG, Sugar moiety | mPEG-VS mPEG2-MAL In vitro coupling | Nektar Inc. 2003 Catalog; Delgado et al, Critical Reviews in Therapeutic Drug Carrier Systems 9(3, 4): 249-304 (1992) |

TABLE 4-continued

Useful attachment groups and examples of corresponding non-polypeptide moieties

| Attachment group | Amino acid | Examples of non-polypeptide moieties | Examples of conjugation method/activated PEG | Reference |
|---|---|---|---|---|
| —OH | Ser, Thr, OH— | Sugar moiety | In vivo O-linked glycosylation | |
| —CONH$_2$ | Asn as part of an N-glycosylation site | Sugar moiety | In vivo N-glycosylation | |
| Aromatic residue | Phe, Tyr, Trp | Sugar moiety | In vitro coupling | |
| —CONH$_2$ | Gln | Sugar moiety | In vitro coupling | Yan and Wold, Biochemistry, 1984, Jul 31; 23(16): 3759-65 |
| Aldehyde Ketone | Oxidized carbohydrate | Polymer, e.g. PEG, PEG-hydrazide | PEGylation | Andresz et al., 1978, Makromol. Chem. 179: 301; WO 92/16555, WO 00/23114 |
| Guanidino | Arg | Sugar moiety | In vitro coupling | Lundblad and Noyes, Chemical Reagents for Protein Modification, CRC Press Inc. Boca Raton, Fl |
| Imidazole ring | His | Sugar moiety | In vitro coupling | As for guanidine |

For in vivo N-glycosylation, the term "attachment group" is used in an unconventional way to indicate the amino acid residues constituting an N-glycosylation site (with the sequence N-X-S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present. Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the polypeptide of the invention is to be understood as one, two or all of the amino acid residues constituting an N-glycosylation site is/are to be altered in such a manner that either a functional N-glycosylation site is introduced into the amino acid sequence, removed from said sequence or a functional N-glycosylation site is retained in the amino acid sequence (e.g. by substituting a serine residue, which already constitutes part of an N-glycosylation site, with a threonine residue and vice versa).

The term "introduce" (i.e., an "introduced" amino acid residue, "introduction" of an amino acid residue) is primarily intended to mean substitution of an existing amino acid residue for another amino acid residue, but may also mean insertion of an additional amino acid residue.

The term "remove" (i.e., a "removed" amino acid residue, "removal" of an amino acid residue) is primarily intended to mean substitution of the amino acid residue to be removed for another amino acid residue, but may also mean deletion (without substitution) of the amino acid residue to be removed.

The term "amino acid residue comprising an attachment group for the non-polypeptide moiety" is intended to indicate that the amino acid residue is one to which the non-polypeptide moiety binds (in the case of an introduced amino acid residue) or would have bound (in the case of a removed amino acid residue).

The term "functional in vivo half-life" is used in its normal meaning, i.e. the time at which 50% of the biological activity of the polypeptide is still present in the body/target organ, or the time at which the activity of the polypeptide is 50% of the initial value. The functional in vivo half-life may be determined in an experimental animal, such as rat, mice, rabbit, dog or monkey. Preferably, the functional in vivo half-life is determined in a non-human primate, such as a monkey. Furthermore, the functional in vivo half-life may be determined for a sample that has been administered intravenously or subcutaneously.

As an alternative to determining functional in vivo half-life, "serum half-life" may be determined, i.e. the time at which 50% of the polypeptide circulates in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life". The serum half-life may be determined as described above in connection with determination of functional in vivo half-life.

The term "serum" is used in its normal meaning, i.e. as blood plasma without fibrinogen and other clotting factors.

The term "increased" as used about the functional in vivo half-life or serum half-life is used to indicate that the relevant half-life of the conjugate of the invention is statistically significantly increased relative to that of a reference molecule, such as a wild-type interferon-alpha, e.g., a human interferon-alpha, such as one of SEQ ID NO:45-SEQ ID NO:56 (or other huIFN-alpha sequences as described herein and/or in Allen G. and Diaz M. O. (1996), supra), or the corresponding non-conjugated polypeptide. Thus, interesting conjugates of the invention include those which have an increased functional in vivo half-life or an increased serum half-life as compared to a reference molecule mentioned above.

The term "$AUC_{sc}$" or "Area Under the Curve when administered subcutaneously" is used in its normal meaning, i.e. as the area under the interferon-alpha-activity-in-serum vs. time curve, where the conjugated molecule has been administered subcutaneously to an experimental animal. Once the experimental interferon-alpha activity time points have been determined, the $AUC_{sc}$ may conveniently be calculated by a computer program, such as GraphPad Prism 3.01.

The term "increased" as used about the $AUC_{sc}$ is used to indicate that the Area Under the Curve for a conjugate of the invention, when administered subcutaneously, is statistically significantly increased relative to that of a reference molecule, such as wild-type interferon-alpha, e.g., a human interferon-alpha, such as one of SEQ ID NO:45-SEQ ID NO:56 (or other huIFN-alpha sequences as described herein and/or in Allen G. and Diaz M. O. (1996), supra), or the corresponding non-conjugated polypeptide, when determined under comparable conditions. Evidently, the same amount of interferon-alpha activity should be administered for the conjugate of the invention and the reference molecule. Consequently, in order to make direct comparisons between different interferon-alpha molecules, the $AUC_{sc}$ values should typically be normalized, i.e. be expressed as $AUC_{sc}$/dose administered.

The term "$T_{max,sc}$" is used about the time point in the interferon-alpha-activity-in-serum vs. time curve where the highest interferon-alpha activity in serum is observed.

It will be understood that while the examples and modifications to the parent polypeptide are generally provided herein in regards to the sequence SEQ ID NO:1, the disclosed modifications may also be made in equivalent amino acid positions of any of the other polypeptides of the invention (including SEQ ID NOs:2-35 and 37-44 and variants thereof) described above.

By removing and/or introducing amino acid residues comprising an attachment group for the non-polypeptide moiety it is possible to specifically adapt the polypeptide so as to make the molecule more susceptible to conjugation to the non-polypeptide moiety of choice, to optimize the conjugation pattern (e.g. to ensure an optimal distribution of non-polypeptide moieties on the surface of the interferon-alpha molecule and thereby, e.g., effectively shield epitopes and other surface parts of the polypeptide without significantly impairing the function thereof). For instance, by introduction of attachment groups, the interferon-alpha polypeptide is altered in the content of the specific amino acid residues to which the relevant non-polypeptide moiety binds, whereby a more efficient, specific and/or extensive conjugation is achieved. By removal of one or more attachment groups it is possible to avoid conjugation to the non-polypeptide moiety in parts of the polypeptide in which such conjugation is disadvantageous, e.g. to an amino acid residue located at or near a functional site of the polypeptide (since conjugation at such a site may result in inactivation or reduced interferon-alpha activity of the resulting conjugate due to impaired receptor recognition). Further, it may be advantageous to remove an attachment group located close to another attachment group.

It will be understood that the amino acid residue comprising an attachment group for a non-polypeptide moiety, whether it be removed or introduced, is selected on the basis of the nature of the non-polypeptide moiety and, in some instances, on the basis of the conjugation method to be used. For instance, when the non-polypeptide moiety is a polymer molecule, such as a polyethylene glycol or polyalkylene oxide derived molecule, amino acid residues capable of functioning as an attachment group may be selected from the group consisting of cysteine, lysine (and/or the N-terminal amino group of the polypeptide), aspartic acid, glutamic acid, histidine and arginine. When the non-polypeptide moiety is a sugar moiety, the attachment group is an in vivo or in vitro N- or O-glycosylation site, preferably an N-glycosylation site.

In some instances, when an attachment group for a non-polypeptide moiety is to be introduced into or removed from the interferon-alpha polypeptide, the position of the interferon-alpha polypeptide to be modified may be conveniently selected as follows:

The position to be modified may be located at the surface of the interferon-alpha polypeptide, such as a position occupied by an amino acid residue which has more than 25% of its side chain exposed to the solvent, such as more than 50% of its side chain exposed to the solvent. Such positions have been identified on the basis of an analysis of a 3D structure of the human interferon-alpha 2a molecule as described in the "Materials and Methods" section herein.

In order to determine an optimal distribution of attachment groups, the distance between amino acid residues located at the surface of the interferon-alpha molecule was calculated on the basis of a 3D structure of an interferon-alpha polypeptide. More specifically, the distance between the CB's of the amino acid residues comprising such attachment groups, or the distance between the functional group (NZ for lysine, CG for aspartic acid, CD for glutamic acid, SG for cysteine) of one and the CB of another amino acid residue comprising an attachment group were determined. In case of glycine, CA was used instead of CB. In the interferon-α polypeptide part of a conjugate of the invention, any of said distances may be more than 8 Å, such as more than 10 Å in order to avoid or reduce heterogeneous conjugation and to provide a uniform distribution of attachment groups, e.g. with the aim of epitope shielding.

Furthermore, in the interferon-alpha polypeptide part of a conjugate of the invention, in some instances attachment groups located at or near the receptor binding sites of interferon-alpha are removed, such as by substitution of the amino acid residue comprising such group. In some instances, amino acid residues comprising an attachment group for a non-polypeptide moiety, such as cysteine or lysine, are often not introduced at or near the receptor binding site of the interferon alpha molecule.

Another approach for modifying an interferon-alpha polypeptide is to shield and thereby modify or destroy or otherwise inactivate an epitope present in the parent interferon-alpha, by conjugation to a non-polypeptide moiety. Epitopes of interferon-alpha polypeptides may be identified by use of methods known in the art, also known as epitope mapping, see e.g. Romagnoli et al., *J. Biol. Chem.*, 1999, 380(5):553-9, DeLisser H M, *Methods Mol Biol*, 1999, 96:11-20, Van de Water et al., *Clin Immunol Immunopathol*, 1997, 85(3):229-35, Saint-Remy J M, *Toxicology*, 1997, 119 (1):77-81, and Lane D P and Stephen C W, *Curr Opin Immunol*, 1993, 5(2):268-71. One method is to establish a phage display library expressing random oligopeptides of, e.g., 9 amino acid residues. IgG1 antibodies from specific antisera towards human interferon-alpha are purified by immunoprecipitation and the reactive phages are identified by immunoblotting. By sequencing the DNA of the purified reactive phages, the sequence of the oligopeptide can be determined followed by localization of the sequence on the 3D-structure of the interferon-alpha. Alternatively, epitopes can be identified according to the method described in U.S. Pat. No. 5,041, 376. The thereby identified region on the structure constitutes an epitope that then can be selected as a target region for introduction of an attachment group for the non-polypeptide moiety. Preferably, at least one epitope, such as two, three or four epitopes of interferon-alpha are shielded by a non-polypeptide moiety according to the present invention. Accordingly, in one aspect, the conjugate of the invention has at least one shielded epitope as compared to a wild type human interferon-alpha, including any commercially available interferon-alpha. This may be done by introduction of an attachment group for a non-polypeptide moiety into a position located in the vicinity of (i.e. within 4 amino acid residues in the primary sequence or within about 10 Å in the tertiary sequence) of a given epitope. The 10 Å distance is measured between CB's (CA's in case of glycine). Such specific introductions are described in the following sections.

In case of removal of an attachment group, the relevant amino acid residue comprising such group and occupying a position as defined above may be substituted with a different amino acid residue that does not comprise an attachment group for the non-polypeptide moiety in question, or may be deleted. Removal of an N-glycosylation group, may also be accomplished by insertion or removal of an amino acid reside within the motif N-X-S/T/C.

In case of introduction of an attachment group, an amino acid residue comprising such group is introduced into the position, such as by substitution of the amino acid residue occupying such position.

The exact number of attachment groups available for conjugation and present in the interferon-alpha polypeptide is dependent on the effect desired to be achieved by conjugation. The effect to be obtained is, e.g., dependent on the nature and degree of conjugation (e.g. the identity of the non-polypeptide moiety, the number of non-polypeptide moieties desirable or possible to conjugate to the polypeptide, where they should be conjugated or where conjugation should be avoided, etc.). For instance, if reduced immunogenicity is desired, the number (and location of) attachment groups should be sufficient to shield most or all epitopes. This is normally obtained when a greater proportion of the interferon-alpha polypeptide is shielded. Effective shielding of epitopes is normally achieved when the total number of attachment groups available for conjugation is in the range of 1-6 attachment groups, e.g., 1-5, such as in the range of 1-3, such as 1, 2, or 3 attachment groups.

Functional in vivo half-life is i.a. dependent on the molecular weight of the conjugate, and the number of attachment groups needed for providing increased half-life thus depends on the molecular weight of the non-polypeptide moiety in question. Some such conjugates comprise 1-6, e.g., 1-5, such as 1-3, e.g. 1, 2, or 3 non-polypeptide moieties each having a MW of about 2-40 kDa, such as about 2 kDa, about 5 kDa, about 12 kDa, about 15 kDa, about 20 kDa, about 30 kDa, or about 40 kDa.

In the conjugate of the invention, some, most, or substantially all conjugatable attachment groups are occupied by the relevant non-polypeptide moiety.

The conjugate of the invention may exhibit one or more of the following improved properties:

For example, the conjugate may exhibit a reduced immunogenicity as compared to a human interferon-alpha (such as any of the polypeptides defined herein as SEQ ID NO:45-57, or any other huIFN-alpha described herein and/or in Allen G. and Diaz M. O. (1996), supra) or as compared to the corresponding non-conjugated polypeptide, e.g. a reduction of at least 10%, such as a reduction of at least of 25%, such as a reduction of at least of 50%, e.g. a reduction of at least 75% compared to the non-conjugated polypeptide or compared to a human interferon-alpha.

In another aspect the conjugate may exhibit a reduced reaction or no reaction with neutralizing antibodies from patients treated with a human interferon-alpha (such as any of the polypeptides defined herein as SEQ ID NO: 45-57, or any other huIFN-alpha described herein and/or in Allen G. and Diaz M. O. (1996), supra) or as compared to the corresponding non-conjugated polypeptide, e.g. a reduction of neutralisation of at least 10%, such as at least of 25%, such as of at least 50%, e.g., at least 75%.

In another aspect of the invention the conjugate may exhibit an increased functional in vivo half-life and/or increased serum half-life as compared to a reference molecule such as a human interferon-alpha (e.g. any of the polypeptides defined herein as SEQ ID NO:45-57 or any other huIFN-alpha described herein and/or in Allen G. and Diaz M. O. (1996), supra) or as compared to the corresponding non-conjugated polypeptide. Particular preferred conjugates are such conjugates where the ratio between the functional in vivo half-life (or serum half-life) of said conjugate and the functional in vivo half-life (or serum half-life) of said reference molecule is at least 1.25, such as at least 1.50, such as at least 1.75, such as at least 2, such as at least 3, such as at least 4, such as at least 5, such as at least 6, such as at least 7, such as at least 8. As mentioned above, the half-life is conveniently determined in an experimental animal, such as rat or monkey, and may be based on intravenously or subcutaneously administration.

In a further aspect the conjugate may exhibit an increased bioavailability as compared to a reference molecule such as a human interferon-alpha (e.g. any of the polypeptides defined herein as SEQ ID NO:45-57, or any other huIFN-alpha described herein and/or in Allen G. and Diaz M. O. (1996), supra) or the corresponding non-conjugated polypeptide. For example, the conjugate may exhibit an increased $AUC_{sc}$ as compared to a reference molecule such as a human interferon-alpha or the corresponding non-conjugated polypeptide. Thus, exemplary conjugates are such conjugates where the ratio between the $AUC_{sc}$ of said conjugate and the $AUC_{sc}$ of said reference molecule is at least 1.25, such as at least 1.5, such as at least 2, such as at least 3, such as at least 4, such as at least 5 or at least 6, such as at least 7, such as at least 8, such as at least 9 or at least 10, such as at least 12, such as at least 14, e.g. at least 16, at least 18 or at least 20 when administered subcutaneously, in particular when administered subcutaneously in an experimental animal such as rat or monkey. Analogously, some conjugates of the invention are such conjugates wherein the ratio between $T_{max}$ for said conjugate and $T_{max}$ for said reference molecule, such as a human interferon-alpha or the corresponding non-conjugated polypeptide, is at least 1.2, such as at least 1.4, e.g. at least 1.6, such as at least 1.8, such as at least 2, e.g. at least 2.5, such as at least 3, such as at least 4, e.g. at least 5, such as at least 6, such as at least 7, e.g. at least 8, such as at least 9, such as at least 10, when administered subcutaneously, in particular when administered subcutaneously in an experimental animal such as rat or monkey.

In some instances, the magnitude of the antiviral activity of a conjugate of the invention may be reduced (e.g. by at least about 75%, at least about 50%, at least about 25%, at least about 10%) or increased (e.g. by at least about 10%) or is about equal (e.g. within about +/−10% or about +/−5%) to that of a human interferon-alpha (e.g. any of the polypeptides identified herein as SEQ ID NO:45-57, or any other huIFN-alpha described herein and/or in Allen G. and Diaz M. O. (1996), supra) or to that of the corresponding non-conjugated polypeptide. In some instances the degree of antiviral activity as compared to antiproliferative activity of a conjugate of the invention may vary, and thus be higher, lower or about equal to that of a human interferon-alpha or to that of the corresponding non-conjugated polypeptide.

Conjugate of the Invention where the Non-Polypeptide Moiety Binds to a Lysine Residue or the N-Terminal Amine In one aspect, the invention relates to a conjugate exhibiting an interferon-alpha activity and comprising at least one non-polypeptide moiety conjugated to at least one lysine residue and/or to the N-terminal amino group of an interferon-alpha polypeptide comprising a sequence selected from SEQ ID NOs:2-35 and 37-44. Some such conjugates comprise a non-polypeptide moiety attached to a lysine residue selected from K31, K50, K71, K84, K122, K134, K135, and K165; such as, for example, a lysine residue selected from K31, K122, K135, and K165. Some such conjugates comprise a non-polypeptide moiety attached to a lysine residue selected from K31, K122, and K135. Some such conjugates comprise a non-polypeptide moiety attached to a lysine residue selected from K122 and K135. Some such conjugates comprise a non-polypeptide moiety attached to a lysine residue selected from K31 and K122; or K31 and K135.

In another aspect, the invention relates to a conjugate exhibiting an interferon-alpha activity and comprising at least one non-polypeptide moiety conjugated to at least one lysine residue, or to the N-terminal amino group, of an interferon-alpha polypeptide comprising a sequence which (a) differs in 1 to 16 amino acid positions (such as in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions) from SEQ ID NO:1 and (b) comprises one or more substitutions relative to SEQ ID NO:1 selected from the group consisting of F48A/L; V51P; F55A; F65A; F68P; L111A; and V114P. Some such conjugates comprise a polypeptide sequence further comprising one or more additional amino acid(s), such as a methionine added to the N-terminus. Some conjugates according to this aspect comprise at least one removed lysine residue and/or at least one removed histidine residue, and/or at least one introduced lysine residue.

The invention also provides a conjugate exhibiting an interferon-alpha activity and comprising at least one non-polypeptide moiety conjugated to at least one lysine residue, or to the N-terminal amino group, of an interferon-alpha polypeptide comprising a sequence which (a) differs in 0 to 16 amino acid positions from SEQ ID NO:13 (such as in 0-15 amino acid positions, in 0-14 amino acid positions, in 0-13 amino acid positions, in 0-12 amino acid positions, in 0-11 amino acid positions, in 0-10 amino acid positions, in 0-9 amino acid positions, in 0-8 amino acid positions, in 0-7 amino acid positions, in 0-6 amino acid positions, in 0-5 amino acid positions, in 0-4 amino acid positions, in 0-3 amino acid positions, in 0-2 amino acid positions, or in 0-1 amino acid positions) and (b) comprises one or more of: Ala or Leu at position 48; Pro at position 51; Ala at position 55; Ala at position 65; Pro at position 68; Ala at position 111; and Pro at position 114 (position numbering relative to SEQ ID NO:13). Some such conjugates comprise a polypeptide sequence which comprises an Ala or a Leu at position 48. Some such conjugates comprise a polypeptide sequence which comprises an Ala at position 48. In some instances, the polypeptide part of the conjugate further comprises one or more substitution(s) relative to SEQ ID NO:13 selected from the group consisting of H47Q; V51A; Q52P/E; A53T; F55S; L56V; F57L; Y58H; M61I; N113K; V114E; and E160D. Some such conjugates comprise a polypeptide sequence further comprising one or more additional amino acid(s), such as a methionine added to the N-terminus. Some conjugates according to this aspect comprise at least one removed lysine residue and/or at least one removed histidine residue, and/or at least one introduced lysine residue.

In another aspect, the invention relates to a conjugate exhibiting an interferon-alpha activity and comprising at least one non-polypeptide moiety conjugated to at least one lysine residue, or to the N-terminal amino group, of an interferon-alpha polypeptide comprising a sequence which (a) differs in 1 to 16 amino acid positions (such as in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions) from SEQ ID NO:36 and (b) comprises one or more substitutions relative to SEQ ID NO:36 selected from the group consisting of M21A; I24P; F48A/L; T51P; S55A; F65A; F68P; F90A; M93P; L111A; V114P; F124A; I127P; and E160D. Some such conjugates comprise a polypeptide sequence further comprising one or more additional amino acid(s), such as a methionine added to the N-terminus. Some conjugates according to this aspect comprise at least one removed lysine residue and/or at least one removed histidine residue, and/or at least one introduced lysine residue.

The invention also provides a conjugate exhibiting an interferon-alpha activity and comprising at least one non-polypeptide moiety conjugated to at least one lysine residue, or to the N-terminal amino group, of an interferon-alpha polypeptide comprising a sequence which (a) differs in 0 to 16 amino acid positions (such as in 0-15 amino acid positions, in 0-14 amino acid positions, in 0-13 amino acid positions, in 0-12 amino acid positions, in 0-11 amino acid positions, in 0-10 amino acid positions, in 0-9 amino acid positions, in 0-8 amino acid positions, in 0-7 amino acid positions, in 0-6 amino acid positions, in 0-5 amino acid positions, in 0-4 amino acid positions, in 0-3 amino acid positions, in 0-2 amino acid positions, or in 0-1 amino acid positions) from SEQ ID NO:38 and (b) comprises one or more of: Ala at position 21; Pro at position 24; Ala or Leu at position 48; Pro at position 51; Ala at position 55; Ala at position 65; Pro at position 68; Ala at position 90; Pro at position 93; Ala at position 111; Pro at position 114; Ala at position 124; Pro at position 127; and Glu at position 160 (position numbering relative to SEQ ID NO:38). Some such conjugates comprise a polypeptide sequence which comprises an Ala or a Leu at position 48. Some such conjugates comprise a polypeptide sequence which comprises an Ala at position 48. In some instances, the polypeptide part of the conjugate further comprises one or more substitution(s) relative to SEQ ID NO:38 selected from the group consisting of P26L; H47Q; V51T; F55P/S; L56V; Y58H; L60M; F90Y; M93L; N95D; N113K; V114E; R125Q; T132K; and F154L. Some such conjugates comprise a polypeptide sequence further comprising one or more additional amino acid(s), such as a methionine added to the N-terminus. Some conjugates according to this aspect comprise at least one removed lysine residue and/or at least one removed histidine residue, and/or at least one introduced lysine residue.

Some conjugates of the invention comprise a polypeptide sequence comprising a substitution of an amino acid residue for a different amino acid residue, or a deletion of an amino acid residue, which removes one or more lysines, such as, one or more of K31, K50, K71, K84, K122, K133, K134, K135, and/or K165 from a polypeptide of the invention such as, for example, one of SEQ ID NOs:2-35 and 37-44. The one or more lysine residue(s) to be removed may be substituted with any other amino acid, may be substituted with an Arg (R) or Gln (O), or may be deleted.

In instances where amine-reactive conjugation chemistries are employed, it may be advantageous to avoid or to minimize the potential for conjugation to histidine residues. Therefore, some conjugates of the invention comprise a polypeptide sequence comprising a substitution or a deletion which removes one or more histidines, e.g., H7, H11, H34, and/or H47 (relative to SEQ ID NO:1) from any polypeptide sequence of the invention such as, for example, one of one of SEQ ID NOs:2-35 and 37-44. The one or more histidine residue(s) to be removed may be substituted with any other amino acid, may be substituted with an Arg (R) or Gln (O), or may be deleted. Some such conjugates comprise the substitutions H34Q; H47Q; or H34Q+H47Q.

Alternatively, or in addition, some conjugates of the invention comprise a polypeptide sequence comprising a modification which introduces a lysine into a position that is occupied in the parent sequence (e.g., one of SEQ ID NOs:2-35 and 37-44) by an amino acid residue that is exposed to the surface of the molecule, e.g., one that has at least 25%, such as at least 50% of its side chain exposed to the surface. Some such conjugates comprise a polypeptide sequence comprising one or more of the following substitutions, relative to SEQ ID NO:1, which introduces a lysine residue into a position which is predicted to be exposed at the surface of the molecule with more than a 25% fractional ASA: D2K, L3K, P4K, Q5K, T6K, H7K, S8K, L9K, G10K, R12K, R13K, M16K, A19K, Q20K, R22K, R23K, I24K, S25K, L26K, F27K, S28K, L30K, R33K, H34K, D35K, R37K, Q40K, E41K, E42K, D44K, N46K, H47K, Q49K, V51K, Q52K, E59K, Q62K, Q63K, N66K, S69K, T70K, D72K, S74K, A75K, D78K, E79K, T80K, L81K, E83K, I87K, F90K, Q91K, N94K, D95K, E97K, A98K, V100K, M101K, Q102K, E103K, V104K, G105K, E107K, E108K, T109K, P110K, L111K, M112K, N113K, V114K, D115K, L118K, R121K, Q125K, R126K, T128K, L129K, T132K, E133K, Y136K, S137K, P138K, A146K, M149K, R150K, S153K, F154K, N157K, Q159K, E160K, S161K, L162K, R163K, S164K, and E166K, said amino acid residue positions relative to SEQ ID NO:1.

Some such conjugates of the invention comprise a polypeptide sequence comprising one or more of the following substitutions, relative to SEQ ID NO:1, which introduces a lysine residue into a position which is predicted to be exposed at the surface of the molecule with more than a 50% fractional ASA: D2K, L3K, P4K, Q5K, T6K, H7K, S8K, L9K, R12K, R13K, M16K, A19K, S25K, F27K, S28K, R33K, H34K, D35K, R37K, E41K, D44K, N46K, H47K, Q49K, N66K, A75K, D78K, E79K, T80K, E83K, I87K, F90K, Q91K, N94K, D95K, M101K, Q102K, E103K, G105K, E107K, E108K, T109K, P110K, L111K, V114K, D115K, L118K, R121K, Q125K, R126K, L129K, T132K, E133K, P138K, R150K, E160K, L162K, R163K, S164K and E166K, said amino acid residue positions relative to SEQ ID NO:1.

It is to be understood that while the examples of modifications to the parent polypeptide are generally provided herein relative to the sequence SEQ ID NO:1 (or relative to some other specified sequence), the disclosed modifications may also be made in equivalent amino acid positions of the other polypeptides of the invention (including SEQ ID NOs:2-35 and 37-44 and variants thereof) described herein. Thus, as an example, the substitution H47K relative to SEQ ID NO:1 is understood to correspond to Q47K in SEQ ID NO:37, and so on.

Non-polypeptide moieties contemplated for this aspect of the invention include polymer molecules, such as any of the molecules mentioned in the section entitled "Conjugation to a polymer molecule", such as PEG or mPEG or mPEG2. The conjugation between the lysine-containing polypeptide and the polymer molecule may be achieved in any suitable manner, e.g. as described in the section entitled "Conjugation to a polymer molecule", e.g. in using a one step method or in the stepwise manner referred to in said section. An exemplary method for PEGylating the interferon-alpha polypeptide is to covalently attach PEG to lysine residues using lysine-reactive PEGs, such as described in Example 5 herein. A number of highly specific, lysine-reactive PEGs (such as for example, succinimidyl propionate (SPA), succinimidyl butanoate (SBA), N-hydroxylsuccinimide (NHS), and aldehyde (e.g., ButyrALD)) and different size linear or branched PEGs (e.g., 2-40 kDa, such as 2 kDa, 5 kDa, 12 kDa, 15 kDa, 20 kDa, 30 kDa, or 40 kDa) are commercially available, e.g. from Nektar Therapeutics Inc., Huntsville, Ala., USA, or SunBio, Anyang City, South Korea.

In another aspect, the invention includes a composition comprising a population of conjugates wherein the majority of the conjugates of said population each contain a single non-polypeptide moiety (such as, a single polymer molecule, e.g., a single PEG, such as a linear PEG or a branched PEG) covalently attached to a single lysine residue or N-terminal amino group of the polypeptide. For example, a "monoconjugated" (such as, a "monoPEGylated") composition of the invention comprises one or more "positional isomers" of said conjugate, wherein each positional isomer contains a single non-polypeptide moiety (e.g., a single PEG molecule) covalently attached to a single lysine residue of the polypeptide.

The invention includes a monoPEGylated composition comprising a population of conjugates, wherein the majority of the conjugates of said population are positional isomers each containing a single PEG molecule (such as, a linear or branched PEG, such as a 2 kDa, 5 kDa, 12 kDa, 15 kDa, 20 kDa, 30 kDa, or 40 kDa mPEG or mPEG2 molecule) covalently attached to a single lysine residue of a polypeptide of the invention.

Some such positional isomers contain a single PEG molecule covalently attached to a lysine residue selected from K31, K50, K71, K84, K122, K134, K135, and K165. Some such positional isomers contain a single PEG molecule covalently attached to a lysine residue selected from K31, K122, K135, and K165. Some such positional isomers contain a single PEG molecule covalently attached to a lysine residue selected from K31, K122, and K135, such as, a single PEG molecule covalently attached to a lysine reside selected from K31 and K122; K31 and K135; or K122 and K135.

Example 5 herein describes the preparation of monoPEGylated compositions of the invention. A monoPEGylated composition of a polypeptide of the invention identified herein as 14epi18 (SEQ ID NO:13) reacted with a 40 kDa branched PEG (mPEG2-NHS) according to the procedure of Example 5 contains predominantly two positional isomers, one with a single PEG moiety covalently attached to Lys122 and another with a single PEG moiety covalently attached to Lys135. Accordingly, the invention includes a composition (e.g. a monoPEGylated composition), said composition comprising a polypeptide conjugate comprising the sequence SEQ ID NO:13 wherein a PEG moiety is covalently attached to Lys122 or Lys135. The invention also includes a composition (e.g. a monoPEGylated composition), said composition comprising a polypeptide conjugate comprising the sequence SEQ ID NO:13 wherein a 40 kDa PEG moiety (e.g., a 40 kDa branched PEG moiety) is covalently attached to Lys122 or Lys135.

A monoPEGylated composition of another exemplary polypeptide of the invention, identified herein as 25epi19 (SEQ ID NO:38), when reacted with a 40 kDa branched PEG (mPEG2-NHS) according to the procedure of Example 5 predominantly contains three positional isomers, one with a single PEG moiety covalently attached to Lys 31, another with a single PEG moiety covalently attached to Lys122, and another with a single PEG moiety covalently attached to Lys135. Accordingly, the invention includes a composition (e.g. a monoPEGylated composition), said composition comprising a polypeptide conjugate comprising the sequence SEQ ID NO:38 wherein a PEG moiety is covalently attached to Lys31, Lys122, or Lys135. The invention also includes a composition (e.g. a monoPEGylated composition), said composition comprising a polypeptide conjugate comprising the sequence SEQ ID NO:38 wherein a 40 kDa PEG moiety (e.g., a 40 kDa branched PEG moiety) is covalently attached to Lys31, Lys122, or Lys135.

Conjugate of the Invention where the Non-Polypeptide Moiety Binds to a Cysteine Residue In one aspect, the invention relates to a conjugate exhibiting an interferon-alpha activity and comprising at least one non-polypeptide moiety conjugated to at least one cysteine residue of an interferon-alpha polypeptide comprising a sequence which (a) differs in 1 to 16 amino acid positions (such as in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions) from SEQ ID NO:1 and (b) comprises one or more substitutions relative to SEQ ID NO:1 selected from the group consisting of F48A/L; V51P; F55A; F65A; F68P; L111A; and V114P. Some conjugates according to this aspect comprise at least one introduced cysteine residue.

In another aspect, the invention relates to a conjugate exhibiting an interferon-alpha activity and comprising at least one non-polypeptide moiety conjugated to at least one cysteine residue of an interferon-alpha polypeptide comprising a sequence which (a) differs in 1 to 16 amino acid positions (such as in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions) from SEQ ID NO:36 and (b) comprises one or more substitutions relative to SEQ ID NO:36 selected from the group consisting of M21A; I24P; F48A/L; T51P; S55A; F65A; F68P; F90A; M93P; L111A; V114P; F124A; I127P; and E160D. Some conjugates according to this aspect comprise at least one introduced cysteine residue.

For example, some conjugates of the invention comprise a polypeptide sequence further comprising one or more of the following substitutions, relative to SEQ ID NO:1, which introduces a cysteine residue into a position which is predicted to be exposed at the surface of the molecule with more than a 25% fractional ASA: D2C, L3C, P4C, Q5C, T6C, H7C, S8C, L9C, G10C, R12C, R13C, M16C, A19C, Q20C, R22C, R23C, I24C, S25C, L26C, F27C, S28C, L30C, K31C, R33C, H34C, D35C, R37C, Q40C, E41C, E42C, D44C, N46C, H47C, Q49C, K50C, V51C, Q52C, E59C, Q62C, Q63C, N66C, S69C, T70C, K71C, D72C, S74C, A75C, D78C, E79C, T80C, L81C, E83C, K84C, I87C, F90C, Q91C, N94C, D95C, E97C, A98C, V100C, M101C, Q102C, E103C, V104C, G105C, E107C, E108C, T109C, P110C, L111C, M112C, N113C, V114C, D115C, L118C, R121C, K122C, Q125C, R126C, T128C, L129C, T132C, E133C, K134C, K135C, Y136C, S137C, P138C, A146C, M149C, R150C, S153C, F154C, N157C, Q159C, E160C, S161C, L162C, R163C, S164C, K165C and E166C, said amino acid residue positions relative to SEQ ID NO:1.

Some such conjugates of the invention comprise a polypeptide sequence further comprising one or more of the following substitutions, relative to SEQ ID NO:1, which introduces a cysteine residue into a position which is predicted to be exposed at the surface of the molecule with more than a 50% fractional ASA: D2C, L3C, P4C, Q5C, T6C, H7C, S8C, L9C, R12C, R13C, M16C, A19C, S25C, F27C, S28C, K31C, R33C, H34C, D35C, R37C, E41C, D44C, N46C, H47C, Q49C, K50C, N66C, K71C, A75C, D78C, E79C, T80C, E83C, K84C, I87C, F90C, Q91C, N94C, D95C, M101C, Q102C, E103C, G105C, E107C, E108C, T109C, P110C, L111C, V114C, D115C, L118C, R121C, K122C, Q125C, R126C, L129C, T132C, E133C, K135C, P138C, R150C, E160C, L162C, R163C, S164C, K165C and E166C, said amino acid residue positions relative to SEQ ID NO:1.

It is to be understood that while the examples of modifications to the parent polypeptide are generally provided herein relative to the sequence SEQ ID NO:1 (or relative to some other specified sequence), the disclosed modifications may also be made in equivalent amino acid positions of the other polypeptides of the invention (including SEQ ID NOs:2-35 and 37-44 and variants thereof) described herein. Thus, as an example, the substitution H47C relative to SEQ ID NO:1 is understood to correspond to Q47C in SEQ ID NO:37, and so on.

In some instances, only a single cysteine residue is introduced in order to avoid formation of disulfide bridges between two or more introduced cysteine residues.

In interferon alphas, disulfide bonds are formed between cysteines at positions 1/99 and 29/139. The disulfide bond 29/139 is essential for biological activity, while the 1/99 bond can be reduced without significantly affecting biological activity (Beilharz M. W. et al. (1986) J. Interferon Res. 6(6): 677-685). Thus, in another aspect of the invention one of C1 or C99 is removed, preferably by substitution, e.g. C1S or C99S, thereby leaving the other cysteine residue available for conjugation to a non-polypeptide moiety.

Non-polypeptide moieties contemplated in this aspect of the invention include polymer molecules, such as any of the molecules mentioned in the section entitled "Conjugation to a polymer molecule", such as PEG or mPEG. The conjugation between the cysteine-containing polypeptide and the polymer molecule may be achieved in any suitable manner, e.g. as described in the section entitled "Conjugation to a polymer molecule", e.g. in using a one step method or in the stepwise manner referred to in said section. An exemplary method for PEGylating the interferon-alpha polypeptide is to covalently attach PEG to cysteine residues using cysteine-reactive PEGs. A number of highly specific, cysteine-reactive PEGs with different groups (e.g. orthopyridyl-disulfide (OPSS), maleimide (MAL) and vinylsulfone (VS)) and different size linear or branched PEGs (e.g., 2-40 kDa, such as 2 kDa, 5 kDa, 12 kDa, 15 kDa, 20 kDa, 30 kDa, or 40 kDa) are commercially available, e.g. from Nektar Therapeutics Inc., Huntsville, Ala., USA, or SunBio, Anyang City, South Korea.

Non-Polypeptide Moiety of the Conjugate of the Invention

As indicated above, the non-polypeptide moiety of the conjugate of the invention is generally selected from the group consisting of a polymer molecule, a lipophilic compound, a sugar moiety (e.g., by way of in vivo N-glycosylation) and an organic derivatizing agent. All of these agents may confer desirable properties to the polypeptide part of the conjugate, such as reduced immunogenicity, increased functional in vivo half-life, increased serum half-life, increased bioavailability and/or increased $AUC_{sc}$. The polypeptide part of the conjugate is often conjugated to only one type of non-polypeptide moiety, but may also be conjugated to two or more different types of non-polypeptide moieties, e.g. to a polymer molecule and a sugar moiety, etc. The conjugation to two or more different non-polypeptide moieties may be done simultaneously or sequentially. The choice of non-polypeptide moiety/moieties, depends especially on the effect desired to be achieved by the conjugation. For instance, sugar moieties have been found particularly useful for reducing immunogenicity, whereas polymer molecules such as PEG are of particular use for increasing functional in vivo half-life and/or serum half-life. Using a combination of a polymer molecule and a sugar moiety may enhance the reduction in immunogenicity and the increase in functional in vivo or serum half-life.

In the following sections "Conjugation to a lipophilic compound", "Conjugation to a polymer molecule", "Conjugation to a sugar moiety" and "Conjugation to an organic derivatizing agent" conjugation to specific types of non-polypeptide moieties is described.

Conjugation to a Lipophilic Compound

For conjugation to a lipophilic compound the following polypeptide groups may function as attachment groups: the N-terminus or C-terminus of the polypeptide, the hydroxy groups of the amino acid residues Ser, Thr or Tyr, the ε-amino group of Lys, the SH group of Cys or the carboxyl group of Asp and Glu. The polypeptide and the lipophilic compound may be conjugated to each other either directly or by use of a linker. The lipophilic compound may be a natural compound such as a saturated or unsaturated fatty acid, a fatty acid diketone, a terpene, a prostaglandin, a vitamin, a carotenoid or steroid, or a synthetic compound such as a carbon acid, an alcohol, an amine and sulphonic acid with one or more alkyl, aryl, alkenyl or other multiple unsaturated compounds. The conjugation between the polypeptide and the lipophilic compound, optionally through a linker may be done according to methods known in the art, e.g. as described by Bodanszky in Peptide Synthesis, John Wiley, New York, 1976 and in WO 96/12505.

Conjugation to a Polymer Molecule

The polymer molecule to be coupled to the polypeptide may be any suitable polymer molecule, such as a natural or synthetic homo-polymer or heteropolymer, typically with a molecular weight in the range of about 300-100,000 Da, such as about 1000-50,000 Da, e.g. in the range of about 1000-40,000 Da. More particularly, the polymer molecule, such as PEG, in particular mPEG, will typically have a molecular weight of about 2, 5, 10, 12, 15, 20, 30, 40 or 50 kDa, in particular a molecular weight of about 5 kDa, about 10 kDa, about 12 kDa, about 15 kDa, about 20 kDa, about 30 kDa or about 40 kDa. The PEG molecule may be branched (e.g., mPEG2), or may be unbranched (i.e., linear).

When used about polymer molecules herein, the word "about" indicates an approximate average molecular weight and reflects the fact that there will normally be a certain molecular weight distribution in a given polymer preparation.

Examples of homo-polymers include a polyol (i.e. poly-OH), a polyamine (i.e. poly-$NH_2$) and a polycarboxylic acid (i.e. poly-COOH). A hetero-polymer is a polymer which comprises one or more different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs (PEG2), poly-vinyl alcohol (PVA), poly-carboxylate, poly-(vinylpyrolidone), polyethylene-co-maleic acid anhydride, polystyrene-co-malic acid anhydride, dextran including carboxymethyl-dextran, or any other biopolymer suitable for reducing immunogenicity and/or increasing functional in vivo half-life and/or serum half-life. Generally, polyalkylene glycol-derived polymers are biocompatible, non-toxic, non-antigenic, non-immunogenic, have various water solubility properties, and are easily excreted from living organisms.

PEG is the preferred polymer molecule to be used, since it has only few reactive groups capable of cross-linking compared to e.g. polysaccharides such as dextran. In particular, monofunctional PEG, e.g. monomethoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl propionate (SPA), succinimidyl butanoate (SBA), succinimidyl carboxymethylate (SCM), benzotriazole carbonate (BTC), N-hydroxysuccinimide (NHS), aldehyde, nitrophenylcarbonate (NPC), and tresylate (TRES)). Suitably activated polymer molecules are commercially available, e.g. from Nektar Therapeutics, Inc., Huntsville, Ala., USA; PolyMASC Pharmaceuticals plc, UK; or SunBio Corporation, Anyang City, South Korea. Alternatively, the polymer molecules can be activated by conventional methods known in the art, e.g. as disclosed in WO 90/13540. Specific examples of activated linear or branched polymer molecules suitable for use in the present invention are described in the Nektar Therapeutics, Inc. 2003 Catalog ("Nektar Molecule Engineering: Polyethylene Glycol and Derivatives for Advanced Pegylation, Catalog 2003"), incorporated by reference herein. Specific examples of activated PEG polymers include the following linear PEGs: NHS-PEG, SPA-PEG, SSPA-PEG, SBA-PEG, SS-PEG, SSA-PEG, SC-PEG, SG-PEG, SCM-PEG, NOR-PEG, BTC-PEG, EPOX-PEG, NCO-PEG, NPC-PEG, CDI-PEG, ALD-PEG, TRES-PEG, VS-PEG, OPSS-PEG, IODO-PEG, and MAL-PEG, and branched PEGs, such as PEG2-NHS, PEG2-MAL, and those disclosed in U.S. Pat. Nos. 5,932,462 and 5,643,575, both of which are incorporated herein by reference. Furthermore, the following publications, incorporated herein by reference, dis-close useful polymer molecules and/or PEGylation chemistries: U.S. Pat. No. 5,824,778, 5,476,653, WO 97/32607, EP 229,108, EP 402,378, U.S. Pat. Nos. 4,902,502, 5,281,698, 5,122,614, 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736, 625, WO 98/05363, EP 809 996, U.S. Pat. No. 5,629,384, WO 96/41813, WO 96/07670, U.S. Pat. Nos. 5,473,034, 5,516, 673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g. as described in the following references (which also describe suitable methods for activation of polymer molecules): Harris and Zalipsky, eds., Poly(ethylene glycol) Chemistry and Biological Applications, AZC, Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.

For PEGylation of cysteine residues the polypeptide is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to about 16 hours. Examples of activated PEG polymers for coupling to cysteine residues include the following linear and branched PEGs: vinylsulfone-PEG (PEG-VS), such as vinylsulfone-mPEG (mPEG-VS); orthopyridyl-disulfide-PEG (PEG-OPSS), such as orthopyridyl-disulfide-mPEG (mPEG-OPSS); and maleimide-PEG (PEG-MAL), such as maleimide-mPEG (mPEG-MAL) and branched maleimide-mPEG2 (mPEG2-MAL).

Pegylation of lysines often employs PEG-N-hydroxylsuccinimide (e.g., mPEG-NHS or mPEG2-NHS), or esters such as PEG succinimidyl propionate (e.g., mPEG-SPA) or PEG succinimidyl butanoate (e.g., mPEG-SBA). One or more PEGs can be attached to a protein within 30 minutes at pH 8-9.5 at room temperature if about equimolar amounts of PEG and protein are mixed. A molar ratio of PEG to protein amino groups of 1-5 to 1 will usually suffice. Increasing pH increases the rate of reaction, while lowering pH reduces the rate of reaction. These highly reactive active esters can couple at physiological pH, but less reactive derivatives typically require higher pH. Low temperatures may also be employed if a labile protein is being used. Under low temperature conditions, a longer reaction time may be used.

N-terminal PEGylation is facilitated by the difference between the pKa values of the α-amino group of the N-terminal amino acid (~7.6 to 8.0) and the ε-amino group of lysine (~10). PEGylation of the N-terminal amino group often employs PEG-aldehydes (such as mPEG-propionaldehyde or mPEG-butylaldehyde), which are more selective for amines and thus are less likely to react with the imidazole group of histidine; in addition, PEG reagents used for lysine conjugation (such as mPEG-SPA, mPEG-SBA, or mPEG-NHS) may also be used for conjugation of the N-terminal amine. Conjugation of a PEG-aldehyde to the N-terminal amino group typically takes place in a suitable buffer (such as, 100 mM sodium acetate or 100 mM sodium bisphosphate buffer with 20 mM sodium cyanoborohydride) at pH ~5.0 overnight at temperatures varying from about 4° C. to 25° C. Useful N-terminal PEGylation methods and chemistries are also described in U.S. Pat. Nos. 5,985,265 and 6,077,939, both incorporated herein by reference.

Typically, linear PEG or mPEG polymers will have a molecular weight of about 5 kDa, about 10 kDa, about 12 kDa, about 15 kDa, about 20 kDa, or about 30 kDa. Branched PEG (PEG2 or mPEG2) polymers will typically have a molecular weight of about 10 kDa, about 20 kDa, or about 40 kDa. In some instances, the higher-molecular weight branched PEG2 reagents, such as 20 kDa or 40 kDa PEG2, including e.g. mPEG2-NHS for lysine PEGylation, mPEG2-MAL for cysteine PEGylation, or MPEG2-aldehyde for N-terminal PEGylation (all available from Nektar Therapeutics, Inc, Huntsville Ala.), may be used. The branched structure of the PEG2 compound results in a relatively large molecular volume, so fewer attached molecules (or, one attached molecule) may impart the desired characteristics of the PEGylated molecule.

The skilled person will be aware that the activation method and/or conjugation chemistry to be used depends on the attachment group(s) of the interferon-alpha polypeptide as well as the functional groups of the polymer (e.g., being amino, hydroxyl, carboxyl, aldehyde or sulfhydryl). The PEGylation may be directed towards conjugation to all available attachment groups on the polypeptide (i.e. such attachment groups that are exposed at the surface of the polypeptide) or may be directed towards specific attachment groups, e.g. cysteine residues, lysine residues, or the N-terminal amino group.

Furthermore, the conjugation may be achieved in one step or in a stepwise manner (e.g. as described in WO 99/55377).

In some instances, the polymer conjugation is performed under conditions aiming at reacting as many of the available polymer attachment groups as possible with polymer molecules. This is achieved by means of a suitable molar excess of the polymer in relation to the polypeptide. Typical molar ratios of activated polymer molecules to polypeptide are up to about 1000-1, such as up to about 200-1 or up to about 100-1. In some cases, the ratio may be somewhat lower, however, such as up to about 50-1, 10-1 or 5-1. Also equimolar ratios may be used.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179, 337; Shafer et al., (1986), J. Polym. Sci. Polym. Chem. Ed., 24, 375-378).

Subsequent to the conjugation residual activated polymer molecules are blocked according to methods known in the art, e.g. by addition of primary amine to the reaction mixture, and the resulting inactivated polymer molecules removed by a suitable method.

Covalent in vitro coupling of a sugar moiety to amino acid residues of interferon-alpha may be used to modify or increase the number or profile of sugar substituents. Depending on the coupling mode used, the carbohydrate(s) may be attached to a) arginine and histidine (Lundblad and Noyes, Chemical Reagents for Protein Modification, CRC Press Inc. Boca Raton, Fla.), b) free carboxyl groups (e.g. of the C-terminal amino acid residue, asparagine or glutamine), c) free sulfhydryl groups such as that of cysteine, d) free hydroxyl groups such as those of serine, threonine, tyrosine or hydroxyproline, e) aromatic residues such as those of phenylalanine or tryptophan or f) the amide group of glutamine. These amino acid residues constitute examples of attachment groups for a sugar moiety, which may be introduced and/or removed in the interferon-alpha polypeptide. Suitable methods of in vitro coupling are described in WO 87/05330 and in Aplin et al., CRC Crit Rev. Biochem., pp. 259-306, 1981. The in vitro coupling of sugar moieties or PEG to protein- and peptide-bound Gln-residues can also be carried out by transglutaminases (TGases), e.g. as described by Sato et al., 1996 *Biochemistry* 35, 13072-13080 or in EP 725145.

Coupling to a Sugar Moiety

In order to achieve in vivo glycosylation of an interferon-alpha polypeptide that has been modified by introduction of one or more glycosylation sites, the nucleotide sequence encoding the polypeptide part of the conjugate is inserted in a glycosylating, eukaryotic expression host. The expression host cell may be selected from fungal (filamentous fungal or yeast), insect, mammalian animal cells, from transgenic plant cells or from transgenic animals. Furthermore, the glycosylation may be achieved in the human body when using a nucleotide sequence encoding the polypeptide part of a conjugate of the invention or a polypeptide of the invention in gene therapy. In one aspect the host cell is a mammalian cell, such as a CHO cell, a COS cell, a BHK or HEK cell, e.g. HEK293, or an insect cell, such as an SF9 cell, or a yeast cell, e.g. *Saccharomyces cerevisiae, Pichia pastoris* or any other suitable glycosylating host, e.g. as described further below. Optionally, sugar moieties attached to the interferon-α polypeptide by in vivo glycosylation are further modified by use of glycosyltransferases, e.g. using the GlycoAdvance™ technology marketed by Neose, Horsham, Pa., USA. Thereby, it is possible to, e.g., increase the sialyation of the glycosylated interferon-alpha polypeptide following expression and in vivo glycosylation by CHO cells.

Coupling to an Organic Derivatizing Agent

Covalent modification of the interferon-alpha polypeptide may be performed by reacting (an) attachment group(s) of the polypeptide with an organic derivatizing agent. Suitable derivatizing agents and methods are well known in the art. For example, cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonate at pH 5.5-7.0 because this agent is relatively specific for the histidyl side chain. Para-bromophenacyl bromide is also useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group. Carboxyl side groups (aspartyl or glutamyl or C-terminal amino acid residue) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Blocking of a Functional Site

Since excessive polymer conjugation may lead to a loss of activity of the interferon-α polypeptide to which the polymer is conjugated, it may be advantageous to remove attachment groups located at the functional site or to block the functional site prior to conjugation. These latter strategies constitute further aspects of the invention (the first strategy being exemplified further above, e.g. by removal of lysine residues which may be located close to a functional site). More specifically, according to the second strategy the conjugation between the interferon-alpha polypeptide and the non-polypeptide moiety is conducted under conditions where the functional site of the polypeptide is blocked by a helper molecule capable of binding to the functional site of the polypeptide. Preferably, the helper molecule is one which specifically recognizes a functional site of the polypeptide, such as a receptor, in particular the type I interferon receptor. Alternatively, the helper molecule may be an antibody, in particular a monoclonal antibody recognizing the interferon-alpha polypeptide. In particular, the helper molecule may be a neutralizing monoclonal antibody.

The polypeptide is allowed to interact with the helper molecule before effecting conjugation. This ensures that the functional site of the polypeptide is shielded or protected and consequently unavailable for derivatization by the non-polypeptide moiety such as a polymer. Following its elution from the helper molecule, the conjugate between the non-polypeptide moiety and the polypeptide can be recovered with at least a partially preserved functional site.

The subsequent conjugation of the polypeptide having a blocked functional site to a polymer, a lipophilic compound, an organic derivatizing agent or any other compound is conducted in the normal way, e.g. as described in the sections above entitled "Conjugation to . . . ".

Irrespective of the nature of the helper molecule to be used to shield the functional site of the polypeptide from conjugation, it is desirable that the helper molecule is free from or comprises only a few attachment groups for the non-polypeptide moiety of choice in parts of the molecule where the conjugation to such groups would hamper the desorption of the conjugated polypeptide from the helper molecule. Hereby, selective conjugation to attachment groups present in non-shielded parts of the polypeptide can be obtained and it is possible to reuse the helper molecule for repeated cycles of conjugation. For instance, if the non-polypeptide moiety is a polymer molecule such as PEG, which has the epsilon amino group of a lysine or N-terminal amino acid residue as an attachment group, it is desirable that the helper molecule is substantially free from conjugatable epsilon amino groups, preferably free from any epsilon amino groups. Accordingly, in some instances the helper molecule is a protein or peptide capable of binding to the functional site of the polypeptide, which protein or peptide is free from any conjugatable attachment groups for the non-polypeptide moiety of choice.

In a further aspect the helper molecule is first covalently linked to a solid phase such as column packing materials, for instance Sephadex or agarose beads, or a surface, e.g. reaction vessel. Subsequently, the polypeptide is loaded onto the column material carrying the helper molecule and conjugation carried out according to methods known in the art, e.g. as described in the sections above entitled "Conjugation to . . . ". This procedure allows the polypeptide conjugate to be separated from the helper molecule by elution. The polypeptide conjugate is eluted by conventional techniques under physico-chemical conditions that do not lead to a substantive degradation of the polypeptide conjugate. The fluid phase containing the polypeptide conjugate is separated from the solid phase to which the helper molecule remains covalently linked. The separation can be achieved in other ways: For instance, the helper molecule may be derivatized with a second molecule (e.g. biotin) that can be recognized by a specific binder (e.g. streptavidin). The specific binder may be linked to a solid phase thereby allowing the separation of the polypeptide conjugate from the helper molecule-second molecule complex through passage over a second helper-solid phase column which will retain, upon subsequent elution, the helper molecule-second molecule complex, but not the polypeptide conjugate. The polypeptide conjugate may be released from the helper molecule in any appropriate fashion. De-protection may be achieved by providing conditions in which the helper molecule dissociates from the functional site of the interferon-α to which it is bound. For instance, a complex between an antibody to which a polymer is conjugated and an anti-idiotypic antibody can be dissociated by adjusting the pH to an acid or alkaline pH.

Conjugation of a Tagged Interferon-Alpha Polypeptide

In another aspect the interferon-alpha polypeptide is expressed as a fusion protein with a tag, i.e. an amino acid sequence or peptide made up of typically 1-30, such as 1-20 or 1-15 or 1-10 or 1-5 amino acid residues, e.g. added to the N-terminus or to the C-terminus of the polypeptide. Besides allowing for fast and easy purification, the tag is a convenient tool for achieving conjugation between the tagged polypeptide and the non-polypeptide moiety. In particular, the tag may be used for achieving conjugation in microtiter plates or other carriers, such as paramagnetic beads, to which the tagged polypeptide can be immobilised via the tag. The conjugation to the tagged polypeptide in, e.g., microtiter plates has the advantage that the tagged polypeptide can be immobilised in the microtiter plates directly from the culture broth (in principle without any purification) and subjected to conjugation. Thereby, the total number of process steps (from expression to conjugation) can be reduced. Furthermore, the tag may function as a spacer molecule ensuring an improved accessibility to the immobilised polypeptide to be conjugated. The conjugation using a tagged polypeptide may be to any of the non-polypeptide moieties disclosed herein, e.g. to a polymer molecule such as PEG.

The identity of the specific tag to be used is not critical as long as the tag is capable of being expressed with the polypeptide and is capable of being immobilised on a suitable surface or carrier material. A number of suitable tags are commercially available, e.g. from Unizyme Laboratories, Denmark. Antibodies against such tags are commercially available, e.g. from ADI, Aves Lab and Research Diagnostics.

Polynucleotides of the Invention

The invention provides isolated or recombinant nucleic acids (also referred to herein as polynucleotides), collectively referred to as "nucleic acids (or polynucleotides) of the invention", which encode polypeptides of the invention. The polynucleotides of the invention are useful in a variety of applications. As discussed above, the polynucleotides are useful in producing polypeptides of the invention. In addition, polynucleotides of the invention can be incorporated into expression vectors useful for gene therapy, DNA vaccination, and immunotherapy, as described in more detail below.

In one aspect, the invention provides isolated or recombinant polynucleotides that each comprise a nucleic acid sequence which encodes a polypeptide comprising an amino acid sequence selected from SEQ ID NOs:2-35 and 37-44; or, a complementary nucleic acid sequence thereof. Exemplary nucleic acid sequences according to this aspect of the invention include, but are not limited to, SEQ ID NOs:59-61, which each encode a polypeptide comprising the sequence SEQ ID NO:10; SEQ ID NOs:62-64 and 89, which each encode a polypeptide comprising the sequence SEQ ID NO:13; SEQ ID NOs:65-67, which each encode a polypeptide comprising the sequence SEQ ID NO:15; SEQ ID NOs:68-70, which each encode a polypeptide comprising the sequence SEQ ID NO:23; SEQ ID NOs:71-73, which each encode a polypeptide comprising the sequence SEQ ID NO:27; SEQ ID NOs:74-76, which each encode a polypeptide comprising the sequence SEQ ID NO:30; SEQ ID NOs:77-79, which each encode a polypeptide comprising the sequence SEQ ID NO:37; SEQ ID NOs:80-82 and 90, which each encode a polypeptide comprising the sequence SEQ ID NO:38; SEQ ID NOs:83-85, which each encode a polypeptide comprising the sequence SEQ ID NO:41; and SEQ ID NOs:86-88, which each encode a polypeptide comprising the sequence SEQ ID NO:44.

The invention also provides isolated or recombinant polynucleotides that each comprise a nucleic acid sequence which encodes a polypeptide comprising an amino acid sequence which (a) differs in 1 to 16 amino acid positions (such as in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions) from SEQ ID NO:1 and (b) comprises one or more substitutions relative to SEQ ID NO:1 selected from the group consisting of F48A/L, V51P, F55A, F65A, F68P, L111A, and V114P; or, a complementary nucleic acid sequence thereof. Some polypeptides encoded by polynucleotides of the invention further comprise one or more additional amino acid(s), such as a methionine added to the N-terminus. In some instances the encoded polypeptide exhibits an interferon-alpha activity.

The invention also provides isolated or recombinant polynucleotides that each comprise a nucleic acid sequence which encodes a polypeptide comprising an amino acid sequence which (a) differs in 1 to 16 amino acid positions (such as in 1, 2, 3, 4, 5, 6, 7, 8, 9, 10, 11, 12, 13, 14, 15, or 16 amino acid positions, e.g., in 1-15 amino acid positions, in 1-14 amino acid positions, in 1-13 amino acid positions, in 1-12 amino acid positions, 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions) from SEQ ID NO:36 and (b) comprises one or more substitutions relative to SEQ ID NO:36 selected from the group consisting of M21A, I24P, F48A/L, T51P, S55A, F65A, F68P, F90A, M93P, L111A, V114P, F124A, I127P, and E160D; or, a complementary nucleic acid sequence thereof. Some polypeptides encoded by polynucleotides of the invention further comprise one or more additional amino acid(s), such as a methionine added to the N-terminus. In some instances the encoded polypeptide exhibits an interferon-alpha activity.

The invention also provides isolated or recombinant polynucleotides that each comprise a nucleic acid sequence which encodes a polypeptide comprising an amino acid sequence having at least 90% sequence identity (e.g., at least about 91%, at least about 92%, at least about 93%, at least about 94%, at least about 95%, at least about 96%, at least about 97%, at least about 98%, or at least about 99% amino acid sequence identity) to any one of SEQ ID NOs:1-35, wherein the amino acid sequence comprises one or more of: Ala or Leu at position 48; Pro at position 51; Ala at position 55; Ala at position 65; Pro at position 68; Ala at position 111; and Pro at position 114, position numbering relative to SEQ ID NO:1; or, a complementary nucleic acid sequence thereof. Some polypeptides encoded by polynucleotides of the invention further comprise one or more additional amino acid(s), such as a methionine added to the N-terminus. In some instances the encoded polypeptide exhibits an interferon-alpha activity.

The invention also provides isolated or recombinant polynucleotides that each comprise a nucleic acid sequence which encodes a polypeptide comprising an amino acid sequence having at least 90% sequence identity (e.g., at least about 91%, at least about 92%, at least about 93%, at least about 94%, at least about 95%, at least about 96%, at least about 97%, at least about 98%, or at least about 99% amino acid sequence identity) to any one of SEQ ID NOs:36-44, wherein the amino acid sequence comprises one or more of: Ala at position 21; Pro at position 24; Ala or Leu at position 48; Pro at position 51; Ala at position 55; Ala at position 65; Pro at position 68; Ala at position 90; Pro at position 93; Ala at position 111; Pro at position 114; Ala at position 124; Pro at position 127; and Asp at position 160, position numbering relative to SEQ ID NO:36; or, a complementary nucleic acid sequence thereof. Some polypeptides encoded by polynucleotides of the invention further comprise one or more additional amino acid(s), such as a methionine added to the N-terminus. In some instances the encoded polypeptide exhibits an interferon-alpha activity.

Additional Aspects

Any of the polynucleotides of the invention (which includes those described above) may encode a fusion protein comprising at least one additional amino acid sequence, such as, for example, a secretion/localization sequence, a sequence useful for solubilization or immobilization (e.g., for cell surface display) of the polypeptide, a sequence useful for detection and/or purification of the polypeptide (e.g., a polypeptide purification subsequence, such as an epitope tag, a polyhistidine sequence, and the like). In another aspect, the invention provides cells comprising one or more of the polynucleotides of the invention. Such cells may express one or more polypeptides encoded by the polynucleotides of the invention.

The invention also provides vectors comprising any of the polynucleotides of the invention. Such vectors may comprise a plasmid, a cosmid, a phage, a virus, or a fragment of a virus. Such vectors may comprise an expression vector, and, if desired, the nucleic acid is operably linked to a promoter, including those discussed herein and below. Furthermore, in another aspect, the invention provides compositions comprising an excipient or carrier and at least one of any of the polynucleotides of the invention, or vectors, cells, or host comprising such nucleic acids. Such composition may be pharmaceutical compositions, and the excipient or carrier may be a pharmaceutically acceptable excipient or carrier.

The invention also includes compositions comprising two or more nucleic acids of the invention, or fragments thereof (e.g., as substrates for recombination). The composition can comprise a library of recombinant nucleic acids, where the library contains at least 2, at least 3, at least 5, at least 10, at least 20, at least 50, or at least 100 or more nucleic acids described above. The nucleic acids are optionally cloned into expression vectors, providing expression libraries.

The polynucleotides of the invention and fragments thereof, as well as vectors comprising such polynucleotides, may be employed for therapeutic or prophylactic uses in combination with a suitable carrier, such as a pharmaceutical carrier. Such compositions comprise a therapeutically and/or prophylactically effective amount of the compound, and a pharmaceutically acceptable carrier or excipient. Such a carrier or excipient includes, but is not limited to, saline, buffered saline, dextrose, water, glycerol, ethanol, and combinations thereof. The formulation should suit the mode of administration. Methods of administering nucleic acids, polypeptides, and proteins are well known in the art, and are further discussed below.

The invention also includes compositions produced by digesting one or more of any of the nucleic acids of the invention with a restriction endonuclease, an RNAse, or a DNAse (e.g., as is performed in certain of the recombination formats noted above); and compositions produced by fragmenting or shearing one or more nucleic acids of the invention by mechanical means (e.g., sonication, vortexing, and the like), which can also be used to provide substrates for recombination in the methods described herein. The invention also provides compositions produced by cleaving at least one of any of the nucleic acids of the invention. The cleaving may comprise mechanical, chemical, or enzymatic cleavage, and the enzymatic cleavage may comprise cleavage with a restriction endonuclease, an RNAse, or a DNAse.

Also included in the invention are compositions produced by a process comprising incubating one or more of the fragmented nucleic acids of the invention in the presence of ribonucleotide or deoxyribonucleotide triphosphates and a nucleic acid polymerase. This resulting composition forms a recombination mixture for many of the recombination formats noted above. The nucleic acid polymerase may be an RNA polymerase, a DNA polymerase, or an RNA-directed DNA polymerase (e.g., a "reverse transcriptase"); the polymerase can be, e.g., a thermostable DNA polymerase (e.g., VENT, TAQ, or the like).

Similarly, compositions comprising sets of oligonucleotides corresponding to more than one nucleic acids of the invention are useful as recombination substrates and are a feature of the invention. For convenience, these fragmented, sheared, or oligonucleotide synthesized mixtures are referred to as fragmented nucleic acid sets.

The invention also provides an isolated or recombinant nucleic acid encoding a polypeptide that exhibits an interferon-alpha activity, produced by mutating or recombining at least one nucleic acid of the invention.

Making Polynucleotides

Polynucleotides, oligonucleotides, and nucleic acid fragments of the invention can be prepared by standard solid-phase methods, according to known synthetic methods. Typically, fragments of up to about 100 bases are individually synthesized, then joined (e.g., by enzymatic or chemical ligation methods, or polymerase mediated recombination methods) to form essentially any desired continuous sequence. For example, the polynucleotides and oligonucleotides of the invention can be prepared by chemical synthesis using, e.g., classical phosphoramidite method described by, e.g., Beaucage et al. (1981) Tetrahedron Letters 22:1859-69, or the method described by Matthes et al. (1984) EMBO J. 3:801-05, e.g., as is typically practiced in automated synthetic methods. According to the phosphoramidite method, oligonucleotides are synthesized, e.g., in an automatic DNA synthesizer, purified, annealed, ligated and cloned into appropriate vectors.

In addition, essentially any polynucleotide can be custom ordered from any of a variety of commercial sources, such as Operon Technologies Inc. (Alameda, Calif.) and many others. Similarly, peptides and antibodies can be custom ordered from any of a variety of sources, e.g., Celtek Peptides (Nashville, Tenn.); Washington Biotechnology, Inc. (Baltimore Md.); Global Peptide Services (Ft. Collin Colo.), and many others.

Certain polynucleotides of the invention may also be obtained by screening cDNA libraries (e.g., libraries generated by recombining homologous nucleic acids as in typical recursive sequence recombination methods) using oligonucleotide probes that can hybridize to or PCR-amplify polynucleotides which encode interferon-alpha polypeptides and fragments of those polypeptides. Procedures for screening and isolating cDNA clones are well-known to those of skill in the art. Such techniques are described in, e.g., Berger and Kimmel, Guide to Molecular Cloning Techniques, Methods in Enzymol. Vol. 152, Acad. Press, Inc., San Diego, Calif. ("Berger"); Sambrook, supra, and Current Protocols in Molecular Biology, Ausubel, supra. Some polynucleotides of the invention can be obtained by altering a naturally occurring sequence, e.g., by mutagenesis, recursive sequence recombination (e.g., shuffling), or oligonucleotide recombination. In other cases, such polynucleotides can be made in silico or through oligonucleotide recombination methods as described in the references cited herein.

As described in more detail herein, the polynucleotides of the invention include polynucleotides that encode polypeptides of the invention, polynucleotide sequences complementary to these polynucleotide sequences, and polynucleotides that hybridize under at least stringent conditions to the sequences defined herein. A coding sequence refers to a polynucleotide sequence encoding a particular polypeptide or domain, region, or fragment of said polypeptide. A coding sequence may encode (code for) a polypeptide of the invention exhibiting an interferon alpha activity as described above. The polynucleotides of the invention may be in the form of RNA or in the form of DNA, and include mRNA, cRNA, synthetic RNA and DNA, and cDNA. The polynucleotides may be double-stranded or single-stranded, and if single-stranded, can be the coding strand or the non-coding (anti-sense, complementary) strand. The polynucleotides of the invention include the coding sequence of a polypeptide of the invention (i) in isolation, (ii) in combination with one or more additional coding sequences, so as to encode, e.g., a fusion protein, a pre-protein, a prepro-protein, or the like, (iii) in combination with non-coding sequences, such as introns, control elements, such as a promoter (e.g., naturally occurring or recombinant or shuffled promoter), a terminator element, or 5' and/or 3' untranslated regions effective for expression of the coding sequence in a suitable host, and/or (iv) in a vector, cell, or host environment in which the coding sequence is a heterologous gene.

Polynucleotides of the invention can also be found in combination with typical compositional formulations of nucleic acids, including in the presence of carriers, buffers, adjuvants, excipients, and the like, as are known to those of ordinary skill in the art. Polynucleotide fragments typically comprise at least about 200 nucleotide bases, such as at least about 250, 300, 350, 400, 450, 460, 470, or more bases. The nucleotide fragments of polynucleotides of the invention may hybridize under highly stringent conditions to a polynucleotide sequence described herein and/or encode amino acid sequences having at least one of the properties of polypeptides of the invention described herein.

Modified Coding Sequences

As will be understood by those of ordinary skill in the art, it can be advantageous to modify a coding sequence to enhance its expression in a particular host. The genetic code is redundant with 64 possible codons, but most organisms preferentially use a subset of these codons. The codons that are utilized most often in a species are considered optimal codons, and those not utilized very often are classified as rare or low-usage codons (see, e.g., Zhang, S. P. et al. (1991) Gene 105:61-72). Codons can be substituted to reflect the preferred codon usage of the host, a process sometimes termed "codon optimization" or "controlling for species codon bias."

Modified coding sequence containing codons preferred by a particular prokaryotic or eukaryotic host (see, e.g., Murray, E. et al. (1989) Nuc Acids Res 17:477-508; Griswold et al., (2003) Protein Expr. Purif. 27(1):134-42) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA respectively. The preferred stop codon for monocotyledonous plants is UGA, whereas insects and *E. coli* prefer to use UAA as the stop codon (Dalphin, M. E. et al. (1996) Nucl. Acids Res. 24:216-218).

The polynucleotide sequences of the present invention can be engineered in order to alter a coding sequence of the invention for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns, to introduce or remove attachment groups (e.g., for pegylation or other conjugation), to change codon preference, to introduce splice sites, etc.

Silent Variations

Because of the degeneracy of the genetic code, a large number of functionally identical nucleic acids encode any given polypeptide. For instance, inspection of the codon table below (Table 5) shows that codons AGA, AGG, CGA, CGC, CGG, and CGU all encode the amino acid arginine. Thus, at every position in a nucleic acid sequence where an arginine is specified by a codon, the codon can be altered to any of the corresponding codons described above without altering the encoded polypeptide. Such nucleic acid variations are "silent variations". It is to be understood that U in an RNA sequence corresponds to T in a DNA sequence.

TABLE 5

| Codon Table | | | | | | |
|---|---|---|---|---|---|---|
| Amino acid | | | Codon(s) | | | |
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |

TABLE 5-continued

Codon Table

| Amino acid | | | Codon(s) | | | | | |
|---|---|---|---|---|---|---|---|---|
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will thus be appreciated by those skilled in the art that due to the degeneracy of the genetic code, a multitude of nucleic acids sequences encoding polypeptides of the invention may be produced, some of which may bear minimal sequence identity to the nucleic acid sequences explicitly disclosed herein. One of ordinary skill in the art will recognize that each codon in a nucleic acid (except AUG and UGC, which are ordinarily the only codon for methionine and tryptophan, respectively) can be modified by standard techniques to encode a functionally identical polypeptide. Accordingly, each silent variation of a nucleic acid which encodes a polypeptide is implicit in any described sequence. The invention also provides each and every possible variation of a nucleic acid sequence encoding a polypeptide of the invention that can be made by selecting combinations based on possible codon choices. These combinations are made in accordance with the standard triplet (codon) genetic code (e.g., as set forth in Table 5), as applied to the nucleic acid sequence encoding a polypeptide of the invention. All such variations of every nucleic acid herein are specifically provided and described by consideration of the sequence in combination with the genetic code. One of skill is fully able to generate any silent substitution of the sequences listed herein.

Using Polynucleotides

The polynucleotides of the invention have a variety of uses in, for example, recombinant production (i.e., expression) of the polypeptides of the invention typically through expression of a plasmid expression vector comprising a sequence encoding the polypeptide or fragment thereof; as therapeutics; as prophylactics; as diagnostic tools; as immunogens; as adjuvants; as diagnostic probes for the presence of complementary or partially complementary nucleic acids (including for detection of a wild-type interferon-alpha nucleic acid), as substrates for further reactions, e.g., recursive sequence recombination reactions or mutation reactions to produce new and/or improved variants, and the like.

Vectors, Promoters, and Expression Systems

The present invention also includes recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), and the like, into which a nucleic acid sequence of the invention has been inserted, in a forward or reverse orientation. In some instances, the construct further comprises regulatory sequences, including, for example, a promoter, operably linked to the nucleic acid sequence. Large numbers of suitable vectors and promoters are known to those of skill in the art, and are commercially available.

General texts that describe molecular biological techniques useful herein, including the use of vectors, promoters and many other relevant topics, include Berger, supra; Sambrook (1989), supra, and Ausubel, supra. Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, all supra, as well as Mullis et al. (1987) U.S. Pat. No. 4,683,202; PCR Protocols: A Guide to Methods and Applications (Innis et al., eds.) Academic Press Inc. San Diego, Calif. (1990) ("Innis"); Arnheim & Levinson (Oct. 1, 1990) C&EN 36-47; The Journal Of NIH Research (1991) 3:81-94; (Kwoh et al. (1989) Proc Natl Acad Sci USA 86:1173-1177; Guatelli et al. (1990) Proc Natl Acad Sci USA 87:1874-1878; Lomeli et al. (1989) J Clin Chem 35:1826-1831; Landegren et al. (1988) Science 241:1077-1080; Van Brunt (1990) Biotechnology 8:291-294; Wu and Wallace (1989) Gene 4:560-569; Barringer et al. (1990) Gene 89:117-122, and Sooknanan and Malek (1995) Biotechnology 13:563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369:684-685 and the references therein, in which PCR amplicons of up to 40 kilobases (kb) are generated. One of skill will appreciate that essentially any RNA can be converted into a double stranded DNA suitable for restriction digestion, PCR expansion and sequencing using reverse transcriptase and a polymerase. See Ausubel, Sambrook and Berger, all supra.

The present invention also provides host cells that are transduced with vectors of the invention, and the production of polypeptides of the invention by recombinant techniques. Host cells are genetically engineered (e.g., transduced, transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying genes. The culture conditions, such as temperature, pH, and the like, are those previously used with the host cell selected for expression, and will be apparent to those skilled in the art and in the references cited herein, including, e.g., Freshney (1994) Culture of Animal Cells, a Manual of Basic Technique, third edition, Wiley-Liss, New York and the references cited therein.

The polypeptides of the invention can also be produced in non-animal cells such as plants, yeast, fungi, bacteria and the like. In addition to Sambrook, Berger and Ausubel, details regarding cell culture are found in, e.g., Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg N.Y.); Atlas & Parks (eds.) The Handbook of Microbiological Media (1993) CRC Press, Boca Raton, Fla.

The polynucleotides of the present invention and fragments thereof may be included in any one of a variety of expression vectors for expressing a polypeptide. Such vectors include chromosomal, nonchromosomal and synthetic DNA sequences, e.g., derivatives of SV40, bacterial plasmids, phage DNA, baculovirus, yeast plasmids, vectors derived from combinations of plasmids and phage DNA, viral DNA such as vaccinia, adenovirus, fowl pox virus, pseudorabies, adeno-associated virus, retroviruses and many others. Any vector that transduces genetic material into a cell, and, if replication is desired, which is replicable and viable in the relevant host can be used.

The nucleic acid sequence in the expression vector is operatively linked to an appropriate transcription control sequence (promoter) to direct mRNA synthesis. Examples of such promoters include: LTR or SV40 promoter, *E. coli* lac or trp promoter, phage lambda $P_L$ promoter, CMV promoter, and other promoters known to control expression of genes in prokaryotic or eukaryotic cells or their viruses. The expression vector also contains a ribosome binding site for translation initiation, and a transcription terminator. The vector optionally includes appropriate sequences for amplifying expression, e.g., an enhancer. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

The vector containing the appropriate DNA sequence encoding a polypeptide of the invention, as well as an appropriate promoter or control sequence, may be employed to transform an appropriate host to permit the host to express the polypeptide. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 or Bowes melanoma; plant cells, etc. It is understood that not all cells or cell lines need to be capable of producing fully functional polypeptides of the invention or fragments thereof; for example, antigenic fragments of the polypeptide may be produced in a bacterial or other expression system. The invention is not limited by the host cells employed.

In bacterial systems, a number of expression vectors may be selected depending upon the use intended for the polypeptide or fragment thereof. For example, when large quantities of a polypeptide or fragments thereof are needed for the induction of antibodies, vectors which direct high level expression of fusion proteins that are readily purified may be desirable. Such vectors include, but are not limited to, multifunctional *E. coli* cloning and expression vectors such as BLUESCRIPT (Stratagene), in which the nucleotide coding sequence may be ligated into the vector in-frame with sequences for the amino-terminal Met and the subsequent 7 residues of beta-galactosidase so that a hybrid protein is produced; pIN vectors (Van Heeke & Schuster (1989) J Biol Chem 264:5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the polypeptides of the invention. For reviews, see Ausubel, supra, Berger, supra, and Grant et al. (1987) Methods in Enzymology 153:516-544.

In mammalian host cells, a number of expression systems, such as viral-based systems, may be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome results in a viable virus capable of expressing a polypeptide of the invention in infected host cells (Logan and Shenk (1984) Proc Natl Acad Sci USA 81:3655-3659). In addition, transcription enhancers, such as the rous sarcoma virus (RSV) enhancer, are used to increase expression in mammalian host cells. Host cells, media, expression systems, and methods of production include those known for cloning and expression of various mammalian interferon-alphas (e.g., human interferon-alphas).

Additional Expression Elements

Specific initiation signals can aid in efficient translation of a polynucleotide coding sequence of the invention and/or fragments thereof. These signals can include, e.g., the ATG initiation codon and adjacent sequences. In cases where an coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous nucleic acid transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression can enhanced by the inclusion of enhancers appropriate to the cell system in use (see, e.g., Scharf D. et al. (1994) Results Probl Cell Differ 20:125-62; and Bittner et al. (1987) Methods in Enzymol 153:516-544).

Secretion/Localization Sequences

Polynucleotides encoding polypeptides of the invention can also be fused, for example, in-frame to nucleic acid encoding a secretion/localization sequence, to target polypeptide expression to a desired cellular compartment, membrane, or organelle, or to direct polypeptide secretion to the periplasmic space or into the cell culture media. Such sequences are known to those of skill, and include secretion leader or signal peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

Expression Hosts

In a further aspect, the present invention relates to host cells containing any of the above-described nucleic acids, vectors, or other constructs of the invention. The host cell can be a eukaryotic cell, such as a mammalian cell, a yeast cell, or a plant cell, or the host cell can be a prokaryotic cell, such as a bacterial cell. Introduction of the construct into the host cell can be effected by calcium phosphate transfection, DEAE-Dextran mediated transfection, electroporation, gene or vaccine gun, injection, or other common techniques (see, e.g., Davis, L., Dibner, M., and Battey, I. (1986) Basic Methods in Molecular Biology) for in vivo, ex vivo or in vitro methods.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre" or a "prepro" form of the protein may also be important for correct insertion, folding and/or function. Different host cells such as *E. coli, Bacillus* sp., yeast or mammalian cells such as CHO, HeLa, BHK, MDCK, HEK 293, WI38, etc. have specific cellular machinery and characteristic mechanisms for such post-translational activities and may be chosen to ensure the correct modification and processing of the introduced foreign protein.

Stable expression can be used for long-term, high-yield production of recombinant proteins. For example, cell lines which stably express a polypeptide of the invention are transduced using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. For example, resistant clumps of stably transformed cells can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The polypeptide produced by a recombinant cell may be secreted, membrane-bound, or contained intracellularly, depending on the sequence and/or the vector used. As will be understood by those of skill in the art, expression vectors containing polynucleotides encoding polypeptides of the invention can be designed with signal sequences which direct secretion of the mature polypeptides through a prokaryotic or eukaryotic cell membrane.

Additional Sequences

The polynucleotides of the present invention optionally comprise a coding sequence fused in-frame to a marker sequence which, e.g., facilitates purification and/or detection of the encoded polypeptide. Such purification subsequences include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I. et al. (1984) Cell 37:767), maltose binding protein sequences, the FLAG epitope utilized in the FLAGS extension/affinity purification system, and the like. The inclusion of a protease-cleavable polypeptide linker sequence between the purification domain and the polypeptide sequence is useful to facilitate purification.

For example, one expression vector possible to use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) Protein Expression and Purification 3:263-281) while the enterokinase cleavage site provides a method for separating the desired polypeptide from the polyhistidine region. pGEX vectors (Promega; Madison, Wis.) are optionally used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

An additional construction in the compositions and methods described herein provides for proteins, and their encoding nucleic acids, comprising polypeptides of the invention (or one or more fragments thereof), e.g., as described herein, fused to an Ig molecule, e.g., human IgG Fc ("fragment crystallizable," or fragment complement binding) hinge, CH2 domain and CH3 domain (and nucleotide sequences encoding them). Fc is the portion of the antibody responsible for binding to antibody receptors on cells and the C1q component of complement. These fusion proteins or fragments thereof and their encoding nucleic acids are optionally useful as prophylactic and/or therapeutic drugs or as diagnostic tools (see also, e.g., Challita-Eid, P. et al. (1998) J Immunol 160: 3419-3426; Sturmhoefel, K. et al. (1999) Cancer Res 59:4964-4972).

Polypeptide Production and Recovery

Following transduction of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Eukaryotic or microbial cells employed in expression of the proteins can be disrupted by any convenient method, including freeze-thaw cycling, sonication, mechanical disruption, or use of cell lysing agents, or other methods, which are well know to those skilled in the art.

As noted, many references are available for the culture and production of many cells, including cells of bacterial, plant, animal (especially mammalian) and archebacterial origin. See, e.g., Sambrook, Ausubel, and Berger (all supra), as well as Freshney (1994) Culture of Animal Cells, a Manual of Basic Technique, third edition, Wiley-Liss, New York and the references cited therein; Doyle and Griffiths (1997) Mammalian Cell Culture: Essential Techniques John Wiley and Sons, NY; Humason (1979) Animal Tissue Techniques, fourth edition W.H. Freeman and Company; and Ricciardelli et al. (1989) In vitro Cell Dev Biol 25:1016-1024. For plant cell culture and regeneration see, e.g., Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Plant Molecular Biology (1993) R. R. D. Croy (ed.) Bios Scientific Publishers, Oxford, U.K. ISBN 0 12 198370 6. Cell culture media in general are set forth in Atlas and Parks (eds.) The Handbook of Microbiological Media (1993) CRC Press, Boca Raton, Fla. Additional information for cell culture is found in available commercial literature such as the Life Science Research Cell Culture Catalogue from Sigma-Aldrich, Inc (St Louis, Mo.) ("Sigma-LSRCCC") and, e.g., the Plant Culture Catalogue and supplement also from Sigma-Aldrich, Inc (St Louis, Mo.) ("Sigma-PCCS").

Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein or fragments thereof. Finally, high performance liquid chromatography (HPLC) can be employed in the final purification steps. In addition to the references noted, supra, a variety of purification methods are well known in the art, including, e.g., those set forth in Sandana (1997) Bioseparation of Proteins, Academic Press, Inc.; Bollag et al. (1996) Protein Methods, $2^{nd}$ Edition Wiley-Liss, NY; Walker (1996) The Protein Protocols Handbook Humana Press, N.J.; Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3$^{rd}$ Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, N.J.

In Vitro Expression Systems

Cell-free transcription/translation systems can also be employed to produce polypeptides of the invention using polynucleotides of the present invention. Several such systems are commercially available. A general guide to in vitro transcription and translation protocols is found in Tymms (1995) In vitro Transcription and Translation Protocols: Methods in Molecular Biology Volume 37, Garland Publishing, NY.

In Vivo Uses and Applications

Polynucleotides that encode a polypeptide of the invention, or complements of the polynucleotides (including e.g., antisense or ribozyme molecules), are optionally administered to a cell to accomplish a therapeutically useful process or to express a therapeutically useful product. These in vivo applications, including gene therapy, include a multitude of techniques by which gene expression may be altered in cells. Such methods include, for instance, the introduction of genes for expression of, e.g., therapeutically and/or prophylactically useful polypeptides, such as the polypeptides of the present invention.

In Vivo Polypeptide Expression

Polynucleotides encoding polypeptides of the invention are particularly useful for in vivo therapeutic applications, using techniques well known to those skilled in the art. For example, cultured cells are engineered ex vivo with at least one polynucleotide (DNA or RNA) of the invention and/or other polynucleotide sequences encoding, e.g., at least one of an antigen, cytokine, other co-stimulatory molecule, adjuvant, etc., and the like, with the engineered cells then being returned to the patient. Cells may also be engineered in vivo for expression of one or more polypeptides in vivo, including polypeptides and/or antigenic peptides of the invention.

A number of viral vectors suitable for organismal in vivo transduction and expression are known. Such vectors include retroviral vectors (see, e.g., Miller, Curr Top Microbiol Immunol (1992) 158:1-24; Salmons and Gunzburg (1993) Human Gene Therapy 4:129-141; Miller et al. (1994) Methods in Enzymology 217:581-599) and adeno-associated vectors (reviewed in Carter (1992) Curr Opinion Biotech 3:533-539; Muzcyzka (1992) Curr Top Microbiol Immunol. 158: 97-129). Other viral vectors that are used include adenoviral vectors, herpes viral vectors and Sindbis viral vectors, as generally described in, e.g., Jolly (1994) Cancer Gene Therapy 1:51-64; Latchman (1994) Molec Biotechnol 2:179-195; and Johanning et al. (1995) Nucl Acids Res 23:1495-1501.

In one aspect, a pox virus vector can be used. The pox viral vector is transfected with a polynucleotide sequence encoding a polypeptide of the invention, such as an eIL-2 polypeptide, and is useful in prophylactic, therapeutic and diagnostic applications where enhancement of an immune response, such as e.g., increased or improved T cell proliferation is desired. See viral vectors discussed in, e.g., Berencsi et al., J Infect Dis (2001)183(8):1171-9; Rosenwirth et al., Vaccine 2001 Feb. 8; 19(13-14):1661-70; Kittlesen et al., J Immunol (2000) 164(8):4204-11; Brown et al. Gene Ther 2000 7(19): 1680-9; Kanesa-thasan et al., Vaccine (2000) 19(4-5):483-91; Sten (2000) Drug 60(2):249-71. Compositions comprising such vectors and an acceptable excipient are also a feature of the invention.

Gene therapy and genetic vaccines provide methods for combating chronic infectious diseases (e.g., HIV infection, viral hepatitis), as well as non-infectious diseases including cancer and some forms of congenital defects such as enzyme deficiencies, and such methods can be employed with polynucleotides of the invention, including, e.g., vectors and cells comprising such polynucleotides. Several approaches for introducing nucleic acids and vectors into cells in vivo, ex vivo and in vitro have been used and can be employed with polynucleotides of the invention, and vectors comprising such polynucleotides. These approaches include liposome based gene delivery (Debs and Zhu (1993) WO 93/24640 and U.S. Pat. No. 5,641,662; Mannino and Gould-Fogerite (1988) BioTechniques 6(7):682-691; Rose, U.S. Pat. No. 5,279,833; Brigham (1991) WO 91/06309; and Felgner et al. (1987) Proc Natl Acad Sci USA 84:7413-7414; Brigham et al. (1989) Am J Med Sci 298:278-281; Nabel et al. (1990) Science 249: 1285-1288; Hazinski et al. (1991) Am J Resp Cell Molec Biol 4:206-209; and Wang and Huang (1987) Proc Natl Acad Sci USA 84:7851-7855); adenoviral vector mediated gene delivery, e.g., to treat cancer (see, e.g., Chen et al. (1994) Proc Natl Acad Sci USA 91:3054-3057; Tong et al. (1996) Gynecol Oncol 61:175-179; Clayman et al. (1995) Cancer Res. 5:1-6; O'Malley et al. (1995) Cancer Res 55:1080-1085; Hwang et al. (1995) Am J Respir Cell Mol Biol 13:7-16; Haddada et al. (1995) Curr Top Microbiol Immunol. 1995 (Pt. 3):297-306; Addison et al. (1995) Proc Natl Acad Sci USA 92:8522-8526; Colak et al. (1995) Brain Res 691:76-82; Crystal (1995) Science 270:404-410; Elshami et al. (1996) Human Gene Ther 7:141-148; Vincent et al. (1996) J Neurosurg 85:648-654), and many others. Replication-defective retroviral vectors harboring therapeutic polynucleotide sequence as part of the retroviral genome have also been used, particularly with regard to simple MuLV vectors. See, e.g., Miller et al. (1990) Mol Cell Biol 10:4239 (1990); Kolberg (1992) J NIH Res 4:43, and Cornetta et al. (1991) Hum Gene Ther 2:215). Nucleic acid transport coupled to ligand-specific, cation-based transport systems (Wu and Wu (1988) J Biol Chem, 263:14621-14624) has also been used. Naked DNA expression vectors have also been described (Nabel et al. (1990), supra); Wolff et al. (1990) Science, 247:1465-1468). In general, these approaches can be adapted to the invention by incorporating nucleic acids encoding the polypeptides of the invention into the appropriate vectors.

General texts which describe gene therapy protocols, which can be adapted to the present invention by introducing the nucleic acids of the invention into patients, include, e.g., Robbins (1996) Gene Therapy Protocols, Humana Press, N.J., and Joyner (1993) Gene Targeting: A Practical Approach, IRL Press, Oxford, England.

Antisense Technology

In addition to expression of the nucleic acids of the invention as gene replacement nucleic acids, the nucleic acids are also useful for sense and anti-sense suppression of expression, e.g., to down-regulate expression of a nucleic acid of the invention, once, or when, expression of the nucleic acid is no-longer desired in the cell. Similarly, the nucleic acids of the invention, or subsequences or anti-sense sequences thereof, can also be used to block expression of naturally occurring homologous nucleic acids. A variety of sense and anti-sense technologies are known in the art, e.g., as set forth in Lichtenstein and Nellen (1997) Antisense Technology: A Practical Approach IRL Press at Oxford University, Oxford, England, and in Agrawal (1996) Antisense Therapeutics Humana Press, N.J., and the references cited therein.

Use as Probes

Also contemplated are uses of polynucleotides, also referred to herein as oligonucleotides, typically having at least 12 bases, preferably at least 15, more preferably at least 20, at least 30, or at least 50 or more bases, which hybridize under highly stringent conditions to a polynucleotide of the invention, or fragments thereof. The polynucleotides may be used as probes, primers, sense and antisense agents, and the like, according to methods as noted supra.

Nucleic Acid Hybridization

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology—Hybridization with Nucleic Acid Probes, part I, chapter 2, "Overview of principles of hybridization and the strategy of nucleic acid probe assays," (Elsevier, N.Y.) (hereinafter "Tjissen"), as well as in Ausubel, supra, Hames and Higgins (1995) Gene Probes 1, IRL Press at Oxford University Press, Oxford, England (Hames and Higgins 1) and Hames and Higgins (1995) Gene Probes 2, IRL Press at Oxford University Press, Oxford, England (Hames and Higgins 2) provide details on the synthesis, labeling, detection and quantification of DNA and RNA, including oligonucleotides.

An indication that two nucleic acid sequences are substantially identical is that the two molecules hybridize to each other under at least stringent conditions. The phrase "hybridizing specifically to," refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization wash conditions" and "stringent hybridization conditions" in the context of nucleic acid hybridization experiments, such as Southern and northern hybridizations, are sequence dependent, and are different under different environmental parameters. An extensive guide to hybridization of nucleic acids is found in Tijssen (1993), supra, and in Hames and Higgins 1 and Hames and Higgins 2, supra.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched probe. In other words, the $T_m$ indicates the temperature at which the nucleic acid duplex is 50% denatured under the given conditions and its represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides. Typically, under "stringent conditions," a probe will hybridize to its target subsequence, but to no other sequences. "Very stringent conditions" are selected to be equal to the $T_m$ for a particular probe.

After hybridization, unhybridized nucleic acid material can be removed by a series of washes, the stringency of which can be adjusted depending upon the desired results. Low stringency washing conditions (e.g., using higher salt and lower temperature) increase sensitivity, but can product non-specific hybridization signals and high background signals. Higher stringency conditions (e.g., using lower salt and higher temperature that is closer to the hybridization temperature) lowers the background signal, typically with only the specific signal remaining. See, Rapley, R. and Walker, J. M. eds., Molecular Biomethods Handbook (Humana Press, Inc. 1998) (hereinafter "Rapley and Walker"), which is incorporated herein by reference in its entirety for all purposes.

The $T_m$ of a DNA-DNA duplex can be estimated using equation (1):

$$T_m(° C.)=81.5° C.+16.6(\log_{10} M)+0.41(\% G+C)-0.72(\%f)-500/n,$$

where M is the molarity of the monovalent cations (usually Na+), (% G+C) is the percentage of guanosine (G) and cystosine (C) nucleotides, (% f) is the percentage of formalize and n is the number of nucleotide bases (i.e., length) of the hybrid. See, Rapley and Walker, supra.

The $T_m$ of an RNA-DNA duplex can be estimated using equation (2):

$$T_m(° C.)=79.8° C.+18.5(\log_{10} M)+0.58(\% G+C)^2-11.8(\% G+C)^2-0.56(\%f)-820/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. Id. Equations 1 and 2 above are typically accurate only for hybrid duplexes longer than about 100-200 nucleotides. Id.

The Tm of nucleic acid sequences shorter than 50 nucleotides can be calculated as follows:

$T_m$ (° C.)=4(G+C)+2(A+T), where A (adenine), C, T (thymine), and G are the numbers of the corresponding nucleotides.

An example of stringent hybridization conditions for hybridization of complementary nucleic acids which have more than 100 complementary residues on a filter in a Southern or northern blot is 50% formalin (or formamide) with 1 mg of heparin at 42° C., with the hybridization being carried out overnight. An example of stringent wash conditions is a 0.2×SSC wash at 65° C. for 15 minutes (see Sambrook, supra, for a description of SSC buffer). Often, the high stringency wash is preceded by a low stringency wash to remove background probe signal. An example low stringency wash is 2×SSC at 40° C. for 15 minutes. An example of highly stringent wash conditions is 0.15M NaCl at 72° C. for about 15 minutes. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na+ion, typically about 0.01 to 1.0 M Na+ ion concentration (or other salts) at pH 7.0 to 8.3, and the temperature is typically at least about 30° C. Stringent conditions can also be achieved with the addition of destabilizing agents such as formamide.

In general, a signal to noise ratio of 2× or 2.5×-5× (or higher) than that observed for an unrelated probe in the particular hybridization assay indicates detection of a specific hybridization. Detection of at least stringent hybridization between two sequences in the context of the present invention indicates relatively strong structural similarity or homology to, e.g., the nucleic acids of the present invention provided in the sequence listings herein.

As noted, "highly stringent" conditions are selected to be about 5° C. or less lower than the thermal melting point ($T_m$) for the specific sequence at a defined ionic strength and pH. Target sequences that are closely related or identical to the nucleotide sequence of interest (e.g., "probe") can be identified under highly stringency conditions. Lower stringency conditions are appropriate for sequences that are less complementary. See, e.g., Rapley and Walker; Sambrook, all supra.

Comparative hybridization can be used to identify nucleic acids of the invention, and this comparative hybridization method is a preferred method of distinguishing nucleic acids of the invention. Detection of highly stringent hybridization between two nucleotide sequences in the context of the present invention indicates relatively strong structural similarity/homology to, e.g., the nucleic acids provided in the sequence listing herein. Highly stringent hybridization between two nucleotide sequences demonstrates a degree of similarity or homology of structure, nucleotide base composition, arrangement or order that is greater than that detected by stringent hybridization conditions. In particular, detection of highly stringent hybridization in the context of the present invention indicates strong structural similarity or structural homology (e.g., nucleotide structure, base composition, arrangement or order) to, e.g., the nucleic acids provided in the sequence listings herein. For example, it is desirable to identify test nucleic acids which hybridize to the exemplar nucleic acids herein under stringent conditions.

Thus, one measure of stringent hybridization is the ability to hybridize to one of the listed nucleic acids of the invention (e.g., nucleic acid sequences SEQ ID NOS:59-88, and complementary polynucleotide sequences thereof) under highly stringent conditions (or very stringent conditions, or ultra-high stringency hybridization conditions, or ultra-ultra high stringency hybridization conditions). Stringent hybridization (including, e.g., highly stringent, ultra-high stringency, or ultra-ultra high stringency hybridization conditions) and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions are gradually increased until a probe comprising one or more nucleic acid sequences selected from SEQ ID NOS:59-88, and complementary polynucleotide sequences thereof, binds to a perfectly matched complementary target (again, a nucleic acid comprising one or more nucleic acid sequences selected from SEQ ID NOS: 59-88, and complementary polynucleotide sequences thereof), with a signal to noise ratio that is at least 2.5×, and optionally 5× or more as high as that observed for hybridization of the probe to an unmatched target. In this case, the unmatched target is a nucleic acid corresponding to, e.g., a known interferon-alpha nucleic acid sequence (e.g., an interferon-alpha nucleic acid sequence present in a public database such as GenBank or GENESEQ at the time of filing of the subject application).

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 2.5×-10×, typically 5×-10× as high as that observed for hybridization to any of the unmatched target nucleic acids such as, e.g., a known interferon-alpha nucleic acid sequence as set forth above. For some such nucleic acids, the stringent conditions are selected such that a perfectly complementary oligonucleotide to the coding oligonucleotide hybridizes to the coding oligonucleotide with at least about a 5× higher signal to noise ratio than for hybridization of the perfectly complementary oligonucleotide to a control nucleic acid corresponding to a known interferon-alpha sequence as set forth above.

Ultra high-stringency hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids, such as, e.g., a known interferon-alpha nucleic acid sequence as set forth above. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids, such as, e.g., a known interferon-alpha nucleic acid sequence as set forth above. A target nucleic acid which hybridizes to a probe under such conditions, with a signal to noise ratio of at least ½ that of the perfectly matched complementary target nucleic acid is said to bind to the probe under ultra-ultra-high stringency conditions.

Target nucleic acids which hybridize to one or more nucleic acids represented by SEQ ID NOS:59-88 under high, ultra-high and ultra-ultra high stringency conditions are a feature of the invention. Examples of such nucleic acids include those with one or a few silent or conservative nucleic acid substitutions as compared to a given nucleic acid sequence.

Therapeutic Uses

Various interferon-alpha polypeptides and interferon-alpha conjugates have been approved or are currently in clinical development for treatment of a variety of conditions such as Chronic Hepatitis C, Chronic Hepatitis B, Hairy Cell Leukemia, Malignant Melanoma, Follicular Lymphoma, Condylomata Acuminata, AIDS-related Kaposi's Sarcoma, Non-Hodgkin's Lymphoma, Chronic Melogenous Leukemia, Basal Cell Carcinoma, Multiple Myeloma, carcinoid tumors, bladder cancer, Crohn's Disease, Cutaneous T Cell Lymphoma, Renal Cell Carcinoma, Multiple Sclerosis, and AIDS. Accordingly, the present invention includes a method of treating a condition which is responsive to interferon-alpha, such as for example a condition described above, comprising administering to a subject afflicted with the condition a composition comprising a polypeptide of the invention or a conjugate of the invention in an amount effective to ameliorate a symptom associated with the condition. The invention also includes the use of a composition comprising a polypeptide of the invention or a conjugate of the invention (i.e., a "composition of the invention") to treat a condition which is responsive to interferon-alpha, such as a condition described above, or any other condition which is responsive to a polypeptide of the invention or a conjugate of the invention.

Treatment of Viral Infections and Conditions Associated with Viral Infection

In one aspect, the invention provides a method for treating a subject infected with a virus, comprising administering to the subject a composition of the invention in an amount effective to decrease the level of the virus in the subject and/or to ameliorate a symptom or condition associated with the viral infection. Exemplary viral infections contemplated for treatment methods of the invention include, but are not limited to, infection by a virus of the Flaviviridae family, such as, for example, Hepatitis C Virus, Yellow Fever Virus, West Nile Virus, Japanese Encephalitis Virus, Dengue Virus, or Bovine Viral Diarrhea Virus; infection by a virus of the Hepadnaviridae family, such as, for example, Hepatitis B Virus; infection by a virus of the Picornaviridae family, such as, for example, Encephalomyocarditis Virus, Human Rhinovirus, or Hepatitis A Virus; infection by a virus of the Retroviridae family, such as, for example, Human Immunodeficiency Virus, Simian Immunodeficiency Virus, Human T-Lymphotropic Virus, or Rous Sarcoma Virus; infection by a virus of the Coronaviridae family, such as, for example, SARS coronavirus; infection by a virus of the Rhabdoviridae family, such as, for example, Rabies Virus or Vesicular Stomatitis Virus, infection by a virus of the Paramyxoviridae family, such as, for example, Respiratory Syncytial Virus or Parainfluenza Virus, infection by a virus of the Papillomaviridae family, such as, for example, Human Papillomavirus, and infection by a virus of the Herpesviridae family, such as, for example, Herpes Simplex Virus.

The following provides non-limiting examples for treatment of exemplary viral infections and diseases and conditions associated with such infections using polypeptides and conjugates of the invention, including suggested dosing schedules for polypeptides and conjugates of the invention and approaches to monitoring the efficacy of such treatments. The dosing schedules of polypeptides or conjugates of the invention for the treatment of other viral infections and diseases and conditions associated with viral infections, and approaches to monitoring the efficacy of such treatments, is ascertainable by one skilled in the art.

Hepatitis C Virus

In one aspect the invention provides a method of treating a patient infected with Hepatitis C Virus (HCV), comprising administering to the patient an effective amount of a composition of the invention comprising one or more polypeptide or conjugate of the invention. The invention also provides a composition for use in treating a patient infected with HCV, comprising one or more polypeptide or conjugate of the invention and a pharmaceutically acceptable carrier or excipient. A patient diagnosed as infected with HCV includes a patient exhibiting HCV RNA in the blood and/or exhibiting anti-HCV antibody in the serum.

A composition comprising a polypeptide of the invention will generally be administered at a dose and frequency similar to what is employed in HCV therapeutic regimens using clinically-approved interferon-alpha polypeptides, such as, e.g. ROFERON®-A (Interferon alfa-2a, recombinant; Hoffmann-La Roche Inc.), INTRON® A (Interferon alfa-2b, recombinant; Schering Corporation), and INFERGEN® (interferon alfacon-1; InterMune, Inc.). Exemplary recommended dosing schedules of ROFERON or INTRON A for the treatment of chronic HCV is 3 million IU (approximately 15 micrograms (mcg)) three times a week by subcutaneous injection for, e.g., 24 to 48 weeks. An exemplary recommended dosing schedule of INFERGEN for the treatment of chronic HCV is 9 mcg three times a week by subcutaneous injection for, e.g., 24 to 48 weeks. Depending on a number of factors (including but not limited to the activity and the pharmacokinetics of the polypeptide of the invention and the size and health of the patient), the polypeptide may be administered in lower amounts (such as, for example, about 2, 3, 4, 5, 6, 7, or 8 mcg) and/or less frequently (such as once per week or twice per week) than described above.

Likewise, a composition comprising a conjugate of the invention will generally be administered at a dose and frequency similar to what is employed in HCV therapeutic regimens using clinically-approved interferon-alpha conjugates, such as, e.g., PEGASYS® (Peginterferon alfa-2a; Hoffmann-La Roche, Inc.) or PEG-INTRON® (peginterferon alfa-2b; Schering Corporation). An exemplary recommended dosing schedule of PEGASYS for the treatment of chronic HCV is 180 mcg once weekly by subcutaneous injection for, e.g., 24 to 48 weeks. Depending on a number of factors (including but not limited to the molecular weight, activity, and pharmacokinetics of the conjugate of the invention and the size and health of the patient), the conjugate may be administered in lower amounts (such as, for example, about 25, 50, 75, 100, 125, or 150 mcg) and/or less frequently (such as once every 10 days, or once every 2 weeks) than described above.

In some instances the polypeptide or conjugate of the invention is administered in combination with one or more additional therapeutic agent(s). For example, the polypeptide or conjugate of the invention may be administered in combination with a small-molecule antiviral drug such as Ribavirin, which is sold under the names COPEGUS® (Hoffmann-La Roche, Inc) and REBETOL® (Schering Corporation). Alternatively, or in addition to a small-molecule antiviral drug, the polypeptide or conjugate of the invention may be administered in combination with one or more additional cytokine, such as, for example, IFN-gamma, which is sold under the name Actimmune® (interferon gamma-1b; InterMune, Inc.), IL-2, which is sold under the name PROLEUKIN® IL-2 (aldesleukin recombinant human interleukin-2 (rhIL-2); Chiron Corp.), or IL-12 (interleukin-12).

The precise amount and frequency of administration of the polypeptide or conjugate of the invention will depend on a number of factors such as the specific activity and the pharmacokinetic properties of the polypeptide or the conjugate, as well as the nature of the condition being treated (such as, the genotype of the Hepatitis C virus being treated), among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

The effectiveness of treatment may be determined by measuring viral load, for example by determining the titer or level of virus in serum or plasma using methods known in the art, such as, e.g., by monitoring viral RNA levels using quantitative PCR-based tests, such as the COBAS AMPLICOR® HCV Test, v2.0 or the COBAS AMPLICOR HCV MONITOR® Test, v2.0 (both from Roche Diagnostics). In some instances, an effective amount of a composition of the invention is one that is sufficient to achieve a reduction in viral load by at least 2 log units, at least 3 log units, at least 4 log units, at least 5 log units, at least 6 log units or at least 7 log units over the course of treatment, compared to the viral load prior to treatment (which is generally in the range of $10^5$-$10^7$ copies of HCV RNA/ml for chronic HCV patients). In some instances an effective amount of a composition of the invention is an amount that is sufficient to reduce viral load to levels which are essentially undetectable, such as, for example, less than about 500 copies/ml serum or less than about 100 copies/ml serum. The invention includes a method of reducing the level of HCV RNA in serum of a patient infected with HCV, comprising administering to the patient a composition of the invention in an amount effective to reduce the level of HCV RNA compared to the HCV RNA level present prior to the start of treatment.

The effectiveness of treatment may alternatively or in addition be determined by measuring a parameter indicative of a condition associated with HCV infection, such as, e.g., liver damage. For example, the level of serum alanine aminotransferase (ALT) may be measured using a standard assay. In general, an ALT level of less than about 50 international units/ml (IU/ml) serum is considered normal. A higher ALT level may be indicative of ongoing liver damage. In some instances, an effective amount of a composition of the invention is an amount effective to reduce ALT level, in a patient with a higher than normal ALT level, to less than about 50 IU/ml of serum. Thus, the invention includes a method of reducing the serum ALT level of a patient infected with HCV exhibiting an initial ALT level greater than 50 IU/ml, comprising administering to the patient a composition of the invention in an amount effective to reduce the ALT level to less than about 50 IU/ml.

Human Immunodeficiency Virus

In another aspect the invention provides a method of treating a patient infected with Human Immunodeficiency Virus (HIV), such as HIV-1 or HIV-2, or a disease or condition associated with HIV infection, such as, for example, AIDS-related Kaposi's sarcoma, comprising administering to the patient an effective amount of a composition of the invention comprising one or more polypeptide or conjugate of the invention, optionally in association with other antiviral therapeutic agents as described below. The invention also provides a composition for use in treating a patient infected with HIV or a disease or condition associated with HIV infection, comprising one or more polypeptide or conjugate of the invention and a pharmaceutically acceptable carrier or excipient. A patient diagnosed as infected with HIV includes a patient exhibiting detectable levels of HIV RNA or proviral DNA in the blood, and/or exhibiting detectable levels of p24 antigen or anti-HIV antibody in serum.

A composition comprising a polypeptide of the invention will generally be administered at a dose and frequency similar to what is employed in HIV therapeutic regimens using interferon-alpha polypeptides such as, e.g. ROFERON®-A (Interferon alfa-2a, recombinant; Hoffmann-La Roche Inc.), INTRON® A (Interferon alfa-2b, recombinant; Schering Corporation), and INFERGEN® (interferon alfacon-1; InterMune, Inc.). As was noted above, exemplary recommended dosing schedules of ROFERON or INTRON A for the treatment of chronic HCV is 3 million IU (approximately 15 micrograms (mcg)) three times a week by subcutaneous injection for, e.g., 24 to 48 weeks, and a exemplary recommended dosing schedule of INFERGEN for the treatment of chronic HCV is 9 mcg three times a week by subcutaneous injection for, e.g., 24 to 48 weeks. An exemplary recommended dosing schedule of ROFERON for the treatment of AIDS-related Kaposi's sarcoma is 36 million units daily for 10 to 12 weeks, then 36 million units 3 times a week. An exemplary recommended dosing schedule of INTRON A for the treatment of AIDS-related Kaposi's sarcoma is 30 million IU/m2 three times a week administered subcutaneously. Such dosing schedules provide useful ranges for dosage of a polypeptide of the invention for the treatment of HIV or a disease or condition associated with HIV infection. Depending on a number of factors (including but not limited to the activity and the pharmacokinetics of the polypeptide of the invention and the size, age and health of the patient), the polypeptide of the invention may be administered in lower amounts and/or less frequently than described above.

Likewise, a composition comprising a conjugate of the invention will generally be administered at a dose and frequency similar to what is employed in HIV therapeutic regimens using interferon-alpha conjugates, such as, e.g., PEGASYS® (Peginterferon alfa-2a; Hoffmann-La Roche, Inc.) or PEG-INTRON® (peginterferon alfa-2b; Schering Corporation). An exemplary dosing schedule of PEG-INTRON for the treatment of HIV is between about 1.0 mcg/kg/week and 3.0 mcg/kg/week by subcutaneous injection for, e.g., 24 to 48 weeks. Such a dosing schedule provides a useful range for dosage of a conjugate of the invention for the treatment of HIV. Depending on a number of factors (including but not limited to the molecular weight, activity, and pharmacokinetics of the conjugate of the invention and the size, age and health of the patient), the conjugate may be administered in lower amounts (such as, for example, about 0.1, 0.25, 0.50, or 0.75 mcg/kg/week) and/or less frequently (such as once every 10 days, or once every 2 weeks) than described above.

In some instances the polypeptide or conjugate of the invention is administered in combination with one or more additional therapeutic agent(s). Current clinical treatments of HIV-1 infection in man include multi-drug combination therapies generally termed Highly Active Antiretroviral Therapy ("HAART"). The polypeptide or conjugate of the invention may thus be administered in combination with HAART or other antiviral therapeutic compounds. Typical components of HAART, which involve various combinations of nucleoside reverse transcriptase inhibitors ("NRTI"), non-nucleoside reverse transcriptase inhibitors ("NNRTI") and HIV protease inhibitors ("PI"), are described, for example, in A. M. Vandamme et al. (1998) Antiviral Chemistry & Chemotherapy, 9:187-203; "Drugs for HIV Infection" in The Medical Letter Vol. 39 (Issue 1015) Dec. 5, 1997, pages 111-116; and published United States Patent Application US 20020182179 A1; each of which is incorporated by reference herein. If the HIV-infected patient is also infected with HCV, the polypeptide or conjugate of the invention may be administered in combination with an antiviral drug such as Ribavirin, which is sold under the names COPEGUS® (Hoffmann-La Roche, Inc) and REBETOL® (Schering Corporation), along with HAART.

The precise amount and frequency of administration of the polypeptide or conjugate of the invention, and administration of additional therapeutic agents such as HAART and/or Ribavirin, will depend on a number of factors such as the specific activity and the pharmacokinetic properties of the polypeptide or the conjugate, as well as the nature of the condition being treated (such as, the presence of additional viral infections such as HCV), among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

In addition to general uses described above, a polypeptide or conjugate of the invention may be administered to the following subsets of patients infected with HIV: as an adjuvant therapy, for example to HAART as described above; as monotherapy or combination therapy in early stage patients when the viral load is generally high; as a combined anti-viral and immunodulatory agent for patients undergoing structured treatment interruptions (STI) or "drug holidays"; as salvage therapy in patients whose HAART options are limited; as an antiviral method of treatment to keep viral load in check without initiating HAART therapy in order to delay the appearance of HAART resistant virus.

The effectiveness of treatment may be determined by measuring viral load, for example by determining the titer or level of virus in serum or plasma using methods known in the art, such as, e.g., by monitoring HIV-1 viral RNA levels using quantitative RT-PCR based tests, such as the AMPLICOR HIV-1 MONITOR® Test, v1.5 (Roche Diagnostics). In some instances, an effective amount of a composition of the invention is one that is sufficient to achieve a reduction in viral load by at least 0.5 log units, at least 1 log unit, at least 2 log units, at least 3 log units, at least 4 log units, at least 5 log units, at least 6 log units or at least 7 log units over the course of treatment, compared to the viral load prior to treatment. In some instances an effective amount of a composition of the invention is an amount that is sufficient to reduce viral load to levels which are essentially undetectable, such as, for example, less than about 50-100 copies HIV-1 RNA per ml serum. The invention includes a method of reducing the level of HIV RNA in serum of a patient infected with HIV, comprising administering to the patient a composition of the invention in an amount effective to reduce the level of HIV RNA compared to the HIV RNA level present prior to the start of treatment.

The effectiveness of treatment may alternatively or in addition be determined by a serum markers for HIV replication, such as the presence of HIV p24 antigen in the blood. In some instances an effective amount of a composition of the invention is an amount that is sufficient to reduce the level of p24 antigen in the blood to 50%, 25%, 10% or 5% of the level present prior to the start of treatment. In some instances an effective amount of a composition of the invention is an amount that is sufficient to reduce the level of p24 antigen to a level which is essentially undetectable. The invention includes a method of reducing the level of p24 antigen in serum of a patient infected with HIV, comprising administering to the patient a composition of the invention in an amount effective to reduce the level of p24 antigen compared to the p24 antigen level present prior to the start of treatment.

Hepatitis B Virus

In another aspect, the invention provides a method of treating a patient infected with Hepatitis B Virus (HBV), comprising administering to the patient an effective amount of a composition of the invention comprising one or more polypeptide or conjugate of the invention. The invention also provides a composition for use in treating a patient infected with HBV, comprising one or more polypeptide or conjugate of the invention and a pharmaceutically acceptable carrier or excipient.

A patient diagnosed as infected with HBV exhibits detectable hepatitis B surface antigen (HBsAg) in the serum. Chronic HBV infection is further categorized as either "replicative" or "non-replicative". In replicative infection, the patient usually has a relatively high serum concentration of viral DNA and detectable HBeAg, which is an alternatively processed protein of the HBV pre-core gene that is synthesized under conditions of high viral replication. However, in rare strains of HBV with mutations in the pre-core gene, replicative infection can occur in the absence of detectable serum HBeAg. Patients with chronic hepatitis B and replicative infection have a generally worse prognosis and a greater chance of developing cirrhosis and/or hepatocellular carcinoma than those without HBeAg. In non-replicative infection, the rate of viral replication in the liver is low, serum HBV DNA concentration is generally low and hepatitis Be antigen (HBeAg) is not detected.

A composition comprising a polypeptide of the invention will generally be administered at a dose and frequency similar to what is employed in HBV therapeutic regimens using clinically-approved interferon-alpha polypeptides, such as, e.g. INTRON® A (Interferon alfa-2b, recombinant; Schering Corporation). An exemplary recommended dosing schedule of INTRON A for the treatment of chronic HBV in adults is 30 to 35 million IU per week by subcutaneous or intramuscular injection, either as 5 million IU per day (qd) or as 10 million IU three times per week (tiw) for 16 weeks. Depending on a number of factors (including, but not limited to, the activity and the pharmacokinetics of the polypeptide of the invention, and the size and health of the patient), the polypeptide of the invention may be administered in lower amounts (such as, for example, about 5, 10, 15, 20, or 25 million IU per week) and/or less frequently (such as once per week or twice per week) than described above.

Likewise, a composition comprising a conjugate of the invention will generally be administered at a dose and frequency similar to what is employed in HBV therapeutic regimens using interferon-alpha conjugates currently undergoing clinical trials, such as, e.g., PEGASYS® (Peginterferon alfa-2a; Hoffmann-La Roche, Inc.). Exemplary dosing schedules of PEGASYS for the treatment of chronic HBV is between 90 mcg-270 mcg injected once per week for a total of 24 weeks. Depending on a number of factors (including but not limited to the molecular weight, activity, and pharmacokinetics of the conjugate of the invention and the size and health of the patient), the conjugate may be administered in lower amounts (such as, for example, about 25, 50, 75, 100, 125, 150, or 200 mcg) and/or less frequently (such as once every 10 days, or once every 2 weeks) than described above.

In some instances the polypeptide or conjugate of the invention is administered in combination with one or more additional therapeutic agent(s). For example, the polypeptide or conjugate of the invention may be administered in combination with antiviral drugs such as lamivudine (also known as 3TC), which is sold under the name Epivir-HBV® (GlaxoSmithKline), or adefovir dipivoxil, which is sold under the name Hepsera® (Gilead Sciences).

The precise amount and frequency of administration of the polypeptide or conjugate of the invention will depend on a number of factors such as the specific activity and the pharmacokinetic properties of the polypeptide or the conjugate, as well as the nature of the condition being treated (such as, e.g., in the case of chronic HBV infection, whether the infection is replicative or non-replicative), among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

The effectiveness of treatment may be determined for example by measuring the viral load, e.g. the level of viral DNA in serum or plasma, using methods known in the art. Methods for monitoring HBV DNA levels include quantitative PCR-based tests, such as the COBAS AMPLICOR HBV MONITOR® Test, v2.0 or the AMPLICOR HBV MONITOR® Test, v2.0 (both from Roche Diagnostics). In some instances an effective amount of a composition of the invention is an amount that is sufficient to reduce viral DNA to, e.g., less than about 500,000 copies/ml serum or less than about 100,000 copies/ml serum or less than about 10,000 copies/ml serum, or to levels which are essentially undetectable (such as, for example, less than about 1000 copies/ml serum, less than about 500 copies/ml serum, or less than about 200 copies/ml serum). The invention includes a method of reducing the level of HBV DNA in serum of a patient infected with HBV, comprising administering to the patient a composition of the invention in an amount effective to reduce the level of HBV DNA compared to the HBV DNA level present prior to the start of treatment.

The effectiveness of treatment may alternatively or in addition be determined by measuring other serum markers for HBV replication, such as HBeAg. In some instances an effective amount of a composition of the invention is an amount that is sufficient to reduce the level of HBeAg in serum to 50%, 25%, 10% or 5% of the level present prior to the start of treatment. In some instances an effective amount of a composition of the invention is an amount that is sufficient to reduce the level of HBeAg to a level which is essentially undetectable. The invention includes a method of reducing the level of HBeAg in serum of a patient infected with HBV, comprising administering to the patient a composition of the invention in an amount effective to reduce the level of HBeAg compared to the HBeAg level present prior to the start of treatment.

As discussed above, another serum marker indicative of HBV infection is HBsAg. Thus, the effectiveness of treatment may alternatively or in addition be determined by measuring the level of HBsAg in the serum. In some instances an effective amount of a composition of the invention is an amount that is sufficient to reduce the level of HBsAg in serum to 50%, 25%, 10% or 5% of the level present prior to the start of treatment. In some instances an effective amount of a composition of the invention is an amount that is sufficient to reduce level of HBsAg to a level which is essentially undetectable. The invention includes a method of reducing the level of HBsAg in serum of a patient infected with HBV, comprising administering to the patient a composition of the invention in an amount effective to reduce the level of HBsAg compared to the HBsAg level present prior to the start of treatment.

The effectiveness of treatment may alternatively or in addition be determined by measuring a parameter indicative of a condition associated with HBV infection, such as, e.g., liver damage. For example, the level of serum alanine aminotransferase (ALT) may be measured using a standard assay. In general, an ALT level of less than about 50 international units/ml (IU/ml) serum is considered normal. A higher ALT level may be indicative of ongoing liver damage. In some instances, an effective amount of a composition of the invention is an amount effective to reduce ALT level, in a patient with a higher than normal ALT level, to less than about 50 IU/ml of serum. Thus, the invention includes a method of reducing the serum ALT level of a patient infected with HBV exhibiting an initial ALT level greater than 50 IU/ml, comprising administering to the patient a composition of the invention in an amount effective to reduce the ALT level to less than about 50 IU/ml.

Human T-Lymphotropic Virus Type 1

In another aspect the invention provides a method of treating a patient infected with Human T-Lymphotropic Virus type 1 (HTLV-1), or a disease or condition associated with HTLV-1 infection, such as, for example, adult T-cell leukemia/lymphoma (ATLL), HTLV-1-associated myelopathy (HAM), Tropical Spastic Paraparesis (TSP), uveitis, or arthropathy. The method comprises administering to the patient an effective amount of a composition of the invention comprising one or more polypeptide or conjugate of the invention. The invention also provides a composition for use in treating a patient infected with HTLV-1, or a disease or condition associated with HTLV-1 infection, the composition comprising one or more polypeptide or conjugate of the invention and a pharmaceutically acceptable carrier or excipient. A patient diagnosed with HTLV-1 infection includes a patient exhibiting HTLV-1 proviral DNA in the blood and/or antibody to an HTLV-1 antigen in the serum.

A composition comprising a polypeptide of the invention will generally be administered at a dose and frequency similar to what is employed in HCV or oncology therapeutic regimens using clinically-approved interferon-alpha polypeptides, such as, e.g. ROFERON®-A (Interferon alfa-2a, recombinant; Hoffmann-La Roche Inc.) and INTRON® A (Interferon alfa-2b, recombinant; Schering Corporation). Exemplary recommended dosing schedules of ROFERON or INTRON A for the treatment of chronic HCV is 3 million IU (approximately 15 micrograms (mcg)) three times a week by subcutaneous injection for, e.g., 24 to 48 weeks. An exemplary recommended dosing schedule of ROFERON for the treatment of hairy-cell leukemia is 3-5 million units daily by subcutaneous injection for 16 to 24 weeks, then 3 million units 3 times a week for maintenance. An exemplary recommended dosing schedule of INTRON A for the treatment of hairy-cell leukemia is 2 million IU/m2 (square meter of body surface) administered subcutaneously 3 times a week for 6 months. Such dosing schedules provide useful ranges for dosage of a polypeptide of the invention for the treatment of HTLV-1 infection, or a disease or condition associated with HTLV-1 infection such as adult T-cell leukemia/lymphoma (ATLL), HTLV-1-associated myelopathy (HAM), or Tropical Spastic Paraparesis (TSP). Depending on a number of factors (including but not limited to the activity and the pharmacokinetics of the polypeptide of the invention and the size, age and health of the patient), the polypeptide may be administered in lower amounts and/or less frequently than described above.

Likewise, a composition comprising a conjugate of the invention will generally be administered at a dose and frequency similar to what is employed in HCV therapeutic or oncology therapeutic regimens using clinically-approved interferon-alpha conjugates, such as, e.g., PEGASYS® (Peginterferon alfa-2a; Hoffmann-La Roche, Inc.) or PEG-INTRON® (peginterferon alfa-2b; Schering Corporation). An exemplary recommended dosing schedule of PEGASYS for the treatment of chronic HCV is 180 mcg once weekly by subcutaneous injection for, e.g., 24 to 48 weeks. An exemplary recommended dosing schedule of PEG-INTRON for the treatment of chronic myelogenous leukemia is 6 mcg/kg body weight once weekly by subcutaneous injection for, e.g., 52 weeks. Such dosing schedules provide useful ranges for dosage of a conjugate of the invention for the treatment of HTLV-1 infection, or a disease or condition associated with HTLV-1 infection such as adult T-cell leukemia/lymphoma (ATLL), HTLV-1-associated myelopathy (HAM), or Tropical Spastic Paraparesis (TSP). Depending on a number of factors (including but not limited to the molecular weight, activity, and pharmacokinetics of the conjugate of the invention and the size, age and health of the patient), the conjugate may be administered in lower amounts and/or less frequently than described above.

In some instances the polypeptide or conjugate of the invention is administered in combination with one or more additional therapeutic agent(s). For example, the polypeptide or conjugate of the invention may be administered in combination with an antiretroviral drug such as zidovudine (AZT) and/or lamivudine (3TC). It may also be administered in combination with peripheral blood stem cell transplantation, conventional chemotherapy, or high dose chemotherapy with autologous or allogeneic bone marrow transplantation. Alternatively, the polypeptide or conjugate of the invention may be combined with other immunotherapy, for example with anti-interleukin-2 receptor monoclonal antibodies or injection of cytotoxic T-cells directed against virus antigens.

The precise amount and frequency of administration of the polypeptide or conjugate of the invention will depend on a number of factors such as the specific activity and the pharmacokinetic properties of the polypeptide or the conjugate, as well as the nature of the condition being treated, among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

The effectiveness of treatment may be determined by measuring the HTLV-1 viral load, such as, for example, measuring the level of HTLV-1 proviral DNA in the blood using methods known in the art, for example by quantitative PCR as described by Saito et al., (2004) J. Infect Dis. 189(1):29-40. In some instances, an effective amount of a composition of the invention is one that is sufficient to achieve a reduction in viral load by at least 0.5 log unit, such as at least 1 log unit, at least 2 log units, at least 3 log units, at least 4 log units, at least 5 log units, at least 6 log units, or at least 7 log units over the course of treatment, compared to the viral load prior to treatment. In some instances an effective amount of a composition of the invention is an amount that is sufficient to reduce viral load to levels which are essentially undetectable. The invention includes a method of reducing the level of HTLV-1 proviral DNA in blood of a patient infected with HTLV-1, comprising administering to the patient a composition of the invention in an amount effective to reduce the level of HTLV-1 proviral DNA compared to that present prior to the start of treatment.

The effectiveness of treatment may alternatively or in addition be determined by measuring titer of an anti-HTLV-1 antibody in the serum, using methods known in the art, such as, for example, by commercially-available tests such as INNO-LIA™ HTLV I/II (Innogenetics; Gent Belgium) and Abbott HTLV-I/HTLV-II EIA (Abbott Laboratories; Abbott Park, Ill.). In some instances an effective amount of a composition of the invention is an amount that is sufficient to reduce the titer of an anti-HTLV-1 antibody in the serum to 50%, 25%, 10% or 5% of the titer present prior to the start of treatment. In some instances an effective amount of a composition of the invention is an amount that is sufficient to reduce the titer of an anti-HTLV-1 antibody in the serum to a level which is essentially undetectable. The invention includes a method of reducing the titer of an anti-HTLV-1 antibody in the serum of a patient infected with HTLV-1, comprising administering to the patient a composition of the invention in an amount effective to reduce the titer of the anti-HTLV-1 antibody in the serum compared to that present prior to the start of treatment.

Human Papillomavirus

In another aspect the invention provides a method of treating a patient infected with Human Papillomavirus (HPV), or a disease or condition associated with HPV infection, such as, for example, warts of the hands and feet, and lesions of the mucous membranes of the oral, anal and genital cavities. While many types of HPV are relatively harmless, many other types are spread through sexual contact and give rise to genital or venereal warts (termed condylomata acuminata) which may give rise to cervical cancer and other genital cancers. The method comprises administering to the patient infected with HPV an effective amount of a composition of the invention comprising one or more polypeptide or conjugate of the invention. The invention also provides a composition for use in treating a patient infected with HPV, or a disease or condition associated with HPV infection, the composition comprising one or more polypeptide or conjugate of the invention and a pharmaceutically acceptable carrier or excipient. A patient diagnosed with HPV infection includes a patient exhibiting HPV viral DNA in biopsied genital tissue, and sometimes (but not always) exhibiting visible lesions on genital tissues.

A composition comprising a polypeptide of the invention will generally be administered at a dose and frequency similar to what is employed in HPV therapeutic regimens using clinically-approved interferon-alpha polypeptides, such as, for example, INTRON® A (Interferon alfa-2b, recombinant; Schering Corporation). A recommended dose of INTRON A for the treatment of condylomata acuminata is 1.0 million IU injected into each lesion, for up to 5 lesions, using a tuberculin or similar syringe and a 25-to 30-gauge needle, three times per week on alternate days, for 3 weeks. Patients with 6 to 10 condylomata may receive a second (sequential) course of treatment at the above dosage schedule, to treat up to five additional condylomata per course of treatment. Patients with greater than 10 condylomata may receive additional sequences depending on how large a number of condylomata are present. The interferon may alternatively or in addition be applied topically, e.g. in a cream or ointment form (as described for example in Stentella et al. (1996) Clin. Exp. Obstet. Gynecol. 23(1):29-36). Such dosing schedules provide useful ranges for dosage of a polypeptide of the invention for the treatment of HPV infection, or a disease or condition associated with HPV infection such as condylomata acuminata. Depending on a number of factors (including but not limited to the activity and the pharmacokinetics of the polypeptide of the invention and the size, age and health of the patient), the polypeptide of the invention may be administered in lower amounts and/or less frequently than described above. Likewise, a composition comprising a conjugate of the invention will generally be administered, e.g. intralesionally or topically, at a dose effective to reduce the amount of HPV viral DNA in the effected tissues or to reduce the size/or number of genital lesions in the infected individual.

In some instances the polypeptide or conjugate of the invention is administered in combination with one or more additional therapeutic agent(s). For example, the polypeptide or conjugate of the invention may be administered in combination with an anti-HPV therapeutic such as Podofilox (Condylox) and/or Podophyllin (Pododerm, Podocon-25).

The precise amount and frequency of administration of the polypeptide or conjugate of the invention will depend on a number of factors such as the specific activity and the pharmacokinetic properties of the polypeptide or the conjugate, as well as the nature of the condition being treated, among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

The effectiveness of treatment may be determined by measuring the HPV viral load, such as, for example, measuring the level of HPV viral DNA in biopsied tissue. In some instances, an effective amount of a composition of the invention is one that is sufficient to achieve a reduction in viral load by at least 0.5 log unit, such as at least 1 log unit, at least 2 log units, at least 3 log units, at least 4 log units, at least 5 log units, at least 6 log units, or at least 7 log units over the course of treatment, compared to the viral load prior to treatment. In some instances an effective amount of a composition of the invention is an amount that is sufficient to reduce viral load to levels which are essentially undetectable. The invention includes a method of reducing the level of HPV viral DNA in tissue of a patient infected with HPV, comprising administering to the patient a composition of the invention in an amount effective to reduce the level of HPV viral DNA compared to that present prior to the start of treatment.

The effectiveness of treatment may alternatively or in addition be determined by observing the size or number of genital lesions (condylomata) in the infected individual. In some instances an effective amount of a composition of the invention is an amount that is sufficient to reduce the size and/or number of condylomata in the infected individual. The invention includes a method of reducing reduce the size and/or number of condylomata in a patient infected with HPV, comprising administering to the patient a composition of the invention in an amount effective to reduce the size and/or number of condylomata in the patient compared to those present prior to the start of treatment.

Formulations and Routes of Administration

Therapeutic formulations of the polypeptide or conjugate of the invention are typically administered in a composition that includes one or more pharmaceutically acceptable carriers or excipients. Such pharmaceutical compositions may be prepared in a manner known per se in the art to result in a polypeptide pharmaceutical that is sufficiently storage-stable and is suitable for administration to humans or animals.

Drug Form

The polypeptide or conjugate of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

Excipients

"Pharmaceutically acceptable" means a carrier or excipient that at the dosages and concentrations employed does not cause any untoward effects in the patients to whom it is administered. Such pharmaceutically acceptable carriers and excipients are well known in the art (see Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)).

Mix of Drugs

The composition of the invention may be administered alone or in conjunction with other therapeutic agents. Ribavirin, for example, is often co-administered with IFN-alpha and has been shown to increase efficacy in antiviral treatments, such as HCV treatment. A variety of small molecules are being developed against both viral targets (viral proteases, viral polymerase, assembly of viral replication complexes) and host targets (host proteases required for viral processing, host kinases required for phosphorylation of viral targets such as NS5A and inhibitors of host factors required to efficiently utilize the viral IRES). Other cytokines may be co-administered, such as for example IL-2, IL-12, IL-23, IL-27, or IFN-gamma. These agents may be incorporated as part of the same pharmaceutical composition or may be administered separately from the polypeptide or conjugate of the invention, either concurrently or in accordance with another treatment schedule. In addition, the polypeptide, conjugate or composition of the invention may be used as an adjuvant to other therapies.

Patients

A "patient" for the purposes of the present invention includes both humans and other mammals. Thus the methods are applicable to both human therapy and veterinary applications.

Types of Composition and Administration Route

The pharmaceutical composition comprising the polypeptide or conjugate of the invention may be formulated in a variety of forms, e.g. as a liquid, gel, lyophilized, or as a compressed solid. The preferred form will depend upon the particular indication being treated and will be apparent to one skilled in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner. The formulations can be administered continuously by infusion, although bolus injection is acceptable, using techniques well known in the art, such as pumps (e.g., subcutaneous osmotic pumps) or implantation. In some instances the formulations may be directly applied as a solution or spray.

Parenterals

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

Parenterals may be prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives are added to retard microbial growth, and are typically added in amounts of about 0.2%-1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

In one aspect of the invention the composition is a liquid composition, such as an aqueous composition, and comprises a sulfoalkyl ether cyclodextrin derivative of the formula

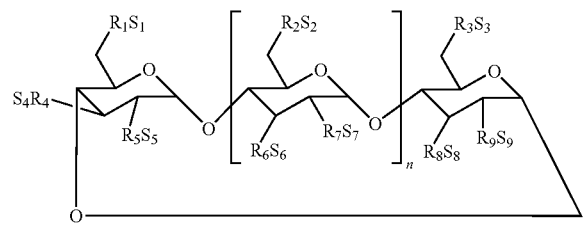

wherein n is 4, 5 or 6; $R_1$, $R_2$, $R_3$, $R_4$, $R_5$, $R_6$, $R_7$, $R_8$, and $R_9$ are each, independently, —O— or a —O—($C_2$-$C_6$ alkyl)-$SO_3$— group, wherein at least one of $R_1$, $R_2$ or $R_3$ is independently a —O—($C_2$-$C_6$ alkyl)-$SO_3$— group; and $S_1$, $S_2$, $S_3$, $S_4$, $S_5$, $S_6$, $S_7$, $S_8$, and $S_9$ are each, independently, a pharmaceutically acceptable cation, including $H^+$.

It should be noted that when n=4, the sulfoalkyl ether cyclodextrin may also be referred to as a α-sulfoalkyl ether cyclodextrin. In a similar way, when n=5, the term β-sulfoalkyl ether cyclodextrin may be employed and when n=6, the sulfoalkyl ether cyclodextrin may also be referred to as a γ-sulfoalkyl ether cyclodextrin.

In a further embodiment, n is 5 or 6. In a preferred embodiment n=6.

In a still further embodiment $R_1$, $R_2$ or $R_3$ is independently selected from the group consisting of —$OCH_2CH_2CH_2SO_3$—, —$OCH_2CH_2CH_2CH_2SO_3$— and —$OCH_2CH_2CH_2CH_2CH_2SO_3$—. Most preferably, $R_1$, $R_2$ or $R_3$ is independently —$OCH_2CH_2CH_2CH_2SO_3$—.

In a further embodiment $S_1$, $S_2$, $S_3$, $S_4$, $S_5$, $S_6$, $S_7$, $S_8$, and $S_9$ are each, independently, a pharmaceutically acceptable cation selected from $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$-$C_6$) alkylamines, piperidine, pyrazine, ($C_1$-$C_6$) alkanolamine and ($C_4$-$C_8$)cycloalkanolamine. Most preferably, $S_1$, $S_2$, $S_3$, $S_4$, $S_5$, $S_6$, $S_7$, $S_8$, and $S_9$ are each, independently, a pharmaceutically acceptable cation selected from the group consisting of $H^+$, $Li^+$, $Na^+$, $K^+$, in particular $Na^+$.

The sulfoalkyl ether cyclodextrin may contain from 1 to 18 sulfoalkyl groups (when n=4), from 1-21 sulfoalkyl groups (when n=5) or from 1-21 (when n=6). In a preferred embodiment of the invention n=5 and the sulfoalkylether derivative comprises, on average, 2-20 sulfoalkyl groups (in particular sulfobutyl groups), such as 3-10 sulfoalkyl groups (in particular sulfobutyl groups), more preferably 4-9 sulfoalkyl groups (in particular sulfobutyl groups), even more preferably 5-9 sulfoalkyl groups (in particular sulfobutyl groups), such as 6-8 sulfoalkyl groups (in particular sulfobutyl groups), e.g. 7 sulfoalkyl groups (in particular sulfobutyl groups).

In some instances the sulfoalkyl ether cyclodextrin derivative is a salt, in particular a sodium salt, of β-cyclodextrin sulfobutyl ether (i.e. n=5), which on average contains 7 sulfobutyl groups. This sulfoalkyl ether cyclodextrin derivative is also termed SBE7-β-CD and is available as Captisol® (Cyclex, Overland Park, Kans.).

The term "$C_1$-$C_6$ alkyl" represents a branched or straight alkyl group having from one to six carbon atoms. Typical $C_1$-$C_6$ alkyl groups include, but are not limited to, methyl ethyl, n-propyl, iso-propyl, n-butyl, iso-butyl, sec-butyl, tert-butyl, n-pentyl, iso-pentyl, n-hexyl and iso-hexyl.

The term "$C_2$-$C_6$ alkyl" represents a branched or straight alkyl group having from two to six carbon atoms. Typical $C_2$-$C_6$ alkyl groups include, but are not limited to, ethyl, n-propyl, iso-propyl, n-butyl, iso-butyl, sec-butyl, tert-butyl, n-pentyl, iso-pentyl, n-hexyl and iso-hexyl.

Further details concerning compositions comprising the polypeptides disclosed herein and sulfoalkyl ether cyclodextrin derivatives can be found in WO 03/002152, particularly the section entitled "The sulfoalkyl ether cyclodextrin derivative" on pp. 37-49, incorporated herein by reference.

Parenteral formulations to be used for in vivo administration must be sterile. This is readily accomplished, for example, by filtration through sterile filtration membranes.

Sustained Release Preparations

Suitable examples of sustained-release preparations include semi-permeable matrices of solid hydrophobic polymers containing the polypeptide or conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Oral Administration

For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The polypeptides or conjugates may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilization and/or may contain conventional adjuvants such as preservatives, stabilizers, wetting agents, emulsifiers, buffers, fillers, etc., e.g. as disclosed elsewhere herein.

Liquid dosage forms for oral administration may include pharmaceutically acceptable emulsions, solutions, suspensions, syrups and elixirs containing inert diluents commonly used in the art, such as water. Such compositions may also comprise adjuvants such as wetting agents, sweeteners, flavoring agents and perfuming agents.

Pulmonary Delivery

Formulations suitable for use with a nebulizer, either jet or ultrasonic, will typically comprise the polypeptide or conjugate dissolved in water at a concentration of, e.g., about 0.01 to 25 mg of conjugate per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer will have a composition and molarity suitable to adjust the solution to a pH in the range of 3 to 9. Generally, buffer molarities of from 1 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in WO 94/20069, U.S. Pat. Nos. 5,915,378, 5,960,792, 5,957,124, 5,934,272, 5,915,378, 5,855,564, 5,826,570 and 5,522,385 which are hereby incorporated by reference.

Formulations for use with a metered dose inhaler device will generally comprise a finely divided powder. This powder may be produced by lyophilizing and then milling a liquid conjugate formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. This mixture is then loaded into the delivery device. An example of a commercially available metered dose inhaler suitable for use in the present invention is the Ventolin metered dose inhaler, manufactured by Glaxo Inc., Research Triangle Park, N.C., USA.

Formulations for powder inhalers will comprise a finely divided dry powder containing conjugate and may also include a bulking agent, such as lactose, sorbitol, sucrose, or mannitol in amounts which facilitate dispersal of the powder from the device, e.g., 50% to 90% by weight of the formulation. The particles of the powder shall have aerodynamic properties in the lung corresponding to particles with a density of about 1 g/cm$^2$ having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass., USA.

The powders for these devices may be generated and/or delivered by methods disclosed in U.S. Pat. Nos. 5,997,848, 5,993,783, 5,985,248, 5,976,574, 5,922,354, 5,785,049 and 5,654,007.

Mechanical devices designed for pulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo., USA; the Acorn II nebulizer, manufactured by Marquest Medical Products, Englewood, Colo., USA; the Ventolin metered dose inhaler, manufactured by Glaxo Inc., Research Triangle Park, N.C., USA; the Spinhaler powder inhaler, manufactured by Fisons Corp., Bedford, Mass., USA the "standing cloud" device of Nektar Therapeutics, Inc., San Carlos, Calif., USA; the AIR inhaler manufactured by Alkermes, Cambridge, Mass., USA; and the AERx pulmonary drug delivery system manufactured by Aradigm Corporation, Hayward, Calif., USA.

Kits

The present invention also provides kits including the polypeptides, conjugates, polynucleotides, expression vectors, cells, methods, compositions, and systems, and apparatuses of the invention. Kits of the invention optionally comprise at least one of the following of the invention: (1) an apparatus, system, system component, or apparatus component as described herein; (2) at least one kit component comprising a polypeptide or conjugate or polynucleotide of the invention; a plasmid expression vector encoding a polypeptide of the invention; a cell expressing a polypeptide of the invention; or a composition comprising at least one of any such component; (3) instructions for practicing any method described herein, including a therapeutic or prophylactic method, instructions for using any component identified in (2) or any composition of any such component; and/or instructions for operating any apparatus, system or component described herein; (4) a container for holding said at least one such component or composition, and (5) packaging materials.

In a further aspect, the present invention provides for the use of any apparatus, component, composition, or kit described above and herein, for the practice of any method or assay described herein, and/or for the use of any apparatus, component, composition, or kit to practice any assay or method described herein.

EXAMPLES

The following examples are offered to illustrate the present invention, but not to limit the spirit or scope of the present invention in any way.

Materials and Methods

I. Determination of Surface-Accessible Residues

Accessible Surface Area (ASA)

The computer program Access (B. Lee and F. M. Richards, J. Mol. Biol. 55: 379-400 (1971)) version 2 (©1983 Yale University) was used to compute the accessible surface area (ASA) of the individual atoms in the structure. This method typically uses a probe-size of 1.4 Å and defines the Accessible Surface Area (ASA) as the area formed by the center of the probe. Prior to this calculation all water molecules and all hydrogen atoms should be removed from the coordinate set, as should other atoms not directly related to the protein.

Fractional ASA of Side Chain

The fractional ASA of the side chain atoms is computed by division of the sum of the ASA of the atoms in the side chain by a value representing the ASA of the side chain atoms of that residue type in an extended ALA-x-ALA tripeptide. See Hubbard, Campbell & Thornton (1991) *J. Mol. Biol.* 220, 507-530. For this example the CA atom is regarded as a part of the side chain of glycine residues but not for the remaining residues. The following values are used as standard 100% ASA for the side chain (Table 6):

| Ala | 69.23 | Å$^2$ |
|-----|-------|-------|
| Arg | 200.35 | Å$^2$ |
| Asn | 106.25 | Å$^2$ |
| Asp | 102.06 | Å$^2$ |
| Cys | 96.69 | Å$^2$ |
| Gln | 140.58 | Å$^2$ |
| Glu | 134.61 | Å$^2$ |
| Gly | 32.28 | Å$^2$ |
| His | 147.00 | Å$^2$ |
| Ile | 137.91 | Å$^2$ |
| Leu | 140.76 | Å$^2$ |
| Lys | 162.50 | Å$^2$ |
| Met | 156.08 | Å$^2$ |
| Phe | 163.90 | Å$^2$ |
| Pro | 119.65 | Å$^2$ |
| Ser | 78.16 | Å$^2$ |
| Thr | 101.67 | Å$^2$ |
| Trp | 210.89 | Å$^2$ |
| Tyr | 176.61 | Å$^2$ |
| Val | 114.14 | Å$^2$ |

Residues not detected in the structure are defined as having 100% exposure as they are thought to reside in flexible regions. In the case where an ensemble of NMR structures is analyzed, the average ASA value of the ensemble is used.

Determination of Surface Exposed Residues when No Three-Dimensional Structure is Available:

When no three-dimensional structure is available or if the structure is not detailed enough to determine surface accessibility (e.g. if only the position of the CA atoms is known) the surface accessibility may be inferred from a sequence alignment created as follows:

A: If the structure is known but not detailed enough to determine surface accessibility:

The low detail structure is included in a structure-based sequence alignment to the known structures of the sequence family using the MODELER program available from Molecular Simulations, Inc.

B: If no structure is known:

The sequence is aligned to a predefined sequence alignment, including the sequences of the known structures of the sequence family, that may be prepared using the "profile/structure alignment" option of the program ClustalW (Thompson et al. (1994) *Nucleic Acids Research* 22:4673-4680).

From the sequence alignment obtained in A or B, residues in the sequence to be analyzed at positions equivalent to residues exposed in at least one of the other sequences having a known structure are defined as being exposed. The degree of exposure is taken to be the largest value for the equivalent residues in the other sequences. In cases where the sequence to be analyzed is at an insertion (i.e. there are no equivalent residues in the other sequences) this residue is defined as being fully exposed, as it most probably is located in a turn/loop region. In cases where a low detailed structure exists, those residues not observed in the structure are defined as being fully exposed, as they are thought to be in flexible regions.

Determining Distances Between Atoms:

The distance between atoms is readily determined using molecular graphics software, e.g. InsightII® 98.0 from Molecular Simulations, Inc.

II. Protein Expression and Purification

A. Expression and Purification from CHO Cells

Some polypeptides of the invention were produced in Chinese Hamster Ovary (CHO) K1 cells (ATCC: CCL-61) that were stably transfected and selected with G418 to establish clonal cell lines.

1. CHO Expression Construct:

Nucleic acids encoding polypeptides of the invention were cloned into a CHO expression vector, under control of the SV40 promoter and in-frame with a sequence which encodes an N-terminal leader sequence, and, optionally, one or two a C-terminal tag sequences. The leader sequence was either a generic leader sequence, IFN alpha 6 leader or a modified IFN alpha 6 leader sequence, and C-terminal tags included an E-tag (Amersham Biosciences) &/or a His-tag. Plasmid production was in XL1-Blue cells.

2. Selection of Stable Subclones Expressing IFN-Alpha Polypeptides:

Materials:

Culture medium: DMEM-F12 with G418, FBS and Penicillin, Streptomycin and Glutamine (PSG; Gibco/Invitrogen);

1×PBS (Gibco/Invitrogen);

Trypsin/EDTA

Anti E-Tag Antibody-HRP conjugate (Amersham BioSciences)

ECL Plus Western Blotting detection Reagents (Amersham BioSciences)

Procedure: Stable transfectants were generated under selection with G418 in DMEM/F-12 medium with FBS and penicillin. Cells were split into T175 flasks with 50 ml of selection medium and incubated in a 37° C. $CO_2$ incubator for ~24 hr. or until cells reached 80% confluence. Cells were harvested by washing with PBS followed by addition of 2.5 ml Trypsin/EDTA and incubation at 37° C. for 3-5 min. Cells were collected and recovered by centrifugation at 1000 g for 30 min in a Beckman Model bench top centrifuge. Cells were washed once in PBS and resuspended in 3 ml PBS with 1% FBS. The cell density was determined and adjusted to $1 \times 10^6$ cell/ml with PBS/FBS. For each IFN-alpha, polypeptide cells were sorted in a DakoCytomation MoFlo sorter into 2-5 96 well plates containing 200 ml of selection medium. The plates were incubated in a 37° C. incubator for 10-14 days to allow the sorted cells to grow. Two subclones were selected for each IFN-alpha polypeptide for high level expression first by dot blot analysis and subsequently confirmed by Western blot analysis using an anti-E tag antibody-HRP conjugate and chemiluminescent detection.

3. Protein Expression:

Materials:

DMEM-F12 medium (Gibco/Invitrogen)

Ultra CHO medium (BioWhittaker)

CHO III A medium (Gibco/Invitrogen)

Ex-Cyte Growth Enhancing Media supplement (Serologicals Proteins)

ITSA (Insulin, Transferrin, Selenium supplement for adherent culture; Gibco/Invitrogen)

Penicillin/Streptomycin (P/S)

FBS, PBS, Trypsin

Procedure:

Day 1: Cells from one T-175 flask were transferred to one roller bottle (1700 cm$^2$) in 300 ml DMEM-F12 with 10% FBS and 1×P/S and grown in a 37° C. $CO_2$ incubator.

Day 3: Medium was changed to 300 ml fresh DMEM-F12-FBS-P/S.

Day 5: The medium was changed to 300 ml Ultra CHO with 1/1000 Ex-Cyte and P/S.

Day 7: The media was replaced with 300 ml CHO III A+P/S production medium.

Supernatants were harvested on Day 8, 9 and 10. The supernatants were centrifuged at 2000 g for 20 min in a Beckman Coulter Allegra 6R bench top centrifuge and filtered using a 0.2μ PES bottle top sterile filter and stored at 4° C. for purification.

4. Protein Purification:

Some polypeptides of the invention were expressed as fusion proteins containing a 13 amino acid E-tag sequence at the C-terminus. Such polypeptides were purified using an E-tag affinity column, as follows.

Materials: Recombinant Phage Antibody System Purification Module (Amersham BioSciences, Cat. No. 17-1362-01). Purification kit contains a 16 mm diameter×25 mm height (5 ml bed volume) anti E-Tag column and associated buffers.

Procedure: Supernatants collected from CHO-HK1 cells in roller bottles were clarified using a combination of centrifugation at 2800×g for 20 min and filtration using a 0.2μ PES bottle top filter module. Supernatants were loaded onto the E-tag column equilibrated in RPAS binding buffer at 150 cm/h (5 ml/min). The column was washed with 5 CV (column volume) of binding buffer and the protein was eluted at 75 cm/h (2.5 ml/min) with RPAS elution buffer. Elution fractions were neutralized with 0.05 volumes of 1M Tris-Cl pH 8.0, dialyzed into PBS, concentrated to 0.1-1.5 mg/ml and stored frozen in aliquots at −80° C. Samples for assays were formulated at 50 μg/ml in PBS with 0.5% BSA and stored frozen in aliquots at −80° C. Samples were routinely analyzed by SDS-PAGE followed by Coomassie staining using materials, reagents and protocols obtained from Invitrogen.

Protein concentrations were routinely determined by the BCA assay using an IFN-alpha standard, the concentration of which had been verified by amino acid analysis.

B. Expression and Purification from *E. coli*

Some polypeptides of the invention were produced in *E. coli* as inclusion bodies, which were purified and refolded as follows.

1a. *E. coli* Expression Construct

In some instances, nucleic acids encoding polypeptides of the invention were modified for improved expression in *E. coli*. Such modifications comprised replacing rare Arg-Arg codon pairs AGGAGG at nucleotide positions 34-39 and AGGAGA at nucleotide positions 64-69 (position numbering relative to SEQ ID NO:59) each with Arg-Arg codon pairs such as CGTCGC which are preferred in *E. coli*, or replacing most or all rare Arg codons AGA and AGG in the coding sequence with preferred *E. coli* Arg codons CGC or CGT. A methionine codon (ATG) was also added to the 5' end of the coding sequence. Exemplary coding sequences modified in such a manner include SEQ ID NOs: 60-61, 63-64, 66-67, 69-70, 72-73, 75-76, 78-79, 81-82, 84-85, and 87-88. The coding sequence was placed into the pET-42 expression vector (Novagen) under control of a T7 promoter with kanamycin selection marker, or into the pQE80-Kan expression vector (Qiagen) under the control of a T5 promoter with kanamycin selection marker.

1b. Protein Expression pET-42 vectors containing interferon coding sequences were transformed into an *E. coli* strain such as BL21(DE3) using standard methods, and plated on to agar plates containing 50 μg/ml kanamycin and incubated at 37° C. After 18-24 h, three separate colonies were picked and transferred into tubes containing 5 ml of 2×YT with 50 μg/ml kanamycin and incubated overnight at 37° C. The overnight culture was used to inoculate 2 sets of flasks containing 100 ml of 2×YT with 50 μg/ml kanamycin. The growth of the culture at 37° C. was monitored at $OD_{600}$. The culture was induced at an $OD_{600}$ of 0.5-0.8 with 1 mM IPTG for 3 h at 37° C. IPTG induced cultures were analyzed for expression by SDS-PAGE by lysing pelleted cells in SDS sample buffer. The corresponding uninduced sets of cultures were used to prepare frozen stocks by addition of 25% glycerol and freezing cells in 1 ml aliquots at −80° C. pQE80-Kan vectors containing interferon coding sequences were transformed into *E. coli* strains W3110 or W3110-fhuA. Expression was verified as described above.

Larger scale shake flask expression was performed by inoculating 4×1 L 2×YT media+kanamycin with 25 ml of an overnight culture. Cultures were monitored at OD600 and induced with 1 mM IPTG at 0.5-0.8 OD units. After 3 h of induction cells are harvested by centrifugation at 5000 g and stored frozen at −80° C. Cells were disrupted using 2-3 passes through a French press or a APV 1000 homogenizer at 10,000 psi and processed as described under "Isolation of IB" and subsequent sections.

Fed-batch fermentation was conducted at 10 L scale in a B. Braun bioreactor in Terrific Broth (TB) medium supplemented with trace element solution and 40 mg/L kanamycin. Fermentation was initiated by inoculating the bioreactor with a 400 ml overnight culture in TB medium. During the initial growth phase the dissolved oxygen (DO) was maintained at 50% by varying the agitation rate. When the OD600 of the culture reached 5.0, the glycerol/amino acid feed was initiated at 0.5 ml/min and the agitation was set to 1000 rpm. The feed rate was adjusted to maintain the DO at 40% for the rest of the fermentation process. When the OD600 reached 25 the culture was induced by addition of IPTG to a final concentration of 1 mM. Three hours post induction the cells were harvested by centrifugation at 10000×g in a Beckman centrifuge and the cell paste was stored at −60° C. The OD600 at harvest was typically around 35-40.

2a. E. coli Expression Construct (for High-Level Expression)

The following example shows the expression of two exemplary polypeptides of the invention cloned into an E. coli expression system (as described in EP 0972838) allowing high level expression of eukaryotic genes in E. Coli. Coding sequences corresponding to the amino acid sequences of 14epi18 (SEQ ID NO:13) and 25epi19 (SEQ ID NO:38), both containing an additional Met at the N-terminus, were optimized according to codon-usage and mRNA secondary structure (Griswold et al., Protein Expr Purif. 2003 January; 27(1): 134-42) using the sequence analysis program GCG (Genetic Computer Group, Inc., Wisconsin USA, Version 7.1, March 1992) function "backtranslate"/"EcoHigh-database" to prevent rare codons, and function MFold/Plotfold (−menu=f or −menu=g) for prediction and prevention of potential secondary structures detrimental to the gene expression. Coding sequences optimized in this manner are provided as SEQ ID NO:89 and SEQ ID NO:90, respectively.

Figure 7:
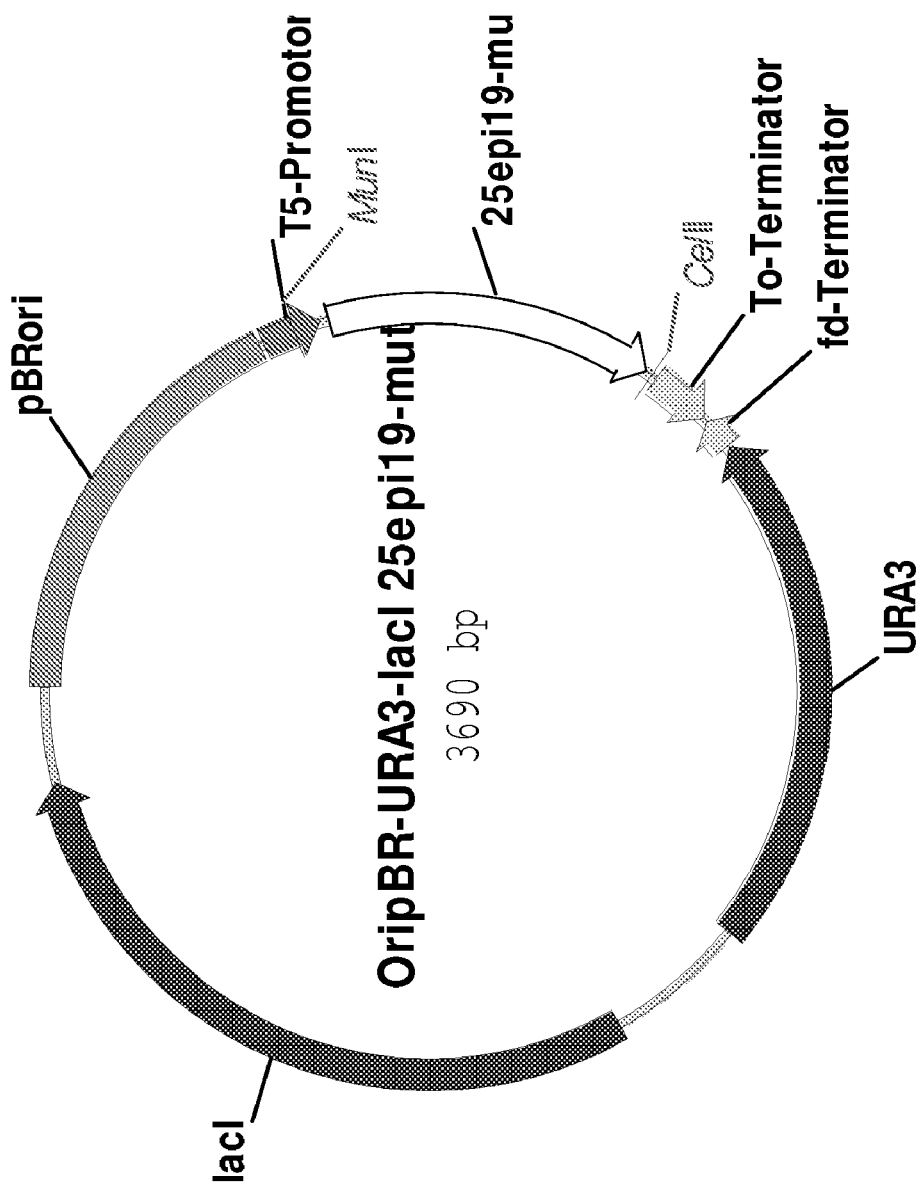

The optimized DNA sequences were cloned into OripBR-URA3 with an additional lacI gene. The resulting vectors, designated OripBR-URA3-lacI__14epi18-mut2 (FIG. 6) and OripBR-URA3-lacI__25epi19-mut (FIG. 7), were transformed into competent E. coli UT5600 (ΔpyrF) cells (as described in EP 0972838). Transformed cells were selected on minimal M9-medium agar plates without addition of Uracil.

M9-Agar Plates:

| | |
|---|---|
| Sterile agarose stock solution (final conc. 15 g/l) | 430 ml |
| M9-salt solution | 50 ml |
| 1M MgSO$_4$ | 0.5 ml |
| 1M CaCl$_2$ | 0.05 ml |
| 20% Glucose | 5 ml |
| Vitamin B1 (c = 1 mg/ml) | 2.5 ml |
| 10% Casaminoacids | 25 ml |
| L-Tryptophan (c = 5 mg/ml) | 5 ml |
| L-Leucine (c = 5 mg/ml) | 5 ml |
| L-Proline (c = 5 mg/ml) | 2.5 ml |

2b. Protein Expression

Transformed cells according to 2a. above were inoculated in shake flasks and cultured at 37° C. Induction was performed at OD$_{578}$=1 by addition of 1 mM IPTG. Cells were harvested after 7 h and cell pellets were analyzed on an SDS-PAGE gel. The media used is as follows:

| | |
|---|---|
| Casaminoacids | 120 g |
| NH$_4$Cl | 3.9 g |
| Tryptophan | 5.5 g |
| Leucine | 5.5 g |
| Proline | 5.5 g |
| Glycerin | 85 g |
| dissolved in 4300 ml H$_2$O and | |
| K$_2$HPO$_4$*3H$_2$O | 91.5 g |
| Citric acid | 8.0 g |
| dissolved in 600 ml H2O and | |
| Thiamin (5 mg/ml) | 17.5 ml |
| MgSO$_4$x7H$_2$O (1M) | 17.5 ml |
| pH = 7.0 | |
| adjust to 5000 ml with H$_2$O | |

3. Isolation, Solubilization, Sulfonation and Refolding of Inclusion Bodies (IB)

For isolating IB the thawed cell paste was resuspended in 1×PBS at 10 ml per gram of cell paste and mixed until a uniform slurry was obtained. The cells were disrupted by two passes through a microfluidizer at 17,000-19,000 psi. The cell lysate was adjusted to 1% Triton-X100, mixed for 10 min and the IB were recovered by centrifugation at 10,000 g for 60 min at 2-8° C. The IB pellet was washed once by resuspending in PBS with 1% Triton-X100 and recovered by centrifugation as above and stored frozen at −80° C.

3a. Solubilization/Refolding Method 1:

For solubilizing IB, the IB pellet was resuspended in Urea buffer (50 mM Tris-Cl, 200 mM NaCl, 8 M urea, 2 mM DTT, 1 mM EDTA, pH 8.0) at 10 ml buffer per gram of cell paste. The suspension was mixed for 30 min and centrifuged at 10,000 g for 30 min at 2-8° C. The pellet was washed once by resuspending in the Urea buffer without DTT, centrifuged as above and washed twice with water. The washed pellet was solubilized in Guanidine buffer (50 mM Tris-Cl, 200 mM NaCl, 8 M guanidine-HCl, 1 mM EDTA, pH 8.0) at 10 ml buffer per gram pellet, mixed for 30-60 min and centrifuged at 10,000 g for 30 min at 2-8° C. The supernatant containing the solubilized IFN was adjusted to 10 mg/ml sodium sulfite and 5 mg/ml sodium tetrathionate to initiate the sulfonation process which was performed at 2-8° C. for 16 hours. Post-sulfonation the IFN solution was diluted 2-fold with water and the IFN pellet was recovered by centrifugation at 10,000 g at 2-8° C. The pellet was washed twice with water and resuspended in Guanidine buffer as above. The protein concentration of the sulfonated IFN was determined by absorbance at 280 nm.

The refolding process was initiated by diluting the sulfonated IFN in Guanidine buffer at 2-8° C. to a final concentration of 100 mg/ml in Refolding buffer (50 mM Tris-Cl, 20 mM NaCl, 2 mM reduced glutathione, 1 mM oxidized glutathione). Refolding was performed at 2-8° C. with slow mixing for 6-8 h, followed by addition of CuSO$_4$ to a final concentration of 2 μM followed by an additional refolding period of 16-20 h. The progress of the refolding reaction was monitored by SDS-PAGE and reverse phase HPLC.

3b. Solubilization/Refolding Method 2:

For solubilization of 14epi18, the IB pellet was resuspended in Guanidine buffer (7 M Guanidine, 20 mM Na$_2$HPO$_4$, 10 mM DTE, pH 8.0) at 4 ml buffer per gram of IB paste. The suspension was mixed for 2 hours and, after solubilization, diafiltered at least 8 volumes at room temperature against a buffer containing 7 M Guanidine buffer and 20 mM NaH$_2$PO$_4$ pH 5.0 using 10 kDa cut-off membranes.

For refolding, the solubilized protein was diluted into a folding buffer containing 20 mM Na$_2$HPO$_4$, 0.8 M arginine and 2 μM CuSO$_4$, pH 7.5. Refolding was performed at 2-8° C. with slow mixing for 72 hours at a final protein concentration of about 0.5 mg/ml protein. The progress of the refolding reaction was monitored by reverse phase HPLC.

3b. Solubilization/Refolding Method 3:

For solubilization of 25epi19, the IB slurry was resuspended in solubilisation buffer (8 M Guanidinium chloride, 100 mM DTT, 50 mM Tris pH 8.3). The suspension was mixed for 30 minutes at room temperature. Subsequently the pH was adjusted to 4.5 with HCl. The solubilisate was further concentrated using a 5 K membrane and diafiltrated against a 10 fold volume of 7.2 M Guanidinium chloride adjusted to pH 4.5 with HCl.

For refolding, the solubilized protein was diluted into a folding buffer (0.8 M Arginine, 50 mM potassium phosphate, 2 mM GSH, 1 mM GSSG pH 7.8). Refolding was performed at 2-8° C. overnight at a final concentration of about 1 mg/ml protein.

4. Purification

4a. Purification Method 1:

The refolded IFN was purified using three chromatography steps. The refolding solution was adjusted to 80% saturating concentration of ammonium sulfate (weight/volume), filtered through a 0.2 μM filter and loaded at 200 cm/h onto a 20 ml Butyl Sepharose Fast Flow Hydrophobic Interaction Chromatography (HIC) column (Amersham Biosciences) equilibrated in Equil buffer (50 mM Tris-Cl, 0.8 M ammonium sulfate, pH 8.0). The HIC column was washed with 8 column volumes (CV) of Equil buffer, followed by 8 CV of Wash buffer (50 mM Tris-Cl, 0.5 M ammonium sulfate, pH 8.0). IFN was eluted with 50 mM Tris-Cl, pH 8.0 with or without 15% saturating concentration of ammonium sulfate.

The HIC pool was adjusted to 50 mM sodium acetate using 0.5 M sodium acetate, pH 4.5 stock and diluted two fold. This adjusted pool was loaded at 90 cm/h on to a 5 ml HiTrap CM Sepharose Fast Flow column (Amersham Biosciences), equilibrated in 50 mM sodium acetate, 100 mM NaCl, pH 5.0. Post loading the column was washed with 5 CV under equilibration buffer conditions and IFN was eluted using a 20 CV gradient from 100-650 mM NaCl. Peak fractions containing IFN were pooled based on absorbance at 280 nm.

The CM Sepharose pool was adjusted to 20 mM 1,3 diaminopropane using a 2 M 1,3 diaminopropane stock to set pH at ~10. The sample was loaded at 200 cm/h on to a 5 ml HiTrap Q Sepharose Fast Flow column (Amersham Biosciences), equilibrated in 50 mM 1,3 diaminopropane, 100 mM NaCl, pH 10.0. Post loading the column was washed with 5 CV of buffer under equilibration conditions and IFN was eluted using a 20 CV gradient from 100-650 mM NaCl or from 100-1000 mM NaCl. The fractions containing IFN are pooled based on absorbance at 280 nm and immediately dialyzed against 250-500 volumes of 50 mM sodium acetate, 150 mM NaCl, pH 5.0 or 50 mM sodium borate, pH 9.0. Post-dialysis the IFN samples were sterile filtered using a 0.2 μM filter in a biosafety cabinet, the concentration was measured by absorbance at 280 nm and the samples are stored at 2-8° C. for periods up to a week or in aliquots at −80° C. for extended storage. For activity assays the sample was generally formulated in 0.5% BSA, PBS pH 7.4 at 5, 20 and 50 ug/ml, and stored frozen in aliquots at −80° C.

4b. Purification Method 2:

Refolded 14epi18 was purified using two chromatographic steps. The refolding solution was adjusted to pH 8.0 and around 190 mS/cm with KCl, filtered through a 5 μm filter and loaded at 75 cm/h onto a Butyl-Sepharose Fast Flow Hydrophobic Interaction Chromatography (HIC) column (General Electric Healthcare) equilibrated in equilibration buffer consisting of 2.0 M KCl, 20 mM $K_2HPO_4$, 0.8 M arginine, pH 8.0. The HIC column was washed with 5 column volumes (CV) of 2.0 M KCl, 20 mM $K_2HPO_4$, 0.8 M arginine pH 8.0. 14epi18 was eluted with 0.4 M KCl, 20 mM $K_2HPO_4$, pH 8.0. The elution was monitored by reverse phase HPLC.

The eluate was diluted with distilled water to a conductivity of around 3 mS/cm. The pH was adjusted to 6.8. This adjusted pool was loaded at 50 cm/h onto a Q-Sepharose Fast Flow column (GE Healthcare) equilibrated in 25 mM ammonium acetate pH 6.8. Post loading, the column was washed with equilibration buffer. 14epi18 was eluted with a linear gradient to pH 4.0. Peak fractions containing the folded 14epi18 were pooled based on reversed phase HPLC analytics.

4c. Purification Method 3:

Refolded 25epi19 was purified using two chromatographic steps. The refolding solution was adjusted to 1.3 M NaCl and the solution was filtered over a combination of two filters (0.8/0.3 μm followed by 0.45/0.2 μm). The protein was loaded onto a Butyl Sepharose Fast Flow column (General Electric Healthcare) equilibrated with equilibration buffer (0.8 M Arginine, 1.3 M sodium chloride, 50 mM potassium phosphate pH 8.0) at 50-150 cm/h. After sample application, the column was washed with 3 CV equilibration buffer and 3 CV wash buffer (20 mM potassium phosphate, 2 M sodium chloride pH 7.5). Step elution was performed by applying elution buffer (20 mM potassium phosphate, pH 7.5) with a flow of 50-100 cm/h. The peak was pooled according to UV280 measurement.

After assuring that the conductivity was below 10 mS/cm, the pool was loaded at 50-75 cm/h onto a Q-Sepharose Fast Flow column (GE Healthcare) equilibrated in 30 mM ammonium acetate, pH 5.9. Post loading, the column was washed with equilibration buffer until baseline (UV280) was reached. 25epi19 was eluted with a linear gradient to pH 3.5. Peak fractions containing the folded 25epi19 were pooled according to reversed phase HPLC analytics and SDS-PAGE.

III. Activity Assays

A1. HuH7-EMCV Antiviral Assay

Provided below is an exemplary assay for antiviral activity of interferon-alpha polypeptides and conjugates of the invention. The assay is a cell-based dose-response assay used to assess the anti-viral potency of a drug, and is sometimes referred to as "protection from cytopathic effect" (or PCPE) assay, also termed inhibition of cytopathic effect (CPE) assay. Briefly, cells are incubated with drug and exposed to virus. In the absence of drug, cells exposed to virus die. With increasing concentrations of drug, an increasing proportion of cells survive. The number of surviving cells can be measured directly (e.g., by visual counts) or indirectly by estimating metabolic rate. For example, metabolic dyes such as MTT or WST-1 may be used as an indirect measure of cell survival. Live cells metabolize such dyes to form metabolic products which can be quantified by spectrophotometry (optical density).

Materials and Reagents:

HuH7 Cells: Human hepatoma cell line (obtained from Dr. Michael Lai, USC-Surgery Department, Los Angeles, Calif.). The cell line may also be obtained from the Cell Bank of the Japanese Collection of Research Bioresources (JCRB)/Health Science Research Resources Bank (HSRRB), Osaka, Japan. The HuH7 cell line was originally established in the laboratory of Dr. J. Sato (Okayama University School of Medicine) from a 57-year old Japanese male with well-differentiated hepatocellular carcinoma (Nakabayashi, H., et al. (1982) Cancer Res. 42(9):3858-63). The cell line is negative for Hepatitis B surface antigen.

VERO Cells: African green monkey kidney cell line (ATCC # CCL-81). The cell line was derived in 1962 at Chiba University in Chiba, Japan from the kidney of a normal adult African green monkey. Passage # 93 of the VERO cell line was transferred to the National Institute of Health (NIH) in 1964.

Encephalomyocarditis virus (EMCV): tissue culture adapted strain (ATCC # VR-129B). A tissue culture adapted strain of encephalomyocarditis virus (EMCV) was purchased from the ATCC (# VR-129B). For the HuH7 antiviral assays, a high titer viral stock was produced in Vero African green monkey kidney cells. The viral titer of the Vero produced EMCV stock was determined by plaque assay on L929 cells to be $1.1\times10^8$ PFU/ml.

Complete DMEM:

Dulbecco's Modified Eagle Medium (DMEM, Gibco Cat. No. 11965-092)

10% Fetal Bovine Serum (FBS, Hyclone Cat. No. SH30071.03)

1× Penicillin-streptomycin (PS, Gibco Cat. No. 15140-122)

Reduced Serum DMEM:

Dulbecco's Modified Eagle Medium (DMEM, Gibco Cat. No. 11965-092)

2% Fetal Bovine Serum (FBS, Hyclone Cat. No. SH30071.03)

1× Penicillin-streptomycin (PS, Gibco Cat. No. 15140-122)

Trypsin/EDTA (Gibco Cat. No. 25300-054)

WST-1 (Roche; Cat. No. 1 644 807)

HuH7 cells were maintained in Complete DMEM at 37° C. in a humidified 5% $CO_2$ incubator. The cells were harvested with trypsin and split twice weekly when confluent to a final density of $1\text{-}2\times10^6$ cells per 25 ml in a T175 flask. One day prior to the assay, the cells were trypsinized and seeded into new T175 flasks at a density of $4.5\times10^6$ cells per 25 ml to ensure that the cells were in log phase prior to the assay.

HuH7-EMCV Antiviral Assay Procedure:

A high titer EMCV virus stock was amplified in VERO cells. The lethal concentration at which 95% of the cells were killed ($LC_{95}$) was determined by an EMCV viral killing curve on HuH7 cell monolayers. Briefly, HuH7 cells were plated on day one in 96-well microtiter plates at $6\times10^4$ cells per well. Virus was serial diluted 1:3 in DMEM+2% FBS with 10 dilution points and added to the cells on day two. Twenty-four hours post-infection, cell survival was determined by a tetrazolium salt metabolism assay, WST-1 (Roche). The $LC_{95}$ determined for the HuH7-EMCV assay corresponded to an MOI of 0.034 (PFU/cell). Titer of the virus stock was determined by a standard plaque assay on L929 cells.

On day one of the assay, log phase HuH7 cells were harvested with trypsin, resuspended in Reduced Serum DMEM and concentrated by centrifugation. The cell pellets, corresponding to 5 T175 flasks of cells, were resuspended in 10 ml of Reduced Serum DMEM, filtered through a 40 micron Nylon cell strainer and counted with a hemocytometer. Cell viability was determined by trypan blue exclusion. The cells were resuspended in Reduced Serum DMEM to a final density of $6\times10^5$ cells/ml. One hundred microliters of the diluted cells were added to each well of a 96-well assay plates ($6\times10^4$ cells/well) and the plates were incubated at 37° C. in a humidified 5% $CO_2$ incubator for 4 hours.

The potencies of "reference" interferon alphas and interferon-alpha polypeptides of the invention (also called "test samples") were determined by dose-response analysis. There was generally one test sample and one reference IFN-alpha per plate, each with three replicate curves of IFN-alpha treated/EMCV challenged cells and two replicate curves of IFN-alpha treatment alone. The later was assayed to control for potential antiproliferative effects of IFN-alpha on HuH7 cells. The dose-response curves for the reference IFN-alphas generally consisted of 8 three-fold dilutions ranging from 100 ng/ml to 0.05 ng/ml. For the IFN-alpha test samples, the three-fold dilutions generally ranged from 5 ng/ml to 0.002 ng/ml. Eight wells each of cells treated with virus but no IFN-alpha and cells alone were also run as controls.

The IFN-alpha dilutions were prepared using Reduced Serum DMEM. One hundred microliters of the diluted IFN-alpha preparations were transferred to the assay plates. The assay plates were incubated at 37° C. in a humidified 5% $CO_2$ incubator for 16 hours.

On day two, the cells were challenged with EMC virus. Medium was aspirated from each well of the assay plate. The EMCV stock was diluted 1:5400 in DMEM+2% FBS. One hundred microliters of the diluted virus, corresponding to 0.034 viral particles per cell initially seeded, was added to each well. The cells were incubated with virus at 37° C. in a humidified 5% $CO_2$ incubator for 24 hours.

On day three, the number of viable cells in each well was quantified by WST-1 assay. Medium was aspirated from each well of the assay plate. The WST-1 reagent was diluted 1:20 in Reduced Serum DMEM, 100 μl of the diluted WST-1 reagent was added to each well and the cells were incubated at 37° C. in a humidified 5% $CO_2$ incubator for 60 minutes. The number of viable cells in each well was quantified by measuring OD at 450 nm on a plate reader.

Analysis:

The antiviral potency of the IFN-alpha reference and test samples were calculated with the equation:

$$\text{Antiviral potency}=(\text{Viable cells}_{C+I+V}-\text{Viable cells}_{C+V})/(\text{Viable cells}_{C+I}-\text{Viable cells}_{C+V})*100\%$$

where C+V=HuH7 cells+EMCV, C+I=HuH7 cells+IFN-α, and C+I+V=HuH7 cells+IFN-α+EMCV Dose-response curves were analyzed by non-linear regression using GraphPad Prism 4 (GraphPad Software Inc.) The following equation was used for the curve fits:

$$Y = \text{Bottom} + \frac{(\text{Top} - \text{Bottom})}{1 + 10^{(LogEC50 - X)\cdot HillSlope}}$$

Bottom is the Y value at the bottom plateau; Top is the Y value at the top plateau, and LogEC50 is the X value when the response is halfway between Bottom and Top. The Levenberg-Marquardt method was used as optimization algorithm.

A2. HeLa-EMCV and WISH-EMCV Antiviral Assays

The inhibition of the cytopathic effect of EMCV on HeLa (a human cervical carcinoma derived cell line) and WISH (a human amniotic tissue derived cell line) cells also provide useful surrogate assays to assess the antiviral potencies of interferon alpha polypeptides and conjugates of the invention. These assays were performed in a similar fashion to the HuH7-EMCV assay described above, with the following modifications.

Materials and Reagents:

HeLa Cells: Human cervical carcinoma cell line (ATCC # CCL-2). The HeLa cell line was derived from a cervical adenocarcinoma from a 35-year-old female. The HeLa cells are reported to contain human papilloma virus (HPV-18) sequences. The cell line was received from the ATCC at passage number 107.

WISH Cells: Human epithelial cell line (ATCC # CCL-25). The WISH cell line was established from altered colonies appearing in a subculture of primary human amniotic cells after 35 days in culture. The WISH cell line contains HeLa marker chromosomes. The cells were received from the ATCC at passage # 170.

L-929 Cells: Murine fibroblast cell line (ATCC # CCL-1). The L-929 cell line is a single cell clone isolated from the 95$^{th}$ passage of the parental strain, Strain L, in 1948. Strain L was isolated from the subcutaneous areolar and adipose tissue of a normal 100 day old male C[3]H/An mouse.

EMCV: tissue culture adapted strain (ATCC # VR-129B). A tissue culture adapted strain of encephalomyocarditis virus (EMCV) was purchased from the ATCC (# VR-129B). For the HeLa and WISH antiviral assays, the high titer EMCV stock was produced in L929 cells. The viral titer of the L929 produced viral stock was $4.0 \times 10^8$ PFU/ml based on the results of a plaque assay on L929 cells.

Complete MEM:
Minimal Essential Media (MEM, Gibco Cat. No. 10370-021)
10% Fetal Bovine Serum (FBS, Hyclone Cat. No. SH30071.03)
1× Penicillin-streptomycin-glutamine (PSG, Gibco Cat. No. 10378-016)
1 mM Sodium pyruvate (Gibco Cat. No. #11360-070)
Reduced Serum MEM:
Minimal Essential Media (MEM, Gibco Cat. No. 10370-021)
2% Fetal Bovine Serum (FBS, Hyclone Cat. No. SH30071.03)
1× Penicillin-streptomycin-gluatimine (PSG, Gibco Cat. No. 10378-016)
1 mM Sodium pyruvate (Gibco Cat. No. #11360-070)

HeLa cells were maintained in Complete MEM at 37° C. in a humidified 5% $CO_2$ incubator. The cells were harvested with trypsin and split twice weekly when confluent to a final density of $2\text{-}4 \times 10^6$ cells per 25 ml in a T175 flask. One day prior to the assay, the cells were trypsinized and seeded into new T175 flasks at a density of $6 \times 10^6$ cells per 25 ml to ensure that the cells were in log phase prior to the assay.

WISH cells were maintained in Complete MEM at 37° C. in a humidified 5% $CO_2$ incubator. The cells were harvested with trypsin and split twice weekly when confluent to a final density of $5\text{-}6 \times 10^6$ cells per 25 ml in a T175 flask. One day prior to the assay, the cells were trypsinized and seeded into new T175 flasks at a density of $10 \times 10^6$ cells per 25 ml to ensure that the cells were in log phase prior to the assay.

HeLa-EMCV Antiviral Assay Procedure:

On day one of the assay, log phase HeLa cells were harvested with trypsin, resuspended in Reduced Serum MEM and concentrated by centrifugation. The cell pellets, corresponding to 5 T175 flasks of cells, were resuspended in 10 ml of Reduced Serum MEM, filtered through a 40 micron Nylon cell strainer and counted with a Coulter Counter. Cell viability was determined by trypan blue exclusion with a hemocytometer. The cells were resuspended in Reduced Serum MEM to a final density of $1 \times 10^5$ cells/ml. One hundred microliters of the diluted cells were added to each well of a 96-well assay plates ($1 \times 10^4$ cells/well) and the plates were incubated at 37° C. in a humidified 5% $CO_2$ incubator for 24 hours.

The potencies of "reference" interferon alphas and interferon-alpha polypeptides of the invention (also called "test samples") were determined by dose-response analysis. There was generally one test sample and one reference IFN-alpha per plate, each with three replicate curves of IFN-alpha treated/EMCV challenged cells and two replicate curves of IFN-alpha treatment alone. The later was assayed to control for potential antiproliferative effects of IFN-alpha on HeLa cells. The dose-response curves for the reference IFN-alphas generally consisted of 8 five-fold dilutions ranging from 60 ng/ml to 0.0008 ng/ml. For the IFN-alpha test samples, the five-fold dilutions generally ranged from 5 ng/ml to 0.00006 ng/ml. Eight wells each of cells treated with virus but no IFN-alpha and cells alone were also run as controls.

The IFN-alpha dilutions were prepared using Reduced Serum MEM. One hundred microliters of the diluted IFN-alpha preparations were transferred to the assay plates. The assay plates were incubated at 37° C. in a humidified 5% $CO_2$ incubator for 16 hours.

On day three, the cells were challenged with EMC virus. Medium was aspirated from each well of the assay plate. The EMCV stock was diluted 1:133 in MEM+2% FBS. One hundred microliters of the diluted virus, corresponding to $3 \times 10^5$ viral particles was added to each well. The cells were incubated with virus at 37° C. in a humidified 5% $CO_2$ incubator for 24 hours.

On day four, the number of viable cells in each well was quantified by WST-1 assay. Medium was aspirated from each well of the assay plate. The WST-1 reagent was diluted 1:20 in Reduced Serum MEM, 100 µl of the diluted WST-1 reagent was added to each well and the cells were incubated at 37° C. in a humidified 5% $CO_2$ incubator for 60 minutes. The number of viable cells in each well was quantified by measuring OD at 450 nm on a plate reader.

WISH-EMCV Antiviral Assay Procedure:

On day one of the assay, log phase WISH cells were harvested with trypsin, resuspended in Reduced Serum MEM and concentrated by centrifugation. The cell pellets, corresponding to five T175 flasks of cells, were resuspended in 10 ml of Reduced Serum MEM, filtered through a 40 micron Nylon cell strainer and counted with a Coulter Counter. Cell viability was determined by trypan blue exclusion with a hemocytometer. The cells were resuspended in Reduced Serum MEM to a final density of $3 \times 10^5$ cells/ml. One hundred microliters of the diluted cells were added to each well of a 96-well assay plates ($3 \times 10^4$ cells/well) and the plates were incubated at 37° C. in a humidified 5% $CO_2$ incubator for 4 hours.

The potencies of "reference" interferon alphas and interferon-alpha polypeptides of the invention (also called "test samples") were determined by dose-response analysis. There was generally one test sample and one reference IFN-alpha per plate, each with three replicate curves of IFN-alpha treated/EMCV challenged cells and two replicate curves of IFN-alpha treatment alone. The later was assayed to control for potential antiproliferative effects of IFN-alpha on HeLa cells. The dose-response curves for the reference IFN-alphas generally consisted of 8 ten-fold dilutions ranging from 100 ng/ml to 0.0001 ng/ml. For the IFN-alpha test samples, the five-fold dilutions generally ranged from 5 ng/ml to 0.00006 ng/ml. Eight wells each of cells treated with virus but no IFN-alpha and cells alone were also run as controls.

The IFN-alpha dilutions were prepared using Reduced Serum MEM. One hundred microliters of the diluted IFN-alpha preparations were transferred to the assay plates. The assay plates were incubated at 37° C. in a humidified 5% $CO_2$ incubator for 16 hours.

On day two, the cells were challenged with EMC virus. Medium was aspirated from each well of the assay plate. The EMCV stock was diluted 1:267 in MEM+2% FBS. One hundred microliters of the diluted virus, corresponding to an MOI of approximately 5 was added to each well. The cells were incubated with virus at 37° C. in a humidified 5% $CO_2$ incubator for 24 hours.

On day three, the number of viable cells in each well was quantified by WST-1 assay. Medium was aspirated from each well of the assay plate. The WST-1 reagent was diluted 1:20 in Reduced Serum MEM, 100 µl of the diluted WST-1 reagent was added to each well and the cells were incubated at 37° C. in a humidified 5% $CO_2$ incubator for 60 minutes. The number of viable cells in each well was quantified by measuring OD at 450 nm on a plate reader.

B. $T_H1$ Differentiation Assay

Provided below is an exemplary assay for $T_H1$ differentiation activity of interferon-alpha polypeptides and conjugates of the invention.

Assay Procedure:

Human buffy coats (25-30 ml) containing leukocytes and erythrocytes prepared from 500 ml blood were collected from Stanford Blood Bank the day of assay initiation (one day before the assay day) and kept at room temperature overnight. Each buffy coat was carefully transferred to a T75 flask and diluted to 100 ml with PBS. For each buffy coat, 13 ml of Histopaque/Ficoll (Sigma H8889) was pipetted into four 50 ml centrifuge tubes, and 25 ml of diluted blood sample was carefully overlaid on top of the Histopaque/Ficoll without disrupting the interface. The tubes were then centrifuged (20° C., 2500 rpm) for 20 minutes. Using 3 ml plastic transfer pipettes the mononuclear cell layer containing PBMCs was transferred to two 50 ml conical tubes (cells from 2 Histopaque/Ficoll/buffy coat tubes to one tube). The PBMCs were then diluted to 50 ml/tube with PBS and centrifuged (20° C., 1000 rpm) for 10 minutes to remove platelets. After removal of PBS, the PBMCs and remaining RBCs were mixed to prevent aggregation. Ten milliliters of RBC lysis buffer (ammonium chloride buffer) were added and two tubes of cells were combined to one tube. Each tube, now containing the total PBMC and RBC isolate from one donor, was incubated at room temperature for 10 min. Potential clots of blood cells were removed by filtering the cells with a cell strainer (70 um, Falcon Cat. No. 2350). PBS was added to a total volume of 50 ml followed by centrifugation (20° C., 1000 rpm) for 10 min. The cell number was finally counted using a hemocytometer.

Next, a fraction of each PBMC preparation was prestained and analyzed by FACS to select PBMC preparations with a percentage of naïve $T_H0$ cells above 15%. Three hundred microliters of PBMCs were stained with 20 µl FITC-conjugated anti-human CD45RA (Pharmigen, Cat. No. 555488), 20 µl Cy-chrome conjugated anti-human CD4 (Pharmigen, Cat. No. 555348), 5 µl PE-conjugated anti-human CD8 (Pharmigen, Cat. No. 555367), 5 µl PE-conjugated anti-human CD14 (Pharmigen, Cat. No. 555398), and 5 µl PE-conjugated anti-human CD20 (Pharmigen, Cat. No. 555623), and incubated on ice for 45 minutes. The cells were washed with PBS, resuspended in 1 ml PBS, and filtered with a 40 µm cell strainer (Falcon, Cat. No. 2340). The percentage of naïve $T_H0$ cells (positive to CD4 and CD45RA and negative to CD8, CD14, CD20) were quantified by FACS, and PBMC preparations with more than 15% naïve $T_H0$ cells were selected for the assay.

The selected PBMC preparations were stained with 500 µl FITC-conjugated anti-human CD45RA, 500 µl Cy-chrome conjugated anti-human CD4, 200 µl PE-conjugated anti-human CD8, 50 µl PE-conjugated anti-human CD14, and 50 µl PE-conjugated anti-human CD20, and incubated on ice for 60 minutes. The cells were washed with PBS, PI was added, and the cells were diluted with 10 ml of PBS followed by filtering with a 40 µm cell strainer. The cells were FACS sorted, and $1 \times 10^4$ naïve $T_H0$ cells (positive to CD4 and CD45RA and negative to CD8, CD14, CD20) were transferred by MOFLO into each well of 96 well round bottom plates, containing 160 µl DMEM plus Penicillin-streptomycin plus 2 mM Glutamine and 10% Fetal Bovine Serum (Hyclone Cat. No. SH30071.03).

One point seven microliters of Dynabeads CD3/CD28 T cell expander (Dynal, Cat. No. 111.32) were added to each well. The stimulatory effect of the Dynabeads was calibrated prior to the experiment to avoid lot-to-lot variance. Next, 20 µl/well of protein samples were added to the assay plates. Generally, concentration ranges for IL-4 and IL-12 standards (obtained from R&D Systems) were from 0.04 pg/ml to 10 ng/ml, and concentration ranges for IFN-alpha test samples and IFN-alpha reference sample were from 0.76 pg/ml to 200 ng/ml.

The cells were incubated at 37° C. in a humidified 5% $CO_2$ incubator for 6 days. Supernatants from each well were harvested to determine the degree of $T_H1$ differentiation through quantification of the IFN-γ content, using a standard ELISA (R&D Systems, Cat. # DIF50).

Analysis:

Response=IFN-γ concentrations in pg/ml.

The following equation was used for curve fitting:

$$Y = \text{Bottom} + \frac{(\text{Top} - \text{Bottom})}{1 + 10^{(LogEC50-X) \cdot HillSlope}}$$

The variable Bottom is the Y value at the bottom plateau; Top is the Y value at the top plateau, and LogEC50 is the X value when the response is halfway between Bottom and Top. The Levenberg-Marquardt method was used as optimization algorithm.

C. Daudi Antiproliferation Assay

Provided below is an exemplary assay for antiproliferative activity of interferon-alpha polypeptides and conjugates of the invention.

Materials:

Daudi Cells: Human Burkitt's lymphoma cells (ATCC Number: # CCL-213). The Daudi line was derived from a 16-year-old black male with Burkitt's lymphoma in 1967. The cell line is positive for Epstein-Barr virus.

Complete RPMI:

RPMI 1640 (RPMI, Gibco Cat. No. 11875-143)

10% Fetal Bovine Serum (FBS, Hyclone Cat. No. SH30071.03)

1× Penicillin-streptomycin-gluatimine (PSG, Gibco Cat. No. 10378-01)

Daudi Burkitt's lymphoma cells grown in suspension were maintained in T175 tissue culture flasks, containing 50 ml of complete RPMI at 37° C. in a humidified 5% $CO_2$ incubator. The cells were split 1:10 when confluent.

Assay Procedure:

Daudi cells were spun down and washed with 1×PBS. The cell number was adjusted to $10^5$ cells/ml. 80 µl culture medium was added to each well in 96 well round bottom assay plates followed by transfer of 100 µl cells ($10^4$ cells/well) to each well.

Eleven dilutions of the IFN-alpha reference material and IFN-alpha test samples, ranging from 200 ng/ml to 0.2 pg/ml (4-fold dilutions), were prepared in dilution plates using culture medium. Twenty µl of the diluted IFN-alpha preparations were then transferred to the assay plates.

The cells were incubated at 37° C. in a humidified 5% $CO_2$ incubator. After 48 hours, 1 µCi of methyl-$^3$H thymidine (Amersham Pharmacia, Cat. No. TRK758) was added to each well followed by incubation for 24 hours at 37° C. in a humidified 5% $CO_2$ incubator. The cells were harvested on the following day and incorporation of thymidine was determined.

Alternatively, the Daudi antiproliferation assay may be performed by measuring the number of viable, metabolically active Daudi cells based on the amount of ATP present in a culture well following interferon treatment. In this procedure, 8000 Daudi cells are plated in a volume of 50 µl in a 96 well round bottom assay plate. The cells are allowed to incubate at 37° C. for 2 hours in a 5% $CO_2$ incubator prior to the addition of the interferon dilutions. The interferons are diluted 6-fold (9-points) generally starting from 5-10 ng/ml. Following addition of the interferons, the cells are incubated for 72 hours at 37° C. in a humidified 5% $CO_2$ incubator. The number of viable cells in each well is then determined by the addition of 100 µl of CellTiter-Glo™ (Promega, Cat #G7572). The cells plus CellTiter-Glo™ reagent are mixed for 2 minutes and incubated at room temperature in the dark for 30-60 minutes. The amount of luminescent signal for each well is determined using an Analyst HT instrument.

Analysis:

The $EC_{50}$ of the IFN-alpha reference and samples were calculated using the equation:

$$Y = \text{Bottom} + \frac{(\text{Top} - \text{Bottom})}{1 + 10^{(LogEC50 - X) \cdot HillSlope}}$$

where Bottom is the Y value at the bottom plateau; Top is the Y value at the top plateau, and LogEC50 is the X value when the response is halfway between Bottom and Top. The Levenberg-Marquardt method was used as optimization algorithm.

Example 1

Determination of Surface-Accessible Residues of Interferon-Alphas

Surface Exposure of Human Interferon-α2a Residues:

Based on the 24 NMR structures of human interferon-alpha 2a reported by Klaus et al., *J. Mol. Biol.*, 274: 661-675 (1997), the fractional ASA of side chains was calculated. The sequence numbering used below is based on the mature sequence of the human interferon-alpha 2a protein (identified herein as SEQ ID NO:47). It is noted that this structure contains two disulphide bridges involving Cys1-Cys98 and Cys29-Cys138, respectively. By computing the ASA and the fractional ASA and taking the average of the 24 structures, focusing on the ASA of the side chains, it was determined that the following residues have more than 25% fractional ASA: D2, L3, P4, Q5, T6, H7, S8, L9, G10, R12, R13, M16, A19, Q20, R22, K23, I24, S25, L26, F27, S28, L30, K31, R33, H34, D35, G37, Q40, E41, E42, G44, N45, Q46, Q48, K49, A50, E51, E58, Q61, Q62, N65, S68, T69, K70, D71, S73, A74, D77, E78, T79, L80, D82, K83, T86, Y89, Q90, N93, D94, E96, A97, V99, I100, Q101, G102, V103, G104, T106, E107, T108, P109, L110, M111, K112, E113, D114, L117, R120, K121, Q124, R125, T127, L128, K131, E132, K133, K134, Y135, S136, P137, C138, A145, M148, R149, S152, L153, N156, C158, E159, S160, L161, R162, S163, K164 and E165, with position numbering relative to that of the interferon-alpha 2a sequence identified herein as SEQ ID NO:47.

The following residues were determined to have on average more than 50% fractional ASA of their side chain: D2, L3, P4, Q5, T6, H7, S8, L9, R12, R13, M16, A19, S25, F27, S28, K31, R33, H34, D35, G37, E41, G44, N45, Q46, Q48, K49, N65, K70, A74, D77, E78, T79, D82, K83, T86, Y89, Q90, N93, D94, I100, Q101, G102, G104, T106, E107, T108, P109, L110, E113, D114, L117, R120, K121, Q124, R125, L128, K131, E132, K134, P137, R149, E159, L161, R162, S163, K164 and E165, with position numbering relative to that of the interferon-alpha 2a sequence identified herein as SEQ ID NO:47.

Surface Exposure of Residues Corresponding to SEQ ID NO:1:

Owing to an insertion of an amino acid after position 44 of the human interferon-alpha 2 subtypes—such as, for example, interferon-alpha 2b (SEQ ID NO:46) and interferon-alpha 2a (SEQ ID NO:47)—in many interferon alpha sequences, including all of the known human interferon alpha sequences (apart from the IFN-alpha 2 subtypes) and certain polypeptides of the invention, the position numbering of the surface-exposed residues will be shifted by one residue past position number 44 in, for example, the sequences shown in the alignment FIG. 2, relative to the numbering of the sequence denoted hIFNalpha 2b (SEQ ID NO:46).

Based on the above analysis, the following positions, numbered relative to SEQ ID NO:1, are considered to contain amino acid residues having more than 25% fractional ASA: positions 2, 3, 4, 5, 6, 7, 8, 9, 10, 12, 13, 16, 19, 20, 22, 23, 24, 25, 26, 27, 28, 30, 31, 33, 34, 35, 37, 40, 41, 42, 44, 46, 47, 49, 50, 51, 52, 59, 62, 63, 66, 69, 70, 71, 72, 74, 75, 78, 79, 80, 81, 83, 84, 87, 90, 91, 94, 95, 97, 98, 100, 101, 102, 103, 104, 105, 107, 108, 109, 110, 111, 112, 113, 114, 115, 118, 121, 122, 125, 126, 128, 129, 132, 133, 134, 135, 136, 137, 138, 139, 146, 149, 150, 153, 154, 157, 159, 160, 161, 162, 163, 164, 165, and 166.

Likewise, the following positions, again numbered relative to SEQ ID NO:1, are considered contain amino acid residues having on average more than 50% fractional ASA of their side chain: 2, 3, 4, 5, 6, 7, 8, 9, 12, 13, 16, 19, 25, 27, 28, 31, 33, 34, 35, 37, 41, 44, 46, 47, 49, 50, 66, 71, 75, 78, 79, 80, 83, 84, 87, 90, 91, 94, 95, 101, 102, 103, 105, 107, 108, 109, 110, 111, 114, 115, 118, 121, 122, 125, 126, 129, 132, 133, 135, 138, 150, 160, 162, 163, 164, 165, and 166.

Example 2

Antiviral Activites of Interferon-Alpha Polypeptides

Patients with chronic HCV infection have initial viral loads in the range of $10^4$-$10^7$ copies of HCV RNA/ml. Upon treatment with IFN-alpha, the viral load characteristically undergoes two distinct log-linear phases of decline reflecting two distinct mechanisms (FIG. 1B). The initial drop in viral load occurs in about the first two days and is believed to be due to the reduction in rate of virus production by infected liver cells in the face of the IFN-alpha therapy.

The major technical challenge with HCV is that the virus cannot be grown in vitro and has only recently been cultured in tractable animal models. There are, however, viruses that replicate in vitro which are considered to be useful surrogates for HCV viral replication. In vitro surrogate assays believed to be predictive of in vivo HCV antiviral activity include the assays described in the Materials and Methods section above, which measure the ability of test molecules to protect cells from the cytopathic effect (CPE) of viral infection, using Encephalomyocarditis virus (EMCV) in the human cell lines HuH7 (hepatoma derived), HeLa (cervical carcinoma derived) and WISH (amniotic tissue derived).

Table 7 below provides relative antiviral activities of various IFN-alpha polypeptides in representative CPE assays performed as described in the Materials and Methods section above. Significant differences in activity were determined by TwoWay ANOVA (factors: sample, experiment) ($\alpha=0.05$) followed by Bonferroni's post-hoc test for mean comparisons ($\alpha=0.05$) or Fisher's post-hoc test. The symbol (+/−) indicates antiviral activity which is statistically indistinguishable from that of the reference interferon; ND, not determined.

TABLE 7

| Sample Name | SEQ ID NO | HuH7/EMCV Antiviral activity relative to huIFN-alpha 2b | HeLa/EMCV Antiviral activity relative to huIFN-alpha 2b |
|---|---|---|---|
| B9X14EC4 | SEQ ID NO: 1 | >8x | >8x |
| 14EPI15 | SEQ ID NO: 10 | >8x | >8x |
| 14EPI16 | SEQ ID NO: 11 | >8x | >8x |
| 14EPI17 | SEQ ID NO: 12 | >8x | >8x |
| 14EPI18 | SEQ ID NO: 13 | >8x | >8x |
| 14EPI19 | SEQ ID NO: 14 | >8x | >8x |
| 14EPI20 | SEQ ID NO: 15 | >8x | >8x |
| 14EPI21 | SEQ ID NO: 16 | >8x | >8x |
| 14EPI25 | SEQ ID NO: 20 | >8x | >8x |
| 14EPI32 | SEQ ID NO: 27 | >8x | >8x |
| 14EPI33 | SEQ ID NO: 28 | >8x | >8x |
| 14EPI34 | SEQ ID NO: 29 | >8x | >8x |
| 25EPI19 | SEQ ID NO: 38 | >8x | >8x |
| 14EPI22 | SEQ ID NO: 17 | 4x to 8x | >8x |
| 14EPI26 | SEQ ID NO: 21 | 4x to 8x | >8x |
| 14EPI29 | SEQ ID NO: 24 | 4x to 8x | >8x |
| 14EPI31 | SEQ ID NO: 26 | 4x to 8x | >8x |
| 14EPI23 | SEQ ID NO: 18 | 4x to 8x | 4x to 8x |
| 14EPI24 | SEQ ID NO: 19 | 4x to 8x | 4x to 8x |
| 25EPI08 | SEQ ID NO: 36 | 4x to 8x | 4x to 8x |
| 25EPI26 | SEQ ID NO: 41 | 4x to 8x | 4x to 8x |
| 14EPI42 | SEQ ID NO: 35 | 4x to 8x | 2x to 4x |
| 25EPI18 | SEQ ID NO: 37 | 4x to 8x | 2x to 4x |
| 25EPI25 | SEQ ID NO: 40 | 4x to 8x | 2x to 4x |
| 14EPI30 | SEQ ID NO: 25 | 2x to 4x | 4x to 8x |
| 25EPI28 | SEQ ID NO: 43 | 2x to 4x | 2x to 4x |
| 14EPI27 | SEQ ID NO: 22 | 2x to 4x | 2x to 4x |
| 14EPI35 | SEQ ID NO: 30 | 2x to 4x | ND |
| 14EPI36 | SEQ ID NO: 31 | 2x to 4x | ND |
| 14EPI37 | SEQ ID NO: 32 | 2x to 4x | ND |
| 14EPI38 | SEQ ID NO: 33 | 2x to 4x | ND |
| 25EPI20 | SEQ ID NO: 39 | 2x to 4x | 0.5x to 2x |
| 14EPI28 | SEQ ID NO: 23 | 0.5x to 2x | 0.5x to 2x |
| 25EPI27 | SEQ ID NO: 42 | 0.1x to 0.5x | 0.1x to 0.5x |
| IFN-alpha Con1 | SEQ ID NO: 58 | 2x to 4x | 4x to 8x |
| IFN-alpha 2a | SEQ ID NO: 47 | 0.5x to 2x | 0.5x to 2x |
| IFN-alpha 2b | SEQ ID NO: 46 | 1 (ref) | 1 (ref) |

Example 3

$T_H1$ Activites of Interferon-Alpha Polypeptides

The $T_H1$ assay was designed to monitor the enhancement of differentiation of naïve T cells into $T_H1$ cells by IFN-alpha as determined by the amount of IFN-gamma detected in the culture supernatants. Table 8 provides relative $T_H1$ activities of various IFN-alpha polypeptides assayed as described in the Materials and Methods section above.

TABLE 8

| Sample | SEQ ID NO | Fold over IFN-alpha 2a |
|---|---|---|
| 14Epi18 | SEQ ID NO: 13 | >30x |
| 25Epi19 | SEQ ID NO: 38 | >30x |
| IFN-alpha Con1 | SEQ ID NO: 58 | 10x to 15x |
| IFN-alpha 2a | SEQ ID NO: 47 | 1 (ref) |

Example 4

Antiproliferative Activities of Interferon-Alpha Polypeptides

IFN-alpha inhibits proliferation of many cell types, although the antiproliferative effects often occur at higher doses than are required for the antiviral response. Daudi cells are a human derived EVB-transformed B cell line that is IFN-alpha sensitive. This IFN-alpha responsive cell line serves as a useful probe of the antiproliferative effects of the IFN-alpha polypeptides of the invention. Furthermore, antiproliferative activity of IFN-alpha on megakaryocytes and neutrophils at high dose is believed to contribute to thrombocytopenia and neutropenia, respectively. The Daudi antiproliferation assay may serve as a useful surrogate assay for antiproliferative effects on these other lymphoid cell types.

Table 9 provides relative antiproliferative activities of various IFN-alpha polypeptides assayed as described in the Materials and Methods section above, expressed as fold antiproliferative activity relative to huIFN-alpha 2a ($EC_{50}$ huIFN-alpha 2a/$EC_{50}$ sample). Under the assay conditions employed, antiproliferative activities at least 0.01x of the reference interferon were detectable.

TABLE 9

| sample name | SEQ ID NO: | Fold activity vs. IFNα-2a |
|---|---|---|
| B9X14EC4 | SEQ ID NO: 1 | 0.8x to 0.5x |
| 14Epi15 | SEQ ID NO: 10 | 0.25x to 0.1x |
| 14Epi17 | SEQ ID NO: 12 | 0.25x to 0.1x |
| 14Epi18 | SEQ ID NO: 13 | 0.8x to 0.5x |
| 14Epi19 | SEQ ID NO: 14 | 0.5x to 0.25x |
| 14Epi20 | SEQ ID NO: 15 | 0.5x to 0.25x |
| 14Epi21 | SEQ ID NO: 16 | 0.25x to 0.1x |
| 14Epi22 | SEQ ID NO: 17 | 0.25x to 0.1x |
| 14Epi23 | SEQ ID NO: 18 | 0.25x to 0.1x |
| 14Epi24 | SEQ ID NO: 19 | 0.5x to 0.25x |
| 14Epi25 | SEQ ID NO: 20 | 0.5x to 0.25x |
| 14Epi26 | SEQ ID NO: 21 | 0.5x to 0.25x |
| 14Epi27 | SEQ ID NO: 22 | 0.5x to 0.25x |
| 14Epi28 | SEQ ID NO: 23 | 0.8x to 0.5x |
| 14Epi29 | SEQ ID NO: 24 | 0.25x to 0.1x |
| 14Epi30 | SEQ ID NO: 25 | 0.5x to 0.25x |
| 14Epi31 | SEQ ID NO: 26 | 0.5x to 0.25x |
| 14Epi32 | SEQ ID NO: 27 | 1.2x to 0.8x |
| 14Epi33 | SEQ ID NO: 28 | 0.8x to 0.5x |
| 14Epi34 | SEQ ID NO: 29 | 0.8x to 0.5x |
| 14Epi35 | SEQ ID NO: 30 | 0.8x to 0.5x |
| 14Epi36 | SEQ ID NO: 31 | 0.5x to 0.25x |
| 14Epi37 | SEQ ID NO: 32 | 0.8x to 0.5x |
| 14Epi38 | SEQ ID NO: 33 | 0.8x to 0.5x |
| 14Epi42 | SEQ ID NO: 35 | 0.5x to 0.25x |
| 25Epi08 | SEQ ID NO: 36 | 0.5x to 0.25x |
| 25Epi18 | SEQ ID NO: 37 | 0.25x to 0.1x |
| 25Epi19 | SEQ ID NO: 38 | 0.8x to 0.5x |
| 25Epi20 | SEQ ID NO: 39 | 0.25x to 0.1x |
| 25Epi25 | SEQ ID NO: 40 | 0.25x to 0.1x |
| 25Epi26 | SEQ ID NO: 41 | 0.25x to 0.1x |
| 25Epi27 | SEQ ID NO: 42 | 0.5x to 0.25x |

TABLE 9-continued

| sample name | SEQ ID NO: | Fold activity vs. IFNα-2a |
|---|---|---|
| 25Epi28 | SEQ ID NO: 43 | 0.5x to 0.25x |
| 25Epi29 | SEQ ID NO: 44 | 0.8x to 0.5x |
| IFN-alpha Con1 | SEQ ID NO: 58 | 1.2x to 0.8x |
| IFN-alpha 2a | SEQ ID NO: 47 | 1x (ref) |

Example 5

Pegylation of Interferon-Alpha Polypeptides

The following provides exemplary procedures for preparing conjugates of the invention.

Cys-PEGylation

A polypeptide of the invention which contains a free cysteine may be cysteine-PEGylated as follows. The polypeptide is first partially reduced with an equimolar concentration of TCEP (Triscarboxyethylphosphine) at 4° C. for 30 min in 50 mM MES, 100 mM NaCl, pH 6.0. The reduced polypeptide is then reacted with a 4 fold molar excess of mPEG-MAL reagent (with a PEG moiety such as a 20 kDa or 30 kDa linear mPEG, or a 40 kDa branched mPEG2) for 1 h at 4° C. under the same conditions. The PEGylated reaction mixture is loaded on to a SP-Sepharose HP column equilibrated with 50 mM MES, pH 6.0, 100 mM NaCl. After a 10 CV (column volume) wash step a gradient from 0-600 mM NaCl is applied to fractionate the PEGylated and unPEGylated fractions. Fractions are collected and aliquots are analyzed by SDS-PAGE. Fractions containing monoPEGylated species are pooled and formulated for assays for interferon-alpha activity as described above.

N-Terminal PEGylation

N-terminal PEGylation with mPEG-butyraldehyde (having a PEG moiety such as a 20 kDa or 30 kDa linear mPEG, or a 40 kDa branched mPEG2) may be performed at 4° C. using a 5 fold molar excess of PEG reagent:polypeptide for 4-8 h in 50 mM MES, pH 5.5, 100 mM NaCl, and 20 mM sodium cyanoborohydride, or in 50 mM sodium acetate, pH 5.5, 100 mM NaCl and 20 mM sodium cyanoborohydride. Conjugates are isolated by chromatography over a SP-Sepharose HP column equilibrated in 50 mM MES pH 5.5, 100 mM NaCl, using a gradient from 100-600 mM NaCl in 50 mM MES pH 5.5. Fractions containing monoPEGylated species are pooled and formulated for assays for interferon-alpha activity as described above, and may be further characterized by, for example, using analytical HPLC, amino acid analysis and/or MALDI-TOF mass spectrometry.

Lysine PEGylation

In general, lysine-PEGylation was performed using a procedure essentially as described by Foser et al. (2003) Protein Expression & Purification 30:78-87. Briefly, the polypeptide was reacted with 40 kDa mPEG2-NHS at about a 3:1 to 5:1 molar ratio of mPEG2-NHS:polypeptide in 50 mM borate buffer, pH 9.0, at 4° C. for about 1 hr to overnight. Conjugates were isolated by cation exchange chromatography. Fractions containing monoPEGylated species were pooled and formulated for interferon-alpha activity assays as described above. MonoPEGylated IFN-alpha conjugates prepared according to the above procedure exhibited antiviral activity in the HeLa-EMCV assay, albeit lower than that of the parent unPEGylated polypeptides.

In some instances, the monoPEGylated pool obtained as described above was further analyzed by cation exchange HPLC using a Polysulfoethyl A column (2.1 mmID×200 mL, 5 m, 1000 A°, from PolyLC) to characterize the PEG-isomer profile. The mobile phases were buffer A: 5 mM $KH_2PO_4$, 40% 1-propanol, 1% diethylene glycol, pH 3.0 and bufferB: same as A with 200 mM NaCl. The PEG positional isomers were separated using a gradient from 50%-75% mobile phase B over 80 min at 0.1 ml/min, 20° C. with detection at 214 nm.

Figure 8:
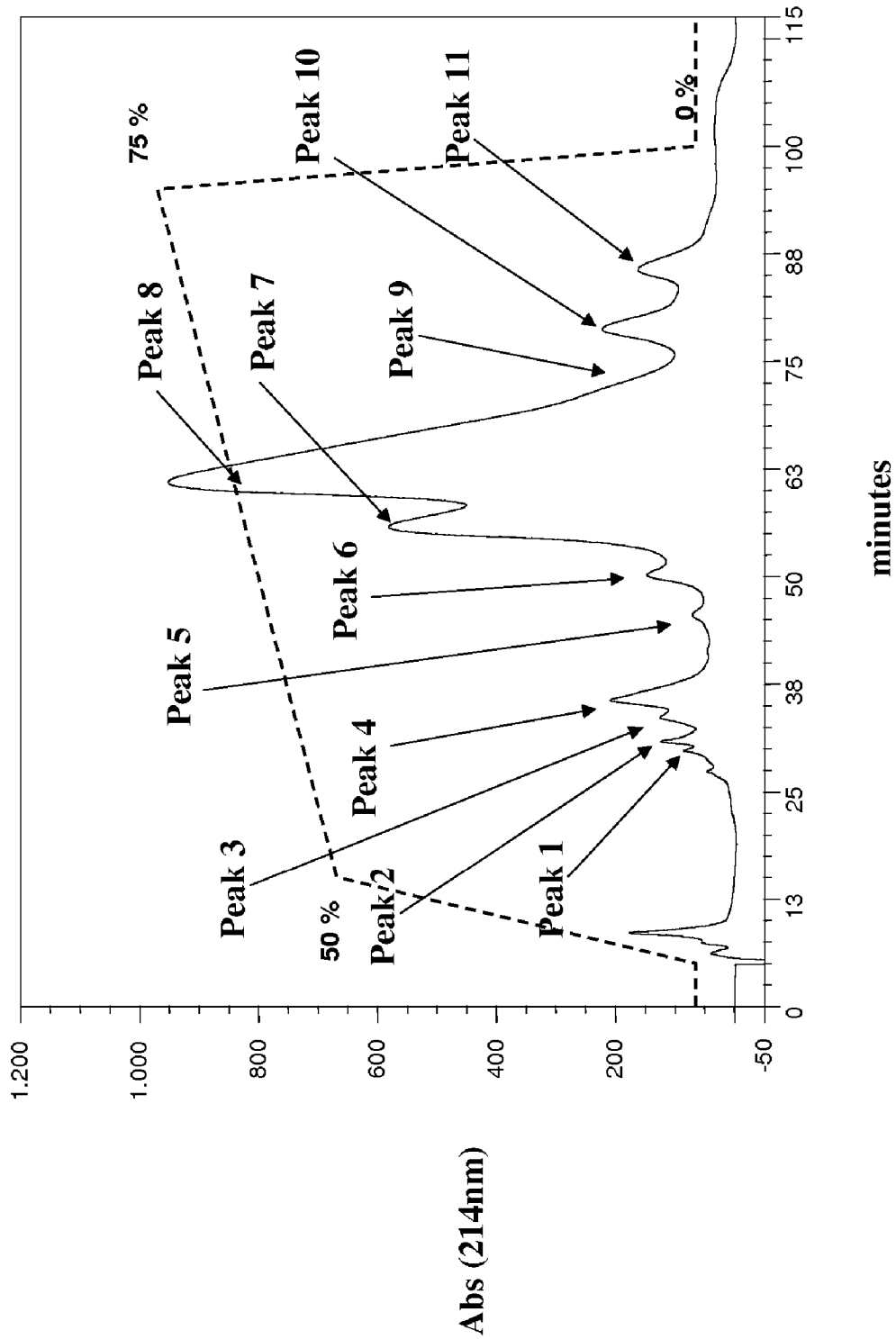
FIG. 8 shows the separation via cation exchange HPLC of positional isomers of an exemplary PEGylated interferon-alpha conjugate.
Figure 9:
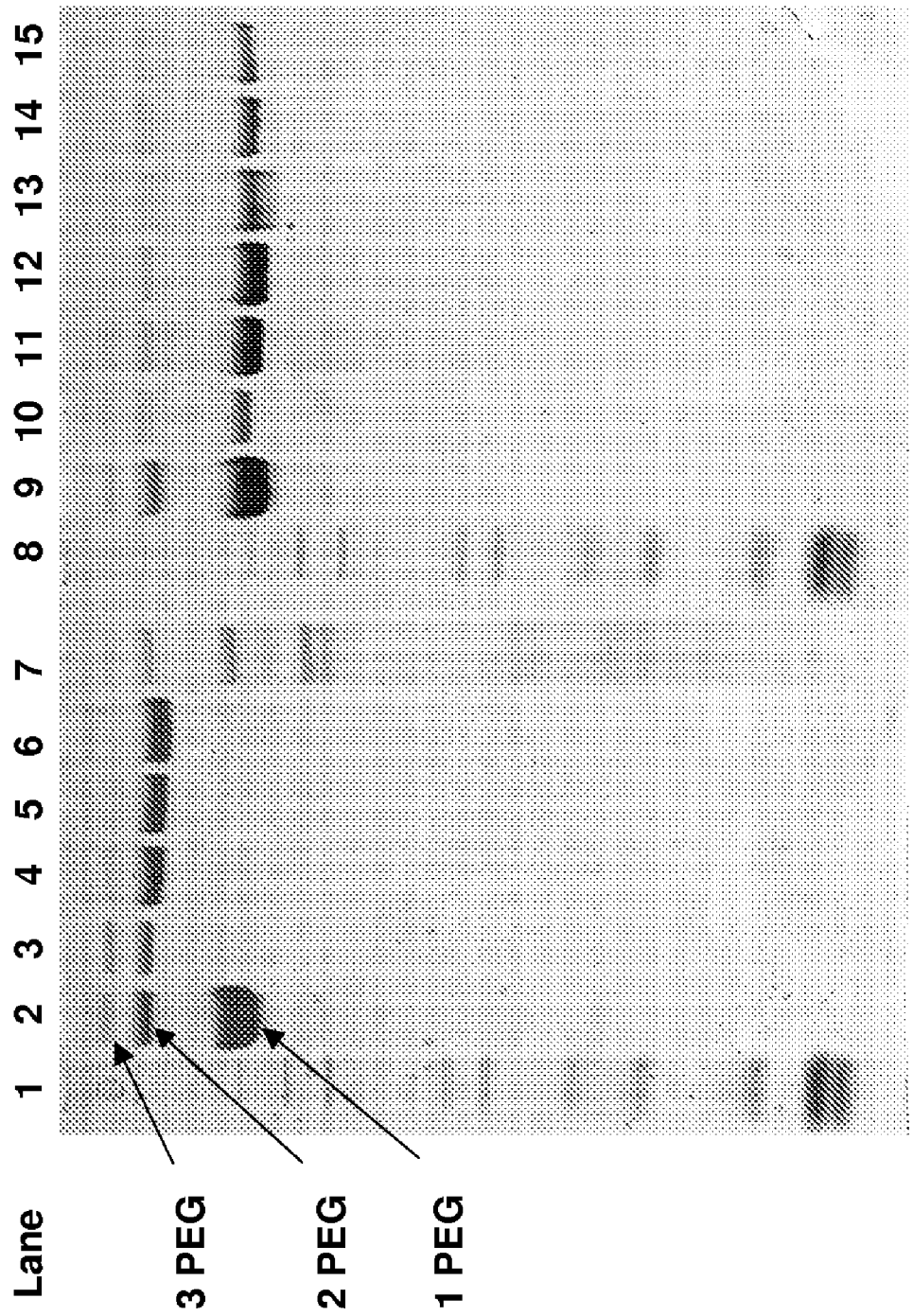
FIG. 9 shows an SDS_PAGE gel of fractions from the cation exchange HPLC separation of FIG. 8.

FIG. 8 shows the separation by cation exchange HPLC of the monoPEGylated pool obtained from the reaction of interferon-alpha polypeptide B9×14EC4 with 40 kDa mPEG2-NHS according to the above procedure. The peaks were collected and analyzed on SDS-PAGE (FIG. 9). Lanes 2 and 9 of FIG. 9 shows that the sample prior to application onto the HPLC column contains predominantly monoPEGylated protein. Peaks 1-4 (lanes 3-6 of FIG. 9) correspond to the small proportion of diPEGylated IFN in the monoPEGylated pool. Minor peak 5 (lane 7 of FIG. 9) contains approximately equal proportions of diPEGylated, monoPEGylated and a lower molecular weight species. Peaks 6-11 (lanes 10-15 of FIG. 9) correspond to positional isomers of the monoPEGylated IFN polypeptide.

Polypeptide 14epi18 (SEQ ID NO:13) was lysine-PEGylated as follows. The eluate of the Q-Sepharose chromatography step (obtained according to the Materials and Methods section above) was concentrated to c<2 mg/ml. For PEGylation the buffer was exchanged to 50 mM sodium borate, pH 9.0. The polypeptide was reacted with 40 kDa mPEG2-NHS essentially as described by Foser et al. (2003; Protein Expression & Purification 30:78-87) at a molar ratio of PEG reagent over protein of 4:1 or 5:1. The PEGylation reaction was allowed to proceed at 4° C. for 1.5 h. MonoPEGylated 14epi18 was purified from the reaction mixture by cation exchange chromatography. Elution was performed in three steps using increasing salt concentrations up to 1 M NaCl to separate oligoPEGylated, monoPEGylated and non-PEGylated species. The monoPEGylated 14epi18 peak was formulated at a concentration of 0.33 mg/ml for further analysis. The monoPEGylated 14epi18 composition so obtained yielded a population of positional isomers predominantly monoPEGylated at Lys122 and Lys135.

Polypeptide 25epi19 (SEQ ID NO:38) was lysine-PEGylated as follows. The eluate of the Q-Sepharose chromatography step (obtained according to the Materials and Methods section above) was concentrated to c<2 mg/ml. For PEGylation the buffer was exchanged to 50 mM sodium borate, pH 9.0. The polypeptide was reacted with 40 kDa mPEG2-NHS essentially as described by Foser et al. (2003; Protein Expression & Purification 30:78-87) at a molar ratio of PEG reagent over protein of 4:1. The PEGylation reaction was allowed to proceed at 4° C. overnight. MonoPEGylated 25epi19 was purified from the reaction mixture by cation exchange chromatography. Elution was performed in three steps using increasing salt concentrations up to 750 mM NaCl to separate oligoPEGylated, monoPEGylated and non-PEGylated species. The monoPEGylated 25epi19 peak was concentrated in the elution buffer to <2 mg/ml and formulated for further analysis. The monoPEGylated 25epi19 composition so obtained yielded a population of positional isomers predominantly monoPEGylated at Lys31, Lys122 and Lys135.

MonoPEGylated 14epi18 and monoPEGylated 25epi19 prepared as described above both exhibited greater than 10-fold higher antiviral activity than monoPEGylated IFN-alpha 2a in the HeLa-EMCV antiviral assay.

Example 6

Differential Scanning Calorimetry

Differential scanning calorimetry (DSC) experiments were performed to estimate the stability of some polypeptides of the invention. Samples of protein at concentrations from 100 to 325 µg/ml were buffer-exchanged into phosphate buffered saline (PBS) and subjected to DSC using a MicroCal VP-DSC (MicroCal, Northampton, Mass.). The melting temperature ($T_m$) was estimated from the plot of heat capacity ($C_p$) vs temperature. Estimated $T_m$s are: B9X14EC4 (SEQ ID NO:1) 58.4° C.; 14epi16 (SEQ ID NO:11) 64.2° C.; and 14epi18 (SEQ ID NO:13) 59.5° C. The substitution of a buried phenylalanine residue at position 48 (in SEQ ID NO:1) for either a leucine (in SEQ ID NO:11) or an alanine (in SEQ ID NO:13) appears to have no detrimental effect on the stability of the polypeptide.

Example 7

In Vivo Assays

Measurement of Pharmacokinetic (PK) and Pharmacodynamic (PD) Profiles of a Polypeptide or Conjugate of the Invention Measurement of biological or serum half-life may be carried out in a number of ways described in the literature. For example, biological half-life may be determined using an ELISA method to detect serum levels of interferon-alpha after e.g. subcutaneous or intramuscular administration. Use of an ELISA method to determine the pharmacokinetics of interferon-alpha administered subcutaneously is e.g. described by Rostaing et al. (1998), J. Am. Soc. Nephrol. 9(12): 2344-48. Merimsky et al. (1991), Cancer Chemother. Pharmacol. 27(5); 406-8, describe the determination of the serum level of an interferon-alpha administered intramuscularly.

For example, the pharmacokinetic (PK) and pharmacodynamic (PD) profiles of a conjugate of the invention may be studied in cynomolgus monkeys (*Macaca fascicularis*) according to the following procedure. Three to four year old female animals with an average weight of 5-6 kg are used in the study. Animals are acclimatized for a minimum of 6 weeks between arrival and start of treatment with a minimum period of 3 weeks acclimatization to the study housing conditions. They are housed singly in stainless-steel mesh cages (at least 540×810×760 mm) and are kept on an expanded complete commercial primate diet (100 grams/animal/day) analyzed for the absence of chemical and bacterial contaminants. In addition, animals receive fruit daily (apple or banana). Animals are fasted before all procedures requiring anesthesia.

Three days before study initiation and on the day of study initiation prior to administration of the compounds, blood samples are collected from all animals. Throughout the study, blood samples (1 ml of whole blood) are withdrawn from a femoral or cephalic/saphenous vessel of the unanesthetised manually restrained animal. The normal feeding regime is maintained during collection. Samples are collected in tubes without anticoagulant, followed by centrifugation at 3000 rpm (about 1760 g) for 10 minutes at 4° C. The serum samples are then separated into two aliquots (approximately 200 µl each) and stored at −20° C.

Prior to initiation of the study, the conjugate of the invention is formulated in 20 mM sodium acetate (pH 6.0) and 140 mM sodium chloride. At study initiation, the conjugate is administered once per animal at either 30 mcg conjugate/kg animal weight (four animals), or 300 mcg/kg (four animals), using a sterile syringe and needle introduced subcutaneously after local disinfection with an aqueous solution of ethyl alcohol. Blood samples are collected at the following time points after administration of the conjugate: 4 hours, 8 hours, 12 hours, 24 hours, 48 hours, 72 hours, 144 hours, 240 hours, 336 hours, 456 hours, 552 hours, 600 hours, 624 hours, 648 hours, 672 hours, 696 hours, 720 hours and 744 hours.

The animals are observed daily to detect any clinical signs or reaction to treatment. Injection sites are visually assessed daily in order to evaluate local tolerance. A detailed clinical examination is performed before the initiation of treatment and at study termination.

The concentration of conjugate in the isolated serum samples are determined after completion of the study, using an ELISA assay. The in vivo half-life of the conjugate in cynomolgus monkeys is then determined based on the serum concentration of the compounds at the specified time points.

The pharmacodynamic response in cynomolgus monkeys to treatment with a conjugate of the invention is evaluated by measuring the levels of 2',5'-oligoadenylate synthetase and neopterin in each of the serum samples, using a commercially available RIA (Eiken Chemical Co., Tokyo) and a commercially available ELISA (IBL Immuno Biological Laboratories, Hamburg.), respectively. Based on the measured concentrations of these two biomarkers for interferon activity in the serum samples, the area under the curve (AUC) is determined to quantify the in vivo activity of each compound at each of the two dosages.

Determining In Vitro Immunogenicity

Reduced immunogenicity of a polypeptide or conjugate of the invention relative to a reference molecule can be determined by use of an ELISA method measuring the immunoreactivity of the molecule relative to a reference molecule or preparation, typically a known interferon-alpha protein. The ELISA method is based on antibodies from patients treated with the reference protein. The immunogenicity is considered to be reduced when the polypeptide or conjugate of the invention has a statistically significant lower response in the assay than the reference molecule or preparation.

While the foregoing invention has been described in some detail for purposes of clarity and understanding, it will be clear to one skilled in the art from a reading of this disclosure that various changes in form and detail can be made without departing from the true scope of the invention. It is understood that the examples and embodiments described herein are for illustrative purposes only and that various modifications or changes in light thereof will be suggested to persons skilled in the art and are to be included within the spirit and purview of this application and scope of the appended claims. For example, all the techniques and apparatus described above may be used in various combinations. All publications, patents, patent applications, and/or other documents cited in this application are incorporated herein by reference in their entirety for all purposes to the same extent as if each individual publication, patent, patent application, and/or other document were individually indicated to be incorporated herein by reference in its entirety for all purposes.

What is claimed is:

1. An isolated or recombinant polynucleotide comprising a nucleic acid sequence which encodes a polypeptide having the sequence SEQ ID NO:13 or a sequence which differs from SEQ ID NO:13 in 1-8 amino acid positions, which comprises Ala or Leu at position 48 and optionally comprises a methionine at the N-terminus, which polypeptide exhibits antiviral activity.

2. The polynucleotide of claim 1, comprising a nucleic acid sequence which encodes a polypeptide comprising the sequence SEQ ID NO:13.

3. The polynucleotide of claim 2, comprising a nucleic acid sequence selected from SEQ ID NO:62, SEQ ID NO:63, SEQ ID NO:64, and SEQ ID NO:89.

4. An isolated host cell comprising the nucleic acid of claim 1.

5. A vector comprising the polynucleotide of claim 1.

6. The vector of claim 5, which is an expression vector comprising the polynucleotide operably linked to a promoter.

7. An isolated host cell comprising the vector of claim 6.

8. A composition comprising the polynucleotide of claim 1 and an excipient.

9. A method for preparing a polypeptide, the method comprising:
   providing a culture comprising a host cell, the host cell comprising an expression vector comprising a promoter operably linked to the polynucleotide of claim 1,
   culturing the culture under conditions which permit expression of the polypeptide, and
   recovering the polypeptide.

10. The method of claim 9, wherein the host cell is a glycosylating host cell.

11. The method of claim 9, wherein the host cell is a bacterial host cell.

12. The method of claim 9, wherein the bacterial host cell is *E. coli*.

13. The method of claim 12, wherein the step of recovering the polypeptide comprises:
(a) isolating inclusion bodies (IB) comprising the polypeptide;
(b) solubilizing the IB, thereby obtaining unfolded polypeptide;
(c) refolding the unfolded polypeptide, thereby obtaining refolded polypeptide; and
(d) purifying the refolded polypeptide.

* * * * *

SEQUENCE LISTING

<160> NUMBER OF SEQ ID NOS: 90

<210> SEQ ID NO 1
<211> LENGTH: 166
<212> TYPE: PRT
<213> ORGANISM: Artificial Sequence
<220> FEATURE:
<223> OTHER INFORMATION: Synthetic construct B9x14EC4

<400> SEQUENCE: 1

```
Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

<210> SEQ ID NO 2
<211> LENGTH: 166
<212> TYPE: PRT
<213> ORGANISM: Artificial Sequence
<220> FEATURE:
<223> OTHER INFORMATION: Synthetic construct 14epi07

<400> SEQUENCE: 2

```
Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Pro Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110
```

```
Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 3
<211> LENGTH: 166
<212> TYPE: PRT
<213> ORGANISM: Artificial Sequence
<220> FEATURE:
<223> OTHER INFORMATION: Synthetic construct 14epi08

<400> SEQUENCE: 3

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Ala Pro Ala Ile Ser Val Leu His Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 4
<211> LENGTH: 166
<212> TYPE: PRT
<213> ORGANISM: Artificial Sequence
<220> FEATURE:
<223> OTHER INFORMATION: Synthetic construct 14epi09

<400> SEQUENCE: 4

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Ala Glu Thr Ile Pro Val Leu His Glu Met Met Gln Gln Thr
    50                  55                  60

Phe Asn Leu Phe Ser Thr Lys Asp Ser Ser Ala Ala Trp Asp Glu Thr
65                  70                  75                  80
```

```
Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 5
<211> LENGTH: 166
<212> TYPE: PRT
<213> ORGANISM: Artificial Sequence
<220> FEATURE:
<223> OTHER INFORMATION: Synthetic construct 14epi10

<400> SEQUENCE: 5

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Ala Glu Ala Ile Ser Val Leu His Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 6
<211> LENGTH: 166
<212> TYPE: PRT
<213> ORGANISM: Artificial Sequence
<220> FEATURE:
<223> OTHER INFORMATION: Synthetic construct 14epi11

<400> SEQUENCE: 6

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45
```

```
Gln Lys Ala Gln Ala Ile Ser Ala Phe His Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 7
<211> LENGTH: 166
<212> TYPE: PRT
<213> ORGANISM: Artificial Sequence
<220> FEATURE:
<223> OTHER INFORMATION: Synthetic construct 14epi12d

<400> SEQUENCE: 7

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn His Leu
             35                  40                  45

Gln Lys Val Gln Ala Ile Phe Leu Phe Tyr Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Asp
145                 150                 155                 160

Ser Leu Arg Ser Lys Glu
                165

<210> SEQ ID NO 8
<211> LENGTH: 166
<212> TYPE: PRT
<213> ORGANISM: Artificial Sequence
<220> FEATURE:
<223> OTHER INFORMATION: Synthetic construct 14epi13
```

<400> SEQUENCE: 8

```
Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
            165

<210> SEQ ID NO 9
<211> LENGTH: 166
<212> TYPE: PRT
<213> ORGANISM: Artificial Sequence
<220> FEATURE:
<223> OTHER INFORMATION: Synthetic construct 14epi14

<400> SEQUENCE: 9

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
            165
```

```
<210> SEQ ID NO 10
<211> LENGTH: 166
<212> TYPE: PRT
<213> ORGANISM: Artificial Sequence
<220> FEATURE:
<223> OTHER INFORMATION: Synthetic construct 14epi15

<400> SEQUENCE: 10

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
             20                  25                  30

Arg His Asp Phe Arg Phe Pro Gln Glu Glu Phe Asp Gly Asn His Leu
         35                  40                  45

Gln Lys Val Gln Ala Ile Phe Leu Phe Tyr Glu Met Met Gln Gln Thr
     50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 11
<211> LENGTH: 166
<212> TYPE: PRT
<213> ORGANISM: Artificial Sequence
<220> FEATURE:
<223> OTHER INFORMATION: Synthetic construct 14epi16

<400> SEQUENCE: 11

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
             20                  25                  30

Arg His Asp Phe Arg Phe Pro Gln Glu Glu Phe Asp Gly Asn His Leu
         35                  40                  45

Gln Lys Val Gln Ala Ile Ala Leu Phe Tyr Glu Met Met Gln Gln Thr
     50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140
```

```
Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 12
<211> LENGTH: 166
<212> TYPE: PRT
<213> ORGANISM: Artificial Sequence
<220> FEATURE:
<223> OTHER INFORMATION: Synthetic construct 14epi17

<400> SEQUENCE: 12

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Leu
        35                  40                  45

Gln Lys Val Gln Ala Ile Ser Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 13
<211> LENGTH: 166
<212> TYPE: PRT
<213> ORGANISM: Artificial Sequence
<220> FEATURE:
<223> OTHER INFORMATION: Synthetic construct 14epi18

<400> SEQUENCE: 13

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110
```

```
Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 14
<211> LENGTH: 166
<212> TYPE: PRT
<213> ORGANISM: Artificial Sequence
<220> FEATURE:
<223> OTHER INFORMATION: Synthetic construct 14epi19

<400> SEQUENCE: 14

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Ala Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 15
<211> LENGTH: 166
<212> TYPE: PRT
<213> ORGANISM: Artificial Sequence
<220> FEATURE:
<223> OTHER INFORMATION: Synthetic construct 14epi20

<400> SEQUENCE: 15

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Ser Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80
```

```
Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 16
<211> LENGTH: 166
<212> TYPE: PRT
<213> ORGANISM: Artificial Sequence
<220> FEATURE:
<223> OTHER INFORMATION: Synthetic construct 14epi21

<400> SEQUENCE: 16

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Ala Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 17
<211> LENGTH: 166
<212> TYPE: PRT
<213> ORGANISM: Artificial Sequence
<220> FEATURE:
<223> OTHER INFORMATION: Synthetic construct 14epi22

<400> SEQUENCE: 17

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45
```

```
Gln Lys Val Gln Ala Ile Ser Leu Phe Tyr Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 18
<211> LENGTH: 166
<212> TYPE: PRT
<213> ORGANISM: Artificial Sequence
<220> FEATURE:
<223> OTHER INFORMATION: Synthetic construct 14epi23

<400> SEQUENCE: 18

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn His Ala
             35                  40                  45

Gln Lys Val Gln Ala Ile Ser Leu Phe Tyr Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Ala Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 19
<211> LENGTH: 166
<212> TYPE: PRT
<213> ORGANISM: Artificial Sequence
<220> FEATURE:
<223> OTHER INFORMATION: Synthetic construct 14epi24
```

```
<400> SEQUENCE: 19

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Ser Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 20
<211> LENGTH: 166
<212> TYPE: PRT
<213> ORGANISM: Artificial Sequence
<220> FEATURE:
<223> OTHER INFORMATION: Synthetic construct 14epi25

<400> SEQUENCE: 20

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Leu
        35                  40                  45

Gln Lys Val Gln Ala Ile Ser Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Ala Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

```
<210> SEQ ID NO 21
<211> LENGTH: 166
<212> TYPE: PRT
<213> ORGANISM: Artificial Sequence
<220> FEATURE:
<223> OTHER INFORMATION: Synthetic construct 14epi26

<400> SEQUENCE: 21

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Leu
        35                  40                  45

Gln Lys Val Gln Ala Ile Ser Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 22
<211> LENGTH: 166
<212> TYPE: PRT
<213> ORGANISM: Artificial Sequence
<220> FEATURE:
<223> OTHER INFORMATION: Synthetic construct 14epi27

<400> SEQUENCE: 22

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Ser Leu Phe Tyr Glu Met Met Gln Gln Thr
    50                  55                  60

Ala Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Ala Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140
```

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 23
<211> LENGTH: 166
<212> TYPE: PRT
<213> ORGANISM: Artificial Sequence
<220> FEATURE:
<223> OTHER INFORMATION: Synthetic construct 14epi28

<400> SEQUENCE: 23

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Ser Leu Phe Tyr Glu Met Met Gln Gln Thr
    50                  55                  60

Ala Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Met Asn Asp Leu
                85                  90                  95

Glu Ala Cys Val Met Gln Glu Val Gly Val Glu Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 24
<211> LENGTH: 166
<212> TYPE: PRT
<213> ORGANISM: Artificial Sequence
<220> FEATURE:
<223> OTHER INFORMATION: Synthetic construct 14epi29

<400> SEQUENCE: 24

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Ser Leu Phe Tyr Glu Met Met Gln Gln Thr
    50                  55                  60

Ala Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Met Asn Asp Leu
                85                  90                  95

Glu Ala Cys Val Met Gln Glu Val Gly Val Glu Glu Thr Pro Leu Met
            100                 105                 110

```
Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
            165

<210> SEQ ID NO 25
<211> LENGTH: 166
<212> TYPE: PRT
<213> ORGANISM: Artificial Sequence
<220> FEATURE:
<223> OTHER INFORMATION: Synthetic construct 14epi30

<400> SEQUENCE: 25

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Ala Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Ala Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
            165

<210> SEQ ID NO 26
<211> LENGTH: 166
<212> TYPE: PRT
<213> ORGANISM: Artificial Sequence
<220> FEATURE:
<223> OTHER INFORMATION: Synthetic construct 14epi31

<400> SEQUENCE: 26

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Ala
        35                  40                  45

Gln Lys Val Gln Ala Ile Ala Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80
```

```
Leu Leu Glu Lys Phe Tyr Ile Glu Leu Phe Gln Gln Met Asn Asp Leu
            85                  90                  95

Glu Ala Cys Val Met Gln Glu Val Gly Val Glu Glu Thr Pro Leu Met
            100                 105                 110

Lys Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
            165

<210> SEQ ID NO 27
<211> LENGTH: 166
<212> TYPE: PRT
<213> ORGANISM: Artificial Sequence
<220> FEATURE:
<223> OTHER INFORMATION: Synthetic construct 14epi32

<400> SEQUENCE: 27

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Leu
            35                  40                  45

Gln Lys Val Pro Ala Ile Ser Leu Phe Tyr Glu Met Met Gln Gln Thr
            50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
            85                  90                  95

Glu Ala Cys Val Met Gln Glu Val Gly Val Glu Glu Thr Pro Leu Met
            100                 105                 110

Lys Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Phe Ser Thr Asn Leu Gln Glu
145                 150                 155                 160

Ser Leu Arg Ser Lys Glu
            165

<210> SEQ ID NO 28
<211> LENGTH: 166
<212> TYPE: PRT
<213> ORGANISM: Artificial Sequence
<220> FEATURE:
<223> OTHER INFORMATION: Synthetic construct 14epi33

<400> SEQUENCE: 28

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
            35                  40                  45
```

Gln Lys Val Pro Ala Ile Ser Leu Phe Tyr Glu Met Met Gln Gln Thr
            50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Lys Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 29
<211> LENGTH: 166
<212> TYPE: PRT
<213> ORGANISM: Artificial Sequence
<220> FEATURE:
<223> OTHER INFORMATION: Synthetic construct 14epi34

<400> SEQUENCE: 29

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
                20                  25                  30

Arg His Asp Phe Arg Phe Pro Gln Glu Glu Phe Asp Gly Asn His Phe
            35                  40                  45

Gln Lys Val Pro Ala Ile Ser Leu Phe Tyr Glu Met Met Gln Gln Thr
            50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 30
<211> LENGTH: 166
<212> TYPE: PRT
<213> ORGANISM: Artificial Sequence
<220> FEATURE:
<223> OTHER INFORMATION: Synthetic construct 14epi35

```
<400> SEQUENCE: 30

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Leu
        35                  40                  45

Gln Lys Ala Pro Ala Ile Ser Val Leu His Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 31
<211> LENGTH: 166
<212> TYPE: PRT
<213> ORGANISM: Artificial Sequence
<220> FEATURE:
<223> OTHER INFORMATION: Synthetic construct 14epi36

<400> SEQUENCE: 31

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Ala Glu Thr Ile Pro Val Leu His Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

```
<210> SEQ ID NO 32
<211> LENGTH: 166
<212> TYPE: PRT
<213> ORGANISM: Artificial Sequence
<220> FEATURE:
<223> OTHER INFORMATION: Synthetic construct 14epi37

<400> SEQUENCE: 32

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Ala Gln Ala Ile Ser Val Leu His Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 33
<211> LENGTH: 166
<212> TYPE: PRT
<213> ORGANISM: Artificial Sequence
<220> FEATURE:
<223> OTHER INFORMATION: Synthetic construct 14epi38

<400> SEQUENCE: 33

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Ala Pro Ala Ile Ser Val Leu His Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140
```

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 34
<211> LENGTH: 166
<212> TYPE: PRT
<213> ORGANISM: Artificial Sequence
<220> FEATURE:
<223> OTHER INFORMATION: Synthetic construct 14epi39

<400> SEQUENCE: 34

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
                20                  25                  30

Arg His Asp Phe Arg Phe Pro Gln Glu Glu Phe Asp Gly Asn Gln Ala
            35                  40                  45

Gln Lys Val Gln Ala Ile Ser Leu Phe Tyr Glu Met Met Gln Gln Thr
50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 35
<211> LENGTH: 166
<212> TYPE: PRT
<213> ORGANISM: Artificial Sequence
<220> FEATURE:
<223> OTHER INFORMATION: Synthetic construct 14epi42

<400> SEQUENCE: 35

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
                20                  25                  30

Arg His Asp Phe Arg Phe Pro Gln Glu Glu Phe Asp Gly Asn Gln Ala
            35                  40                  45

Gln Lys Val Gln Ala Ile Ser Val Phe His Glu Met Met Gln Gln Thr
50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

```
Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 36
<211> LENGTH: 166
<212> TYPE: PRT
<213> ORGANISM: Artificial Sequence
<220> FEATURE:
<223> OTHER INFORMATION: Synthetic Construct 25Epi08

<400> SEQUENCE: 36

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 37
<211> LENGTH: 166
<212> TYPE: PRT
<213> ORGANISM: Artificial Sequence
<220> FEATURE:
<223> OTHER INFORMATION: Synthetic Construct 25Epi18

<400> SEQUENCE: 37

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Ala
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80
```

```
Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 38
<211> LENGTH: 166
<212> TYPE: PRT
<213> ORGANISM: Artificial Sequence
<220> FEATURE:
<223> OTHER INFORMATION: Synthetic Construct 25Epi19

<400> SEQUENCE: 38

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Ala
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 39
<211> LENGTH: 166
<212> TYPE: PRT
<213> ORGANISM: Artificial Sequence
<220> FEATURE:
<223> OTHER INFORMATION: Synthetic Construct 25Epi20

<400> SEQUENCE: 39

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Ala
        35                  40                  45
```

```
Gln Lys Val Gln Ala Ile Ser Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Arg Arg Ile Thr
                115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 40
<211> LENGTH: 166
<212> TYPE: PRT
<213> ORGANISM: Artificial Sequence
<220> FEATURE:
<223> OTHER INFORMATION: Synthetic Construct 25Epi25

<400> SEQUENCE: 40

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
                20                  25                  30

Arg His Asp Phe Gly Phe Pro Glu Glu Glu Phe Asp Gly His Gln Ala
            35                  40                  45

Gln Lys Val Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
                115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 41
<211> LENGTH: 166
<212> TYPE: PRT
<213> ORGANISM: Artificial Sequence
<220> FEATURE:
<223> OTHER INFORMATION: Synthetic Construct 25Epi26
```

<400> SEQUENCE: 41

```
Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Ala
        35                  40                  45

Gln Lys Val Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Tyr Gln Gln Leu Asn Asp Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

<210> SEQ ID NO 42
<211> LENGTH: 166
<212> TYPE: PRT
<213> ORGANISM: Artificial Sequence
<220> FEATURE:
<223> OTHER INFORMATION: Synthetic Construct 25Epi27

<400> SEQUENCE: 42

```
Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Ala
        35                  40                  45

Gln Lys Val Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Ala Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

<210> SEQ ID NO 43
<211> LENGTH: 166
<212> TYPE: PRT
<213> ORGANISM: Artificial Sequence
<220> FEATURE:
<223> OTHER INFORMATION: Synthetic Construct 25Epi28

<400> SEQUENCE: 43

```
Cys Asp Leu Pro Gln Thr His Ser Leu Ser Asn Arg Arg Thr Leu Met
 1               5                  10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Ala
        35                  40                  45

Gln Lys Val Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Tyr Gln Gln Leu Asn Asp Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

<210> SEQ ID NO 44
<211> LENGTH: 166
<212> TYPE: PRT
<213> ORGANISM: Artificial Sequence
<220> FEATURE:
<223> OTHER INFORMATION: Synthetic Construct 25Epi29

<400> SEQUENCE: 44

```
Cys Asp Leu Pro Gln Thr His Ser Leu Ser Asn Arg Arg Thr Leu Met
 1               5                  10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140
```

-continued

Arg Ala Glu Ile Met Arg Ser Phe Ser Phe Ser Thr Asn Leu Gln Asp
145                 150                 155                 160

Ser Leu Arg Ser Lys Glu
            165

<210> SEQ ID NO 45
<211> LENGTH: 166
<212> TYPE: PRT
<213> ORGANISM: homo sapiens

<400> SEQUENCE: 45

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Leu Ser Thr Asn Leu Gln Glu
145                 150                 155                 160

Arg Leu Arg Arg Lys Glu
            165

<210> SEQ ID NO 46
<211> LENGTH: 165
<212> TYPE: PRT
<213> ORGANISM: homo sapiens

<400> SEQUENCE: 46

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

```
Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 47
<211> LENGTH: 165
<212> TYPE: PRT
<213> ORGANISM: homo sapiens

<400> SEQUENCE: 47

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 48
<211> LENGTH: 166
<212> TYPE: PRT
<213> ORGANISM: homo sapiens

<400> SEQUENCE: 48

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
                20                  25                  30

Arg His Asp Phe Gly Phe Pro Glu Glu Glu Phe Asp Gly His Gln Phe
            35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110
```

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
            165

<210> SEQ ID NO 49
<211> LENGTH: 166
<212> TYPE: PRT
<213> ORGANISM: homo sapiens

<400> SEQUENCE: 49

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
            35                  40                  45

Gln Lys Ala Gln Ala Ile Ser Val Leu His Glu Met Ile Gln Gln Thr
50                  55                  60

Phe Asn Leu Phe Ser Thr Lys Asp Ser Ser Ala Thr Trp Asp Glu Thr
65                  70                  75                  80

Leu Leu Asp Lys Phe Tyr Thr Glu Leu Tyr Gln Gln Leu Asn Asp Leu
            85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Ala Asn Leu Gln Glu
145                 150                 155                 160

Arg Leu Arg Arg Lys Glu
            165

<210> SEQ ID NO 50
<211> LENGTH: 166
<212> TYPE: PRT
<213> ORGANISM: homo sapiens

<400> SEQUENCE: 50

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
            35                  40                  45

Gln Lys Ala Glu Ala Ile Ser Val Leu His Glu Val Ile Gln Gln Thr
50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
            85                  90                  95

```
Glu Ala Cys Val Met Gln Glu Val Trp Val Gly Gly Thr Pro Leu Met
                100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Ser Arg Asn Leu Gln Glu
145                 150                 155                 160

Arg Leu Arg Arg Lys Glu
                165

<210> SEQ ID NO 51
<211> LENGTH: 166
<212> TYPE: PRT
<213> ORGANISM: homo sapiens

<400> SEQUENCE: 51

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 52
<211> LENGTH: 166
<212> TYPE: PRT
<213> ORGANISM: homo sapiens

<400> SEQUENCE: 52

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80
```

```
Leu Leu Asp Glu Phe Tyr Ile Glu Leu Asp Gln Gln Leu Asn Asp Leu
            85                  90                  95

Glu Ser Cys Val Met Gln Val Gly Val Ile Glu Ser Pro Leu Met
            100                 105                 110

Tyr Glu Asp Ser Ile Leu Ala Val Arg Lys Tyr Phe Gln Arg Ile Thr
            115                 120                 125

Leu Tyr Leu Thr Glu Lys Lys Tyr Ser Ser Cys Ala Trp Glu Val Val
130                 135                 140

Arg Ala Glu Ile Met Arg Ser Phe Ser Leu Ser Ile Asn Leu Gln Lys
145                 150                 155                 160

Arg Leu Lys Ser Lys Glu
            165
```

<210> SEQ ID NO 53
<211> LENGTH: 166
<212> TYPE: PRT
<213> ORGANISM: homo sapiens

<400> SEQUENCE: 53

```
Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
            35                  40                  45

Gln Lys Ala Gln Ala Ile Ser Val Leu His Glu Met Ile Gln Gln Thr
50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
            85                  90                  95

Glu Ala Cys Val Ile Gln Glu Val Gly Val Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Ile Glu Arg Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
            165
```

<210> SEQ ID NO 54
<211> LENGTH: 166
<212> TYPE: PRT
<213> ORGANISM: homo sapiens

<400> SEQUENCE: 54

```
Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
            35                  40                  45

Gln Lys Ala Gln Ala Ile Ser Val Leu His Glu Met Met Gln Gln Thr
50                  55                  60
```

```
Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Ile Gln Glu Val Gly Val Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Met Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Lys
145                 150                 155                 160

Arg Leu Arg Arg Lys Asp
                165

<210> SEQ ID NO 55
<211> LENGTH: 166
<212> TYPE: PRT
<213> ORGANISM: homo sapiens

<400> SEQUENCE: 55

Cys Asp Leu Pro Gln Thr His Ser Leu Gly Asn Arg Arg Ala Leu Ile
  1               5                  10                  15

Leu Leu Ala Gln Met Gly Arg Ile Ser His Phe Ser Cys Leu Lys Asp
                 20                  25                  30

Arg Tyr Asp Phe Gly Phe Pro Gln Glu Val Phe Asp Gly Asn Gln Phe
             35                  40                  45

Gln Lys Ala Gln Ala Ile Ser Ala Phe His Glu Met Ile Gln Gln Thr
        50                  55                  60

Phe Asn Leu Phe Ser Thr Lys Asp Ser Ser Ala Ala Trp Asp Glu Thr
 65                  70                  75                  80

Leu Leu Asp Lys Phe Tyr Ile Glu Leu Phe Gln Gln Leu Asn Asp Leu
                 85                  90                  95

Glu Ala Cys Val Thr Gln Glu Val Gly Val Glu Glu Ile Ala Leu Met
            100                 105                 110

Asn Glu Asp Ser Ile Leu Ala Val Arg Lys Tyr Phe Gln Arg Ile Thr
            115                 120                 125

Leu Tyr Leu Met Gly Lys Lys Tyr Ser Pro Cys Ala Trp Glu Val Val
        130                 135                 140

Arg Ala Glu Ile Met Arg Ser Phe Ser Phe Ser Thr Asn Leu Gln Lys
145                 150                 155                 160

Gly Leu Arg Arg Lys Asp
                165

<210> SEQ ID NO 56
<211> LENGTH: 166
<212> TYPE: PRT
<213> ORGANISM: homo sapiens

<400> SEQUENCE: 56

Cys Asp Leu Pro Gln Thr His Ser Leu Gly Asn Arg Arg Ala Leu Ile
  1               5                  10                  15

Leu Leu Ala Gln Met Gly Arg Ile Ser Pro Phe Ser Cys Leu Lys Asp
                 20                  25                  30

Arg His Asp Phe Gly Leu Pro Gln Glu Glu Phe Asp Gly Asn Gln Phe
             35                  40                  45
```

-continued

```
Gln Lys Thr Gln Ala Ile Ser Val Leu His Glu Met Ile Gln Gln Thr
         50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asn Leu
                 85                  90                  95

Glu Ala Cys Val Ile Gln Glu Val Gly Met Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 57
<211> LENGTH: 166
<212> TYPE: PRT
<213> ORGANISM: homo sapiens

<400> SEQUENCE: 57

Cys Asp Leu Pro Gln Thr His Ser Leu Gly Asn Arg Arg Ala Leu Ile
  1               5                  10                  15

Leu Leu Ala Gln Met Gly Arg Ile Ser Pro Phe Ser Cys Leu Lys Asp
                 20                  25                  30

Arg His Asp Phe Gly Phe Pro Gln Glu Glu Phe Asp Gly Asn Gln Phe
             35                  40                  45

Gln Lys Ala Gln Ala Ile Ser Val Leu His Glu Met Ile Gln Gln Thr
         50                  55                  60

Phe Asn Leu Phe Ser Thr Lys Asp Ser Ser Ala Thr Trp Glu Gln Ser
 65                  70                  75                  80

Leu Leu Glu Lys Phe Ser Thr Glu Leu Asn Gln Gln Leu Asn Asp Leu
                 85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 58
<211> LENGTH: 167
<212> TYPE: PRT
<213> ORGANISM: Artificial Sequence
<220> FEATURE:
<223> OTHER INFORMATION: Synthetic Construct IFN-alpha Con1
```

<400> SEQUENCE: 58

```
Met Cys Asp Leu Pro Gln Thr His Ser Leu Gly Asn Arg Arg Ala Leu
 1               5                  10                  15
Ile Leu Leu Ala Gln Met Arg Arg Ile Ser Pro Phe Ser Cys Leu Lys
            20                  25                  30
Asp Arg His Asp Phe Gly Phe Pro Gln Glu Glu Phe Asp Gly Asn Gln
        35                  40                  45
Phe Gln Lys Ala Gln Ala Ile Ser Val Leu His Glu Met Ile Gln Gln
    50                  55                  60
Thr Phe Asn Leu Phe Ser Thr Lys Asp Ser Ser Ala Ala Trp Asp Glu
65                  70                  75                  80
Ser Leu Leu Glu Lys Phe Tyr Thr Glu Leu Tyr Gln Gln Leu Asn Asp
                85                  90                  95
Leu Glu Ala Cys Val Ile Gln Glu Val Gly Val Glu Glu Thr Pro Leu
            100                 105                 110
Met Asn Val Asp Ser Ile Leu Ala Val Lys Lys Tyr Phe Gln Arg Ile
        115                 120                 125
Thr Leu Tyr Leu Thr Glu Lys Lys Tyr Ser Pro Cys Ala Trp Glu Val
    130                 135                 140
Val Arg Ala Glu Ile Met Arg Ser Phe Ser Leu Ser Thr Asn Leu Gln
145                 150                 155                 160
Glu Arg Leu Arg Arg Lys Glu
                165
```

<210> SEQ ID NO 59
<211> LENGTH: 498
<212> TYPE: DNA
<213> ORGANISM: Artificial Sequence
<220> FEATURE:
<223> OTHER INFORMATION: Synthetic Construct 14epi15c1

<400> SEQUENCE: 59

```
tgtgatctgc ctcagaccca cagcctgggt cacaggagga ccatgatgct cctggcacaa      60
atgaggagaa tctctctttt ctcctgtctg aaggacagac atgacttcag atttccccag     120
gaggagtttg atggcaacca cctccagaag gttcaagcta tcttcctttt ctatgagatg     180
atgcagcaga ccttcaacct cttcagcaca aaggactcat ctgctgcttg ggatgagacc     240
ctcctagaaa aattctacat tgaactttc cagcaaatga atgacctgga agcctgcgtg     300
atgcaggagg ttggagtgga agagactccc ctgatgaatg tggactccat cctggctgtg     360
aggaaatact ttcaaagaat cactctttat ctgacagaga agaagtatag cccttgtgcc     420
tgggaggttg tcagagcaga aatcatgaga tctttctctt tttcaacaaa cttgcaagaa     480
agcttacgca gcaaggaa                                                  498
```

<210> SEQ ID NO 60
<211> LENGTH: 501
<212> TYPE: DNA
<213> ORGANISM: Artificial Sequence
<220> FEATURE:
<223> OTHER INFORMATION: Synthetic Construct 14epi15c2

<400> SEQUENCE: 60

```
atgtgtgatc tgcctcagac ccacagcctg ggtcaccgtc gcaccatgat gctcctggca      60
caaatgcgtc gcatctctct tttctcctgt ctgaaggacc gccatgactt ccgctttccc     120
caggaggagt tgatggcaa ccacctccag aaggttcaag ctatcttcct tttctatgag     180
```

```
atgatgcagc agaccttcaa cctcttcagc acaaaggact catctgctgc ttgggatgag      240
accctcctag aaaaattcta cattgaactt ttccagcaaa tgaatgacct ggaagcctgc      300
gtgatgcagg aggttggagt ggaagagact cccctgatga atgtggactc catcctggct      360
gtgcgtaaat actttcaacg catcactctt tatctgacag agaagaagta tagcccttgt      420
gcctgggagg ttgtccgcgc agaaatcatg cgctctttct cttttcaac aaacttgcaa       480 gaaagcttac gcagcaagga a                                                501

<210> SEQ ID NO 61
<211> LENGTH: 501
<212> TYPE: DNA
<213> ORGANISM: Artificial Sequence
<220> FEATURE:
<223> OTHER INFORMATION: Synthetic Construct 14epi15c3

<400> SEQUENCE: 61
atgtgtgatc tgcctcagac ccacagcctg ggtcaccgtc gcaccatgat gctcctggca      60
caaatgcgtc gcatctctct tttctcctgt ctgaaggaca gacatgactt cagatttccc     120
caggaggagt ttgatggcaa ccacctccag aaggttcaag ctatcttcct tttctatgag     180
atgatgcagc agaccttcaa cctcttcagc acaaaggact catctgctgc ttgggatgag     240
accctcctag aaaaattcta cattgaactt ttccagcaaa tgaatgacct ggaagcctgc     300
gtgatgcagg aggttggagt ggaagagact cccctgatga atgtggactc catcctggct     360
gtgaggaaat actttcaaag aatcactctt tatctgacag agaagaagta tagcccttgt     420
gcctgggagg ttgtcagagc agaaatcatg agatctttct cttttcaac aaacttgcaa     480 gaaagcttac gcagcaagga a                                               501

<210> SEQ ID NO 62
<211> LENGTH: 498
<212> TYPE: DNA
<213> ORGANISM: Artificial Sequence
<220> FEATURE:
<223> OTHER INFORMATION: Synthetic Construct 14epi18c1

<400> SEQUENCE: 62
tgtgatctgc ctcagaccca gcctgggt cacaggagga ccatgatgct cctggcacaa       60
atgaggagaa tctctctttt ctcctgtctg aaggacagac atgacttcag atttccccag    120
gaggagtttg atggcaacca cgcccagaag gttcaagcta tcttcctttt ctatgagatg    180
atgcagcaga ccttcaacct cttcagcaca aaggactcat ctgctgcttg ggatgagacc    240
ctcctagaaa aattctacat tgaacttttc agcaaatgaa tgacctgga agcctgcgtg     300 atgcaggagg ttggagtgga agagactccc ctgatgaatg tggactccat cctggctgtg    360
aggaaatact ttcaaagaat cactctttat ctgacagaga agaagtatag cccttgtgcc    420
tgggaggttg tcagagcaga aatcatgaga tctttctctt tttcaacaaa cttgcaagaa   480
agcttacgca gcaaggaa                                                   498

<210> SEQ ID NO 63
<211> LENGTH: 501
<212> TYPE: DNA
<213> ORGANISM: Artificial Sequence
<220> FEATURE:
<223> OTHER INFORMATION: Synthetic Construct 14epi18c2
```

```
<400> SEQUENCE: 63
agttgtgatc tgcctcagac ccacagcctg ggtcaccgtc gcaccatgat gctcctggca        60
caaatgcgtc gcatctctct tttctcctgt ctgaaggacc gccatgactt ccgctttccc       120
caggaggagt tgatggcaa ccacgcccag aaggttcaag ctatcttcct tttctatgag        180
atgatgcagc agaccttcaa cctcttcagc acaaaggact catctgctgc ttgggatgag       240
accctcctag aaaaattcta cattgaactt ttccagcaaa tgaatgacct ggaagcctgc       300
gtgatgcagg aggttggagt ggaagagact cccctgatga atgtggactc catcctggct      360
gtgcgtaaat actttcaacg catcactctt tatctgacag agaagaagta tagcccttgt       420
gcctgggagg ttgtccgcgc agaaatcatg cgctctttct cttttcaac aaacttgcaa        480 gaaagcttac gcagcaagga a                                                 501

<210> SEQ ID NO 64
<211> LENGTH: 501
<212> TYPE: DNA
<213> ORGANISM: Artificial Sequence
<220> FEATURE:
<223> OTHER INFORMATION: Synthetic Construct 14epi18c3

<400> SEQUENCE: 64
agttgtgatc tgcctcagac ccacagcctg ggtcaccgtc gcaccatgat gctcctggca        60
caaatgcgtc gcatctctct tttctcctgt ctgaaggaca gacatgactt cagatttccc      120
caggaggagt tgatggcaa ccacgcccag aaggttcaag ctatcttcct tttctatgag        180
atgatgcagc agaccttcaa cctcttcagc acaaaggact catctgctgc ttgggatgag       240
accctcctag aaaaattcta cattgaactt ttccagcaaa tgaatgacct ggaagcctgc       300
gtgatgcagg aggttggagt ggaagagact cccctgatga atgtggactc catcctggct      360
gtgaggaaat actttcaaag aatcactctt tatctgacag agaagaagta tagcccttgt       420
gcctgggagg ttgtcagagc agaaatcatg agatctttct cttttcaac aaacttgcaa        480 gaaagcttac gcagcaagga a                                                 501

<210> SEQ ID NO 65
<211> LENGTH: 498
<212> TYPE: DNA
<213> ORGANISM: Artificial Sequence
<220> FEATURE:
<223> OTHER INFORMATION: Synthetic Construct 14epi20c1

<400> SEQUENCE: 65
tgtgatctgc ctcagaccca cagcctgggt cacaggagga ccatgatgct cctggcacaa       60
atgaggagaa tctctctttt ctcctgtctg aaggacagac atgacttcag atttccccag      120
gaggagtttg atggcaacca cgcccagaag gttcaagcta tctctctttt ctatgagatg      180
atgcagcaga ccttcaacct cttcagcaca aaggactcat ctgctgcttg ggatgagacc      240
ctcctagaaa aattctacat tgaacttttc agcaaatgaa tgacctgga agccgcgtg         300 atgcaggagg ttggagtgga agagactccc ctgatgaatg tggactccat cctggctgtg      360
aggaaatact ttcaaagaat cactctttat ctgacagaga agaagtatag cccttgtgcc      420
tgggaggttg tcagagcaga aatcatgaga tctttctctt tttcaacaaa cttgcaagaa      480
agcttacgca gcaaggaa                                                    498
```

```
<210> SEQ ID NO 66
<211> LENGTH: 501
<212> TYPE: DNA
<213> ORGANISM: Artificial Sequence
<220> FEATURE:
<223> OTHER INFORMATION: Synthetic Construct 14epi20c2

<400> SEQUENCE: 66
atgtgtgatc tgcctcagac ccacagcctg ggtcaccgtc gcaccatgat gctcctggca       60
caaatgcgtc gcatctctct tttctcctgt ctgaaggacc gccatgactt ccgctttccc      120
caggaggagt tgatggcaa ccacgcccag aaggttcaag ctatctctct tttctatgag       180
atgatgcagc agaccttcaa cctcttcagc acaaaggact catctgctgc ttgggatgag      240
accctcctag aaaaattcta cattgaactt ttccagcaaa tgaatgacct ggaagcctgc      300
gtgatgcagg aggttggagt ggaagagact cccctgatga atgtggactc catcctggct      360
gtgcgtaaat actttcaacg catcactctt tatctgacag agaagaagta tagcccttgt      420
gcctgggagg ttgtccgcgc agaaatcatg cgctcttttct cttttcaac aaacttgcaa      480 gaaagcttac gcagcaagga a                                                 501

<210> SEQ ID NO 67
<211> LENGTH: 501
<212> TYPE: DNA
<213> ORGANISM: Artificial Sequence
<220> FEATURE:
<223> OTHER INFORMATION: Synthetic Construct 14epi20c3

<400> SEQUENCE: 67
atgtgtgatc tgcctcagac ccacagcctg ggtcaccgtc gcaccatgat gctcctggca       60
caaatgcgtc gcatctctct tttctcctgt ctgaaggaca gacatgactt cagatttccc      120
caggaggagt tgatggcaa ccacgcccag aaggttcaag ctatctctct tttctatgag       180
atgatgcagc agaccttcaa cctcttcagc acaaaggact catctgctgc ttgggatgag      240
accctcctag aaaaattcta cattgaactt ttccagcaaa tgaatgacct ggaagcctgc      300
gtgatgcagg aggttggagt ggaagagact cccctgatga atgtggactc catcctggct      360
gtgaggaaat actttcaaag aatcactctt tatctgacag agaagaagta tagcccttgt      420
gcctgggagg ttgtcagagc agaaatcatg agatctttct cttttcaac aaacttgcaa       480 gaaagcttac gcagcaagga a                                                 501

<210> SEQ ID NO 68
<211> LENGTH: 498
<212> TYPE: DNA
<213> ORGANISM: Artificial Sequence
<220> FEATURE:
<223> OTHER INFORMATION: Synthetic Construct 14epi28c1

<400> SEQUENCE: 68
tgtgatctgc ctcagaccca cagcctgggt cacaggagga ccatgatgct cctggcacaa       60
atgaggagaa tctctctttt ctcctgtctg aaggacagac atgacttcag atttccccag      120
gaggagtttg atggcaacca cgcccagaag gttcaagcta tctctctttt ctatgagatg      180
atgcagcaga ccgctaacct cttcagcaca aaggactcat ctgctgcttg ggatgagacc      240
ctcctagaaa aattctacat tgaacttttc cagcaaatga atgacctgga agcctgcgtg      300
atgcaggagg ttggagtgga agagactccc ctgatgaagg aggactccat cctggctgtg      360
aggaaatact ttcaaagaat cactctttat ctgacagaga agaagtatag cccttgtgcc      420
```
tgggaggttg tcagagcaga atcatgaga tctttctctt tttcaacaaa cttgcaagaa    480
agcttacgca gcaaggaa                                                 498

<210> SEQ ID NO 69
<211> LENGTH: 501
<212> TYPE: DNA
<213> ORGANISM: Artificial Sequence
<220> FEATURE:
<223> OTHER INFORMATION: Synthetic Construct 14epi28c2

<400> SEQUENCE: 69
atgtgtgatc tgcctcagac ccacagcctg ggtcaccgtc gcaccatgat gctcctggca     60
caaatgcgtc gcatctctct tttctcctgt ctgaaggacc gccatgactt ccgctttccc    120
caggaggagt ttgatggcaa ccacgcccag aaggttcaag ctatctctct tttctatgag    180
atgatgcagc agaccgctaa cctcttcagc acaaaggact catctgctgc ttgggatgag    240
accctcctag aaaaattcta cattgaactt ttccagcaaa tgaatgaccct ggaagcctgc    300 gtgatgcagg aggttggagt ggaagagact cccctgatga aggaggactc catcctggct    360
gtgcgtaaat actttcaacg catcactctt tatctgacag agaagaagta tagcccttgt    420
gcctgggagg ttgtccgcgc agaaatcatg cgctctttct cttttcaac aaacttgcaa    480 gaaagcttac gcagcaagga a                                             501

<210> SEQ ID NO 70
<211> LENGTH: 501
<212> TYPE: DNA
<213> ORGANISM: Artificial Sequence
<220> FEATURE:
<223> OTHER INFORMATION: Synthetic Construct 14epi28c3

<400> SEQUENCE: 70
atgtgtgatc tgcctcagac ccacagcctg ggtcaccgtc gcaccatgat gctcctggca     60
caaatgcgtc gcatctctct tttctcctgt ctgaaggaca gacatgactt cagatttccc    120
caggaggagt ttgatggcaa ccacgcccag aaggttcaag ctatctctct tttctatgag    180
atgatgcagc agaccgctaa cctcttcagc acaaaggact catctgctgc ttgggatgag    240
accctcctag aaaaattcta cattgaactt ttccagcaaa tgaatgaccct ggaagcctgc    300 gtgatgcagg aggttggagt ggaagagact cccctgatga aggaggactc catcctggct    360
gtgaggaaat actttcaaag aatcactctt tatctgacag agaagaagta tagcccttgt    420
gcctgggagg ttgtcagagc agaaatcatg agatctttct cttttcaac aaacttgcaa    480 gaaagcttac gcagcaagga a                                             501

<210> SEQ ID NO 71
<211> LENGTH: 498
<212> TYPE: DNA
<213> ORGANISM: Artificial Sequence
<220> FEATURE:
<223> OTHER INFORMATION: Synthetic Construct 14epi32c1

<400> SEQUENCE: 71
tgtgatctgc ctcagaccca cagcctgggt cacaggagga ccatgatgct cctggcacaa     60
atgaggagaa tctctctttt ctcctgtctg aaggacagac atgacttcag atttccccag    120
gaggagtttg atggcaacca cctccagaag gttccagcta tctctctttt ctatgagatg    180
atgcagcaga ccttcaacct cttcagcaca aaggactcat ctgctgcttg ggatgagacc    240
ctcctagaaa aattctacat tgaactttcc agcaaatga atgacctgga agcctgcgtg    300

```
atgcaggagg ttggagtgga agagactccc ctgatgaagg aggactccat cctggctgtg    360
aggaaatact ttcaaagaat cactctttat ctgacagaga agaagtatag cccttgtgcc    420
tgggaggttg tcagagcaga aatcatgaga tctttctctt tttcaacaaa cttgcaagaa    480
agcttacgca gcaaggaa                                                   498
```

<210> SEQ ID NO 72
<211> LENGTH: 501
<212> TYPE: DNA
<213> ORGANISM: Artificial Sequence
<220> FEATURE:
<223> OTHER INFORMATION: Synthetic Construct 14epi32c2

<400> SEQUENCE: 72

```
atgtgtgatc tgcctcagac ccacagcctg ggtcaccgtc gcaccatgat gctcctggca    60
caaatgcgtc gcatctctct tttctcctgt ctgaaggacc gccatgactt ccgctttccc    120
caggaggagt ttgatggcaa ccacctccag aaggttccag ctatctctct tttctatgag    180
atgatgcagc agaccttcaa cctcttcagc acaaaggact catctgctgc ttgggatgag    240
accctcctag aaaaattcta cattgaactt ttccagcaaa tgaatgacct ggaagcctgc    300
gtgatgcagg aggttggagt ggaagagact ccctgatga aggaggactc catcctggct    360
gtgcgtaaat actttcaacg catcactctt tatctgacag agaagaagta tagcccttgt    420
gcctgggagg ttgtccgcgc agaaatcatg cgctctttct cttttcaac aaacttgcaa    480 gaaagcttac gcagcaagga a                                              501
```

<210> SEQ ID NO 73
<211> LENGTH: 501
<212> TYPE: DNA
<213> ORGANISM: Artificial Sequence
<220> FEATURE:
<223> OTHER INFORMATION: Synthetic Construct 14epi32c3

<400> SEQUENCE: 73

```
atgtgtgatc tgcctcagac ccacagcctg ggtcaccgtc gcaccatgat gctcctggca    60
caaatgcgtc gcatctctct tttctcctgt ctgaaggaca gacatgactt cagatttccc    120
caggaggagt ttgatggcaa ccacctccag aaggttccag ctatctctct tttctatgag    180
atgatgcagc agaccttcaa cctcttcagc acaaaggact catctgctgc ttgggatgag    240
accctcctag aaaaattcta cattgaactt ttccagcaaa tgaatgacct ggaagcctgc    300
gtgatgcagg aggttggagt ggaagagact ccctgatga aggaggactc catcctggct    360
gtgaggaaat actttcaaag aatcactctt tatctgacag agaagaagta tagcccttgt    420
gcctgggagg ttgtcagagc agaaatcatg agatctttct cttttcaac aaacttgcaa    480 gaaagcttac gcagcaagga a                                              501
```

<210> SEQ ID NO 74
<211> LENGTH: 498
<212> TYPE: DNA
<213> ORGANISM: Artificial Sequence
<220> FEATURE:
<223> OTHER INFORMATION: Synthetic Construct 14epi35c1

<400> SEQUENCE: 74

```
tgtgatctgc ctcagaccca cagcctgggt cacaggagga ccatgatgct cctggcacaa    60
atgaggagaa tctctctttt ctcctgtctg aaggacagac atgacttcag atttccccag    120
gaggagtttg atggcaacca cctccagaag gctccagcca tctctgtcct ccatgagatg    180
```

```
atgcagcaga ccttcaacct cttcagcaca aaggactcat ctgctgcttg ggatgagacc    240
ctcctagaaa aattctacat tgaactttc cagcaaatga atgacctgga agcctgcgtg     300
atgcaggagg ttggagtgga agagactccc ctgatgaagg aggactccat cctggctgtg    360
aggaaatact ttcaaagaat cactctttat ctgacagaga agaagtatag cccttgtgcc    420
tgggaggttg tcagagcaga aatcatgaga tctttctctt tttcaacaaa cttgcaagaa    480
agcttacgca gcaaggaa                                                 498
```

<210> SEQ ID NO 75
<211> LENGTH: 501
<212> TYPE: DNA
<213> ORGANISM: Artificial Sequence
<220> FEATURE:
<223> OTHER INFORMATION: Synthetic Construct 14epi35c2

<400> SEQUENCE: 75

```
atgtgtgatc tgcctcagac ccacagcctg ggtcaccgtc gcaccatgat gctcctggca    60
caaatgcgtc gcatctctct tttctcctgt ctgaaggacc gccatgactt ccgctttccc    120
caggaggagt ttgatggcaa ccacctccag aaggctccag ccatctctgt cctccatgag    180
atgatgcagc agaccttcaa cctcttcagc acaaggact catctgctgc ttgggatgag     240
accctcctag aaaaattcta cattgaactt ttccagcaaa tgaatgacct ggaagcctgc    300
gtgatgcagg aggttggagt ggaagagact cccctgatga aggaggactc catcctggct    360
gtgcgtaaat actttcaacg catcactctt tatctgacag agaagaagta tagcccttgt    420
gcctgggagg ttgtccgcgc agaaatcatg cgctcttttct cttttcaac aaacttgcaa    480 gaaagcttac gcagcaagga a                                             501
```

<210> SEQ ID NO 76
<211> LENGTH: 501
<212> TYPE: DNA
<213> ORGANISM: Artificial Sequence
<220> FEATURE:
<223> OTHER INFORMATION: Synthetic Construct 14epi35c3

<400> SEQUENCE: 76

```
atgtgtgatc tgcctcagac ccacagcctg ggtcaccgtc gcaccatgat gctcctggca    60
caaatgcgtc gcatctctct tttctcctgt ctgaaggaca gacatgactt cagatttccc    120
caggaggagt ttgatggcaa ccacctccag aaggctccag ccatctctgt cctccatgag    180
atgatgcagc agaccttcaa cctcttcagc acaaggact catctgctgc ttgggatgag     240
accctcctag aaaaattcta cattgaactt ttccagcaaa tgaatgacct ggaagcctgc    300
gtgatgcagg aggttggagt ggaagagact cccctgatga aggaggactc catcctggct    360
gtgaggaaat actttcaaag aatcactctt tatctgacag agaagaagta tagcccttgt    420
gcctgggagg ttgtcagagc agaaatcatg agatctttct cttttcaac aaacttgcaa     480 gaaagcttac gcagcaagga a                                             501
```

<210> SEQ ID NO 77
<211> LENGTH: 498
<212> TYPE: DNA
<213> ORGANISM: Artificial Sequence
<220> FEATURE:
<223> OTHER INFORMATION: Synthetic Construct 25epi18c1

```
<400> SEQUENCE: 77
tgtgatctgc ctcagaccca cagcctgagt aacaggagga ctctgatgct catggcacaa      60
atgaggagaa tctctccttt ctcctgcctg aaggacagac atgatttcgg attccccgag     120
gaggagtttg atgccacca ggcccagaag actcaagcca tctccgttct ccatgagctg      180
atccagcaga ccttcaatct cttcagcaca aaggactcat ctgctgcttg ggatgagacc     240
ctcctagaaa aattctacat tgaactttc agcaaatga ataacctgga agcatgtgtg       300
atacaggagg ttggggtgga agagattgcc ctgatgaatg tggactccat cctggctgtg     360
aggaaatact tccgtcgcat cactctctat ctgacagaga agaaatacag cccttgtgcc    420
tgggaggttg tcagagcaga aatcatgaga tctttctctt tttcaacaaa cttgcaagaa    480
agcttacgca gcaaggaa                                                   498

<210> SEQ ID NO 78
<211> LENGTH: 501
<212> TYPE: DNA
<213> ORGANISM: Artificial Sequence
<220> FEATURE:
<223> OTHER INFORMATION: Synthetic Construct 25epi18c2

<400> SEQUENCE: 78
atgtgtgatc tgcctcagac ccacagcctg agtaaccgtc gcactctgat gctcatggca     60
caaatgcgtc gcatctctcc tttctcctgc ctgaaggacc gccatgattt cggattcccc    120
gaggaggagt ttgatggcca ccaggcccag aagactcaag ccatctccgt tctccatgag    180
ctgatccagc agaccttcaa tctcttcagc acaaaggact catctgctgc ttgggatgag    240
accctcctag aaaaattcta cattgaactt ttccagcaaa tgaataaccct ggaagcatgt   300 gtgatacagg aggttggggt ggaagagatt gccctgatga atgtggactc catcctggct    360
gtgcgtaaat acttccgtcg catcactctc tatctgacag agaagaaata cagcccttgt    420
gcctgggagg ttgtccgcgc agaaatcatg cgctctttct cttttcaac aaacttgcaa     480 gaaagcttac gcagcaagga a                                              501

<210> SEQ ID NO 79
<211> LENGTH: 501
<212> TYPE: DNA
<213> ORGANISM: Artificial Sequence
<220> FEATURE:
<223> OTHER INFORMATION: Synthetic Construct 25epi18c3

<400> SEQUENCE: 79
atgtgtgatc tgcctcagac ccacagcctg agtaaccgtc gcactctgat gctcatggca     60
caaatgcgtc gcatctctcc tttctcctgc ctgaaggaca gacatgattt cggattcccc    120
gaggaggagt ttgatggcca ccaggcccag aagactcaag ccatctccgt tctccatgag    180
ctgatccagc agaccttcaa tctcttcagc acaaaggact catctgctgc ttgggatgag    240
accctcctag aaaaattcta cattgaactt ttccagcaaa tgaataaccct ggaagcatgt   300 gtgatacagg aggttggggt ggaagagatt gccctgatga atgtggactc catcctggct    360
gtgaggaaat acttccgtcg catcactctc tatctgacag agaagaaata cagcccttgt    420
gcctgggagg ttgtcagagc agaaatcatg agatctttct cttttcaac aaacttgcaa     480 gaaagcttac gcagcaagga a                                              501
```

<210> SEQ ID NO 80
<211> LENGTH: 498
<212> TYPE: DNA
<213> ORGANISM: Artificial Sequence
<220> FEATURE:
<223> OTHER INFORMATION: Synthetic Construct 25epi19c1

<400> SEQUENCE: 80

| | | | | | |
|---|---|---|---|---|---|
| tgtgatctgc | ctcagaccca | cagcctgagt | aacaggagga | ctctgatgct | catggcacaa | 60 |
| atgaggagaa | tctctccttt | tcctgcctg | aaggacagac | atgatttcgg | attccccgag | 120 |
| gaggagtttg | atggccacca | ggcccagaag | gttcaagcca | tcttccttct | ctatgagctg | 180 |
| atccagcaga | ccttcaatct | cttcagcaca | aaggactcat | ctgctgcttg | ggatgagacc | 240 |
| ctcctagaaa | aattctacat | tgaacttttc | cagcaaatga | ataacctgga | agcatgtgtg | 300 |
| atacaggagg | ttggggtgga | agagattgcc | ctgatgaatg | tggactccat | cctggctgtg | 360 |
| aggaaatact | ccgtcgcat | cactctctat | ctgacagaga | agaaatacag | cccttgtgcc | 420 |
| tgggaggttg | tcagagcaga | aatcatgaga | tctttctctt | tttcaacaaa | cttgcaagaa | 480 |
| agcttacgca | gcaaggaa | | | | | 498 |

<210> SEQ ID NO 81
<211> LENGTH: 501
<212> TYPE: DNA
<213> ORGANISM: Artificial Sequence
<220> FEATURE:
<223> OTHER INFORMATION: Synthetic Construct 25epi19c2

<400> SEQUENCE: 81

| | | | | | |
|---|---|---|---|---|---|
| atgtgcgacc | tgccgcagac | ccactccctg | tccaaccgtc | gcaccctgat | gctgatggct | 60 |
| cagatgcgtc | gcatttcccc | gttctcctgc | cttaaggacc | gtcacgactt | cggtttcccg | 120 |
| gaagaggaat | ttgacggtca | ccaggctcag | aaagttcagg | ctatcttcct | gctgtacgag | 180 |
| ctcatccagc | aaaccttcaa | cctgttctcc | accaaagact | cttccgcggc | ttgggacgaa | 240 |
| accctgctgg | agaaatttta | tcgaactg | ttccagcaaa | tgaacaatct | agaagcatgt | 300 |
| gttatccagg | aagttggtgt | tgaagagatc | gctctgatga | acgttgactc | catcctggct | 360 |
| gttcgtaaat | acttccgtcg | catcaccctg | tacctgaccg | aaaaaaagta | ctccccgtgc | 420 |
| gcttgggaag | ttgtacgtgc | tgaaatcatg | agatcttct | ccttctccac | caacctgcag | 480 |
| gaatccctgc | gttccaaaga | a | | | | 501 |

<210> SEQ ID NO 82
<211> LENGTH: 501
<212> TYPE: DNA
<213> ORGANISM: Artificial Sequence
<220> FEATURE:
<223> OTHER INFORMATION: Synthetic Construct  25epi19c3

<400> SEQUENCE: 82

| | | | | | |
|---|---|---|---|---|---|
| atgtgtgatc | tgcctcagac | ccacagcctg | agtaaccgtc | gcactctgat | gctcatggca | 60 |
| caaatgcgtc | gcatctctcc | tttctcctgc | ctgaaggaca | gacatgattt | cggattcccc | 120 |
| gaggaggagt | ttgatggcca | ccaggcccag | aaggttcaag | ccatcttcct | tctctatgag | 180 |
| ctgatccagc | agaccttcaa | tctcttcagc | acaaggact | catctgctgc | ttgggatgag | 240 |
| accctcctag | aaaaattcta | cattgaactt | ttccagcaaa | tgaataacct | ggaagcatgt | 300 |
| gtgatacagg | aggttgggt | ggaagagatt | gccctgatga | atgtggactc | catcctggct | 360 |
| gtgaggaaat | acttccgtcg | catcactctc | tatctgacag | agaagaaata | cagcccttgt | 420 |

```
gcctgggagg ttgtcagagc agaaatcatg agatctttct cttttcaac aaacttgcaa    480 gaaagcttac gcagcaagga a                                             501
```

<210> SEQ ID NO 83
<211> LENGTH: 498
<212> TYPE: DNA
<213> ORGANISM: Artificial Sequence
<220> FEATURE:
<223> OTHER INFORMATION: Synthetic Construct 25epi26c1

<400> SEQUENCE: 83

```
tgtgatctgc ctcagaccca cagcctgagt aacaggagga ctctgatgct catggcacaa     60
atgaggagaa tctctccttt ctcctgcctg aaggacagac atgatttcgg attccccgag    120
gaggagtttg atggccacca ggcccagaag gttcaagcca tctccgttct ccatgagctg    180
atccagcaga ccttcaatct cttcagcaca aaggactcat ctgctgcttg ggatgagacc    240
ctcctagaaa aattctacat tgaactttac agcaactga atgacctgga agcatgtgtg    300
atacaggagg ttggggtgga agagattgcc ctgatgaatg tggactccat cctggctgtg    360
aggaaatact tccgtcgcat cactctctat ctgacagaga gaaaatacag cccttgtgcc    420
tgggaggttg tcagagcaga atcatgaga tctttctctt tttcaacaaa cttgcaagaa    480
agcttacgca gcaaggaa                                                  498
```

<210> SEQ ID NO 84
<211> LENGTH: 501
<212> TYPE: DNA
<213> ORGANISM: Artificial Sequence
<220> FEATURE:
<223> OTHER INFORMATION: Synthetic Construct 25epi26c2

<400> SEQUENCE: 84

```
atgtgtgatc tgcctcagac ccacagcctg agtaaccgtc gcactctgat gctcatggca     60
caaatgcgtc gcatctctcc tttctcctgc ctgaaggacc gccatgattt cggattcccc    120
gaggaggagt tgatggcca ccaggcccag aaggttcaag ccatctccgt tctccatgag    180
ctgatccagc agaccttcaa tctcttcagc acaaaggact catctgctgc tgggatgag    240 accctcctag aaaattcta cattgaactt taccagcaac tgaatgacct ggaagcatgt    300
gtgatacagg aggttgggt ggaagagatt gccctgatga atgtggactc catcctggct    360
gtgcgtaaat acttccgtcg catcactctc tatctgacag agaagaaata cagcccttgt    420
gcctgggagg ttgtccgcgc agaaatcatg cgctctttct cttttcaac aaacttgcaa    480 gaaagcttac gcagcaagga a                                             501
```

<210> SEQ ID NO 85
<211> LENGTH: 501
<212> TYPE: DNA
<213> ORGANISM: Artificial Sequence
<220> FEATURE:
<223> OTHER INFORMATION: Synthetic Construct  25epi26c3

<400> SEQUENCE: 85

```
atgtgtgatc tgcctcagac ccacagcctg agtaaccgtc gcactctgat gctcatggca     60
caaatgcgtc gcatctctcc tttctcctgc ctgaaggaca gacatgattt cggattcccc    120
gaggaggagt tgatggcca ccaggcccag aaggttcaag ccatctccgt tctccatgag    180
ctgatccagc agaccttcaa tctcttcagc acaaaggact catctgctgc tgggatgag    240 accctcctag aaaattcta cattgaactt taccagcaac tgaatgacct ggaagcatgt    300
```

```
gtgatacagg aggttggggt ggaagagatt gccctgatga atgtggactc catcctggct        360
gtgaggaaat acttccgtcg catcactctc tatctgacag agaagaaata cagcccttgt        420
gcctgggagg ttgtcagagc agaaatcatg agatctttct cttttcaac aaacttgcaa         480 gaaagcttac gcagcaagga a                                                  501

<210> SEQ ID NO 86
<211> LENGTH: 498
<212> TYPE: DNA
<213> ORGANISM: Artificial Sequence
<220> FEATURE:
<223> OTHER INFORMATION: Synthetic Construct 25epi29c1

<400> SEQUENCE: 86
tgtgatctgc ctcagaccca cagcctgagt aacaggagga ctctgatgct catggcacaa         60
atgaggagaa tctctccttt ctcctgcctg aaggacagac atgatttcgg attccccgag        120
gaggagtttg atggccacca gttccagaag actcaagcca tctccgttct ccatgagctg        180
atccagcaga ccttcaatct cttcagcaca aaggactcat ctgctgcttg ggatgagacc        240
ctcctagaaa aattctacat tgaacttttc cagcaaatga ataacctgga agcatgtgtg        300
atacaggagg ttggggtgga agagattgcc ctgatgaatg tggactccat cctggctgtg        360
aggaaatact tccgtcgcat cactctctat ctgacagaga gaaatacag cccttgtgcc         420 tgggaggttg tcagagcaga atcatgaga tctttctctt tttcaacaaa cttgcaagat        480
agcttacgca gcaaggaa                                                      498

<210> SEQ ID NO 87
<211> LENGTH: 501
<212> TYPE: DNA
<213> ORGANISM: Artificial Sequence
<220> FEATURE:
<223> OTHER INFORMATION: Synthetic Construct 25epi29c2

<400> SEQUENCE: 87
atgtgcgacc tgccgcagac ccactccctg tccaaccgtc gtaccctgat gctgatggct         60
cagatgcgca gaatctcccc gttctcctgc cttaaggacc gtcacgactt cggtttccca        120
gaagaagaat ttgacggtca ccagttccag aaaacccagg ctatctccgt tcttcatgaa        180
ctgatccagc agaccttcaa cctgttctcc accaaagact cctccgcggc ttgggacgaa        240
accctgctgg aaaaattcta catcgaactg tttcagcaga tgaacaacct agaggcatgt        300
gttatccagg aagtaggtgt tgaggaaatc gctctgatga cgttgactc catcctggct         360 gtccggaaat acttccgtcg catcaccctg tacctgaccg aaaaaaata ctccccgtgc        420 gcttgggaag ttgtgcgcgc tgaaatcatg cgttccttct ccttctccac caacctgcag        480
gactccctgc gttccaaaga a                                                  501

<210> SEQ ID NO 88
<211> LENGTH: 501
<212> TYPE: DNA
<213> ORGANISM: Artificial Sequence
<220> FEATURE:
<223> OTHER INFORMATION: Synthetic Construct 25epi29c3

<400> SEQUENCE: 88
atgtgtgatc tgcctcagac ccacagcctg agtaaccgtc gcactctgat gctcatggca         60
caaatgcgtc gcatctctcc tttctcctgc ctgaaggaca gacatgattt cggattcccc        120
gaggaggagt ttgatggcca ccagttccag aagactcaag ccatctccgt tctccatgag        180
```

```
ctgatccagc agaccttcaa tctcttcagc acaaaggact catctgctgc ttgggatgag    240
accctcctag aaaaattcta cattgaactt ttccagcaaa tgaataaccct ggaagcatgt   300 gtgatacagg aggttggggt ggaagagatt gccctgatga atgtggactc catcctggct   360
gtgaggaaat acttccgtcg catcactctc tatctgacag agaagaaata cagcccttgt   420
gcctgggagg ttgtcagagc agaaatcatg agatctttct cttttcaac aaacttgcaa    480 gatagcttac gcagcaagga a                                             501
```

```
<210> SEQ ID NO 89
<211> LENGTH: 579
<212> TYPE: DNA
<213> ORGANISM: Artificial Sequence
<220> FEATURE:
<223> OTHER INFORMATION: Synthetic Construct 14epi18m2
<220> FEATURE:
<221> NAME/KEY: CDS
<222> LOCATION: (57)...(560)

<400> SEQUENCE: 89
```

```
caattgtgag cggataacaa tttcacacag aattcattaa agaggagaaa ttaact atg     59
                                                                Met
                                                                 1 tgc gac ctg ccg cag acc cac tcc ctt gga cac cgt cgg acc atg atg     107
Cys Asp Leu Pro Gln Thr His Ser Leu Gly His Arg Arg Thr Met Met
          5                  10                  15 ctg cta gct cag atg cgt aga ata tcc ctg ttc tcc tgc ctt aag gac    155
Leu Leu Ala Gln Met Arg Arg Ile Ser Leu Phe Ser Cys Leu Lys Asp
         20                  25                  30 cgt cac gac ttc cgt ttc ccc cag gaa gaa ttt gat ggt aac cac gct    203
Arg His Asp Phe Arg Phe Pro Gln Glu Glu Phe Asp Gly Asn His Ala
     35                  40                  45 cag aaa gtt cag gct atc ttc ctg ttt tac gaa atg atg cag caa acc    251
Gln Lys Val Gln Ala Ile Phe Leu Phe Tyr Glu Met Met Gln Gln Thr
 50                  55                  60                  65 ttc aac ctg ttc tcc acc aaa gac tcc tcc gcg gct tgg gac gaa acc    299
Phe Asn Leu Phe Ser Thr Lys Asp Ser Ser Ala Ala Trp Asp Glu Thr
                 70                  75                  80 ctg ctg gaa aaa ttc tac atc gaa ctg ttc cag cag atg aac gat cta    347
Leu Leu Glu Lys Phe Tyr Ile Glu Leu Phe Gln Gln Met Asn Asp Leu
             85                  90                  95 gaa gca tgc gtt atg cag gaa gta ggt gtt gaa gag acc cca ctg atg    395
Glu Ala Cys Val Met Gln Glu Val Gly Val Glu Glu Thr Pro Leu Met
        100                 105                 110 aac gtt gac tcc atc ctg gct gtc cgg aaa tac ttc cag cgt atc acc    443
Asn Val Asp Ser Ile Leu Ala Val Arg Lys Tyr Phe Gln Arg Ile Thr
    115                 120                 125 ctg tac ctg act gaa aaa aaa tac tcc ccg tgc gct tgg gaa gtt gtg    491
Leu Tyr Leu Thr Glu Lys Lys Tyr Ser Pro Cys Ala Trp Glu Val Val
130                 135                 140                 145 cgc gct gaa atc atg cgt tcc ttc tcc ttc tcc acc aac ctg cag gaa    539
Arg Ala Glu Ile Met Arg Ser Phe Ser Phe Ser Thr Asn Leu Gln Glu
                150                 155                 160 tcc ctg cgt tcc aaa gaa taa taagcttaat tagctgagc                   579
Ser Leu Arg Ser Lys Glu *
            165
```

```
<210> SEQ ID NO 90
<211> LENGTH: 579
<212> TYPE: DNA
<213> ORGANISM: Artificial Sequence
```

-continued

```
<220> FEATURE:
<223> OTHER INFORMATION: Synthetic Construct 25epi19m
<220> FEATURE:
<221> NAME/KEY: CDS
<222> LOCATION: (57)...(560)

<400> SEQUENCE: 90
caattgtgag cggataacaa tttcacacag aattcattaa agaggagaaa ttaact atg      59
                                                                 Met
                                                                  1 tgc gac ctg ccg cag acc cac tcc ctt tct aac cgt aga acc ctg atg      107
Cys Asp Leu Pro Gln Thr His Ser Leu Ser Asn Arg Arg Thr Leu Met
          5                  10                  15 ctg atg gct cag atg cgt cgt att tct ccg ttc tct tgc ctt aag gat      155
Leu Met Ala Gln Met Arg Arg Ile Ser Pro Phe Ser Cys Leu Lys Asp
             20                  25                  30 cgt cac gac ttc ggt ttc cca gaa gag gaa ttt gac ggt cac cag gct      203
Arg His Asp Phe Gly Phe Pro Glu Glu Glu Phe Asp Gly His Gln Ala
     35                  40                  45 cag aaa gtt cag gct atc ttc ctg ctg tac gag ctc atc cag caa acc      251
Gln Lys Val Gln Ala Ile Phe Leu Leu Tyr Glu Leu Ile Gln Gln Thr
 50                  55                  60                  65 ttc aac ctg ttc tct acc aaa gac tct tcc gcg gct tgg gac gaa acc      299
Phe Asn Leu Phe Ser Thr Lys Asp Ser Ser Ala Ala Trp Asp Glu Thr
                 70                  75                  80 ctg ctg gag aaa ttt tac atc gaa ctg ttc cag caa atg aac aat cta      347
Leu Leu Glu Lys Phe Tyr Ile Glu Leu Phe Gln Gln Met Asn Asn Leu
                     85                  90                  95 gaa gca tgt gtt atc cag gaa gtt ggt gtt gaa gag atc gct ctg atg      395
Glu Ala Cys Val Ile Gln Glu Val Gly Val Glu Glu Ile Ala Leu Met
            100                 105                 110 aac gtt gac tcc atc ctg gct gtt cgt aaa tac ttc cgt cgc atc acc      443
Asn Val Asp Ser Ile Leu Ala Val Arg Lys Tyr Phe Arg Arg Ile Thr
        115                 120                 125 ctg tac ctg acc gaa aaa aag tac tcc ccg tgc gct tgg gaa gtt gta      491
Leu Tyr Leu Thr Glu Lys Lys Tyr Ser Pro Cys Ala Trp Glu Val Val
130                 135                 140                 145 cgt gct gaa atc atg aga tct ttc tcc ttc tcc acc aac ctg cag gaa      539
Arg Ala Glu Ile Met Arg Ser Phe Ser Phe Ser Thr Asn Leu Gln Glu
                150                 155                 160 tcc ctg cgt tcc aaa gaa taa taagcttaat tagctgagc                     579
Ser Leu Arg Ser Lys Glu *
                165
```